United States Patent
Yurkovetskiy et al.

(10) Patent No.: US 10,226,535 B2
(45) Date of Patent: Mar. 12, 2019

(54) AURISTATIN COMPOUNDS AND CONJUGATES THEREOF

(71) Applicant: Mersana Therapeutics, Inc., Cambridge, MA (US)

(72) Inventors: Aleksandr V. Yurkovetskiy, Littleton, MA (US); Mao Yin, Needham, MA (US); Timothy B. Lowinger, Carlisle, MA (US); Cheri A. Stevenson, Haverhill, MA (US); Patrick R. Conlon, Wakefield, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 3 days.

(21) Appl. No.: 14/651,097

(22) PCT Filed: Dec. 10, 2013

(86) PCT No.: PCT/US2013/074187
§ 371 (c)(1),
(2) Date: Jun. 10, 2015

(87) PCT Pub. No.: WO2014/093379
PCT Pub. Date: Jun. 19, 2014

(65) Prior Publication Data
US 2015/0314008 A1 Nov. 5, 2015

Related U.S. Application Data

(60) Provisional application No. 61/735,534, filed on Dec. 10, 2012.

(51) Int. Cl.
*A61K 47/59* (2017.01)
*A61K 47/48* (2006.01)
*C08G 4/00* (2006.01)
*C07K 17/08* (2006.01)

(52) U.S. Cl.
CPC ........ *A61K 47/48192* (2013.01); *A61K 47/59* (2017.08); *C07K 17/08* (2013.01); *C08G 4/00* (2013.01)

(58) Field of Classification Search
None
See application file for complete search history.

(56) References Cited

U.S. PATENT DOCUMENTS

| | | |
|---|---|---|
| 5,208,020 A | 5/1993 | Chari et al. |
| 5,410,024 A | 4/1995 | Pettit et al. |
| 5,416,064 A | 5/1995 | Chari et al. |
| 5,475,092 A | 12/1995 | Chari et al. |
| 5,502,032 A | 3/1996 | Haupt et al. |
| 5,585,499 A | 12/1996 | Chari et al. |
| 5,635,483 A | 6/1997 | Pettit et al. |
| 5,663,149 A | 9/1997 | Pettit et al. |
| 5,767,237 A | 6/1998 | Sakakibara et al. |
| 5,780,588 A | 7/1998 | Pettit et al. |
| 5,846,545 A | 12/1998 | Chari et al. |
| 6,214,345 B1 | 4/2001 | Firestone et al. |
| 6,323,315 B1 | 11/2001 | Pettit et al. |
| 6,333,410 B1 | 12/2001 | Chari et al. |
| 6,340,701 B1 | 1/2002 | Chari et al. |
| 6,372,738 B2 | 4/2002 | Chari et al. |
| 6,436,931 B1 | 8/2002 | Chari et al. |
| 6,441,163 B1 | 8/2002 | Chari et al. |
| 6,534,660 B1 | 3/2003 | Yongxin et al. |
| 6,596,757 B1 | 7/2003 | Chari et al. |
| 6,630,579 B2 | 10/2003 | Chari et al. |
| 6,756,397 B2 | 6/2004 | Zhao et al. |
| 7,276,497 B2 | 10/2007 | Chari et al. |

(Continued)

FOREIGN PATENT DOCUMENTS

| | | | |
|---|---|---|---|
| WO | WO 2002088172 A2 | | 11/2002 |
| WO | WO 2004/032828 | * | 4/2004 |

(Continued)

OTHER PUBLICATIONS

Doronina et al., Development of potent monoclonal antibody auristatin conjugates for cancer therapy. *Nature Biotech.* 2003, 21:778-784.
Hamann, Monoclonal Antibody-Drug Conjugates. *Expert Opinion on Therapeutic Patents, Informa Healthcare*, GB, 2005, 15:1087-1103.
Doronina et al., Enhanced Activity of Monomethylauristatin F through Monoclonal Antibody Delivery: Effects of Linker Technology on Efficacy and Toxicity. *Bioconjugate Chem.*, 2006, 17:114-124.
Doronina et al., Novel Peptide Linkers for Highly Potent Antibody-Auristatin Conjugate. *Bioconjugate Chem.*, 2008, 19:1960-1963.
Gianolio et al., Targeting HER2-positive cancer with dolastatin 15 derivatives conjugated to trastuzumab, novel antibody—drug conjugates. *Cancer Chemother Pharmacol*, 2012, 70:439-449.

(Continued)

*Primary Examiner* — Sergio Coffa
(74) *Attorney, Agent, or Firm* — Cooley LLP; Heidi A. Erlacher; Xixi Sun

(57) ABSTRACT

An auristatin compound conjugate is provided herein. The conjugate comprises a protein based recognition-molecule (PBRM) and a polymeric carrier substituted with one or more -$L^D$-D, the protein based recognition-molecule being connected to the polymeric carrier by $L^P$. Each occurrence of D is independently an auristatin compound having a molecular weight ≤5 kDa. $L^D$ and $L^P$ are distinct linkers connecting the auristatin compound and PBRM to the polymeric carrier respectively. Also disclosed are polymeric scaffolds useful for conjugating with a PBRM to form a polymer-auristatin compound-PBRM conjugate described herein, compositions comprising the conjugates, methods of their preparation, and methods of treating various disorders with the conjugates or their compositions.

19 Claims, 4 Drawing Sheets

(56) References Cited

U.S. PATENT DOCUMENTS

| | | |
|---|---|---|
| 7,423,116 B2 | 9/2008 | Doronina et al. |
| 7,498,298 B2 | 3/2009 | Doronina et al. |
| 7,659,241 B2 | 2/2010 | Senter et al. |
| 7,662,387 B2 | 2/2010 | Law et al. |
| 7,829,531 B2 | 11/2010 | Senter et al. |
| 7,968,687 B2 | 6/2011 | McDonagh et al. |
| 8,685,383 B2 | 4/2014 | Yurkovetskiy et al. |
| 8,808,679 B2 | 8/2014 | Yurkovetskiy et al. |
| 8,815,226 B2 | 8/2014 | Yurkovetskiy et al. |
| 8,821,850 B2 | 9/2014 | Yurkovetskiy et al. |
| 9,144,615 B2 | 9/2015 | Yurkovetskiy et al. |
| 2009/0111756 A1 | 4/2009 | Doronina et al. |
| 2011/0020343 A1 | 1/2011 | Senter et al. |
| 2012/0003247 A1 | 1/2012 | Doronina et al. |
| 2013/0066055 A1 | 3/2013 | Lerchen et al. |
| 2013/0095123 A1 | 4/2013 | Lerchen et al. |
| 2013/0129753 A1 | 5/2013 | Doroski et al. |
| 2013/0157960 A1 | 6/2013 | Lerchen et al. |
| 2013/0230543 A1 | 9/2013 | Pons et al. |
| 2014/0080763 A1 | 3/2014 | Lerchen et al. |
| 2014/0127240 A1 | 5/2014 | Lerchen et al. |
| 2015/0064130 A1 | 3/2015 | Yurkovetskiy et al. |
| 2015/0104407 A1 | 4/2015 | Yurkovetskiy et al. |
| 2015/0306240 A1 | 10/2015 | Yurkovetskiy et al. |
| 2015/0366982 A1 | 12/2015 | Bodyak et al. |
| 2015/0366987 A1 | 12/2015 | Bodyak et al. |
| 2016/0022829 A1 | 1/2016 | Yurkovetskiy et al. |

FOREIGN PATENT DOCUMENTS

| | | |
|---|---|---|
| WO | WO 2005023294 A2 | 3/2005 |
| WO | WO 2005081711 A2 | 9/2005 |
| WO | WO 2009117531 A1 | 9/2009 |
| WO | WO 2010138719 A1 | 12/2010 |
| WO | WO 2011/120053 A1 | 9/2011 |
| WO | WO 2011154359 A1 | 12/2011 |
| WO | WO 2012059882 A2 | 5/2012 |
| WO | WO 2012123423 A1 | 9/2012 |
| WO | WO 2012131527 A1 | 10/2012 |
| WO | WO 2012135440 A1 | 10/2012 |
| WO | WO 2012/171020 A1 | 12/2012 |
| WO | WO 2012166560 A1 | 12/2012 |
| WO | WO 2014/008375 A1 | 1/2014 |

OTHER PUBLICATIONS

Lewis Phillips et al., Targeting HER2-Positive Breast Cancer with Trastuzumab-DM1, an Antibody—Cytotoxic Drug Conjugate. *Cancer Res.*, 2008, 68:9280-9290.

Krop et al. "Phase I Study of Trastuzumab-DM1, an HER2 Antibody-Drug Conjugate, Given Every 3 Weeks to Patients With HER2-Positive Metastatic Breast Cancer", *Journal of Clinical Oncology*, 2010, vol. 28, p. 2698-2704.

Ricart, A. D., and Tolcher, A. W., "Technology Insight: cytotoxic drug immunoconjugates for cancer therapy", *Nature Clinical Practice*, 2007, vol. 4, p. 245-255.

\* cited by examiner

FIGURE 4

Table 1

|  | At least one polymer attached to one PBRM, PBRM MW > 40 kDa | | |
|---|---|---|---|
| Starting/unmodified PHF MW range, kDa | Acceptable Range | Preferable Range | Most preferable |
|  | 2-40 kDa | 6-20 kDa | 8-15 kDa |
| $m+m_1+m_2+m_3+m_4$ | 15-300 | 45-150 | 60-110 |
| $m_1+m_2$ | 3-140 | 7-75 | 7-55 |
| $m_2$ | 1-40 | 2-20 | 2-15 |
| $m_3+m_4$ | 1-18 | 1-9 | 1-7 |
| $m_4$ | 1-10 | 1-10 | 1-10 |
| Polymer/PBRM ratio | 1-10 | 1-10 | 1-10 |

Table 2

|  | At least one PBRM is attached to one polymer | | |
|---|---|---|---|
|  | PBRM MW <200 kDa, PBRM MW preferably < 80 kDa, PBRM MW more preferably 30-70 kDa, 20-30 kDa, or 4-20 kDa | | |
| Starting/unmodified PHF MW range, kDa | Acceptable Range | Preferable Range | Most preferable |
|  | 20-300 kDa | 20-150 kDa | 30-100 kDa |
| $m+m_1+m_2+m_3+m_4$ | 150-2200 | 150-1100 | 220-740 |
| $m_1+m_2$ | 14-660 | 14-330 | 18-220 |
| $m_2$ | 3-300 | 3-150 | 3-100 |
| $m_3+m_4$ | 1-110 | 1-55 | 1-40 |
| $m_4$ | 1-60 | 1-30 | 1-20 |
| Polymer/PBRM ratio | 0.0167-1.0 | 0.0333-1.0 | 0.05-1.0 |

AURISTATIN COMPOUNDS AND CONJUGATES THEREOF

RELATED APPLICATIONS

This application is a U.S. National Phase application, filed under 35 U.S.C. § 371, of International Application No. PCT/US2013/074187, filed Dec. 10, 2013, which claims the benefit of and priority to U.S. Provisional Application No. 61/735,534, filed Dec. 10, 2012, the contents of each of which are hereby incorporated by reference in their entireties.

BACKGROUND OF THE INVENTION

Traditionally, pharmaceuticals have primarily consisted of small molecules that are dispensed orally (as solid pills and liquids) or as injectables. Over the past three decades, formulations (i.e., compositions that control the route and/or rate of drug delivery and allow delivery of the therapeutic agent at the site where it is needed) have become increasingly common and complex. Nevertheless, many questions and challenges regarding the development of new treatments as well as the mechanisms with which to administer them remain to be addressed. For example, many drugs exhibit limited or otherwise reduced potencies and therapeutic effects because they are either generally subject to partial degradation before they reach a desired target in the body, or accumulate in tissues other than the target, or both.

One objective in the field of drug delivery systems, therefore, is to deliver medications intact to specifically targeted areas of the body through a system that can stabilize the drug and control the in vivo transfer of the therapeutic agent utilizing either physiological or chemical mechanisms, or both.

Antibody-drug conjugates have been developed as target-specific therapeutic agents. Antibodies against various cancer cell-surface antigens have been conjugated with different cytotoxic agents that inhibit various essential cellular targets such as microtubules (maytansinoids, auristatins, taxanes: U.S. Pat. Nos. 5,208,020; 5,416,064; 6,333,410; 6,441,163; 6,340,701; 6,372,738; 6,436,931; 6,596,757; and 7,276,497); DNA (calicheamicin, doxorubicin, CC-1065 analogs; U.S. Pat. Nos. 5,475,092; 5,585,499; 5,846,545; 6,534,660; 6,756,397; and 6,630,579). Antibody conjugates with some of these cytotoxic drugs are actively being investigated in the clinic for cancer therapy (Ricart, A. D., and Tolcher, A. W., 2007, *Nature Clinical Practice*, 4, 245-255; Krop et al., 2010, *J. Clin. Oncol.*, 28, 2698-2704). However, existing antibody-drug conjugates have exhibited a few limitations. A major limitation is their inability to deliver a sufficient concentration of drug to the target site because of the limited number of targeted antigens and the relatively moderate cytotoxicity of cancer drugs like methotrexate, daunorubicin, maytansinoids, taxanes, and vincristine. One approach to achieving significant cytotoxicity is by linkage of a large number of drug molecules either directly or indirectly to the antibody. However such heavily modified antibodies often display impaired binding to the target antigen and fast in vivo clearance from the blood stream. Therefore, there is a need to improve the ability to deliver a sufficient concentration of a drug to the target such that maximum cytotoxicity for the drug is achieved.

SUMMARY OF THE INVENTION

The present invention relates to a protein-polymer-drug conjugate (i.e., a protein-polymer-auristatin compound conjugate) that is biodegradable, biocompatible and exhibits high drug load as well as strong binding to target antigen. The present invention also relates to a polymeric scaffold useful to conjugate with a protein based recognition-molecule (PBRM) so as to obtain the protein-polymer-drug conjugate.

In one aspect, the invention relates to a polymeric scaffold of Formula (Ibb) useful to conjugate with a protein based recognition-molecule (PBRM):

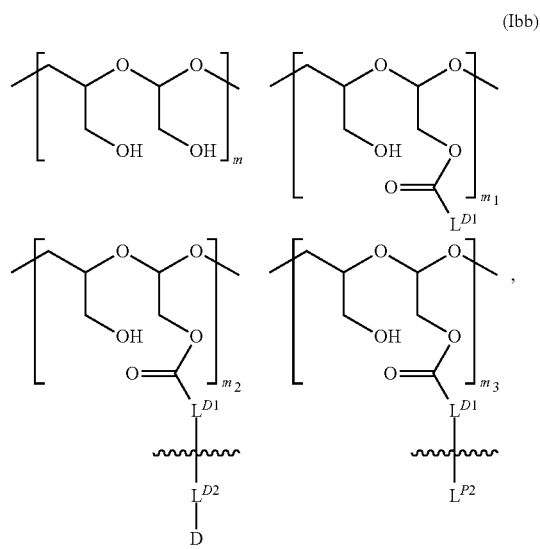

(Ibb)

wherein:

the scaffold comprises poly(1-hydroxymethylethylene hydroxymethyl-formal) (PHF) having a molecular weight (i.e., MW of the unmodified PHF) ranging from 2 kDa to 40 kDa when the PBRM to be conjugated has a molecular weight of greater than 40 kDa, or the scaffold comprises PHF having a molecular weight ranging from 20 kDa to 300 kDa when the PBRM to be conjugated has a molecular weight of less than 200 kDa (e.g., less than 80 kDa);

each occurrence of D is independently an auristatin compound having a molecular weight of ≤5 kDa;

$L^{D1}$ is a carbonyl-containing moiety;

$L^{D2}$ is a moiety of Formula (Iaa):

$$-A_a-W_w-Y_y- \qquad (Iaa)$$

in which

-A- is a Stretcher unit and is proximal to the polymeric carrier;

a is an integer 0 or 1;

each —W— is independently an amino acid unit;

w is an integer from 0 to 12;

—Y— is a self-immolative or non-self-immolative Spacer unit and is proximal to D; and y is an integer from 0 to 2;

each occurrence of

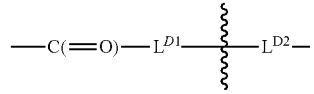

in

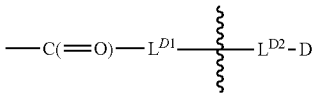

is independently a first linker that contains a biodegradable bond so that when the bond is broken, D is released in an active form for its intended therapeutic effect; in which the

in

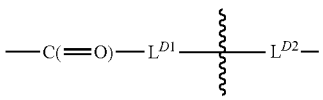

between $L^{D1}$ and $L^{D2}$ denotes direct or indirect attachment of $L^{D2}$ to $L^{D1}$;

each occurrence of

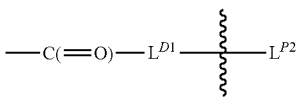

is independently a second linker not yet connected to the PBRM, in which $L^{P2}$ is a moiety containing a functional group that is capable of forming and not yet formed a covalent bond with a functional group of a PBRM, and the

in

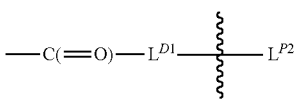

between $L^{D1}$ and $L^{P2}$ denotes direct or indirect attachment of $L^{P2}$ to $L^{D1}$, and each occurrence of the second linker is distinct from each occurrence of the first linker is an integer from 1 to 2200

$m_1$ is an integer from 1 to 660,
$m_2$ is an integer from 1 to 300,
$m_3$ is an integer from 1 to 110, and
the sum of m, $m_1$, $m_2$ and $m_3$ ranges from 15 to about 2200.

The scaffold of (Ibb) can include one or more of the following features:

When the PHF in Formula (Ibb) has a molecular weight ranging from about 2 kDa to about 40 kDa (i.e., the sum of m, $m_1$, $m_2$, and $m_3$ ranging from about 15 to about 300), $m_2$ is an integer from 1 to about 40, $m_3$ is an integer from 1 to about 18, and/or $m_1$ is an integer from 1 to about 140 (e.g., $m_1$ being about 1-90);

When the PHF in Formula (Ibb) has a molecular weight ranging from about 6 kDa to about 20 kDa (i.e., the sum of m, $m_1$, $m_2$, and $m_3$ ranging from about 45 to about 150), $m_2$ is an integer from 2 to about 20, $m_3$ is an integer from 1 to about 9, and/or $m_1$ is an integer from 1 to about 75 (e.g., $m_1$ being about 4-45);

When the PHF in Formula (Ibb) has a molecular weight ranging from about 8 kDa to about 15 kDa (i.e., the sum of m, $m_1$, $m_2$, and $m_3$ ranging from about 60 to about 110), $m_2$ is an integer from 2 to about 15, $m_3$ is an integer from 1 to about 7, and/or $m_1$ is an integer from 1 to about 55 (e.g., $m_1$ being about 4-30);

When the PHF in Formula (Ibb) has a molecular weight ranging from 20 kDa to 300 kDa (i.e., the sum of m, $m_1$, $m_2$, and $m_3$ ranging from about 150 to about 2200), $m_2$ is an integer from 3 to about 300, $m_3$ is an integer from 1 to about 110, and/or $m_1$ is an integer from 1 to about 660 (e.g., $m_1$ being about 10-250);

When the PHF in Formula (Ibb) has a molecular weight ranging from 20 kDa to 150 kDa (i.e., the sum of m, $m_1$, $m_2$ and $m_3$, ranging from about 150 to about 1100), $m_2$ is an integer from 3 to about 150, $m_3$ is an integer from 1 to about 55, and/or $m_1$ is an integer from 1 to about 330 (e.g., $m_1$ being about 10-330 or about 15-100). This scaffold can be used, for example, for conjugating a PBRM having a molecular weight of about 4 kDa to about 80 kDa;

When the PHF in Formula (Ibb) has a molecular weight ranging from 30 kDa to 100 kDa (i.e., the sum of m, $m_1$, $m_2$, and $m_3$ ranging from about 220 to about 740), $m_2$ is an integer from 3 to 100 (e.g., 5-100), $m_3$ is an integer from 1 to about 40, and/or $m_1$ is an integer from 1 to about 220 (e.g., $m_1$ being about 15-80);

For conjugating a PBRM having a molecular weight of 40 kDa or greater (e.g., 80 kDa or greater), the polymeric carrier of the scaffold of the invention is a polyacetal, e.g., a PHF having a molecular weight (i.e., MW of the unmodified PHF) ranging from about 2 kDa to about 40 kDa (e.g., about 6-20 kDa or about 8-15 kDa);

For conjugating a PBRM having a molecular weight of 200 kDa or less (e.g., 80 kDa or less), the polymeric carrier of the scaffold of the invention is a polyacetal, e.g., a PHF having a molecular weight (i.e., MW of the unmodified PHF) ranging from about 20 kDa to about 300 kDa (e.g., about 20-150 kDa or about 30-100 kDa);

The functional group of $L^{P2}$ is selected from —$SR^P$, —S—S-LG, maleimido, and halo, in which LG is a leaving group and $R^P$ is H or a sulfur protecting group;

$L^{D1}$ comprises —X—$(CH_2)_v$—C(=O)— with X directly connected to the carbonyl group of

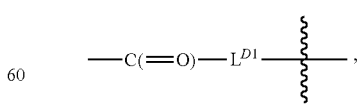

in which X is $CH_2$, O, or NH, and v is an integer from 1 to 6;

$L^{P2}$ contains a biodegradable bond;

At least one of a, w, and y is not 0;

The Stretcher unit -A- is

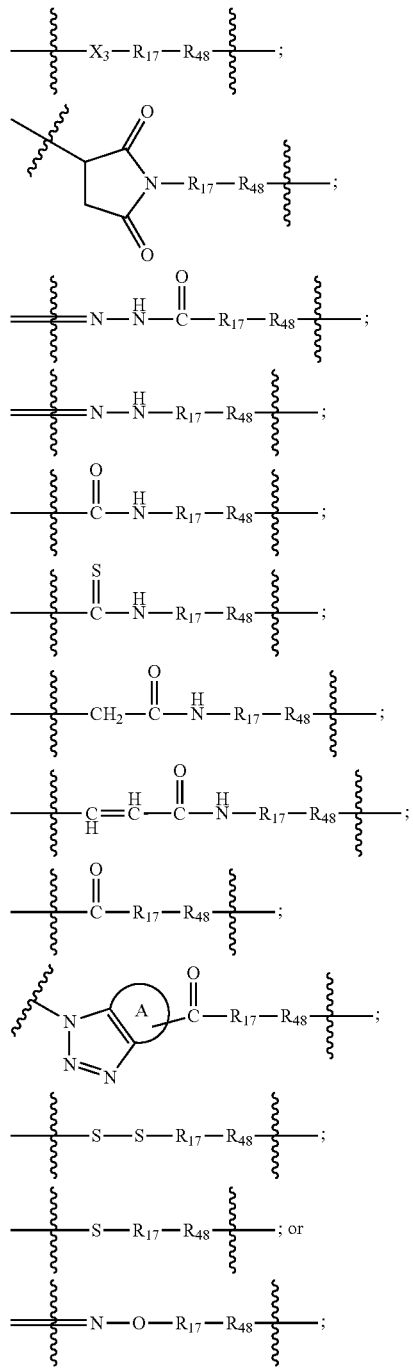

wherein
$R_{48}$ is proximal to D and is —C(O), NH or O;
$X_3$ is —O— or —NH;
$R_{17}$ is —$C_{1-10}$ alkylene-, —$C_{3-8}$ carbocyclo-, $C_{1-30}$ heteroalkylene, —O—($C_{1-8}$ alkyl)-, -arylene-, —$C_{1-10}$ alkylene-arylene-, -arylene-$C_{1-10}$ alkylene-, —$C_{1-10}$ alkylene-($C_{3-8}$ carbocyclo)-, —($C_{3-8}$ carbocyclo)-$C_{1-10}$ alkylene-, —$C_{3-8}$ heterocyclo-, —$C_{1-10}$ alkylene-($C_{3-8}$ heterocyclo)-, —($C_{3-8}$ heterocyclo)-$C_{1-10}$ alkylene-, and —($CH_2CH_2O)_h$—$(CH_2)_c$, in which c is an integer from 0 to 3 and h is an integer from 1 to 12; and
ring A is cycloalkyl or heterocycloalkyl;

Each W is

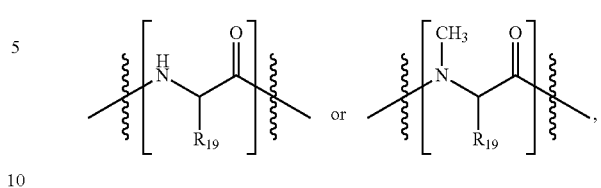

in which the carbonyl group is proximal to D and the amino group is proximal to the PHF; and $R_{19}$ is hydrogen, methyl, isopropyl, isobutyl, sec-butyl, benzyl, p-hydroxybenzyl, —$CH_2OH$, —$CH(OH)CH_3$, —$CH_2CH_2SCH_3$, —$CH_2CONH_2$, —$CH_2COOH$, —$CH_2CH_2CONH_2$, —$CH_2CH_2COOH$, —$(CH_2)_3NHC(=NH)NH_2$, —$(CH_2)_3NH_2$, —$(CH_2)_3NHCOCH_3$, —$(CH_2)_3NHCHO$, —$(CH_2)_4NHC(=NH)NH_2$, —$(CH_2)_4NH_2$, —$(CH_2)_4NHCOCH_3$, —$(CH_2)_4NHCHO$, —$(CH_2)_3NHCONH_2$, —$(CH_2)_4NHCONH_2$, —$CH_2CH_2CH(OH)CH_2NH_2$, 2-pyridylmethyl-, 3-pyridylmethyl-, 4-pyridylmethyl-, phenyl, cyclohexyl, or is selected from

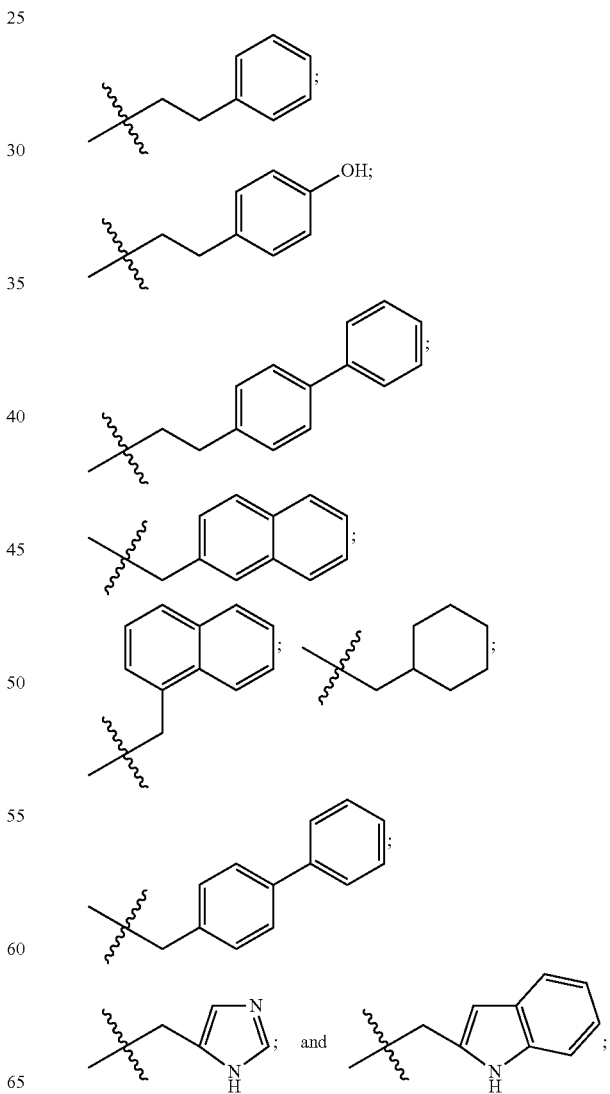

$R_{19}$ is isopropyl or —$(CH_2)_3NHCONH_2$;

$W_w$ is a val-cit linker, in which w is 2, one W unit is valine, and the other W unit is citrulline;

Each Y is

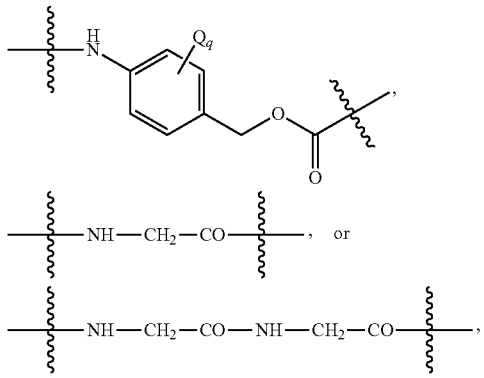

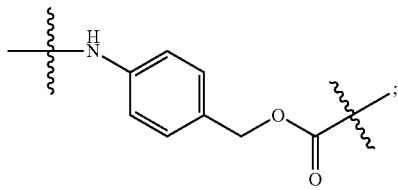 [SMILES: *Nc1ccc(COC(*)=O)cc1], or

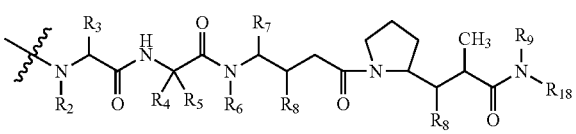

in which the carbonyl group is proximal to D; each Q independently is —$C_{1-8}$ alkyl, —O—$(C_{1-8}$ alkyl), -halogen, -nitro or -cyano; and q is an integer from 0 to 4;

Y is

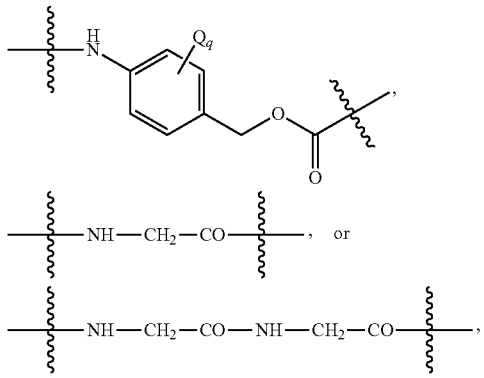

$L^{D2}$ does not contain a Stretcher unit, i.e., a is 0;

The auristatin compound -D is of Formula (Ib):

(Ib)

wherein:

$R_2$ is H or $C_{1-8}$ alkyl;

$R_3$ is H, $C_{1-8}$ alkyl, $C_{3-8}$ carbocycle, $X_4$—$C_{3-8}$ carbocycle, $C_{6-10}$ aryl, $X_4$—$C_{6-10}$ aryl, $C_{3-8}$ heterocycle, or $X_4$—$C_{3-8}$ heterocycle;

$R_4$ is H, $C_{1-8}$ alkyl, $C_{3-8}$ carbocycle, $X_4$—$C_{3-8}$ carbocycle, $C_{6-10}$ aryl, $X_4$—$C_{6-10}$ aryl, $C_{3-8}$ heterocycle, or $X_4$—$C_{3-8}$ heterocycle;

$R_5$ is H or methyl; or $R_4$ and $R_5$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;

$R_6$ is H or $C_{1-8}$ alkyl;

$R_7$ is H, $C_{1-8}$ alkyl, $C_{3-8}$ carbocycle, $X_4$—$C_{3-8}$ carbocycle, $C_{6-10}$ aryl, $X_4$—$C_{6-10}$ aryl, $C_{3-8}$ heterocycle, or $X_4$—$C_{3-8}$ heterocycle;

each $R_8$ independently is H, OH, $C_{1-8}$ alkyl, $C_{3-8}$ carbocycle or O—$(C_{1-8}$ alkyl);

each $X_4$ independently is $C_{1-10}$ alkylene or $C_{3-10}$ cycloalkylene;

$R_9$ is H or $C_{1-8}$ alkyl;

$R_{18}$ is —$C(R_8)_2$—$C(R_8)_2$—$C_{6-10}$ aryl, —$C(R_8)_2$—$C(R_8)_2$—$(C_{3-8}$ heterocycle), —$C(R_8)_2$—$C(R_8)_2$—$(C_{3-8}$ carbocycle), or selected from

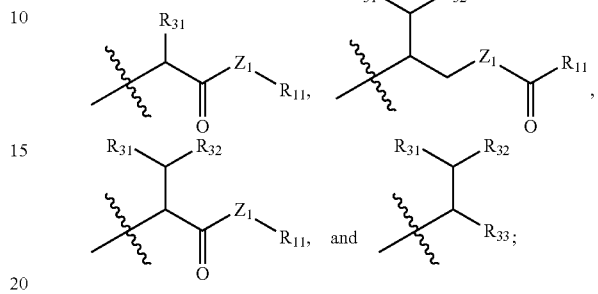

$Z_1$ is O, S, or $NR_{34}$;

$R_{31}$ is H, OH, $N(R_{34})_2$, $C_{1-8}$ alkyl, $C_{3-8}$ carbocycle, O—$(C_{1-8}$ alkyl), $C_{6-10}$ aryl, $X_4$—$C_{6-10}$ aryl, $X_4$—$(C_{3-8}$ carbocycle), $C_{3-8}$ heterocycle, $X_4$—$(C_{3-8}$ heterocycle), $C_{1-8}$ alkylene-$NH_2$, or $(CH_2)_2SCH_3$; or $R_{31}$ is an oxygen atom which forms a carbonyl unit (C=O) with the carbon atom to which it is attached and a hydrogen atom on this carbon atom is replaced by one of the bonds in the (C=O) double bond;

$R_{32}$ is $C_{6-10}$-aryl or $C_{3-8}$ heterocycle;

$R_{33}$ is H, OH, $N(R_{34})_2$, $C_{1-8}$ alkyl, $C_{3-8}$ carbocycle, O—$(C_{1-8}$ alkyl), $C_{6-10}$ aryl, $C_{1-8}$ alkyl-$C_{6-10}$ aryl, $C_{1-8}$ alkyl-$(C_{3-8}$ carbocycle), $C_{3-8}$ heterocycle, or $C_{1-8}$ alkyl-$(C_{3-8}$ heterocycle);

each $R_{34}$ independently is H or $C_{1-8}$ alkyl;

$R_{11}$ is H, OH, $N(R_{34})_2$, $C_{1-20}$ alkyl, $C_{6-10}$ aryl, $C_{3-8}$ heterocycle, —$(R_{13}O)_s$—$R_{14}$, —$(R_{13}O)_s$—$CH(R_{15})_2$ or —$[C(R_{50}R_{51})]_b$—$R_{52}$;

$R_{13}$ is $C_{2-8}$ alkyl;

$R_{14}$ is H or $C_{1-8}$ alkyl;

$R_{15}$ is H, COOH, —$(CH_2)_o$—$N(R_{16})_2$, —$(CH_2)_o$—$SO_3H$, or —$(CH_2)_o$—$SO_3$—$C_{1-8}$ alkyl;

$R_{16}$ is H, $C_{1-8}$ alkyl, or —$(CH_2)_o$—COOH;

each of $R_{50}$ and $R_{51}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{52}$ is OH, $NHR_{53}$, COOH, $R_{82}$—$C(O)(CH_2)_c$—$C(H)(R_{53})$—$N(H)(R_{53})$, $R_{82}$—$C(O)(CH_2)_d$—$(O$—$CH_2$—$CH_2)_h$—$N(H)(R_{53})$ or $R_{82}$—$(C(O)$—$CH(X_2)$—$NH)_d$—$R_{77}$;

each $R_{53}$ independently is hydrogen, $C_{1-6}$ alkyl, $C_{6-10}$ aryl, $C_{3-8}$ cycloalkyl, COOH, or COO—$C_{1-6}$ alkyl;

$X_2$ is a side chain of a natural or unnatural amino acid;

$R_{77}$ is hydrogen or $X_2$ and $NR_{77}$ form a nitrogen containing cyclic compound;

$R_{82}$ is NH or oxygen;

n is an integer from 2 to 7;

s is an integer from 0 to 1000;

o is an integer from 0 to 6.

b is an integer from 1 to 6;

c is an integer from 0 to 3;

d is an integer from 1 to 3; and h is an integer from 1 to 12.

The scaffold of Formula (Ibb) further comprises a PBRM connected to the polymeric carrier via $L^P$.

For example, the scaffold of Formula (Ibb) is of Formula (Icc):

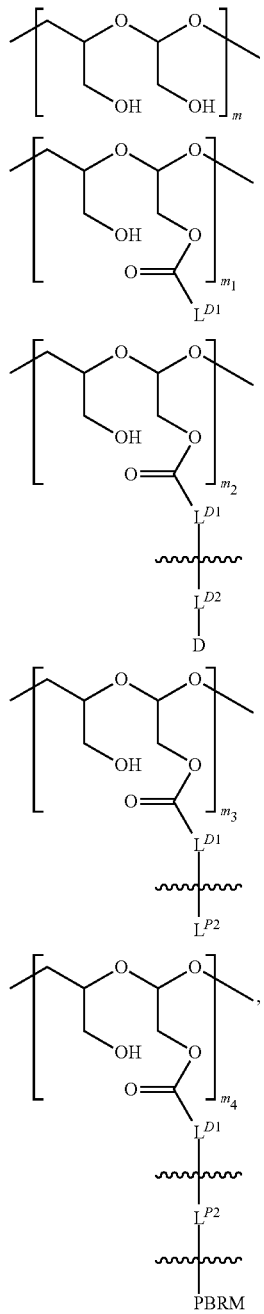

wherein:

between $L^{P2}$ and PBRM in

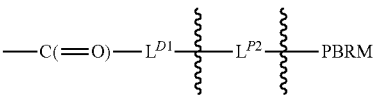

denotes direct or indirect attachment of PBRM to $L^{P2}$, such that the D-carrying polymeric carrier is connected to the PBRM, each occurrence of PBRM independently has a molecular weight of less than 200 kDa (e.g., less than 80 kDa),
m is an integer from 1 to 2200,
$m_1$ is an integer from 1 to 660,
$m_2$ is an integer from 3 to 300,
$m_3$ is an integer from 0 to 110,
$m_4$ is an integer from 1 to 60; and
the sum of m, $m_1$, $m_2$, $m_3$ and $m_4$ ranges from 150 to 2200

In Formula (Icc), $m_1$ is an integer from about 10 to about 660 (e.g., about 10-250).

When the PHF in Formula (Icc) has a molecular weight ranging from 20 kDa to 150 kDa (i.e., the sum of m, $m_1$, $m_2$, $m_3$, and $m_4$ ranging from about 150 to about 1100), $m_2$ is an integer from 3 to about 150, $m_3$ is an integer from 0 to about 55, $m_4$ is an integer from 1 to about 30, and/or $m_1$ is an integer from 1 to about 330 (e.g., $m_1$ being about 10-330 or about 15-100). For example, the sum of $m_1$ and $m_2$ is an integer from 14 to 330, and the sum of $m_3$ and $m_4$ is an integer from 1 to 55.

When the PHF in Formula (Icc) has a molecular weight ranging from 30 kDa to 100 kDa, the $m_1$ an integer from 1 to 220 (e.g., $m_1$ being about 10-220 or about 15-120), $m_2$ is an integer from 3 to 100, $m_3$ is an integer from 0 to 40, and/or $m_4$ is an integer from 1 to 20. For example, the sum of $m_1$ and $m_2$ is an integer from 18 to 220, and the sum of $m_3$ and $m_4$ is an integer from 1 to 40.

In Formula (Icc), the ratio of D to PBRM is between 5:1 and 40:1.

Alternatively or additionally, one or more $L^{D2}$-D-carrying polymeric carriers are connected to one PBRM. The scaffold (e.g., a PBRM-polymer-drug conjugate) comprises a PBRM with a molecular weight of greater than 40 kDa and one or more D-carrying polymeric carriers connected to the PBRM, in which each of the D-carrying polymeric carrier independently is of Formula (Idd):

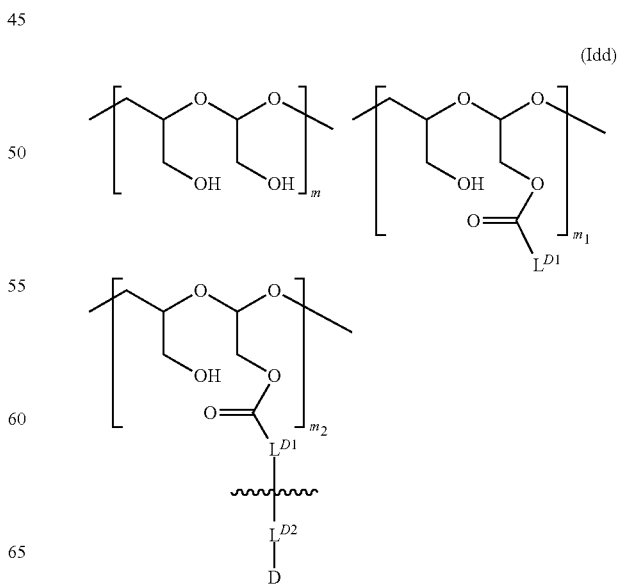

-continued

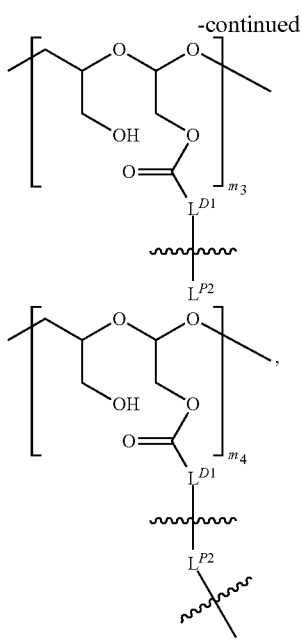

wherein:
the terminal

in

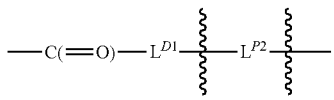

denotes direct or indirect attachment of $L^{P2}$ to PBRM such that the $L^{P2}$-D-carrying polymeric carrier is connected to the PBRM,
m is an integer from 1 to 300,
$m_1$ is an integer from 1 to 140,
$m_2$ is an integer from 1 to 40,
$m_3$ is an integer from 0 to 18,
$m_4$ is an integer from 1 to 10; and
the sum of m, $m_1$, $m_2$, $m_3$, and $m_4$ ranges from 15 to 300; provided that the total number of $L^{P2}$ attached to the PBRM is 10 or less.

In Formula (Idd), $m_1$ is an integer from 1 to about 120 (e.g., about 1-90) and/or $m_3$ is an integer from 1 to about 10 (e.g., about 1-8).

When the PHF in Formula (Idd) has a molecular weight ranging from about 6 kDa to about 20 kDa (i.e., the sum of m, $m_1$, $m_2$, $m_3$, and $m_4$ ranging from about 45 to about 150), $m_2$ is an integer from 2 to about 20, $m_3$ is an integer from 1 to about 9, and/or $m_1$ is an integer from 1 to about 75 (e.g., $m_1$ being about 4-45).

When the PHF in Formula (Idd) has a molecular weight ranging from about 8 kDa to about 15 kDa (i.e., the sum of m, $m_1$, $m_2$, $m_3$, and $m_4$ ranging from about 60 to about 110), $m_2$ is an integer from 2 to about 15, $m_3$ is an integer from 1 to about 7, and/or $m_1$ is an integer from 1 to about 55 (e.g., $m_1$ being about 4-30).

In Formula (Idd), the ratio of D to PBRM is between 5:1 and 40:1 (e.g., 25:1, 20:1, 15:1, 10:1, 9:1, 8:1, 7:1, 6;1, 5:1, 4:1, 3:1, or 2:1).

Each

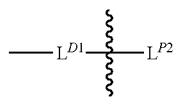

when not connected to PBRM, independently comprises a terminal group $W^P$, in which each $W^P$ independently is:

(1)
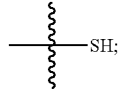

(2)
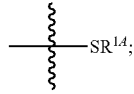

(3)
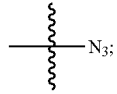

(4)
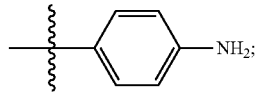

(5)
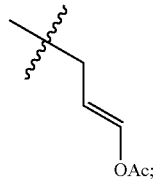

(6)
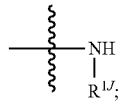

(7)
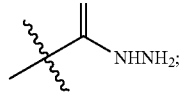

(8)
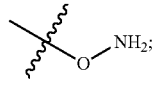

(9)
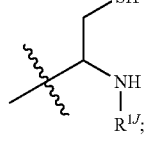

-continued

(10) 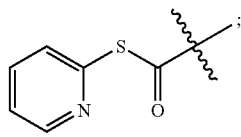

(11) 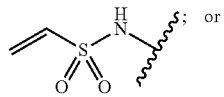

(12) 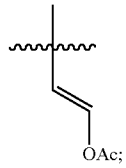

in which $R^{1K}$ is a leaving group (e.g., halide or RC(O)O— in which R is hydrogen, an aliphatic, heteroaliphatic, carbocyclic, or heterocycloalkyl moiety), $R^{1A}$ is a sulfur protecting group, and ring A is cycloalkyl or heterocycloalkyl, and $R^{1J}$ is hydrogen, an aliphatic, heteroaliphatic, carbocyclic, or heterocycloalkyl moiety.

Each $R^{1A}$ independently is

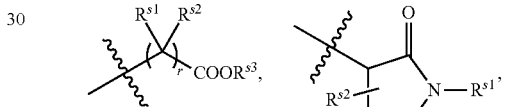

in which r is 1 or 2 and each of $R^{s1}$, $R^{s2}$, and $R^{s3}$ is hydrogen, an aliphatic, heteroaliphatic, carbocyclic, or heterocycloalkyl moiety.

Each $$—L^{D1}\text{—}L^{P2},$$

when connected to PBRM, independently is —$X^P$-$M^{P1}$-$Y^P$-$M^{P2}$-$Z^P$-$M^{P3}$-$Q^P$-$M^{P4}$, with $X^P$ directly connected to the carbonyl group of $$—C(=O)—L^{D1}\text{—}$$

and $M^{P4}$ directly connected to PBRM, in which $X^P$ is —O—, —S—, —N($R^1$)—, or absent, in which $R^1$ is hydrogen, an aliphatic, heteroaliphatic, carbocyclic, or heterocycloalkyl moiety, —C(=O)$R^{1B}$, —C(=O)O$R^{1B}$, or

(13) 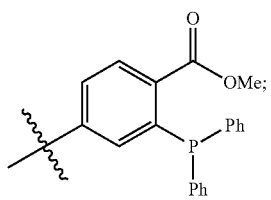

(14) 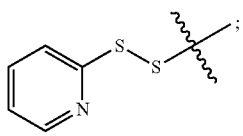

(15) 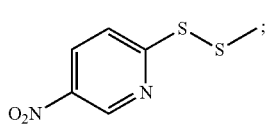

(16) 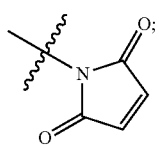

(17) 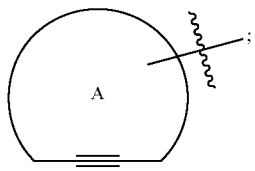

(18) 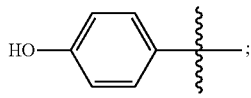

(19) 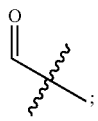

(20) 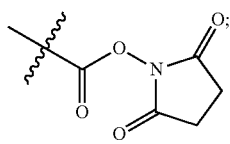

(21) 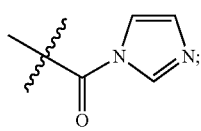

(22) 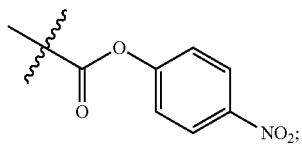

(23) 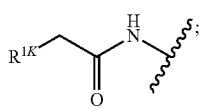

—SO$_2$R$^{1B}$, or —N(R$^1$)— is a heterocycloalkyl moiety, wherein R$^{1B}$ is hydrogen, an aliphatic, heteroaliphatic, carbocyclic, or heterocycloalkyl moiety;

each of Y$^P$, Z$^P$, and Q$^P$, independently, is absent or a biodegradable linker moiety selected from the group consisting of —S—S—, —C(=O)O—, —C(=O)NR$^2$—, —OC(=O)—, —NR$^2$C(=O)—, —OC(=O)O—, —OC(=O)NR$^2$—, —NR$^2$C(=O)O—, —NR$^2$C(=O)NR$^3$—, —C(OR$^2$)O—, —C(OR$^2$)S—, —C(OR$^2$)NR$^3$—, —C(SR$^2$)O—, —C(SR$^2$)S—, —C(SR$^2$)NR$^3$—, —C(NR$^2$R$^3$)O—, —C(NR$^2$R$^3$)S—, —C(NR$^2$R$^3$)NR$^4$—, —C(=O)S—, —SC(=O)—, —SC(=O)S—, —OC(=O)S—, —SC(=O)O—, —C(=S)S—, —SC(=S)—, —OC(=S)—, —C(=S)O—, —SC(=S)O—, —OC(=S)S—, —OC(=S)O—, —SC(=S)S—, —C(=NR$^2$)O—, —C(=NR$^2$)S—, —C(=NR$^2$)NR$^3$—, —OC(=NR$^2$)—, —SC(=NR$^2$)—, —NR$^3$C(=NR$^2$)—, —NR$^2$SO$_2$—, —NR$^2$NR$^3$—, —C(=O)NR$^2$NR$^3$—, —NR$^2$NR$^3$C(=O)—, —OC(=O)NR$^2$NR$^3$—, —NR$^2$NR$^3$C(=O)O, C(=S)NR$^2$NR$^3$—, —NR$^2$NR$^3$C(=S)—, —C(=NR$^4$)NR$^2$NR$^3$—, —NR$^2$NR$^3$C(=NR$^4$)—, —O(N=CR$^3$)—, —(CR$^3$=N)O—, —C(=O)NR$^2$(N=CR$^3$)—, —(CR$^3$=N)—NR$^2$C(=O)—, —SO$_3$—, —NR$^2$SO$_2$NR$^3$—, —SO$_2$NR$^2$—, and polyamide, wherein each occurrence of R$^2$, R$^3$, and R$^4$ independently is hydrogen or an aliphatic, heteroaliphatic, carbocyclic, or heterocyclic moiety, or each occurrence of —NR$^2$— or —NR$^2$NR$^3$— is a heterocycloalkyl moiety; and each of M$^{P1}$, M$^{P2}$, M$^{P3}$, and M$^{P4}$ independently, is absent or a non-biodegradable linker moiety selected from the group consisting of alkyl, alkenyl, alkynyl, heteroalkyl, heteroalkenyl, heteroalkynyl, a carbocyclic moiety, a heterocyclic moiety, and a combination thereof, and each of M$^{P1}$, M$^{P2}$, and M$^{P3}$ optionally contains one or more —(C=O)— but does not contain any said biodegradable linker moiety;

provided that for each

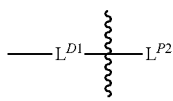

connected to PBRM, at least one of X$^P$, Y$^P$, Z$^P$, and Q$^P$ is not absent.

Each M$^{P1}$ independently is C$_{1-6}$ alkyl or C$_{1-6}$ heteroalkyl.

Each M$^{P2}$, M$^{P3}$, and M$^{P4}$, independently, is absent, C$_{1-6}$ alkyl, cycloalkyl, heteroalkyl, heterocycloalkyl, or a combination thereof.

In each

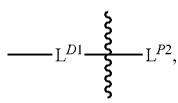

at most one of M$^{P2}$ and M$^{P3}$ has one of the following structures:

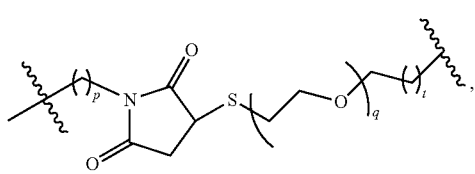

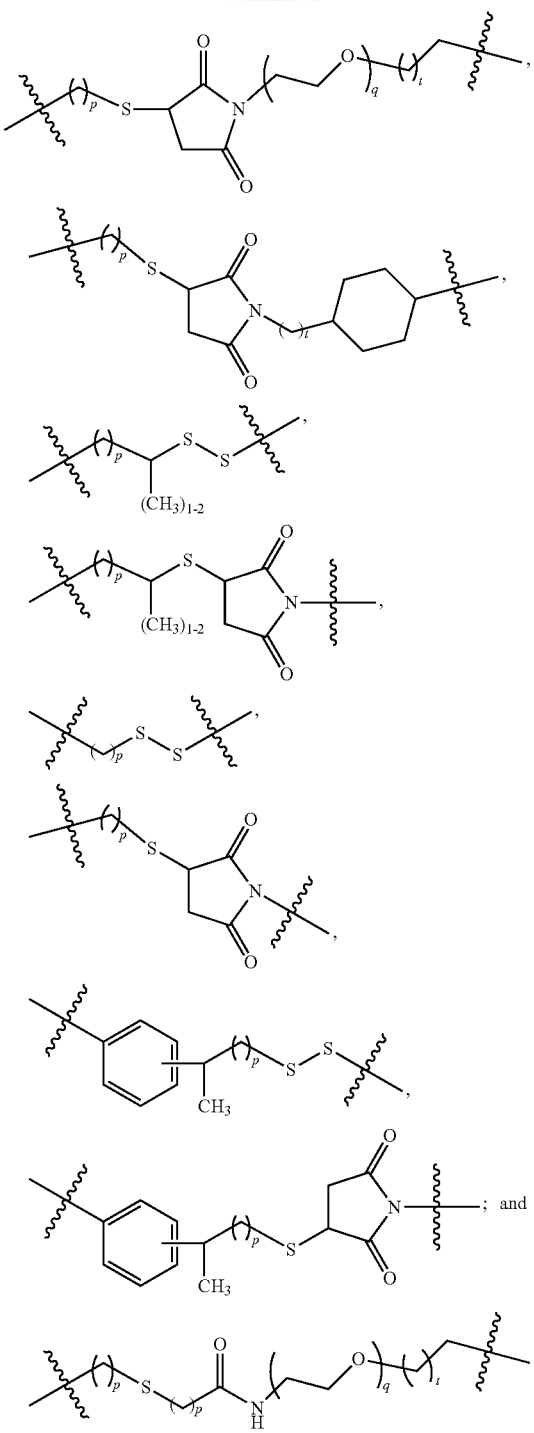

in which q is an integer from 0 to 12 and each of p and t independently is an integer from 0 to 3.

Other features of the polymeric scaffold of Formula (Ibb), (Icc) or (Idd) include those described herein where applicable.

In another aspect, the invention features a polymeric scaffold of Formula (V1) or (V2):

(V1)
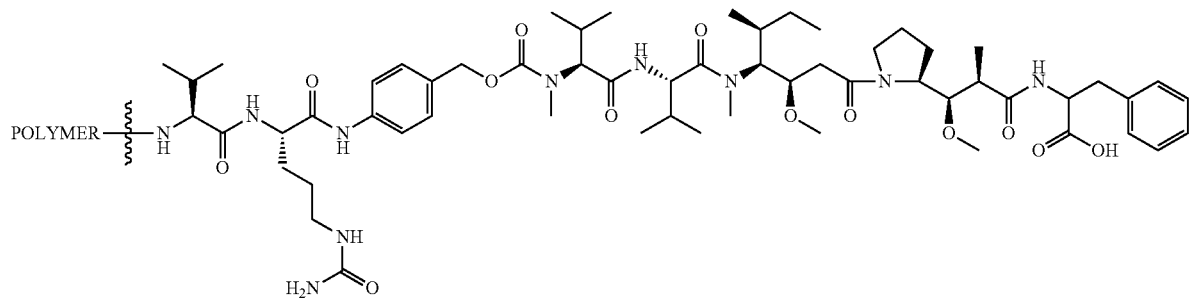
(V2)
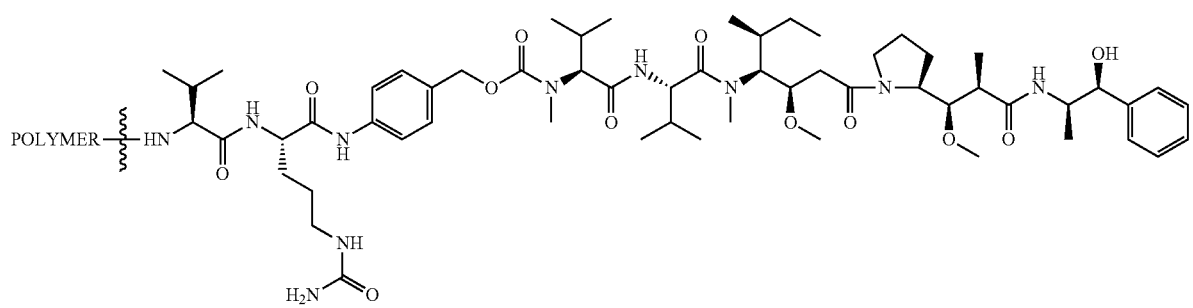
wherein the POLYMER is a polyal or polyketal, for example, a PHF scaffold having the structure:
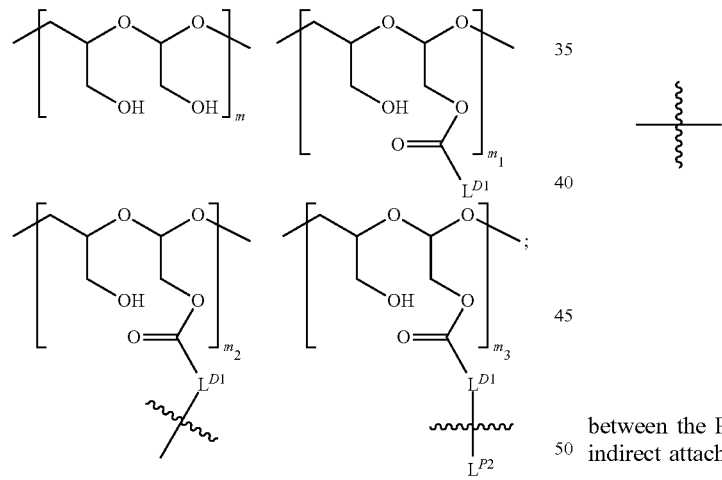
the wavy line between the POLYMER and amino acid denotes direct or indirect attachment.
In yet another aspect, the invention features a polymeric scaffold of Formula (V3), (V4), (V5), or (V6):
(V3)
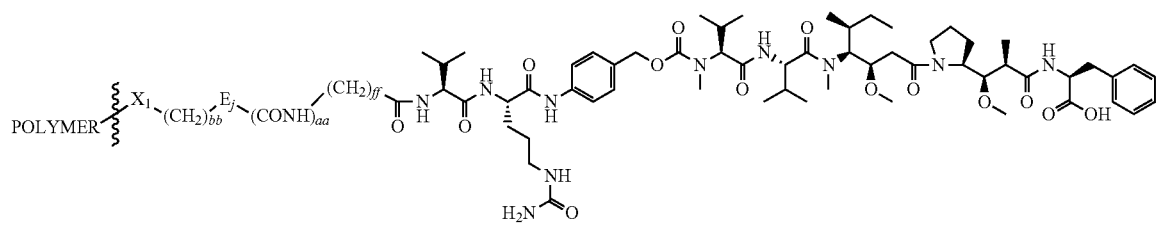

-continued (V4)
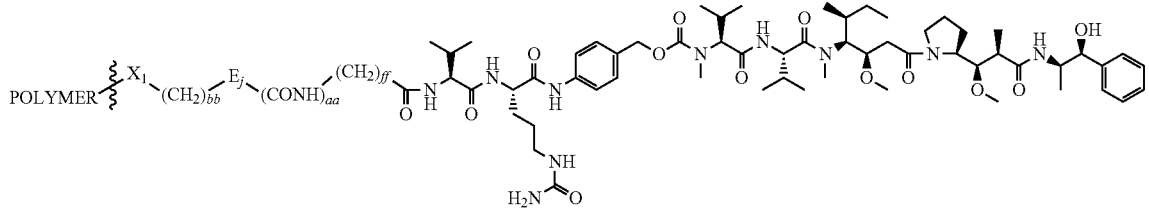

(V5)
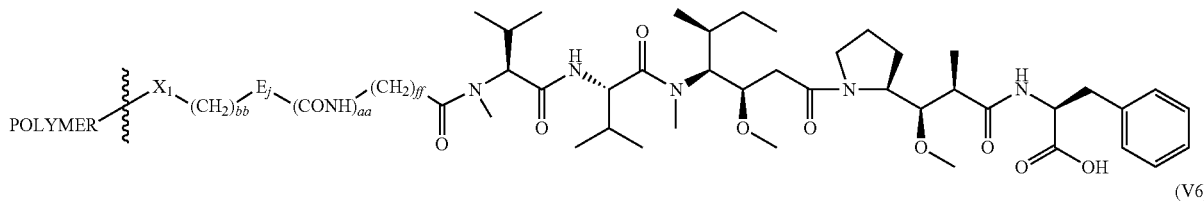

(V6)
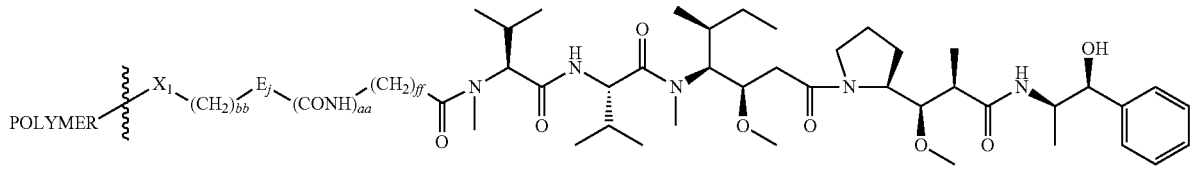

wherein:

E is —CH$_2$— or —OCH$_2$CH$_2$—;

aa is an integer 0 or 1;

bb is an integer 0 or 2;

ff is an integer from 0 to 10;

j is an integer from 0 to 12; and when E is —CH$_2$—, bb is 0 and j is an integer from 0 to 10; and when E is —CH$_2$CH$_2$—O—, bb is 2 and j is an integer from 1 to 12;

X$_1$ is NH, O or

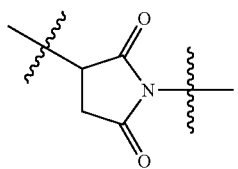

wherein N— is distal to the polymer;

the POLYMER is a polyal or polyketal, for example, a PHF scaffold having the structure

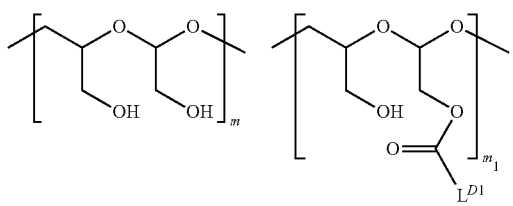

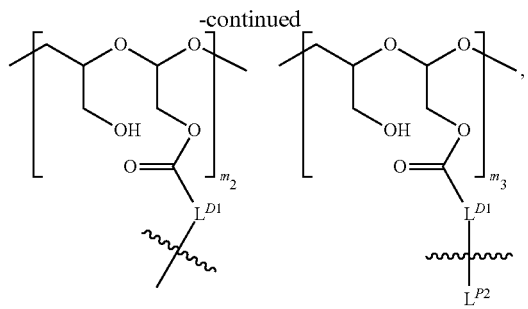

wherein

between the POLYMER and X$_1$ denotes direct or indirect attachment.

The polymeric scaffold of any of Formulae (V1)-(V6) can also include one or more features of Formula (Ibb), (Icc), or (Idd) described herein where applicable.

In still another aspect, the invention features a polymeric scaffold useful to conjugate with a PBRM. The scaffold comprises a polymeric carrier, one or more -L$^D$-D connected to the polymeric carrier, and one or more L$^P$ connected to the polymeric carrier which is suitable for connecting a PBRM to the polymeric carrier, wherein:

each occurrence of D is independently an auristatin compound having a molecular weight ≤5 kDa;

the polymeric carrier is a polyacetal or a polyketal, $L^D$ is a first linker having the structure:

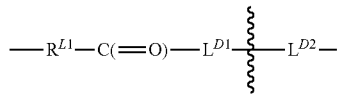

with $R^{L1}$ connected to an oxygen atom of the polymeric carrier and $L^{D1}$ connected to D, and

denotes direct or indirect attachment of $L^{D2}$ to $L^{D1}$, and $L^D$ contains a biodegradable bond so that when the bond is broken, D is released in an active form for its intended therapeutic effect;

$L^{D1}$ is a carbonyl-containing moiety;

$L^{D2}$ is a moiety of Formula (Iaa) as defined herein;

$L^P$ is a second linker having the structure: $-R^{L2}-C(=O)-L^{P1}$ with $R^{L2}$ connected to an oxygen atom of the polymeric carrier and $L^{P1}$ being suitable for connecting directly or indirectly to a PBRM which is not yet connected, and each occurrence of the second linker is distinct from each occurrence of the first linker;

each of $R^{L1}$ and $R^{L2}$ independently is absent, alkyl, heteroalkyl, cycloalkyl, or heterocycloalkyl; and $L^{P1}$ is a moiety containing a functional group that is capable of forming a covalent bond with a functional group of a PBRM but has not yet formed a covalent bond.

The polymeric scaffold can include one or more of the following features:

The polymeric carrier of the scaffold of the invention is a polyacetal, e.g., a PHF having a molecular weight (i.e., MW of the unmodified PHF) ranging from about 2 kDa to about 300 kDa.

The polymeric carrier is PHF having a molecular weight ranging from 2 kDa to 40 kDa when the PBRM to be conjugated with has a molecular weight of more than 40 kDa, or the polymeric carrier is PHF having a molecular weight ranging from 20 kDa to 300 kDa when the PBRM to be conjugated with has a molecular weight of less than 80 kDa.

$L^P$ is a linker having the structure:

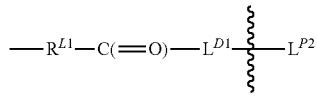

in which $L^{P2}$ is a moiety containing a functional group that is capable of forming and not yet formed a covalent bond with a functional group of a PBRM, and

denotes direct or indirect attachment of $L^{P2}$ to $L^{D1}$.

The functional group of $L^{P1}$ or $L^{P2}$ is selected from $-SR^P$, $-S-S-LG$, maleimido, and halo, in which LG is a leaving group and $R^P$ is H or a sulfur protecting group.

$L^{D1}$ comprises $-X-(CH_2)_v-C(=O)-$ with X directly connected to the carbonyl group of)

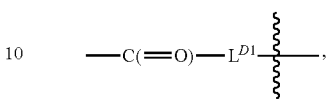

in which X is $CH_2$, O, or NH, and v is an integer from 1 to 6.

$L^{P1}$ or $L^{P2}$ contains a biodegradable bond.

Each of $R^{L1}$ and $R^{L2}$ is absent.

The polymeric scaffold further contains one or more PBRMs.

The polymeric scaffold is of Formula (I):

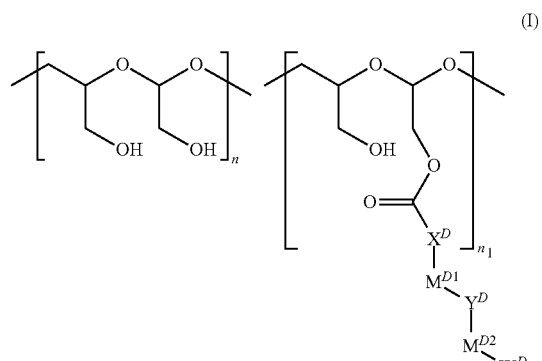
(I)

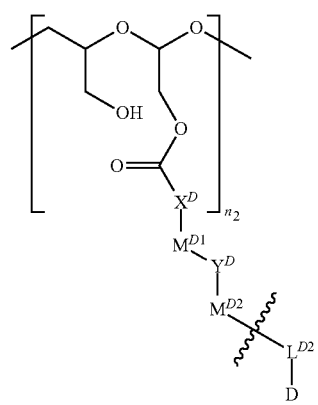

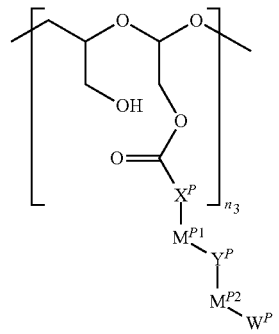

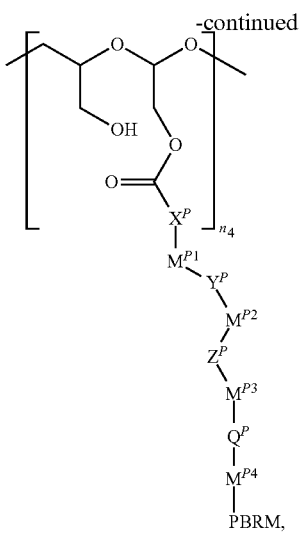

wherein each of n, $n_1$, $n_2$, $n_3$, and $n_4$, is the molar fraction of the corresponding polymer unit ranging between 0 and 1; $n+n_1+n_2+n_3+n_4=1$; provided that none of n, $n_2$, and $n_4$ is 0,
$X^D$ is —O—, —S—, —N($R^1$)—, or absent, in which $R^1$ is hydrogen, an aliphatic, heteroaliphatic, carbocyclic, or heterocycloalkyl moiety, —C(=O)$R^{1B}$, —C(=O)O$R^{1B}$, or —SO$_2R^{1B}$, or —N(R')— is a heterocycloalkyl moiety, wherein $R^{1B}$ is hydrogen, an aliphatic, heteroaliphatic, carbocyclic, or heterocycloalkyl moiety;

$Y^D$ is absent or a biodegradable linker moiety selected from the group consisting of —S—S—, —C(=O)O—, —C(=O)N$R^2$—, —OC(=O)—, —N$R^2$C(=O)—, —OC(=O)O—, —OC(=O)N$R^2$—, —N$R^2$C(=O)O—, —N$R^2$C(=O)N$R^3$—, —C(O$R^2$)O—, —C(O$R^2$)S—, —C(O$R^2$)N$R^3$—, —C(S$R^2$)O—, —C(S$R^2$)S—, —C(S$R^2$)N$R^3$—, —C(N$R^2R^3$)O—, —C(N$R^2R^3$)S—, —C(N$R^2R^3$)N$R^4$—, —SC(=O)—, —SC(=O)S—, —OC(=O)S—, —SC(=O)O—, —C(=S)S—, —SC(=S)—, —OC(=S)—, —SC(=S)O—, —OC(=S)S—, —OC(=S)O, —SC(=S)S—, —C(=N$R^2$)O—, —C(=N$R^2$)S—, —C(=N$R^2$)N$R^3$—, —OC(=N$R^2$)—, —SC(=N$R^2$)—, —N$R^3$C(=N$R^2$)—, —N$R^2$SO$_2$—, —N$R^2$N$R^3$—, —C(=O)N$R^2$N$R^3$—, —N$R^2$N$R^3$C(=O)—, —OC(=O)N$R^2$N$R^3$—, —N$R^2$N$R^3$C(=O)O—, —C(=S)N$R^2$N$R^3$—, —N$R^2$N$R^3$C(=S)—, —C(=N$R^4$)N$R^2$N$R^3$—, —N$R^2$N$R^3$C(=N$R^4$)—, —O(N=C$R^3$)—, —(C$R^3$=N)O—, —C(=O)N$R^2$—(N=C$R^3$)—, —(C$R^3$=N)—N$R^2$C(=O)—, —SO$_3$—, —N$R^2$SO$_2$N$R^3$—, —SO$_2$N$R^2$—, and polyamide, wherein each occurrence of $R^2$, $R^3$, and $R^4$ independently is hydrogen or an aliphatic, heteroaliphatic, carbocyclic, or heterocyclic moiety, or each occurrence of —N$R^2$— or —N$R^2$N$R^3$— is a heterocycloalkyl moiety; and each of $M^{D1}$ and $M^{D2}$ independently, is absent or a non-biodegradable linker moiety selected from the group consisting of alkyl, alkenyl, alkynyl, heteroalkyl, heteroalkenyl, heteroalkynyl, a carbocyclic moiety, a heterocyclic moiety, and a combination thereof, and each of $M^{D1}$ and $M^{D2}$ optionally contains one or more —(C=O)— but does not contain any said biodegradable linker moiety;

provided that at least one of $X^D$ and $Y^D$ is not absent.

In the Formulae described herein, e.g., Formula (I) above, the disconnection or gap between the polyacetal units indicates that the units can be connected to each other in any order. In other words, the appending groups that contain $L^{D2}$-D, PBRM, $W^D$, and $W^P$, can be randomly distributed along the polymer backbone.

In the protein-polymer-drug conjugate of Formula (I), each D can be the same or different auristatin compound and each PBRM can be the same or different moiety.

The ratio between $n_2$ and $n_4$ can be greater than 1:1, and up to 200:1 (e.g., up to 100:1), e.g., between 2:1 and 40:1; between 5:1 and 20:1; between 10:1 and 50:1, between 25:1 and 50:1, or between 30:1 and 50:1.

The ratio between $n_2$ and $n_4$ can be about 50:1, 40:1, 25:1, 20:1, 10:1, 5:1 or 2:1.

For example the ratio between D and PBRM can be greater than 1:1, and up to 200:1 (e.g., up to 100:1), e.g., between 2:1 and 40:1; between 5:1 and 20:1; between 10:1 and 50:1, between 25:1 and 50:1, or between 30:1 and 50:1. Examples of PBRM include but are not limited to, full length antibodies such as IgG and IgM, antibody fragments such as Fabs, scFv, camelids, Fab2, and the like, small proteins, and peptides.

In one embodiment the ratio between D and PBRM can be about 50:1, 40:1, 25:1, 20:1, 15:1, 10:1, 9:1, 8:1, 7:1, 6;1, 5:1, 4:1, 3:1, or 2:1.

In another embodiment the ratio between D and PBRM can be about 25:1, 20:1, 15:1, 10:1, 5:1 or 2:1

The polymeric scaffold, e.g., that of Formula (I), can also include one or more features of Formula (Ibb), (Icc), or (Idd) described herein where applicable. In another aspect, the invention provides compositions comprising the conjugates, methods for their preparation, and methods of use thereof in the treatment of various disorders, including, but not limited to cancer.

The invention also features a drug-polymer conjugate (e.g., auristatin compound-polymer conjugate) that is similar to the protein-polymer-drug conjugate described above except that drug-polymer conjugate does not contain a PBRM. In this embodiment the polymer-drug conjugate may comprise a plurality of drug moieties in which each D can be the same or different. In this embodiment, $n_4$ is 0 in the conjugate of Formula (I). The methods of producing the drug-polymer conjugates and methods of treating various disorders (e.g., cancer) are also contemplated and described herein.

The invention also features a protein-polymer conjugate (e.g., PBRM-polymer conjugate) that is similar to the protein-polymer-drug conjugate described above except that protein-polymer conjugate does not contain a drug. In this embodiment the protein-polymer conjugate may comprise a plurality of protein moieties in which each PBRM can be the same or different. In this embodiment, $n_2$ is 0 in the conjugate of Formula (I). The methods of producing the drug-polymer conjugates or polymeric scaffolds and methods of treating various disorders (e.g., cancer) are also contemplated and described herein. The target cancer can be anal, astrocytoma, leukemia, lymphoma, head and neck, liver, testicular, cervical, sarcoma, hemangioma, esophageal, eye, laryngeal, mouth, mesothelioma, skin, myeloma, oral, rectal, throat, bladder, breast, uterus, ovary, prostate, lung, colon, pancreas, renal, or gastric cancer.

The invention further relates to a pharmaceutical composition comprising a polymeric scaffold or conjugate described herein and a pharmaceutically acceptable carrier.

In yet another aspect, the invention relates to a method of diagnosing a disorder in a subject suspected of having the disorder. The method comprises administering an effective amount of the conjugate described herein to the subject suspected of having the disorder or performing an assay to detect a target antigen/receptor in a sample from the subject so as to determine whether the subject expresses target antigen or receptor.

Also within the scope of the invention is a method of preparing a scaffold described above. The method comprises providing a polymeric carrier that is substituted with one or more -L$^{D2}$-D and one or more —R$^{L1}$—C(=O)-L$^{D1}$, and reacting the polymeric carrier with a compound containing an L$^{P2}$ moiety to produce a scaffold comprising a polymeric carrier substituted both with one or more -L$^{D2}$-D and with one or more

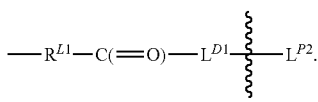

Alternatively, the method comprises providing a polymeric carrier that is substituted with one or more

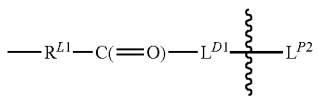

and one or more —R$^{L1}$—C(=O)-L$^{D1}$, and reacting the polymeric carrier with L$^{D3}$-D wherein L$^{D3}$ contains a functional group that is capable of forming and not yet formed a covalent bond with L$^{D1}$ in —R$^{L1}$—C(=O)-L$^{D1}$ to produce a scaffold comprising a polymeric carrier substituted both with one or more -L$^{D2}$-D and with one or more

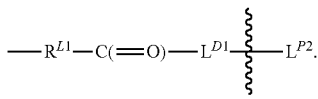

As used herein, the terms "polymeric scaffold" or simply "scaffold" and "conjugate" are used interchangeably when the scaffold comprises one or more PBRM and one or more D molecules (i.e., auristatin compounds).

As used herein the terms "polymer," and "polymeric carrier" are used interchangeably.

As used herein, the expression "capable of" or "suitable for" connecting to, conjugating with, or forming, in one embodiment, refers to the ability to form an association (e.g., a bond such as a covalent bond) but such association (e.g., bond) is not yet present.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. All publications, patent applications, patents and other references mentioned herein are incorporated by reference. The references cited herein are not admitted to be prior art to the claimed invention. In the case of conflict, the present specification, including definitions, will control. In addition, the materials, methods and examples are illustrative only and are not intended to be limiting.

One of the advantages of the present invention is that the protein-polymer-drug conjugates or the polymeric scaffolds described herein greatly enhances the bioavailability of the drugs to be delivered and/or enhances the bioavailability of the protein attached to the polymeric carrier. Another advantage of the present invention is that the efficacy of the protein-polymer-drug conjugates described herein increases or at least remains substantially the same with increases in the drug load of the conjugates. Yet another advantage of the present invention is that the protein-polymer conjugates via thiol conjugation to the cysteine moiety of the protein exhibits substantially improved stability. Other features and advantages of the invention will be apparent from the following detailed description and claims.

BRIEF DESCRIPTION OF FIGURES

FIG. 4 is a group of tables listing "m" values per PHF scaffold and polymer/PBRM ratios of embodiments of the invention. Table 1 relates to PBRM-drug polymer conjugates in which the PBRMs have a molecular weight of 40 kDa or greater (e.g., 60 kDa or greater, 80 kDa or greater, 100 kDa or greater, 120 kDa or greater, 140 kDa or greater, 160 kDa or greater or 180 kDa or greater) and one or more PHF-Drug scaffolds are attached to one PBRM, Table 2 relates to PBRM-drug polymer conjugates in which the PBRMs have a molecular weight of 200 kDa or less (e.g., 120 kDa or less, 80 kDa or less, 60 kDa or less, 40 kDa or less, 20 kDa or less or 10 kDa or less) and one or more PBRMs are attached to one PHF-Drug scaffold.

DETAILED DESCRIPTION OF CERTAIN PREFERRED EMBODIMENTS OF THE INVENTION

Figure 1:
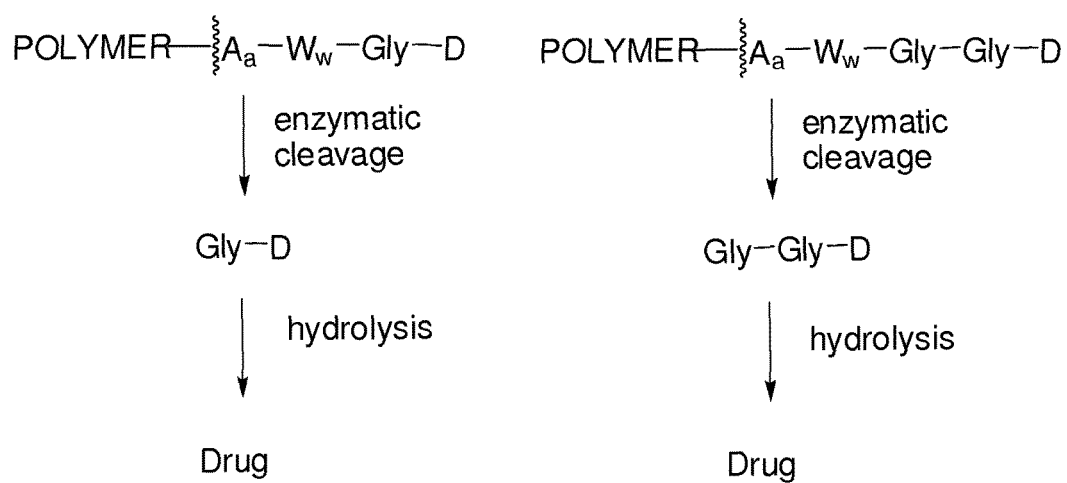
FIG. 1 shows examples of compounds with a non-self-immolative Spacer unit.

The present invention provides novel protein-polymer-auristatin compound conjugates, polymeric scaffolds for making the conjugates, synthetic methods for making the conjugates or polymeric scaffolds, pharmaceutical compositions containing them and various uses of the conjugates.

The present invention also provides novel polymer-auristatin compound conjugates, synthetic methods for making the conjugates, pharmaceutical compositions containing them and various uses of the conjugates.

The present invention further provides novel auristatin compound derivatives, synthetic methods for making the derivatives, pharmaceutical compositions containing them and various uses of the drug derivatives.

Definition/Terminology

Certain compounds of the present invention, and definitions of specific functional groups are also described in more detail herein. For purposes of this invention, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999, the entire contents of which are incorporated herein by reference. Furthermore, it will be appreciated by one of ordinary skill in the art that the synthetic methods, as described herein, utilize a variety of protecting groups.

The use of the articles "a", "an", and "the" in both the following description and claims are to be construed to cover both the singular and the plural, unless otherwise indicated herein or clearly contradicted by context. The terms "comprising", "having", "including", and "containing" are to be construed as open terms (i.e., meaning "including but not limited to") unless otherwise noted. Additionally whenever "comprising" or another open-ended term is used in an embodiment, it is to be understood that the same embodiment can be more narrowly claimed using the intermediate term "consisting essentially of" or the closed term "consisting of."

The term "about", "approximately", or "approximate", when used in connection with a numerical value, means that a collection or range of values is included. For example, "about X" includes a range of values that are ±20%, ±10%, ±5%, ±2%, ±1%, ±0.5%, ±0.2%, or ±0.1% of X, where X is a numerical value. In one embodiment, the term "about" refers to a range of values which are 5% more or less than the specified value. In another embodiment, the term "about" refers to a range of values which are 2% more or less than the specified value. In another embodiment, the term "about" refers to a range of values which are 1% more or less than the specified value.

Recitation of ranges of values are merely intended to serve as a shorthand method of referring individually to each separate value falling within the range, unless otherwise indicated herein, and each separate value is incorporated into the specification as if it were individually recited herein. A range used herein, unless otherwise specified, includes the two limits of the range. For example, the expressions "x being an integer between 1 and 6" and "x being an integer of 1 to 6" both mean "x being 1, 2, 3, 4, 5, or 6".

"Protecting group": as used herein, the term protecting group means that a particular functional moiety, e.g., O, S, or N, is temporarily blocked so that a reaction can be carried out selectively at another reactive site in a multifunctional compound. In preferred embodiments, a protecting group reacts selectively in good yield to give a protected substrate that is stable to the projected reactions; the protecting group must be selectively removed in good yield by readily available, preferably nontoxic reagents that do not attack the other functional groups; the protecting group forms an easily separable derivative (more preferably without the generation of new stereogenic centers); and the protecting group has a minimum of additional functionality to avoid further sites of reaction. As detailed herein, oxygen, sulfur, nitrogen and carbon protecting groups may be utilized. For example, in certain embodiments, certain exemplary oxygen protecting groups may be utilized. These oxygen protecting groups include, but are not limited to methyl ethers, substituted methyl ethers (e.g., MOM (methoxymethyl ether), MTM (methylthiomethyl ether), BOM (benzyloxymethyl ether), and PMBM (p-methoxybenzyloxymethyl ether)), substituted ethyl ethers, substituted benzyl ethers, silyl ethers (e.g., TMS (trimethylsilyl ether), TES (triethylsilyl ether), TIPS (triisopropylsilyl ether), TBDMS (t-butyldimethylsilyl ether), tribenzyl silyl ether, and TBDPS (t-butyldiphenyl silyl ether), esters (e.g., formate, acetate, benzoate (Bz), trifluoroacetate, and dichloroacetate), carbonates, cyclic acetals and ketals. In certain other exemplary embodiments, nitrogen protecting groups are utilized. Nitrogen protecting groups, as well as protection and deprotection methods are known in the art. Nitrogen protecting groups include, but are not limited to, carbamates (including methyl, ethyl and substituted ethyl carbamates (e.g., Troc), amides, cyclic imide derivatives, N-Alkyl and N-Aryl amines, imine derivatives, and enamine derivatives. In yet other embodiments, certain exemplary sulfur protecting groups may be utilized. The sulfur protecting groups include, but are not limited to those oxygen protecting group describe above as well as aliphatic carboxylic acid (e.g., acrylic acid), maleimide, vinyl sulfonyl, and optionally substituted maleic acid. Certain other exemplary protecting groups are detailed herein, however, it will be appreciated that the present invention is not intended to be limited to these protecting groups; rather, a variety of additional equivalent protecting groups can be readily identified using the above criteria and utilized in the present invention. Additionally, a variety of protecting groups are described in "Protective Groups in Organic Synthesis" Third Ed. Greene, T. W. and Wuts, P. G., Eds., John Wiley & Sons, New York: 1999, the entire contents of which are hereby incorporated by reference.

"Leaving group" refers to a molecular fragment that departs with a pair of electrons in heterolytic bond cleavage. Leaving groups can be anions or neutral molecules. Leaving groups include, but are not limited to halides such as Cl$^-$, Br$^-$, and I$^-$, sulfonate esters, such as para-toluenesulfonate ("tosylate", TsO$^-$), methanesulfonyl (mesyl), p-toluenesulfonyl (tosyl), trifluoromethylsulfonyl (triflate), trifluoromethylsulfonate and RC(O)O— in which R is hydrogen, an aliphatic, heteroaliphatic, carbocyclic, or heterocycloalkyl moiety.

All methods described herein can be performed in any suitable order unless otherwise indicated herein or otherwise clearly contradicted by context. The use of any and all examples, or exemplary language (e.g., "such as") provided herein, is intended merely to better illustrate the invention and is not to be construed as a limitation on the scope of the claims unless explicitly otherwise claimed. No language in the specification is to be construed as indicating that any non-claimed element is essential to what is claimed.

"Antibody" refers to a full-length antibody or functional fragment of an antibody comprising an immunoglobulin. By a "functional fragment" it is meant a sufficient portion of the immunoglobulin or antibody is provided that the moiety effectively binds or complexes with the cell surface molecule for its target cell population.

An immunoglobulin may be purified, generated recombinantly, generated synthetically, or combinations thereof, using techniques known to those of skill in the art. While immunoglobulins within or derived from IgG antibodies are particularly well-suited for use in this invention, immunoglobulins from any of the classes or subclasses may be selected, e.g., IgG, IgA, IgM, IgD and IgE. Suitably, the immunoglobulin is of the class IgG including but not limited to IgG subclasses (IgG1, 2, 3 and 4) or class IgM which is able to specifically bind to a specific epitope on an antigen. Antibodies can be intact immunoglobulins derived from natural sources or from recombinant sources and can be immunoreactive portions of intact immunoglobulins. Antibodies may exist in a variety of forms including, for example, polyclonal antibodies, monoclonal antibodies, camelized single domain antibodies, intracellular antibodies ("intrabodies"), recombinant antibodies, anti-idiotypic antibodies, domain antibodies, linear antibody, multispecific antibody, antibody fragments, such as, Fv, Fab, F(ab)$_2$, F(ab)$_3$, Fab', Fab'-SH, F(ab')$_2$, single chain variable fragment antibodies (scFv), tandem/bis-scFv, Fc, pFc', scFvFc, (or scFv-Fc), disulfide Fv (dsfv), bispecific antibodies (bc-scFv) such as BiTE antibodies; camelid antibodies, resurfaced antibodies, humanized antibodies, fully human antibodies, single-domain antibody (sdAb, also known as NANOBODY®), chimeric antibodies, chimeric antibodies comprising at least one human constant region, dual-affinity antibodies such as, dual-affinity retargeting proteins (DART™), divalent (or bivalent) single-chain variable fragments (di-scFvs, bi-scFvs) including but not limited to minibodies, diabodies, triabodies or tribodies, tetrabodies, and the like, and multivalent antibodies. "Antibody fragment" refers to at least a portion of the variable region of the immunoglobulin molecule that binds to its target, i.e., the antigen-binding region. As used herein, the term "antibody" refers to both the full-length antibody and antibody fragments unless otherwise specified.

"Protein based recognition-molecule" or "PBRM" refers to a molecule that recognizes and binds to a cell surface marker or receptor such as, a transmembrane protein, surface immobilized protein, or proteoglycan. Examples of PBRMs include but are not limited to, antibodies (e.g., Trastuzumab, Cetuximab, Rituximab, Bevacizumab, Epratuzumab, Veltuzumab, Labetuzumab, B7-H4, B7-H3, CA125, CD33, CXCR2, EGFR, FGFR1, FGFR2, FGFR3, FGFR4, HER2, PD-L1 and anti-5T4) or peptides (LHRH receptor targeting peptides, EC-1 peptide), lipocalins, such as, for example, anticalins, proteins such as, for example, interferons, lymphokines, growth factors, colony stimulating factors, and the like, peptides or peptide mimics, and the like. The protein based recognition molecule, in addition to targeting the modified polymer conjugate to a specific cell, tissue or location, may also have certain therapeutic effect such as antiproliferative (cytostatic and/or cytotoxic) activity against a target cell or pathway. The protein based recognition molecule comprises or may be engineered to comprise at least one chemically reactive group such as, —COOH, primary amine, secondary amine —NHR, —SH, or a chemically reactive amino acid moiety or side chains such as, for example, tyrosine, histidine, cysteine, or lysine. In one embodiment, a PBRM may be a ligand (LG) or targeting moiety which specifically binds or complexes with a cell surface molecule, such as a cell surface receptor or antigen, for a given target cell population. Following specific binding or complexing of the ligand with its receptor, the cell is permissive for uptake of the ligand or ligand-drug-conjugate, which is then internalized into the cell. As used herein, a ligand that "specifically binds or complexes with" or "targets" a cell surface molecule preferentially associates with a cell surface molecule via intermolecular forces. For example, the ligand can preferentially associate with the cell surface molecule with a Kd of less than about 50 nM, less than about 5 nM, or less than 500 pM. Techniques for measuring binding affinity of a ligand to a cell surface molecule are well-known; for example, one suitable technique, is termed surface plasmon resonance (SPR). In one embodiment, the ligand is used for targeting and has no detectable therapeutic effect as separate from the drug which it delivers. In another embodiment, the ligand functions both as a targeting moiety and as a therapeutic or immunomodulatory agent (e.g., to enhance the activity of the active drug or prodrug).

"Biocompatible" as used herein is intended to describe compounds that exert minimal destructive or host response effects while in contact with body fluids or living cells or tissues. Thus a biocompatible group, as used herein, refers to an aliphatic, cycloalkyl, heteroaliphatic, heterocycloalkyl, aryl, or heteroaryl moiety, which falls within the definition of the term biocompatible, as defined above and herein. The term "Biocompatibility" as used herein, is also taken to mean that the compounds exhibit minimal interactions with recognition proteins, e.g., naturally occurring antibodies, cell proteins, cells and other components of biological systems, unless such interactions are specifically desirable. Thus, substances and functional groups specifically intended to cause the above minimal interactions, e.g., drugs and prodrugs, are considered to be biocompatible. Preferably (with exception of compounds intended to be cytotoxic, such as, e.g., antineoplastic agents), compounds are "biocompatible" if their addition to normal cells in vitro, at concentrations similar to the intended systemic in vivo concentrations, results in less than or equal to 1% cell death during the time equivalent to the half-life of the compound in vivo (e.g., the period of time required for 50% of the compound administered in vivo to be eliminated/cleared), and their administration in vivo induces minimal and medically acceptable inflammation, foreign body reaction, immunotoxicity, chemical toxicity and/or other such adverse effects. In the above sentence, the term "normal cells" refers to cells that are not intended to be destroyed or otherwise significantly affected by the compound being tested.

"Biodegradable": As used herein, "biodegradable" polymers are polymers that are susceptible to biological processing in vivo. As used herein, "biodegradable" compounds or moieties are those that, when taken up by cells, can be broken down by the lysosomal or other chemical machinery or by hydrolysis into components that the cells can either reuse or dispose of without significant toxic effect on the cells. The term "biocleavable" as used herein has the same meaning of "biodegradable". The degradation fragments preferably induce little or no organ or cell overload or pathological processes caused by such overload or other adverse effects in vivo. Examples of biodegradation processes include enzymatic and non-enzymatic hydrolysis, oxidation and reduction. Suitable conditions for non-enzymatic hydrolysis of the biodegradable protein-polymer-drug conjugates (or their components, e.g., the biodegradable polymeric carrier and the linkers between the carrier and the antibody or the drug molecule) described herein, for example, include exposure of the biodegradable conjugates to water at a temperature and a pH of lysosomal intracellular compartment. Biodegradation of some protein-polymer-drug conjugates (or their components, e.g., the biodegradable polymeric carrier and the linkers between the carrier and the antibody or the drug molecule), can also be enhanced extracellularly, e.g., in low pH regions of the animal body, e.g., an inflamed area, in the close vicinity of activated macrophages or other cells releasing degradation facilitating factors. In certain preferred embodiments, the effective size of the polymer carrier at pH~7.5 does not detectably change over 1 to 7 days, and remains within 50% of the original polymer size for at least several weeks. At pH~5, on the other hand, the polymer carrier preferably detectably degrades over 1 to 5 days, and is completely transformed into low molecular weight fragments within a two-week to several-month time frame. Polymer integrity in such tests can be measured, for example, by size exclusion HPLC. Although faster degradation may be in some cases preferable, in general it may be more desirable that the polymer degrades in cells with the rate that does not exceed the rate of metabolization or excretion of polymer fragments by the cells. In preferred embodiments, the polymers and polymer biodegradation byproducts are biocompatible.

"Bioavailability": The term "bioavailability" refers to the systemic availability (i.e., blood/plasma levels) of a given amount of drug or compound administered to a subject. Bioavailability is an absolute term that indicates measurement of both the time (rate) and total amount (extent) of drug or compound that reaches the general circulation from an administered dosage form.

"Hydrophilic": The term "hydrophilic" as it relates to substituents, e.g., on the polymer monomeric units does not essentially differ from the common meaning of this term in the art, and denotes chemical moieties which contain ionizable, polar, or polarizable atoms, or which otherwise may be solvated by water molecules. Thus a hydrophilic group, as used herein, refers to an aliphatic, cycloalkyl, heteroaliphatic, heterocycloalkyl, aryl or heteroaryl moiety, which falls within the definition of the term hydrophilic, as defined above. Examples of particular hydrophilic organic moieties which are suitable include, without limitation, aliphatic or heteroaliphatic groups comprising a chain of atoms in a range of between about one and twelve atoms, hydroxyl, hydroxyalkyl, amine, carboxyl, amide, carboxylic ester, thioester, aldehyde, nitryl, isonitryl, nitroso, hydroxylamine, mercaptoalkyl, heterocycle, carbamates, carboxylic acids and their salts, sulfonic acids and their salts, sulfonic acid esters, phosphoric acids and their salts, phosphate esters, polyglycol ethers, polyamines, polycarboxylates, polyesters and polythioesters. In certain embodiments, hydrophilic substituents comprise a carboxyl group (COOH), an aldehyde group (CHO), a ketone group ($COC_{1-4}$ alkyl), a methylol ($CH_2OH$) or a glycol (for example, CHOH—$CH_2OH$ or CH—($CH_2OH)_2$), $NH_2$, F, cyano, $SO_3H$, $PO_3H$, and the like.

The term "hydrophilic" as it relates to the polymers of the invention generally does not differ from usage of this term in the art, and denotes polymers comprising hydrophilic functional groups as defined above. In a preferred embodiment, hydrophilic polymer is a water-soluble polymer. Hydrophilicity of the polymer can be directly measured through determination of hydration energy, or determined through investigation between two liquid phases, or by chromatography on solid phases with known hydrophobicity, such as, for example, C4 or C18.

"Polymeric Carrier": The term polymeric carrier, as used herein, refers to a polymer or a modified polymer, which is suitable for covalently attaching to or can be covalently attached to one or more drug molecules with a designated linker and/or one or more PBRMs with a designated linker.

"Physiological conditions": The phrase "physiological conditions", as used herein, relates to the range of chemical (e.g., pH, ionic strength) and biochemical (e.g., enzyme concentrations) conditions likely to be encountered in the extracellular fluids of living tissues. For most normal tissues, the physiological pH ranges from about 7.0 to 7.4. Circulating blood plasma and normal interstitial liquid represent typical examples of normal physiological conditions.

"Polysaccharide", "carbohydrate" or "oligosaccharide": The terms "polysaccharide", "carbohydrate", or "oligosaccharide" are known in the art and refer, generally, to substances having chemical formula $(CH_2O)_n$, where generally n>2, and their derivatives. Carbohydrates are polyhydroxyaldehydes or polyhydroxyketones, or change to such substances on simple chemical transformations, such as hydrolysis, oxidation or reduction. Typically, carbohydrates are present in the form of cyclic acetals or ketals (such as, glucose or fructose). These cyclic units (monosaccharides) may be connected to each other to form molecules with few (oligosaccharides) or several (polysaccharides) monosaccharide units. Often, carbohydrates with well-defined number, types and positioning of monosaccharide units are called oligosaccharides, whereas carbohydrates consisting of mixtures of molecules of variable numbers and/or positioning of monosaccharide units are called polysaccharides. The terms "polysaccharide", "carbohydrate", and "oligosaccharide", are used herein interchangeably. A polysaccharide may include natural sugars (e.g., glucose, fructose, galactose, mannose, arabinose, ribose, and xylose) and/or derivatives of naturally occurring sugars (e.g., 2'-fluororibose, 2'-deoxyribose, and hexose).

"Prodrug": As used herein the term "prodrug" refers to a precursor of an active drug, that is, a compound that can be transformed to an active drug. Typically such a prodrug is subject to processing in vivo, which converts the drug to a physiologically active form. In some instances, a prodrug may itself have a desired physiologic effect. A desired physiologic effect may be, e.g., therapeutic, cytotoxic, immunomodulatory, or the like.

"Cytotoxic": As used herein the term "cytotoxic" means toxic to cells or a selected cell population (e.g., cancer cells). The toxic effect may result in cell death and/or lysis. In certain instances, the toxic effect may be a sub lethal destructive effect on the cell, e.g., slowing or arresting cell growth. In order to achieve a cytotoxic effect, the drug or prodrug may be selected from a group consisting of a DNA damaging agent, a microtubule disrupting agent, or a cytotoxic protein or polypeptide, amongst others.

"Cytostatic": As used herein the term "cytostatic" refers to a drug or other compound which inhibits or stops cell growth and/or multiplication.

"Drug": As used herein, the term "drug" refers to a compound which is biologically active and provides a desired physiological effect following administration to a subject in need thereof (e.g., an active pharmaceutical ingredient).

"Drug derivative" or "modified drug" or the like as used herein, refers to a compound that comprises the drug molecule intended to be delivered by the conjugate of the invention and a functional group capable of attaching the drug molecule to the polymeric carrier.

"Active form" as used herein refers to a form of a compound that exhibits intended pharmaceutical efficacy in vivo or in vitro. In particular, when a drug molecule intended to be delivered by the conjugate of the invention is released from the conjugate, the active form can be the drug itself or its derivatives, which exhibit the intended therapeutic properties. The release of the drug from the conjugate can be achieved by cleavage of a biodegradable bond of the linker which attaches the drug to the polymeric carrier. The active drug derivatives accordingly can comprise a portion of the linker.

"Diagnostic label": As used herein, the term diagnostic label refers to an atom, group of atoms, moiety or functional group, a nanocrystal, or other discrete element of a composition of matter, that can be detected in vivo or ex vivo using analytical methods known in the art. When associated with a conjugate of the present invention, such diagnostic labels permit the monitoring of the conjugate in vivo. Alternatively or additionally, constructs and compositions that include diagnostic labels can be used to monitor biological functions or structures. Examples of diagnostic labels include, without limitation, labels that can be used in medical diagnostic procedures, such as, radioactive isotopes (radionuclides) for gamma scintigraphy and Positron Emission Tomography (PET), contrast agents for Magnetic Resonance Imaging (MRI) (for example paramagnetic atoms and superparamagnetic nanocrystals), contrast agents for computed tomography and other X-ray-based imaging methods, agents for ultrasound-based diagnostic methods (sonography), agents for neutron activation (e.g., boron, gadolinium), fluorophores for various optical procedures, and, in general moieties which can emit, reflect, absorb, scatter or otherwise affect electromagnetic fields or waves (e.g., gamma-rays, X-rays, radiowaves, microwaves, light), particles (e.g., alpha particles, electrons, positrons, neutrons, protons) or other forms of radiation, e.g., ultrasound.

"Aliphatic": In general, the term aliphatic, as used herein, includes both saturated and unsaturated, straight chain (i.e., unbranched) or branched aliphatic hydrocarbons, which are optionally substituted with one or more functional groups. As will be appreciated by one of ordinary skill in the art, "aliphatic" is intended herein to include, but is not limited to, alkyl, alkenyl, alkynyl moieties. Thus, as used herein, the term "alkyl" includes straight and branched alkyl groups. An analogous convention applies to other generic terms such as "alkenyl", "alkynyl" and the like. In certain embodiments, as used herein, "lower alkyl" is used to indicate those alkyl groups (substituted, unsubstituted, branched or unbranched) having about 1-6 carbon atoms. "Substituted alkyl" refers to alkyl groups that are substituted with one or more functional groups. Substituents include, but are not limited to, any of the substituents mentioned below, i.e., the substituents recited below resulting in the formation of a stable compound.

"Alkenyl": the term alkenyl denotes a monovalent group derived from a hydrocarbon moiety having at least one carbon-carbon double bond by the removal of a single hydrogen atom. "Substituted alkenyl" groups are substituted with one or more functional groups. Substituents include, but are not limited to, any of the substituents mentioned below, i.e., the substituents recited below resulting in the formation of a stable compound. Alkenyl groups include, for example, ethenyl, propenyl, butenyl, 1-methyl-2-buten-1-yl, and the like.

"Alkynyl": the term alkynyl as used herein refers to a monovalent group derived from a hydrocarbon having at least one carbon-carbon triple bond by the removal of a single hydrogen atom. "Substituted alkenyl" groups are substituted with one or more functional groups. Substituents include, but are not limited to, any of the substituents mentioned below, i.e., the substituents recited below resulting in the formation of a stable compound. Representative alkynyl groups include ethynyl, 2-propynyl (propargyl), 1-propynyl, and the like.

In certain embodiments, the alkyl, alkenyl and alkynyl groups employed in the invention contain about 1-20 aliphatic carbon atoms. In certain other embodiments, the alkyl, alkenyl, and alkynyl groups employed in the invention contain about 1-10 aliphatic carbon atoms. In yet other embodiments, the alkyl, alkenyl, and alkynyl groups employed in the invention contain about 1-8 aliphatic carbon atoms. In still other embodiments, the alkyl, alkenyl, and alkynyl groups employed in the invention contain about 1-6 aliphatic carbon atoms. In yet other embodiments, the alkyl, alkenyl, and alkynyl groups employed in the invention contain about 1-4 carbon atoms. Illustrative aliphatic groups thus include, but are not limited to, for example, methyl, ethyl, n-propyl, isopropyl, allyl, n-butyl, sec-butyl, isobutyl, tert-butyl, n-pentyl, sec-pentyl, isopentyl, tert-pentyl, n-hexyl, sec-hexyl, moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargy 1), 1-propynyl and the like.

"Alkylene" as used herein, the term alkylene by itself or as part of another term refers to a saturated, branched or straight chain having two monovalent radical centers derived by the removal of two hydrogen atoms from the same or two different carbon atoms of a parent alkane. Alkylene radicals include, but are not limited to, methylene, 1,2, ethylene, 1,3-propyl, and the like. Suitable alkylenes include, but are not limited to methylene, ethylene, propylene, butylene, pentylene, hexylene, heptylene, octylene, nonylene, decalene, and the like. The term "cycloalkylene" similarly refers to bivalent cycloalkyl. Cycloalkylene radicals include, but are not limited to, 1,1-cyclopentylene, 1,2-cyclopentylene, 1,1-cyclobutylene, 1,3-cyclobutylene, etc.

"Heteroaliphatic": as used herein, the term heteroaliphatic refers to aliphatic moieties in which one or more carbon atoms in the main chain have been substituted with a heteroatom. Thus, a heteroaliphatic group refers to an aliphatic chain which contains one or more oxygen, sulfur, nitrogen, phosphorus or silicon atoms, e.g., in place of carbon atoms. Heteroaliphatic moieties may be branched or linear unbranched. In certain embodiments, heteroaliphatic moieties are substituted ("substituted heteroaliphatic") by independent replacement of one or more of the hydrogen atoms thereon with one or more moieties including, but not limited to aliphatic; heteroaliphatic; cycloalkyl; heterocycloalkyl; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —$N_{O2}$; —CN; —$C_{F3}$; —$C_{H2}C_{F3}$; —$CHC_{12}$; —$C_{H2}OH$; —$C_{H2}C_{H2}OH$; —$C_{H2}N_{H2}$; —$C_{H2}S_{O2}C_{H3}$; or -$G^{RG1}$ wherein G is —O—, —S—, —$N^{RG2}$—, —C(=O)—, —S(=O)—, —$S_{O2}$—, —C(=O)O—, —C(=O)$N^{RG2}$—, —OC(=O)—, —$N^{RG2}$C(=O)—, —OC(=O)O—, —OC(=O)$N^{RG2}$—, —$N^{RG2}$C(=O)O—, —$N^{RG2}$C(=O)$N^{RG2}$—, —C(=S)—, —C(=S)S—, —SC(=S)—, —SC(=S)S—, —C(=$N^{RG2}$)—, —C(=$N^{RG2}$)O—, —C(=$N^{RG2}$)$N^{RG3}$—, —OC(=$N^{RG2}$)—, —$N^{RG2}$C(—$N^{RG3}$)—, —$N^{RG2}$SO$_2$—, —$N^{RG2}$S$_{O2}$$N^{RG3}$—, or —$S_{O2}$$N^{RG2}$—, wherein each occurrence of $^{RG1}$, $^{RG2}$ and $^{RG3}$ independently includes, but is not limited to, hydrogen, halogen, or an aliphatic, heteroaliphatic, cycloalkyl, heterocycloalkyl, aryl, heteroaryl, alkylaryl, or alkylheteroaryl moiety, each of which is optionally substituted. Additional examples of generally applicable substituents are illustrated by the specific embodiments shown in the Examples that are described herein.

"Cycloalkyl": as used herein, the term cycloalkyl refers to a saturated or unsaturated nonaromatic hydrocarbon mono- or multi-ring system having 3 to 30 carbon atoms (e.g., $C_3$-$C_{10}$). Suitable cycloalkyls include, but are not limited to cyclopropyl, cyclobutyl, cyclopentyl, cyclohexyl, cycloheptyl, cyclooctyl, cyclopentenyl, cyclohexenyl, cycloheptenyl, cycloheptynyl, adamantyl, and the like.

"Heterocycloalkyl" as used herein refers to a saturated or unsaturated nonaromatic 3-8 membered monocyclic, 8-12 membered bicyclic, or 11-19 membered tricyclic ring system having one or more heteroatoms (such as O, N, S, or Se), unless specified otherwise. In certain embodiments, the term "heterocycloalkyl" refers to a non-aromatic 5-, 6-, 7- or 8-membered ring or a polycyclic group, including, but not limited to a bi- or tri-cyclic group comprising fused six-membered rings having between one and three heteroatoms independently selected from oxygen, sulfur and nitrogen, wherein (i) each 5-membered ring has 0 to 2 double bonds and each 6-membered ring has 0 to 2 double bonds, (ii) the nitrogen and sulfur heteroatoms may optionally be oxidized, (iii) the nitrogen heteroatom may optionally be quaternized, and (iv) any of the above heterocycloalkyl; rings may be fused to an aryl or heteroaryl ring. Examples of heterocycloalkyl groups include, but are not limited to, piperidinyl, piperazinyl, pyrrolidinyl, dioxanyl, tetrahydrofuranyl, tetrahydrothienyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydro-2H-pyranyl, 3,6-dihydro-2H-pyranyl, morpholinyl, and the like.

"Aryl": as used herein, refers to groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl": as used herein, refers to aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g., 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and S(O)$_p$, where p=1 or 2). It is to be noted that total number of S and O atoms in the aromatic heterocycle is not more than 1. Examples of heteroaryl include pyridyl, pyrazinyl, pyrimidinyl, pyrrolyl, pyrazolyl, imidazolyl, thiazolyl, isothiazolyl, tetrazolyl, oxazolyl, isooxazolyl, thiadiazolyl, oxadiazolyl, thiophenyl, furanyl, quinolinyl, isoquinolinyl, tetrazolyl, pyridazinyl, quinazolinyl, dihydroquinazolyl, and tetrahydroquinazolyl and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

"Carbocycle" or "carbocyclic moiety" as used herein, is intended to include any stable monocyclic, bicyclic or tricyclic ring having the specified number of carbons, any of which may be saturated, unsaturated, or aromatic. Carbocycle includes cycloalkyl and aryl. For example, a $C_3$-$C_{14}$ carbocycle is intended to include a monocyclic, bicyclic or tricyclic ring having 3, 4, 5, 6, 7, 8, 9, 10, 11, 12, 13 or 14 carbon atoms. Examples of carbocycles include, but are not limited to, cyclopropyl, cyclobutyl, cyclobutenyl, cyclopentyl, cyclopentenyl, cyclohexyl, cycloheptenyl, cycloheptyl, cycloheptenyl, cyclooctyl, cyclooctenyl, cyclooctadienyl, fluorenyl, phenyl, naphthyl, indanyl, adamantyl and tetrahydronaphthyl. Bridged rings are also included in the definition of carbocycle, including, for example, [3.3.0]bicyclooctane, [4.3.0]bicyclononane, [4.4.0]bicyclodecane and [2.2.2]bicyclooctane. A bridged ring occurs when one or more carbon atoms link two non-adjacent carbon atoms. In one embodiment, bridge rings are one or two carbon atoms. It is noted that a bridge always converts a monocyclic ring into a tricyclic ring. When a ring is bridged, the substituents recited for the ring may also be present on the bridge. Fused (e.g., naphthyl, tetrahydronaphthyl) and spiro rings are also included.

"Heterocycle" or "heterocyclic moiety" as used herein, includes any ring structure (saturated, unsaturated, or aromatic) which contains at least one ring heteroatom (e.g., N, O or S). Heterocycle includes heterocycloalkyl and heteroaryl. Examples of heterocycles include, but are not limited to, morpholine, pyrrolidine, tetrahydrothiophene, piperidine, piperazine and tetrahydrofuran.

Examples of heterocyclic groups include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, 1,2,4-oxadiazol5(4H)-one, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl and xanthenyl. Multiple-ring heterocycle can include fused, bridged or spiro rings.

The cycloalkyl, heterocycloalkyl, aryl, or heteroaryl ring (or the carbocyclic or heterocyclic group) can be substituted at one or more ring positions (e.g., the ring-forming carbon or heteroatom such as N) with such substituents as described above, for example, aliphatic; heteroaliphatic; cycloalkyl; heterocycloalkyl; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an aliphatic, heteroaliphatic, cycloalkyl, heterocycloalkyl; aryl, heteroaryl, alkylaryl, or alkylheteroaryl moiety, each of which is optionally substituted. Aryl and heteroaryl groups can also be fused or bridged with cycloalkyl or heterocyclic rings, which are not aromatic so as to form a multicyclic system (e.g., tetralin, methylenedioxyphenyl).

"Alkoxy" (or "alkyloxy"): as used herein, the term alkoxy (or alkyloxy) refers to an alkyl group, as previously defined, attached to the parent molecular moiety through an oxygen atom ("alkoxy"). In certain embodiments, the alkyl group contains about 1-20 aliphatic carbon atoms. In certain other embodiments, the alkyl group contains about 1-10 aliphatic carbon atoms. In yet other embodiments, the alkyl group contains about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkoxy groups, include but are not limited to, methoxy, ethoxy, propoxy, isopropoxy, n-butoxy, tert-butoxy, neopentoxy and n-hexoxy.

"Aryloxy": as used herein, the term aryloxy refers to an aryl group, as defined herein, attached to the parent molecular moiety through an oxygen atom. Examples of aryloxy groups include but are not limited to phenoxy and napthyloxy.

"Heteroaryloxy": as used herein, the term heteroaryloxy refers to a heteroaryl group, as defined herein, attached to the parent molecular moiety through an oxygen atom. Examples of heteroaryloxy groups include but are not limited to, quinolyloxy and isoquinolizinyloxy.

"Amine": the term amine refers to a group having the structure —N(R)$_2$ wherein each occurrence of R is independently hydrogen, or an aliphatic or heteroaliphatic moiety, or the R groups, taken together, may form a heterocyclic moiety. In certain instances, an amine group can be charged (protonated) or quaternized, e.g., —HN$^+$(R)$_2$ or —N$^+$(R)$_3$.

"Alkylamino": as used herein, the term alkylamino refers to a group having the structure —NHR' wherein R' is alkyl, as defined herein. The term "aminoalkyl" refers to a group having the structure NH$_2$R'—, wherein R' is alkyl, as defined herein. In certain embodiments, the alkyl group contains about 1-20 aliphatic carbon atoms. In certain other embodiments, the alkyl group contains about 1-10 aliphatic carbon atoms. In yet other embodiments, the alkyl, alkenyl, and alkynyl groups employed in the invention contain about 1-8 aliphatic carbon atoms. In still other embodiments, the alkyl group contains about 1-6 aliphatic carbon atoms. In yet other embodiments, the alkyl group contains about 1-4 aliphatic carbon atoms. Examples of alkylamino include, but are not limited to, methylamino, ethylamino, iso-propylamino and the like.

"Alkylthio" (or "thioalkyl") means an alkyl group as defined herein with the indicated number of carbon atoms attached through a sulfur atom. $C_{1-6}$ alkylthio, is intended to include $C_1$, $C_2$, $C_3$, $C_4$, $C_5$, and $C_6$ alkylthio groups. $C_{1-8}$ alkylthio, is intended to include $C_1$, $C_2$, $C_3$, $C_4$, $C_5$, $C_6$, $C_7$, and $C_8$ alkylthio groups. The thioalkyl groups can be substituted with groups such as alkyl, alkenyl, alkynyl, halogen, hydroxyl, alkylcarbonyloxy, arylcarbonyloxy, alkoxycarbonyloxy, aryloxycarbonyloxy, carboxylate, carboxyacid, alkylcarbonyl, arylcarbonyl, alkoxycarbonyl, aminocarbonyl, alkylaminocarbonyl, dialkylaminocarbonyl, alkylthiocarbonyl, alkoxyl, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl alkylaryl, or an aryl or heteroaryl moieties.

"Thiocarbonyl" or "thiocarboxy" includes compounds and moieties which contain a carbon connected with a double bond to a sulfur atom.

"Arylthio" (or "thioaryl") means an aryl group as defined herein with the indicated number of carbon atoms attached through a sulfur atom.

"Carboxylic acid" as used herein refers to a compound comprising a group of formula —CO$_2$H.

"Dicarboxylic acid" refers to a compound comprising two groups of formula —CO$_2$H.

"Halo, halide and halogen": The terms halo, halide and halogen as used herein refer to an atom selected from fluorine, chlorine, bromine, and iodine.

"Methylol": The term methylol as used herein refers to an alcohol group of the structure —CH$_2$OH.

"Hydroxyalkyl": As used herein, the term hydroxyalkyl refers to an alkyl group, as defined above, bearing at least one OH group.

"Mercaptoalkyl": The term mercaptoalkyl as used therein refers to an alkyl group, as defined above, bearing at least one SH group.

"Acyl" includes moieties that contain the acyl radical (—C(O)—) or a carbonyl group. "Substituted acyl" includes acyl groups where one or more of the hydrogen atoms are replaced by, for example, alkyl groups, alkynyl groups, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aryl or heteroaryl moiety.

"Hydrocarbon": The term hydrocarbon, as used herein, refers to any chemical group comprising hydrogen and carbon. The hydrocarbon may be substituted or unsubstituted. The hydrocarbon may be unsaturated, saturated, branched, unbranched, cyclic, polycyclic, or heterocyclic. Illustrative hydrocarbons include, for example, methyl, ethyl, n-propyl, iso-propyl, cyclopropyl, allyl, vinyl, n-butyl, tert-butyl, ethynyl, cyclohexyl, methoxy, diethylamino, heterocycloalkyl, aryl, heteroaryl, thioalkyl, and the like. As would be known to one skilled in this art, all valencies must be satisfied in making any substitutions.

"Alkylaryl" as used herein refers to an aryl group substituted with one or more alkyl groups (e.g., methylphenyl).

"Alkylarylamino" as used herein refers to —NR$^{G4}$R$^{G5}$, wherein R$^{G4}$ is alkyl, as defined herein, and R$^{G5}$ is an aryl, as defined herein, or at least one of R$^{G4}$ and R$^{G5}$ is an alkylaryl as defined herein.

"Substituted": The term substituted, whether preceded by the term "optionally" or not, and substituent, as used herein, refers to the replacement of a hydrogen radical in a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Examples of substituents include, but are not limited to aliphatic; heteroaliphatic; cycloalkyl; heterocycloalkyl; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; or -GR$^{G1}$ wherein G is —O—, —S—, —NR$^{G2}$—, —C(=O)—, —S(=O)—, —SO$_2$—, —C(=O)O—, —C(=O)NR$^{G2}$—, —OC(=O)—, —NR$^{G2}$C(=O)—, —OC(=O)O—, —OC(=O)NR$^{G2}$—, —NR$^{G2}$C(=O)O—, —NR$^{G2}$C(=O)NR$^{G2}$—, —C(=S)—, —C(=S)S—, —SC(=S)—, —SC(=S)S—, —C(=NR$^{G2}$)—, —C(=NR$^{G2}$)O—, —C(=NR$^{G2}$)NR$^{G3}$—, —OC(=NR$^{G2}$)—, —NR$^{G2}$C(=NR$^{G3}$)—, —NR$^{G2}$SO$_2$—, —NR$^{G2}$SO$_2$NR$^{G3}$—, or —SO$_2$NR$^{G2}$—, wherein each occurrence of R$^{G1}$, R$^{G2}$ and R$^{G3}$ independently includes, but is not limited to, hydrogen, halogen, or an aliphatic, heteroaliphatic, cycloalkyl, heterocycloalkyl, aryl, heteroaryl, alkylaryl, or alkylheteroaryl moiety, each of which is optionally substituted. Additional examples of generally applicable substituents are illustrated by the specific embodiments shown in the Examples that are described herein.

The following are more general terms used throughout the present application:

"Animal": The term animal, as used herein, refers to humans as well as non-human animals, at any stage of development, including, for example, mammals, birds, reptiles, amphibians, fish, worms and single cells. Cell cultures and live tissue samples are considered to be pluralities of animals. Preferably, the non-human animal is a mammal (e.g., a rodent, a mouse, a rat, a rabbit, a monkey, a dog, a cat, a primate, or a pig). An animal may be a transgenic animal or a human clone. The term "subject" encompasses animals.

"Efficient amount": In general, as it refers to an active agent or drug delivery device, the term "efficient amount" refers to the amount necessary to elicit the desired biological response. As will be appreciated by those of ordinary skill in this art, the efficient amount of an agent or device may vary depending on such factors as the desired biological endpoint, the agent to be delivered, the composition of the encapsulating matrix, the target tissue, etc. For example, the efficient amount of microparticles containing an antigen to be delivered to immunize an individual is the amount that results in an immune response sufficient to prevent infection with an organism having the administered antigen.

"Natural amino acid" as used herein refers to any one of the common, naturally occurring L-amino acids found in naturally occurring proteins: glycine (Gly), alanine (Ala), valine (Val), leucine (Leu), isoleucine (Ile), lysine (Lys), arginine (Arg), histidine (His), proline (Pro), serine (Ser), threonine (Thr), phenylalanine (Phe), tyrosine (Tyr), tryptophan (Trp), aspartic acid (Asp), glutamic acid (Glu), asparagine (Asn), glutamine (Gln), cysteine (Cys) and methionine (Met).

"Unnatural amino acid" as used herein refers to any amino acid which is not a natural amino acid. This includes, for example, amino acids that comprise α-, β-, ω-, D-, L-amino acyl residues. More generally, the unnatural amino acid comprises a residue of the general formula

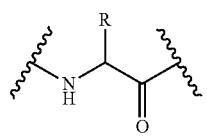

wherein the side chain R is other than the amino acid side chains occurring in nature. Exemplary unnatural amino acids, include, but are not limited to, sarcosine (N-methylglycine), citrulline (cit), homocitrulline, β-ureidoalanine, thiocitrulline, hydroxyproline, allothreonine, pipecolic acid (homoproline), α-aminoisobutyric acid, tert-butylglycine, tert-butylalanine, allo-isoleucine, norleucine, α-methylleucine, cyclohexylglycine, β-cyclohexylalanine, β-cyclopentylalanine, α-methylproline, phenylglycine, α-methylphenylalanine and homophenylalanine.

"Amino acyl": More generally, the term amino acyl, as used herein, encompasses natural amino acid and unnatural amino acids.

"Polyamide": refers to homo- or hetero-polymers of natural amino acid and unnatural amino acids. Illustrative homopolymers include, but are not limited to, poly-lysine, poly-arginine, poly-γ-glutaric acid, and the like. Illustrative hetero-polymers include, but are not limited to, polymers comprising peptides fragments selected from peptidases, lysozymes, metalloproteinases, and the like.

"PHF" refers to poly(1-hydroxymethylethylene hydroxymethyl-formal).

As used herein, the terms "polymer unit", "monomeric unit", "monomer", "monomer unit", "unit" all refer to a repeatable structural unit in a polymer.

"Arylene" as used herein refers to an aryl group which has two covalent bonds and can be in the ortho, meta, or para configurations as shown in the following structures:

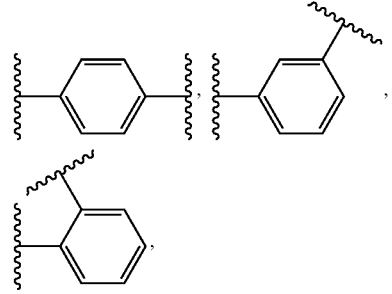

in which the phenyl group can be unsubstituted or substituted with up to four groups including, but not limited to, C$_{1-8}$ alkyl, —O—(C$_{1-8}$ alkyl), C$_{6-10}$ aryl, —C(O)R', —OC(O)R', —C(O)OR', —C(O)NH$_2$, —C(O)NHR', —C(O)N(R')$_2$, NHC(O)R', —S(O)$_2$R', —S(O)R', —OH, -halogen, —N$_3$, —NH$_2$, —NH(R'), —N(R')$_2$ and —CN; wherein each R' independently is H, —C$_{1-3}$ alkyl or C$_{6-10}$ aryl.

"Hydroxy- or oxo-substituted C$_{1-8}$ alkyl" as used herein refers to a lower alkyl group wherein a hydrogen on the lower alkyl group is replaced by —OH (for a hydroxy-substituted lower alkyl), or two hydrogens on a single carbon of the lower alkyl group are replaced by =O (for an oxo-substituted lower alkyl).

"Auristatin compounds" as used herein refers to auristatins such as auristatin E (also known as a derivative of dolastatin-10), auristatin EB (AEB), auristatin EFP (AEFP), monomethyl auristatin E (MMAE), monomethyl auristatin F (MMAF), auristatin F and dolastatin, as well as their derivatives or modified forms, such that they are suitable for conjugation with the polymers or polymeric scaffolds described herein and can convert into active forms when the compounds are released from the polymers.

"PAB" as used herein refers to para-aminobenzoic acid.

As used herein, "molecular weight" or "MW" of a polymer or polymeric carrier/scaffold or polymer conjugates refers to the weight average molecular weight unless otherwise specified.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present invention is intended to include all isomers of the compound, which refers to and includes, optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers.

Polymeric Carriers

In certain exemplary embodiments, the conjugates of the invention find use in biomedical applications, such as drug delivery and tissue engineering, and the carrier is biocompatible and biodegradable. In certain embodiments, the carrier is a soluble polymer, nanoparticle, gel, liposome, micelle, suture, implant, etc. In certain embodiments, the term "soluble polymer" encompasses biodegradable biocompatible polymer such as a polyal (e.g., hydrophilic polyacetal or polyketal). In certain other embodiments, the carrier is a fully synthetic, semi-synthetic or naturally-occurring polymer. In certain other embodiments, the carrier is hydrophilic.

In certain exemplary embodiments, the carriers used in the present invention are biodegradable biocompatible polyals comprising at least one hydrolysable bond in each monomer unit positioned within the main chain. This ensures that the degradation process (via hydrolysis/cleavage of the monomer units) will result in fragmentation of the polymer conjugate to the monomeric components (i.e., degradation), and confers to the polymer conjugates of the invention their biodegradable properties. The properties (e.g., solubility, bioadhesivity and hydrophilicity) of biodegradable biocompatible polymer conjugates can be modified by subsequent substitution of additional hydrophilic or hydrophobic groups. Examples of biodegradable biocompatible polymers suitable for practicing the invention can be found inter alia in U.S. Pat. Nos. 5,811,510; 5,863,990; 5,958,398; 7,838,619 and 7,790,150; and U.S. Publication No. 2006/0058512; each of the above listed patent documents is incorporated herein by reference in its entirety. Guidance on the significance, preparation, and applications of this type of polymers may be found in the above-cited documents. In certain embodiments, it is anticipated that the present invention will be particularly useful in combination with the above-referenced patent documents, as well as U.S. Pat. Nos. 5,582,172 and 6,822,086, each of the above listed patent documents is incorporated herein by reference in its entirety.

The conjugates of this invention are hydrophilic, hydrolysable and comprise drug molecules (e.g., auristatins compounds, and analogs thereof) and antibodies (e.g., Trastuzumab, Cetuximab, Rituximab, Bevacizumab, Epratuzumab, Veltuzumab, Labetuzumab) or peptides (LHRH receptor targeting peptides, EC-1 peptide) covalently attached to the polymer carrier via linkages that contain one or more biodegradable bonds. Thus, in certain exemplary embodiments, carriers suitable for practicing the present invention are polyals having at least one acetal/ketal oxygen atom in each monomer unit positioned within the main chain. As discussed above, this ensures that the degradation process (via hydrolysis/cleavage of the polymer acetal/ketal groups) will result in fragmentation of the polyal conjugate to low molecular weight components (i.e., degradation).

In certain embodiments, biodegradable biocompatible polymer carriers, used for preparation of polymer conjugates of the invention, are naturally occurring polysaccharides, glycopolysaccharides, and synthetic polymers of polyglycoside, polyacetal, polyamide, polyether, and polyester origin and products of their oxidation, fictionalization, modification, cross-linking, and conjugation.

In certain other embodiments, the carrier is a hydrophilic biodegradable polymer selected from the group consisting of carbohydrates, glycopolysaccharides, glycolipids, glycoconjugates, polyacetals, polyketals, and derivatives thereof.

In certain exemplary embodiments, the carrier is a naturally occurring linear and/or branched biodegradable biocompatible homopolysaccharide selected from the group consisting of cellulose, amylose, dextran, levan, fucoidan, carraginan, inulin, pectin, amylopectin, glycogen and lixenan.

In certain other exemplary embodiments, the carrier is a naturally occurring linear and branched biodegradable biocompatible heteropolysaccharide selected from the group consisting of agarose, hyluronan, chondroitinsulfate, dermatansulfate, keratansulfate, alginic acid and heparin.

In yet other exemplary embodiments, the polymeric carrier comprises a copolymer of a polyacetal/polyketal and a hydrophilic polymer selected from the group consisting of polyacrylates, polyvinyl polymers, polyesters, polyorthoesters, polyamides, polypeptides, and derivatives thereof.

In yet another embodiment, the polymeric carrier is dextrin that is produced by the hydrolysis of a starch obtained from various natural products such as, for example, wheat, rice, maize and tapioca. Depending on the structure of the starch starting material each dextrin comprises a unique distribution of α-1,4 linkages and α-1,6 linkages. Since the rate of biodegradability of α-1,6 linkages is typically less than that for α-1,4 linkages, preferably the percentage of α-1,6 linkages is less than 10% and more preferably less than 5%. In one embodiment the molecular weight of the dextrin is in the range of about 1 kDa to about 200 kDa, more preferably from about 2 kDa to about 55 kDa.

In certain embodiments, the carrier comprises polysaccharides activated by selective oxidation of cyclic vicinal diols of 1,2-, 1,4-, 1,6-, and 2,6-pyranosides, and 1,2-, 1,5-, 1,6-furanosides, or by oxidation of lateral 6-hydroxy and 5,6-diol containing polysaccharides prior to conjugation with drug molecules or PBRMs.

In still other embodiments, the polymeric carrier comprises a biodegradable biocompatible polyacetal wherein at least a subset of the polyacetal repeat structural units have the following chemical structure:

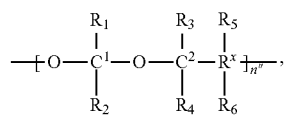

wherein for each occurrence of the n bracketed structure, one of $R_1$ and $R_2$ is hydrogen, and the other is a biocompatible group and includes a carbon atom covalently attached to $C^1$; $R^x$ is a carbon atom covalently attached to $C^2$; n" is an integer; each occurrence of $R_3$, $R_4$, $R_5$ and $R_6$ is a biocompatible group and is independently hydrogen or an organic moiety; and for each occurrence of the bracketed structure n, at least one of $R_1$, $R_2$, $R_3$, $R_4$, $R_5$ and $R_6$ comprises a functional group suitable for coupling. In certain embodiments, the functional group is a hydroxyl moiety.

In one embodiment, the polymeric carrier comprises activated hydrophilic biodegradable biocompatible polymers comprising from 0.1% to 100% polyacetal moieties whose backbone is represented by the following chemical structure:

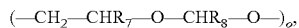

wherein:
$R_7$ and $R_8$ are independently hydrogen, hydroxyl, hydroxy alkyl (e.g., —CH$_2$OH, —CH(OH)—CH(OH), —CHO, —CH(OH)—CHO or -carbonyl; and
o is an integer from 20 to 2000.

In yet other embodiments, the polymeric carrier comprises a biodegradable biocompatible polyketal wherein at least a subset of the polyketal repeatable structural units have the following chemical structure:

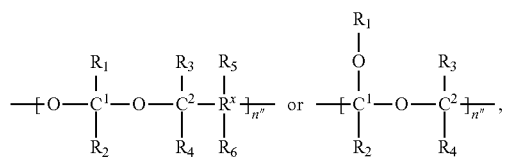

wherein each occurrence of $R_1$ and $R_2$ is a biocompatible group and $R^x$, $R_3$, $R_4$, $R_5$, $R_6$ and are as defined herein In certain embodiments, the ketal units are monomers of Formula (IIa$_1$) or (IIb$_1$):

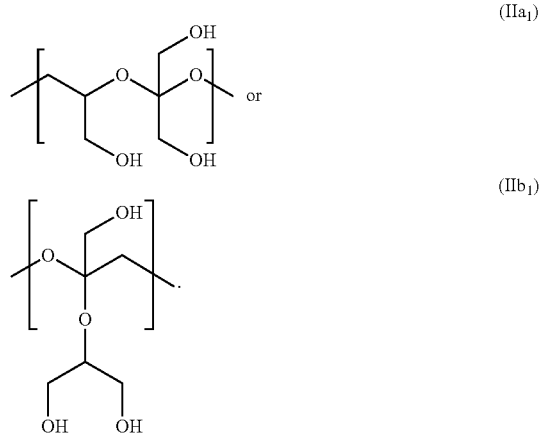

Biodegradable, biocompatible polyketal polymers and their methods of making have been described in U.S. Pat. Nos. 5,811,510, 7,790,150 and 7,838,619, which are hereby incorporated by reference in their entireties.

In one embodiment, the polymeric carrier can be obtained from partially oxidized dextran (β1→6)-D-glucose) followed by reduction. In this embodiment, the polymer comprises a random mixture of the unmodified dextran (A), partially oxidized dextran acetal units (B) and exhaustively dextran acetal units (C) of the following structures:

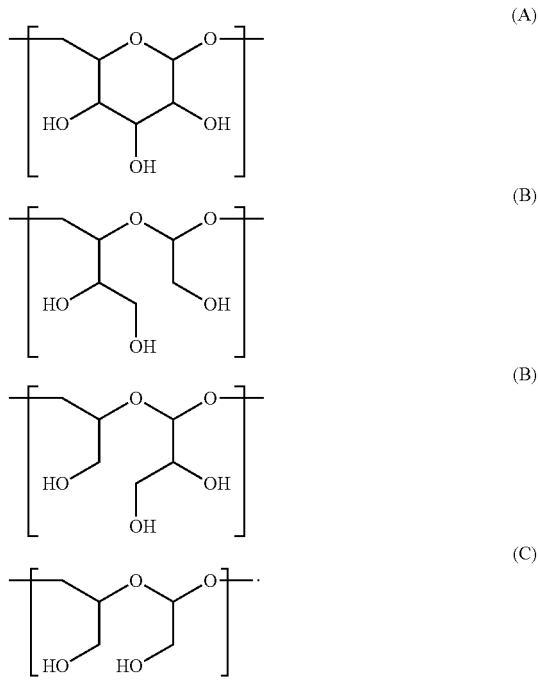

In another embodiment, the polymeric carrier comprises unmodified acetal units, i.e., polyacetal segments. In some embodiments, the polyacetals can be derived from exhaustively oxidized dextran followed by reduction. These polymers have been described in references, see, for example, U.S. Pat. No. 5,811,510, which is hereby incorporated by reference for its description of polyacetals at column 2, line 65 to column 8, line 55 and their synthesis at column 10, line 45 to column 11, line 14. In one embodiment, the unmodified polyacetal polymer is a poly(hydroxymethylethylene hydroxymethyl formal) polymer (PHF).

In addition to poly(hydroxymethylethylene hydroxymethyl formal) polymers, the backbone of the polymeric carrier can also comprise co-polymers of poly(hydroxymethylethylene hydroxymethyl formal) blocks and other acetal or non-acetal monomers or polymers. For example, polyethylene glycol polymers are useful as a stealth agent in the polymer backbone because they can decrease interactions between polymer side chains of the appended functional groups. Such groups can also be useful in limiting interactions such as between serum factors and the modified polymer. Other stealth agent monomers for inclusion in the polymer backbone include, for example, ethyleneimine, methacrylic acid, acrylamide, glutamic acid, and combinations thereof.

The acetal or ketal units are present in the modified polymer in an amount effective to promote biocompatibility. The unmodified acetal or ketal unit can be described as a "stealth agent" that provides biocompatibility and solubility to the modified polymers. In addition, conjugation to a polyacetal or a polyketal polymer can modify the susceptibility to metabolism and degradation of the moieties attached to it, and influence biodistribution, clearance and degradation.

The unmodified acetal units are monomers of Formula (III):

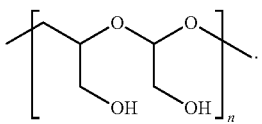

(III)

The molar fraction, n, of unmodified polyacetal units is the molar fraction available to promote biocompatibility, solubility and increase half-life, based on the total number of polymer units in the modified polymer. The molar fraction n may be the minimal fraction of unmodified monomer acetal units needed to provide biocompatibility, solubility, stability, or a particular half-life, or can be some larger fraction. The most desirable degree of cytotoxicity is substantially none, i.e., the modified polymer is substantially inert to the subject. However, as is understood by those of ordinary skill in the art, some degree of cytotoxicity can be tolerated depending on the severity of disease or symptom being treated, the efficacy of the treatment, the type and degree of immune response, and like considerations.

In one embodiment, the modified polymer backbone comprises units of Formula (IVa):

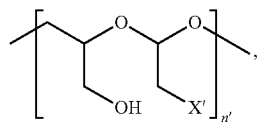

(IVa)

wherein X' indicates the substituent for the hydroxyl group of the polymer backbone. As shown in Formula (IVa) and the other formulae described herein, each polyacetal unit has a single hydroxyl group attached to the glycerol moiety of the unit and an X' group (or another substituent such as -$L^D$-D) attached to the glycolaldehyde moiety of the unit. This is for convenience only and it should be construed that the polymer having units of Formula (IVa) and other formulae described herein can contain a random distribution of units having a X' group (or another substituent such as -$L^D$-D) attached to the glycolaldehyde moiety of the units and those having a single X' group (or another substituent such as -$L^D$-D) attached to the glycerol moiety of the units as well as units having two X' groups (or other substituents such as -$L^D$-D) with one attached to the glycolaldehyde moiety and the other attached to the glycerol moiety of the units.

In one embodiment, biodegradable biocompatible polyals suitable for practicing the present invention have a molecular weight of between about 0.5 and about 300 kDa. In a preferred embodiment of the present invention, the biodegradable biocompatible polyals have a molecular weight of between about 1 and about 300 kDa (e.g., between about 1 and about 200 kDa, between about 2 and about 300 kDa, between about 2 and about 200 kDa, between about 5 and about 100 kDa, between about 10 and about 70 kDa, between about 20 and about 50 kDa, between about 20 and about 300 kDa, between about 40 and about 150 kDa, between about 50 and about 100 kDa, between about 2 and about 40 kDa, between about 6 and about 20 kDa, or between about 8 and about 15 kDa).

In one embodiment, the biodegradable biocompatible polyals suitable for practicing the present invention are modified before conjugating with a drug or a PBRM. For example, the polyals contain —C(=O)—X—(CH$_2$)$_v$—C(=O)— with X being CH$_2$, O, or NH, and v being an integer from 1 to 6. Table A below provides some examples of the modified polyals suitable for conjugating with a drug or PBRM or derivatives thereof. Unless otherwise specified, reference numbers in Tables A through F below correspond to the Example numbers described herein; the term "ND" means not determined; and X is CH$_2$, O, or NH.

TABLE A

| Ref # | Polymer Scaffold |
|---|---|
| X = NH<br>Ex 1 | |

TABLE A-continued

| Ref # | Polymer Scaffold |
|---|---|
| X = CH$_2$ Ex 2 | (chemical structures) |

TABLE A-continued
| Ref # | Polymer Scaffold |
|---|---|
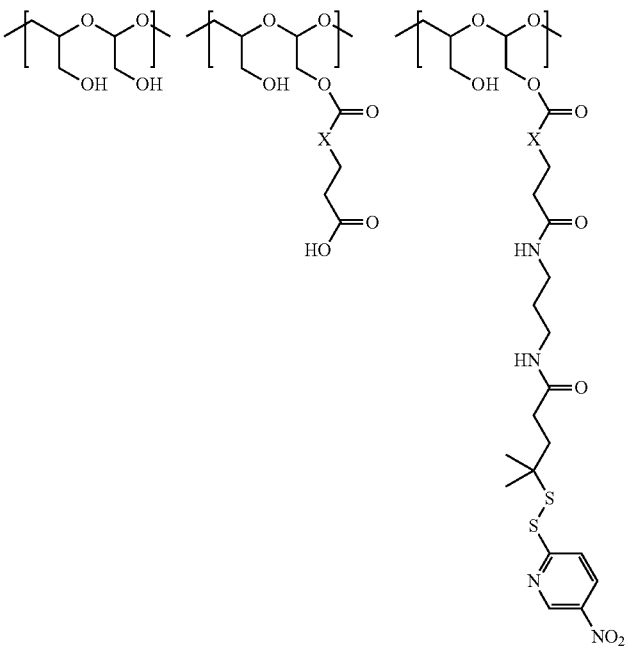
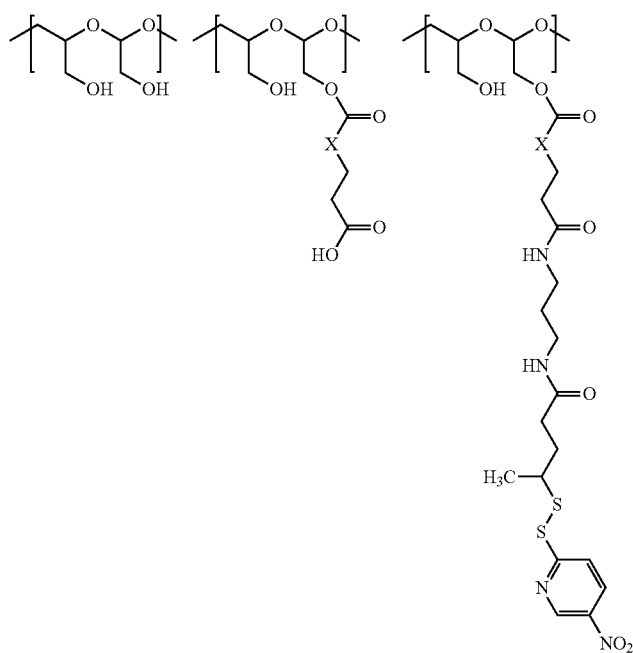

TABLE A-continued
| Ref # | Polymer Scaffold |
|---|---|
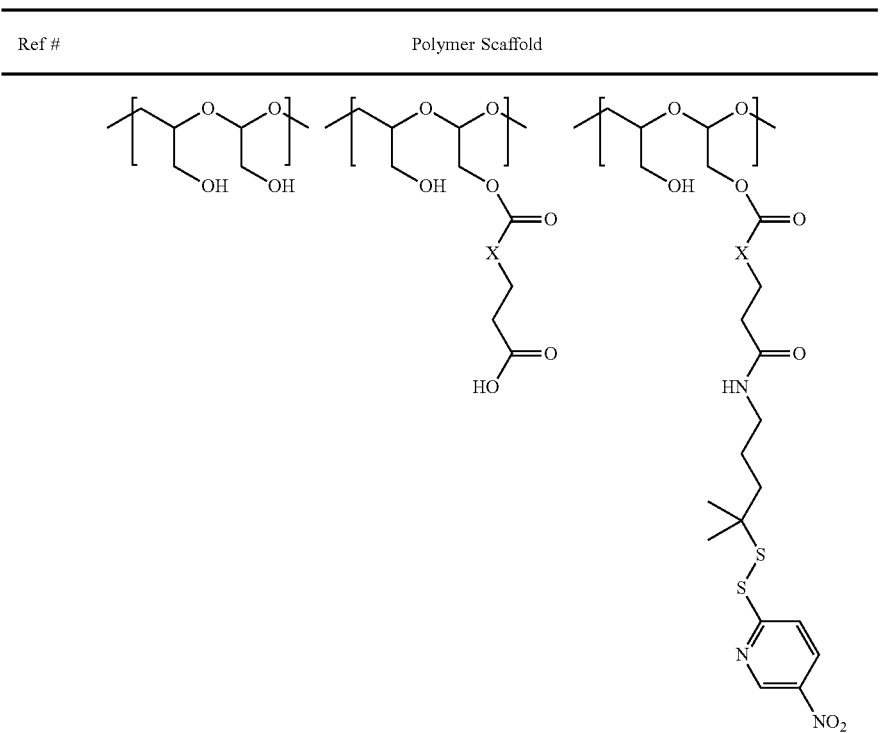
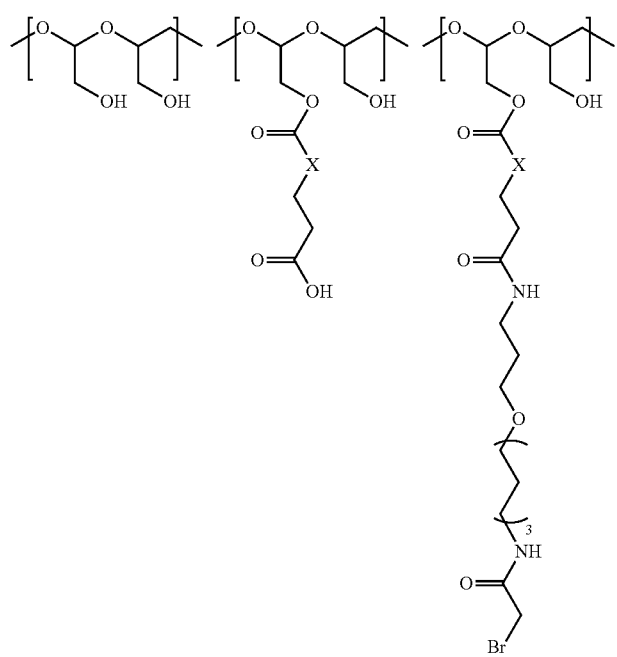

TABLE A-continued
| Ref # | Polymer Scaffold |
|---|---|
| | 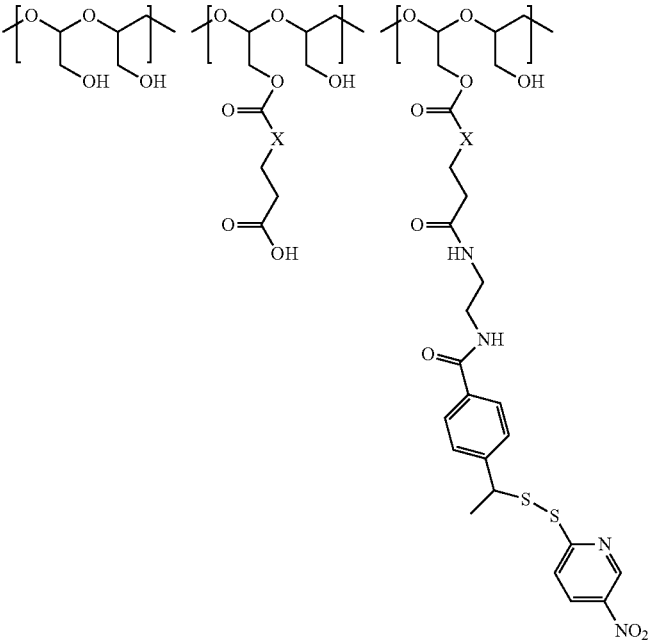 |
| | 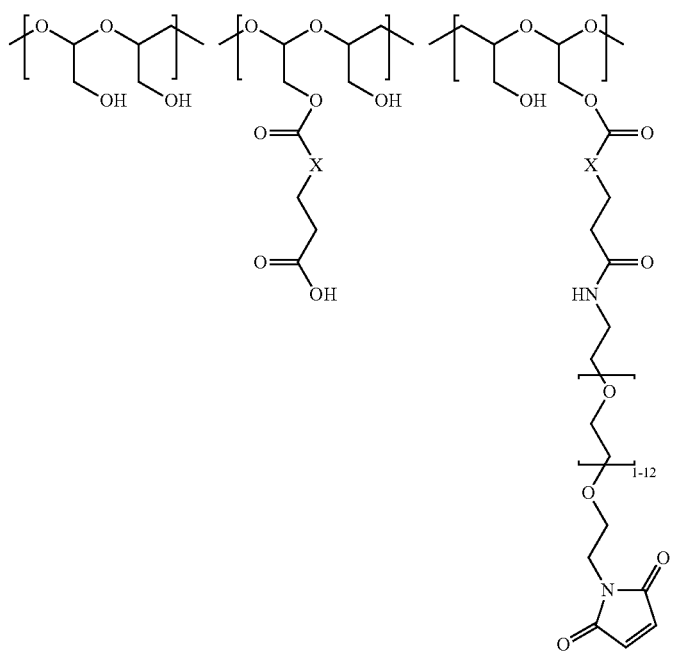 |

TABLE A-continued
| Ref # | Polymer Scaffold |
|---|---|
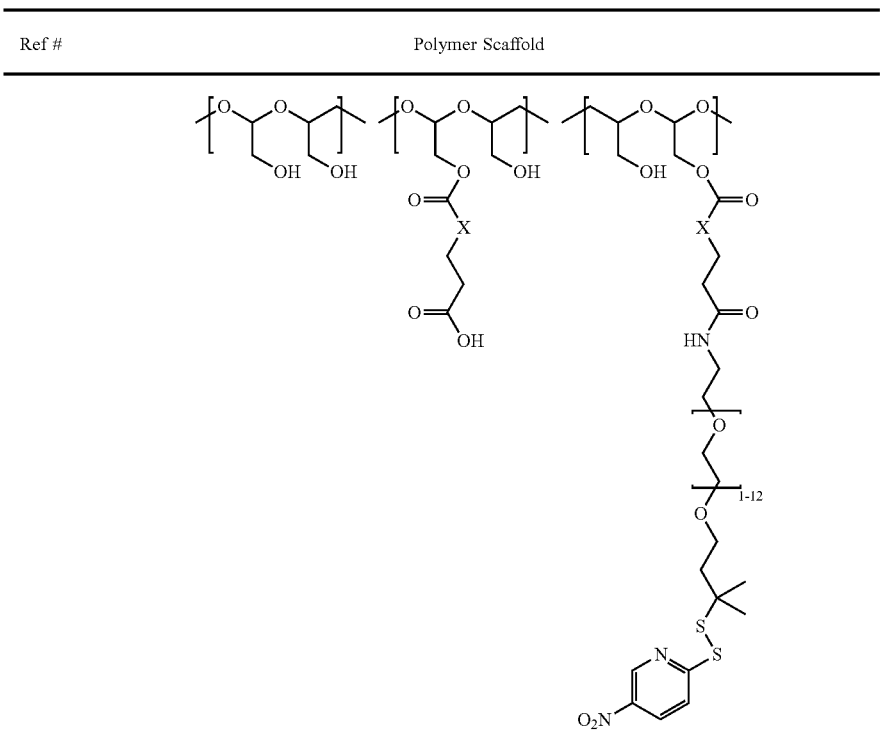
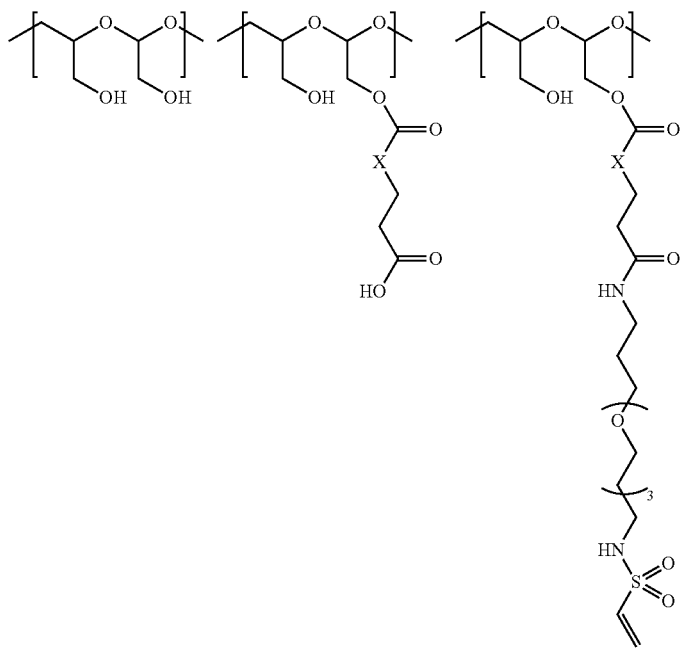

TABLE A-continued

| Ref # | Polymer Scaffold |
|---|---|

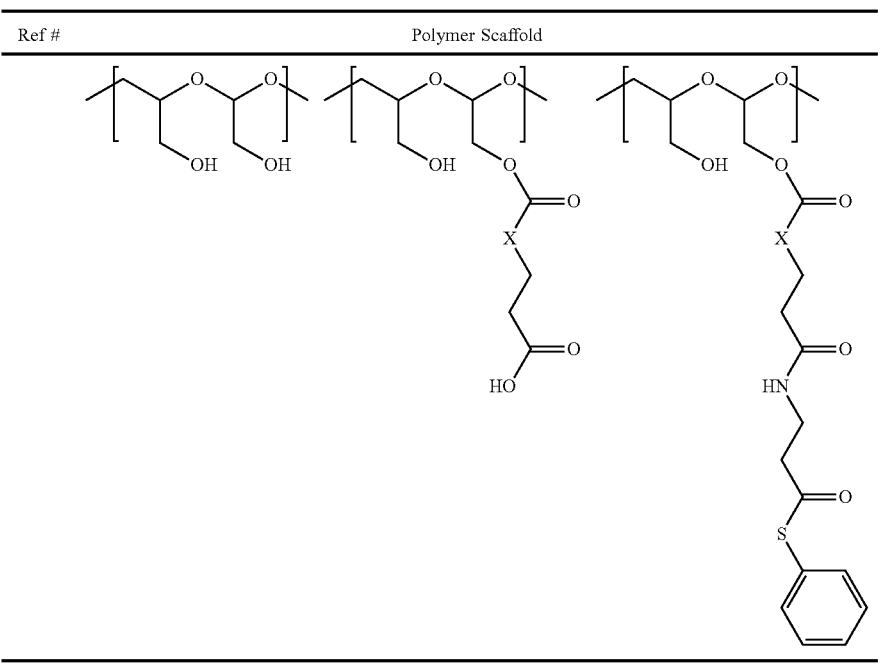

Auristatin Compounds

In some embodiments, D is an auristatin compound that can form a bond with the Linker unit $L^{D2}$ via a nitrogen atom in the primary or secondary amino group of the auristatin compound, or via an oxygen atom of a hydroxyl or carboxyl group of the auristatin compound.

In some embodiments, the auristatin compounds have a nitrogen or oxygen atom that can form a bond with the Spacer unit (i.e., Y) when y=1 or 2 or with the C-terminal carbonyl group of an Amino Acid unit (i.e., W) when y=0.

In embodiments, D is of the Formula (Ib) or a pharmaceutically acceptable salt thereof:

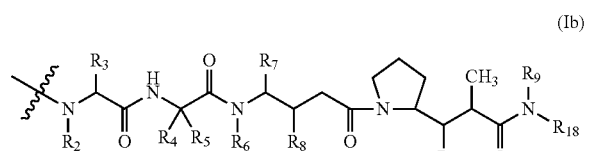

(Ib)

wherein:

$R_2$ is H or $C_{1-8}$ alkyl;

$R_3$ is H, $C_{1-8}$ alkyl, $C_{3-8}$ carbocycle, $X_4$—$C_{3-8}$ carbocycle, $C_{6-10}$ aryl, $X_4$—$C_{6-10}$ aryl, $C_{3-8}$ heterocycle, or $X_4$—$C_{3-8}$ heterocycle;

$R_4$ is H, $C_{1-8}$ alkyl, $C_{3-8}$ carbocycle, $X_4$—$C_{3-8}$ carbocycle, $C_{6-10}$ aryl, $X_4$—$C_{6-10}$ aryl, $C_{3-8}$ heterocycle, or $X_4$—$C_{3-8}$ heterocycle;

$R_5$ is H or methyl; or $R_4$ and $R_5$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;

$R_6$ is H or $C_{1-8}$ alkyl;

$R_7$ is H, $C_{1-8}$ alkyl, $C_{3-8}$ carbocycle, $X_4$—$C_{3-8}$ carbocycle, $C_{6-10}$ aryl, $X_4$—$C_{6-10}$ aryl, $C_{3-8}$ heterocycle, or $X_4$—$C_{3-8}$ heterocycle;

each $R_8$ independently is H, OH, $C_{1-8}$ alkyl, $C_{3-8}$ carbocycle or O—($C_{1-8}$ alkyl);

each $X_4$ independently is $C_{1-10}$ alkylene or $C_{3-10}$ cycloalkylene;

$R_9$ is H or $C_{1-8}$ alkyl;

$R_{18}$ is —$C(R_8)_2$—$C(R_8)_2$—$C_{6-10}$ aryl, —$C(R_8)_2$—$C(R_8)_2$—($C_{3-8}$ heterocycle), —$C(R_8)_2$—$C(R_8)_2$—($C_{3-8}$ carbocycle), or selected from

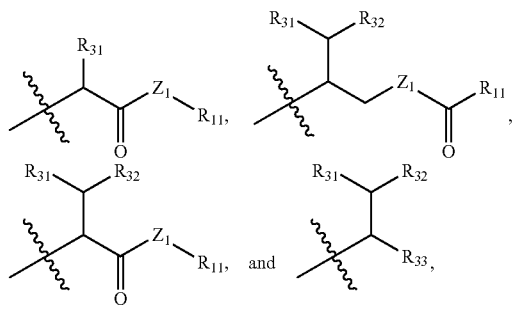

$Z_1$ is O, S, or $NR_{34}$;

$R_{31}$ is H, OH, $N(R_{34})_2$, $C_{1-8}$ alkyl, $C_{3-8}$ carbocycle, O—($C_{1-8}$ alkyl), $C_{6-10}$ aryl, $X_4$—$C_{6-10}$ aryl, $X_4$—($C_{3-8}$ carbocycle), $C_{3-8}$ heterocycle, $X_4$—($C_{3-8}$ heterocycle), $C_{1-8}$ alkylene-$NH_2$, or $(CH_2)_2SCH_3$; or $R_{31}$ is an oxygen atom which forms a carbonyl unit (C=O) with the carbon atom to which it is attached and one hydrogen atom on this carbon atom is replaced by one of the bonds in the (C=O) double bond;

$R_{32}$ is $C_{6-10}$-aryl or $C_{3-8}$ heterocycle;

$R_{33}$ is H, OH, $N(R_{34})_2$, $C_{1-8}$ alkyl, $C_{3-8}$ carbocycle, O—($C_{1-8}$ alkyl), $C_{6-10}$ aryl, $C_{1-8}$ alkyl-$C_{6-10}$ aryl, $C_{1-8}$ alkyl-($C_{3-8}$ carbocycle), $C_{3-8}$ heterocycle, or $C_{1-8}$ alkyl-($C_{3-8}$ heterocycle);

each $R_{34}$ independently is H or $C_{1-8}$ alkyl;

$R_{11}$ is H, OH, $N(R_{34})_2$, $C_{1-20}$ alkyl, $C_{6-10}$ aryl, $C_{3-8}$ heterocycle, $-(R_{13}O)_s-R_{14}$; $-(R_{13}O)_s-CH(R_{15})_2$ or $-[C(R_{50}R_{51})]_b-R_{52}$;

$R_{13}$ is $C_{2-8}$ alkyl;

$R_{14}$ is H or $C_{1-8}$ alkyl;

$R_{15}$ is H, COOH, $-(CH_2)_o-N(R_{16})_2$, $-(CH_2)_o-SO_3H$, or $-(CH_2)_o-SO_3-C_{1-8}$ alkyl;

$R_{16}$ is H, $C_{1-8}$ alkyl, or $-(CH_2)_o-COOH$;

each of $R_{50}$ and $R_{51}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{52}$ is OH, $NHR_{53}$, COOH, $R_{82}-C(O)(CH_2)_c-C(H)(R_{53})-N(H)(R_{53})$, $R_{82}-C(O)(CH_2)_d-(O-CH_2-CH_2)_h-N(H)(R_{53})$ or $R_{82}-(C(O)-CH(X_2)-NH)_d-R_{77}$;

each $R_{53}$ independently is hydrogen, $C_{1-6}$ alkyl, $C_{6-10}$ aryl, $C_{3-8}$ cycloalkyl, COOH, or COO—$C_{1-6}$ alkyl;

$X_2$ is a side chain of a natural or unnatural amino acid;

$R_{77}$ is hydrogen or $X_2$ and $NR_{77}$ form a nitrogen containing cyclic compound;

$R_{82}$ is NH or oxygen;

n is an integer from 2 to 7;

s is an integer from 0 to 1000;

o is an integer from 0 to 6.

b is an integer from 1 to 6;

c is an integer from 0 to 3;

d is an integer from 1 to 3; and h is an integer from 1 to 12.

The compounds of Formula (Ib) can include one or more of the following features.

For example, each $X_4$ independently is $C_{1-8}$ alkylene.

For example, $R_{18}$ is:

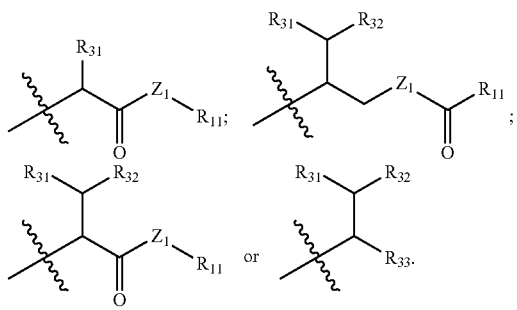

For example, $R_3$, $R_4$ and $R_7$ are each independently isopropyl or sec-butyl and $R_5$ is H. In an exemplary embodiment, $R_3$ and $R_4$ are each isopropyl, $R_5$ is H, and $R_7$ is sec-butyl.

For example, $R_2$ and $R_6$ are each methyl, and $R_9$ is H.

For example, each occurrence of $R_8$ is $OCH_3$.

For example, $R_3$ and $R_4$ are each isopropyl, $R_2$ and $R_6$ are each methyl, $R_5$ is H, $R_7$ is sec-butyl, each occurrence of $R_8$ is $OCH_3$, and $R_9$ is H.

For example, $Z_1$ is O or NH.

For example, $R_{32}$ is $C_{6-10}$ aryl, e.g., phenyl.

For example, when $Z_1$ is O, $R_{11}$ is H, methyl or t-butyl.

For example, when $Z_1$ is NH, $R_{11}$ is $-CH(R_{15})_2$, wherein $R_{15}$ is $-(CH_2)_o-N(R_{16})_2$, and $R_{16}$ is $-C_{1-8}$ alkyl or $-(CH_2)_o-COOH$.

For example, when $Z_1$ is NH, $R_{11}$ is $-CH(R_{15})_2$, wherein $R_{15}$ is $-(CH_2)_o-SO_3H$.

For example, D is a compound of any one of Formulae (XIII) to (XVI) or a pharmaceutically acceptable salt thereof:

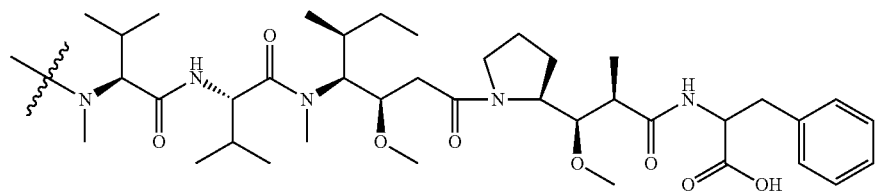

(XIII)

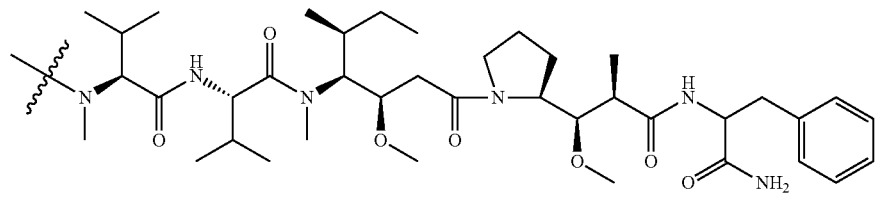

(XIIIA)

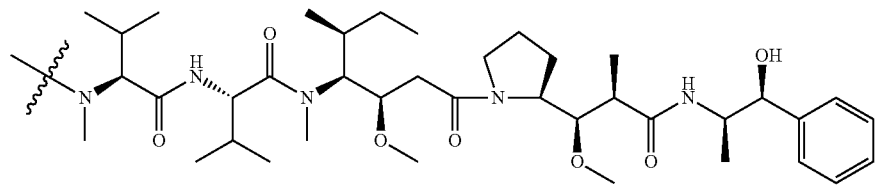

(XIV)

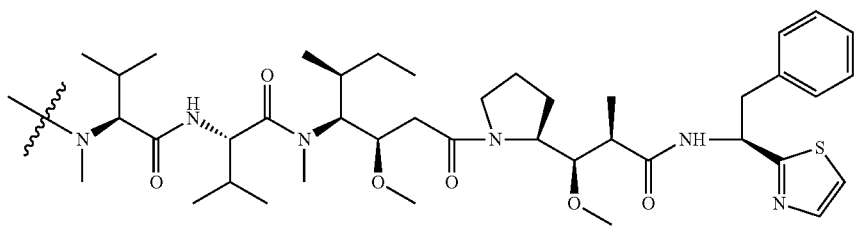
(XV)
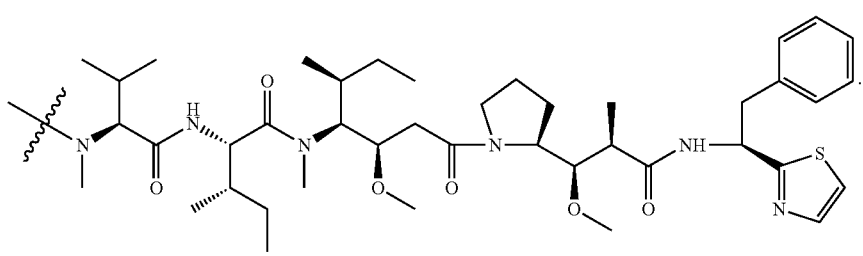
(XVI)
For example, D is any of compounds in Tables B and C below.
TABLE B
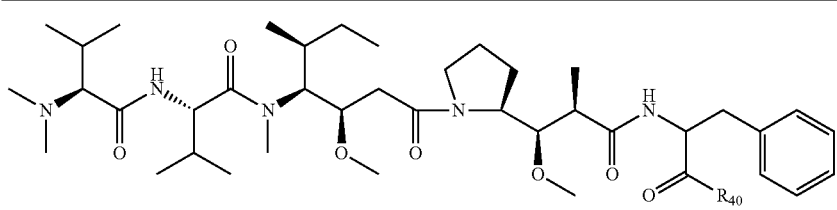
| $R_{40}$ | |
|---|---|
| —OH; | —NH$_2$; |
| | —OCH$_3$; |
| 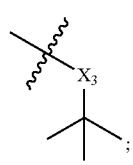 |  |
| 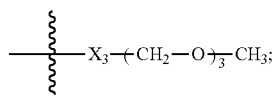 | 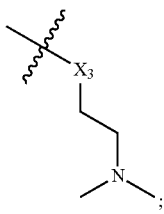 |
| 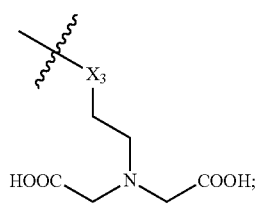 | |

TABLE B-continued
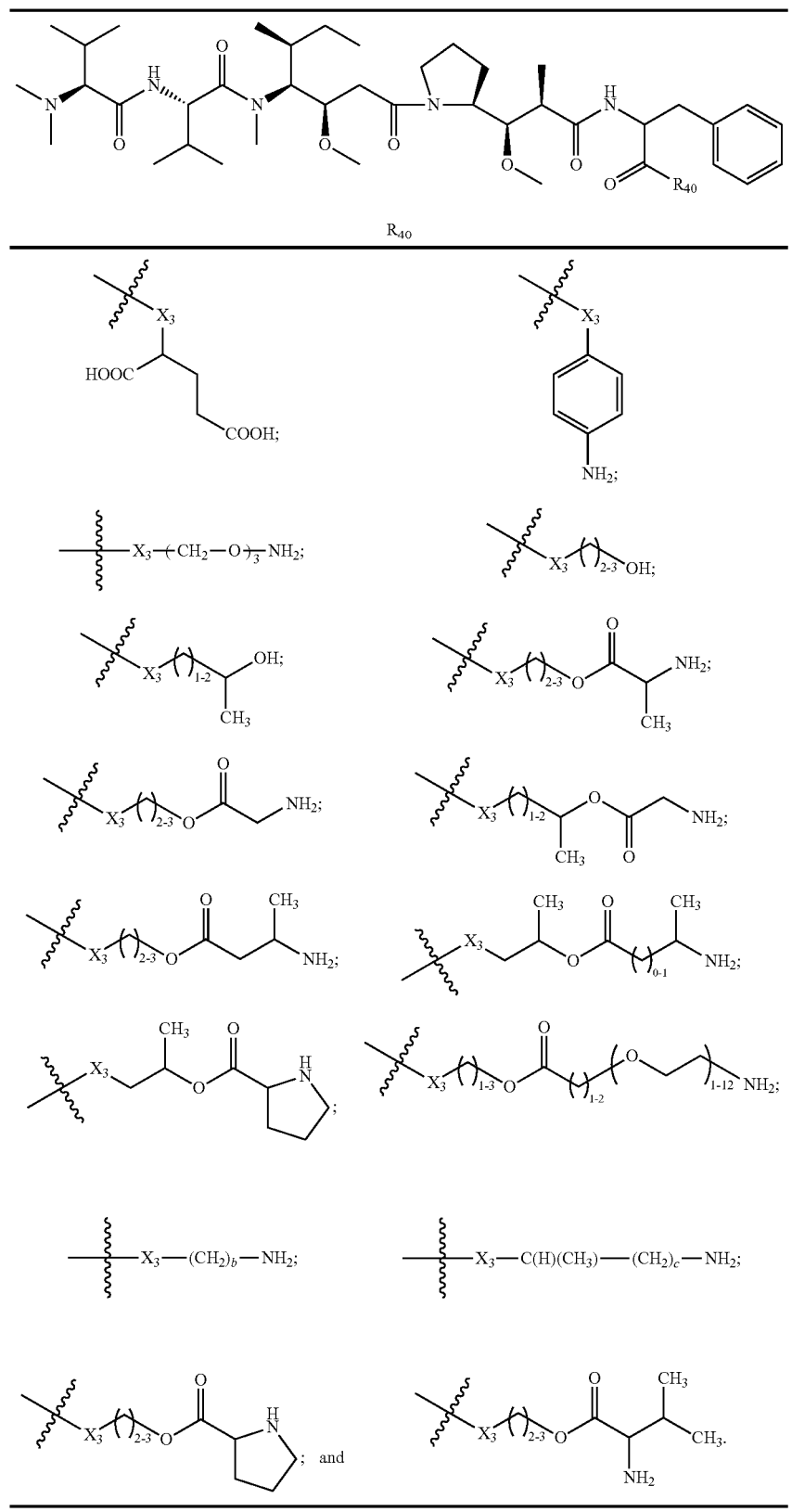
wherein X₃ is —O— or —NH;
b is an integer from 1 to 6, and
c is an integer from 0 to 3.

TABLE C
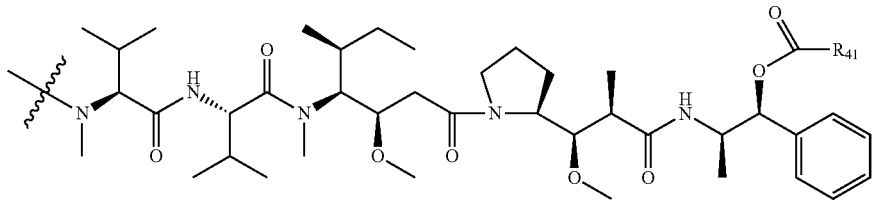
R41
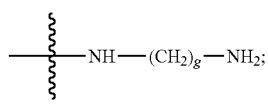
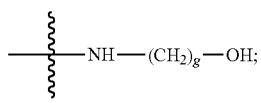
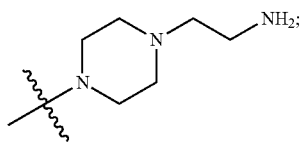 [SMILES: *N1CCN(CCN)CC1]
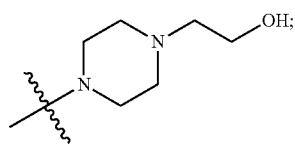 [SMILES: *N1CCN(CCO)CC1]
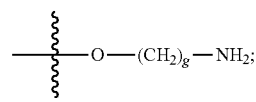
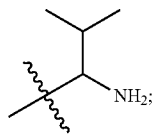 [SMILES: *C(N)C(C)C]
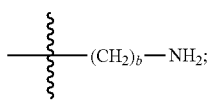
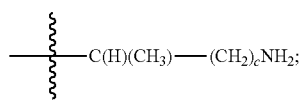
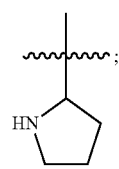
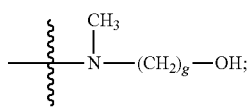
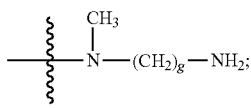
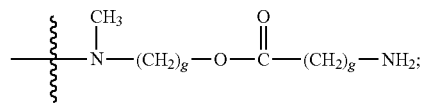
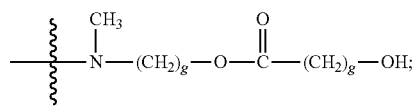
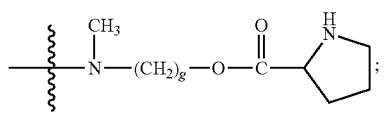
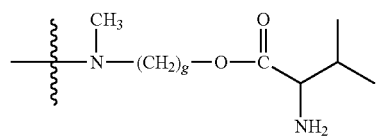

TABLE C-continued
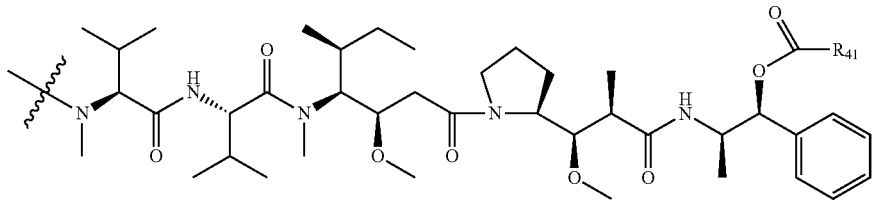
R41
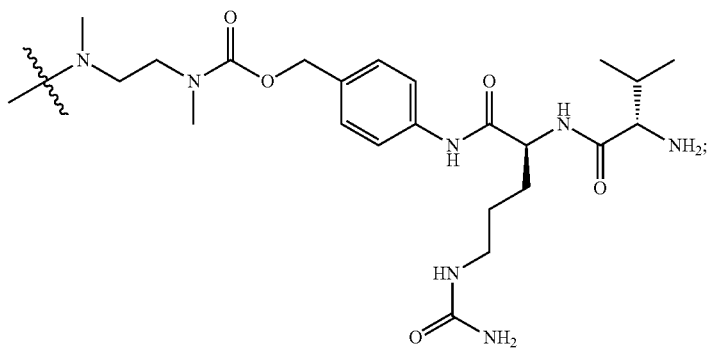 [SMILES: *N(C)CCN(C)C(=O)OCc1ccc(NC(=O)[C@H](CCCNC(N)=O)NC(=O)[C@@H](N)C(C)C)cc1]
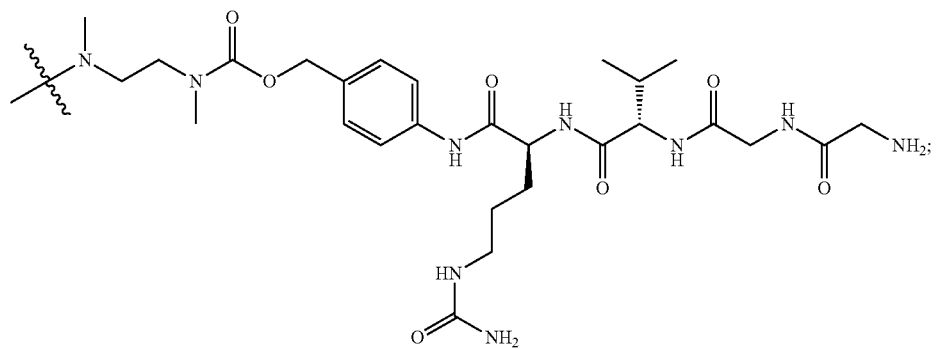 [SMILES: *N(C)CCN(C)C(=O)OCc1ccc(NC(=O)[C@H](CCCNC(N)=O)NC(=O)[C@@H](NC(=O)CNC(=O)CN)C(C)C)cc1]
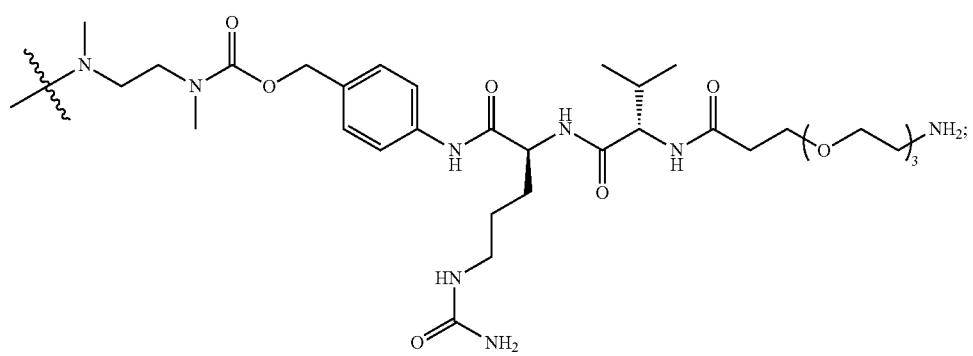

TABLE C-continued
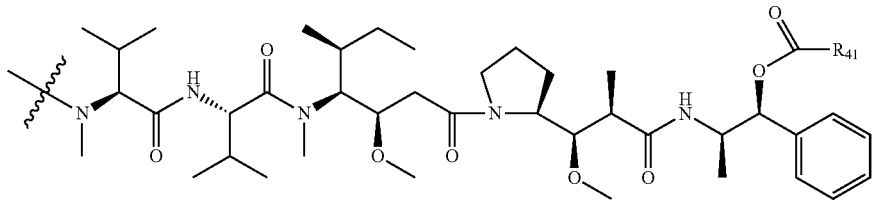
R41
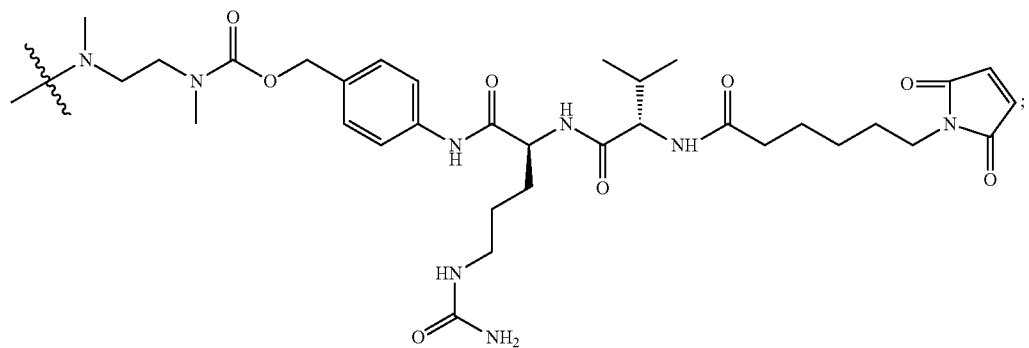
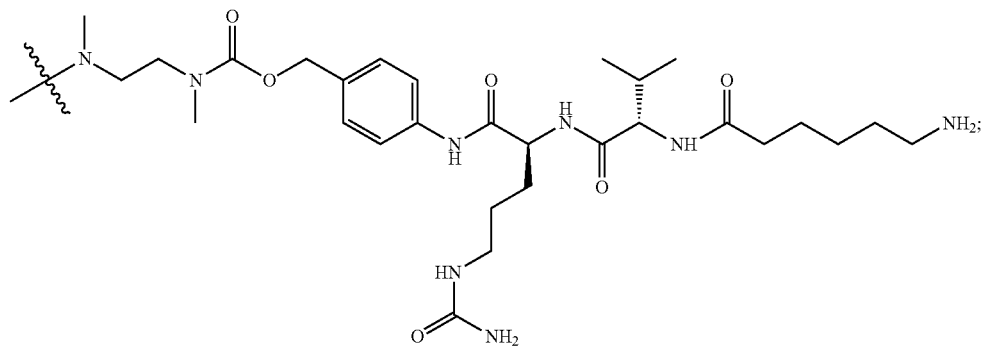
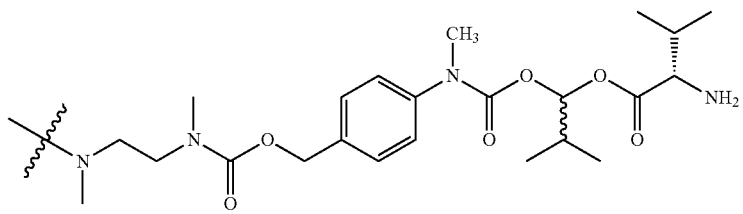

wherein:
b is an integer from 1 to 6;
c is an integer from 0 to 3; and
g is an integer from 2 to 6.

For example, D is a compound of Formula (Id) or a pharmaceutically acceptable salt thereof:

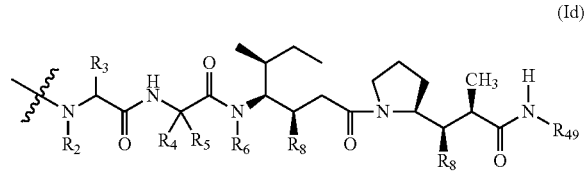

(Id)

wherein:
$R_2$, $R_4$ and $R_6$ are each independently H or methyl;
$R_3$ is H, methyl or isopropyl;
$R_5$ is isopropyl, isobutyl, sec-butyl, methyl or t-butyl; or
$R_4$ and $R_5$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;
n is an integer from 2 to 7;
$R_8$ is —OH, methoxy or ethoxy;

a is an integer 0 or 1; and
$R_{27}$ is —H, —$N_3$, —$C_{1-8}$ alkyl, —$C_{3-8}$ carbocycle, —$C_{6-10}$ aryl, —$C_{1-8}$ alkyl-$C_{6-10}$ aryl, —$C_{1-8}$ alkyl-($C_{3-8}$ carbocycle), —$C_{3-8}$ heterocycle or —$C_{1-8}$ alkyl-($C_{3-8}$ heterocycle) when a is 0; and $R_{27}$ is —H, —$C_{1-8}$ alkyl, —$C_{3-8}$ carbocycle, —$C_{6-10}$ aryl, —$C_{1-5}$ alkyl-$C_{6-10}$ aryl, —$C_{1-8}$ alkyl-($C_{3-8}$ carbocycle), —$C_{3-8}$ heterocycle and —$C_{1-8}$ alkyl-($C_{3-8}$ heterocycle).

For example, $R_{49}$ is

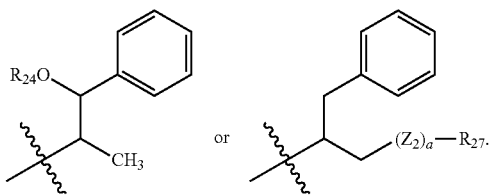

For example, D is a compound of Formula (Ig) or a pharmaceutically acceptable salt thereof:

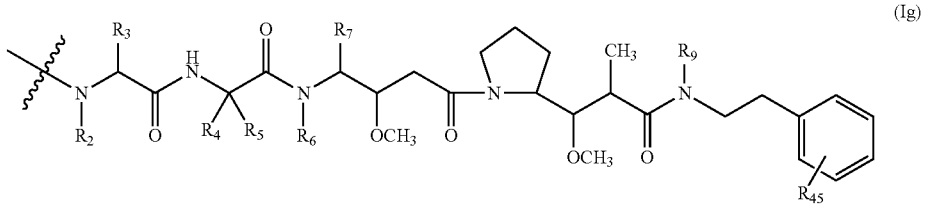

(Ig)

wherein:
$R_2$, $R_4$, $R_6$ and $R_9$ are each independently H or methyl;
$R_3$ is $C_{1-8}$ alkyl;
$R_4$ is $C_{1-8}$ alkyl, $C_{6-10}$ aryl, $CH_2$—($C_{5-7}$ carbocycle);
$R_5$ is H or methyl; or
$R_4$ and $R_5$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;
n is an integer from 2 to 7;
$R_7$ is sec-butyl or iso-butyl; and
$R_{45}$ is a hydroxyl or oxo-substituted $C_{1-8}$ alkyl.

For example, in the compounds of Formula (Ig), $R_2$ is methyl; and/or $R_3$ is iso-propyl; and/or $R_4$ is $C_{1-8}$ alkyl, $C_{6-10}$ aryl or $CH_2$—($C_{5-7}$ carbocycle) and $R_5$ is H or methyl; or $R_4$ is $C_{1-8}$ alkyl and $R_5$ is H or methyl; or $R_4$ and $R_5$ together with the carbon atom to which they are attached form a carbocyclic ring having the formula —$(CR_aR_b)_n$— wherein each of $R_a$ and $R_b$ independently is H or $C_{1-8}$ alkyl; n is an integer from 2 to 7; and/or $R_6$ is $C_{1-8}$ alkyl; and/or $R_7$ is iso-butyl; and/or $R_9$ is H; and/or $R_{45}$ is oxo-substituted $C_{1-8}$ alkyl.

For example, the compound of Formula (Ig) is a compound of Formula (XVII) or a pharmaceutically acceptable salt thereof:

$R_{49}$ is:

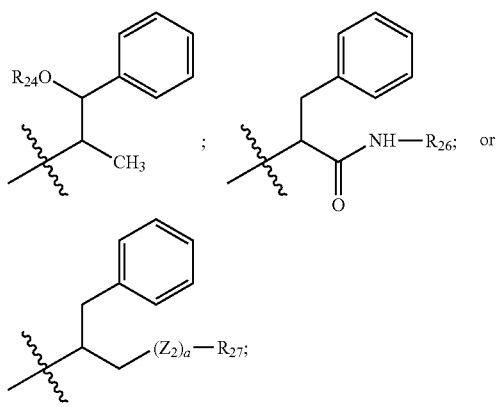

$R_{24}$ is —$C(O)R_{25}$; wherein $R_{25}$ is —$C_{1-8}$ alkyl, —$C_{3-8}$ carbocycle, —$C_{6-10}$ aryl, —$C_{1-8}$ alkyl-$C_{6-10}$ aryl, —$C_{1-8}$ alkyl-($C_{3-8}$ carbocycle), —$C_{3-8}$ heterocycle or —$C_{1-8}$ alkyl-($C_{1-8}$ heterocycle);
$R_{26}$ is —$C_{1-8}$ alkyl, —$C_{3-8}$ carbocycle, —$C_{6-10}$ aryl, —$C_{1-8}$ alkyl-$C_{6-10}$ aryl, —$C_{1-8}$ alkyl-($C_{3-8}$ carbocycle), —$C_{3-8}$ heterocycle or —$C_{1-8}$ alkyl-($C_{3-8}$ heterocycle);
$Z_2$ is —O—, —NH—, —OC(O)—, —NHC(O)—, or —N($R_{28}$)C(O)—; where $R_{28}$ is —H or —$C_{1-8}$ alkyl;

(XVII)

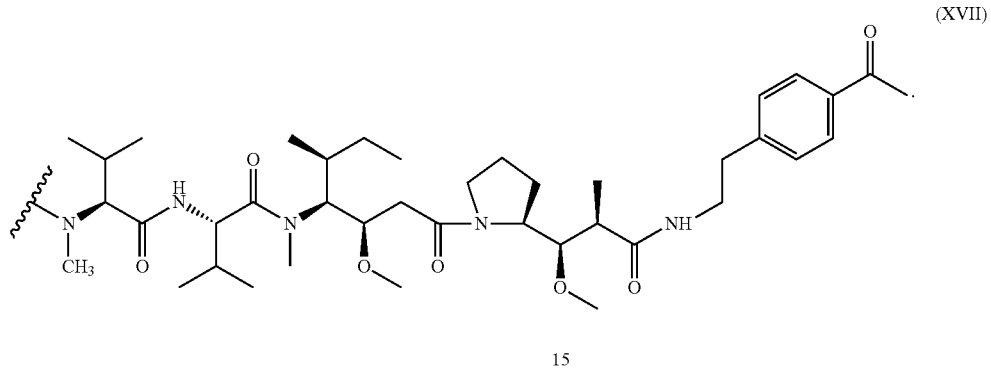

For example, D is a compound of Formula (Ih) or a pharmaceutically acceptable salt thereof:

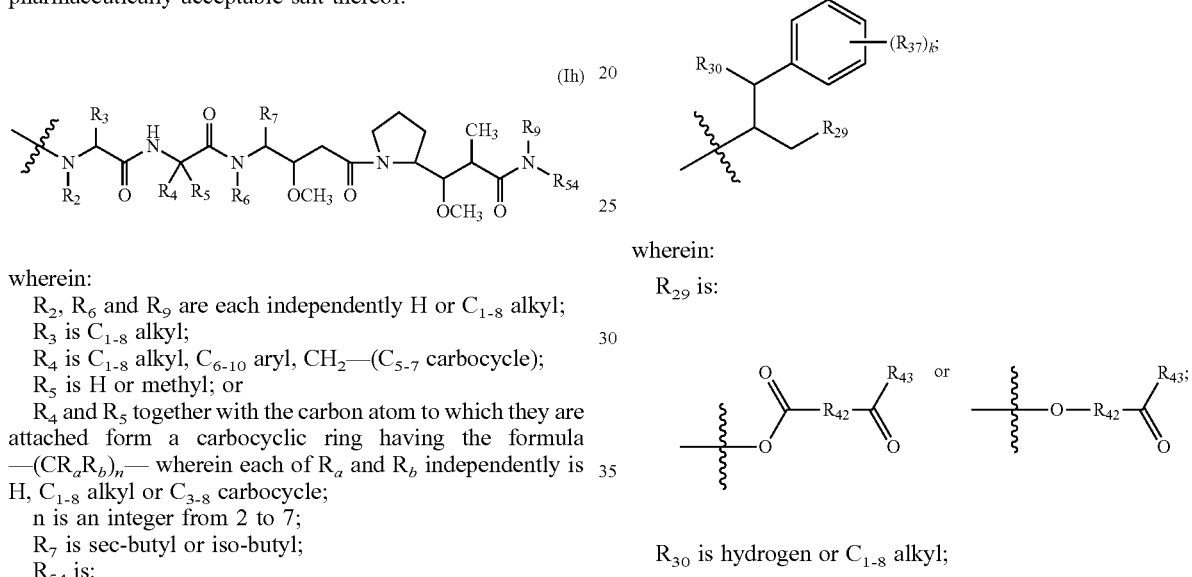

wherein:
R$_2$, R$_6$ and R$_9$ are each independently H or C$_{1-8}$ alkyl;
R$_3$ is C$_{1-8}$ alkyl;
R$_4$ is C$_{1-8}$ alkyl, C$_{6-10}$ aryl, CH$_2$—(C$_{5-7}$ carbocycle);
R$_5$ is H or methyl; or
R$_4$ and R$_5$ together with the carbon atom to which they are attached form a carbocyclic ring having the formula —(CR$_a$R$_b$)$_n$— wherein each of R$_a$ and R$_b$ independently is H, C$_{1-8}$ alkyl or C$_{3-8}$ carbocycle;
n is an integer from 2 to 7;
R$_7$ is sec-butyl or iso-butyl;
R$_{54}$ is:

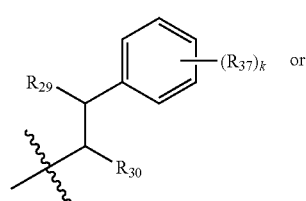

-continued

[structure with R$_{30}$, R$_{29}$, (R$_{37}$)$_k$]

wherein:
R$_{29}$ is:

[two structures with R$_{42}$, R$_{43}$]

R$_{30}$ is hydrogen or C$_{1-8}$ alkyl;
R$_{37}$ at each occurrence independently is selected from C$_{1-8}$ alkyl, halogen, and methoxy;
k is an integer from 0 to 5;
R$_{42}$ is a covalent bond, alkylaryl, C$_{1-10}$ alkylene or C$_{6-10}$ arylene; and
R$_{43}$ is hydrogen, C$_{1-8}$ alkyl and C$_{6-10}$ aryl.

For example, the compounds of Formula (Ih) are compounds of any of Formulae (XVIII), (XIX) and (XX) or pharmaceutically acceptable salts thereof:

(XVIII)

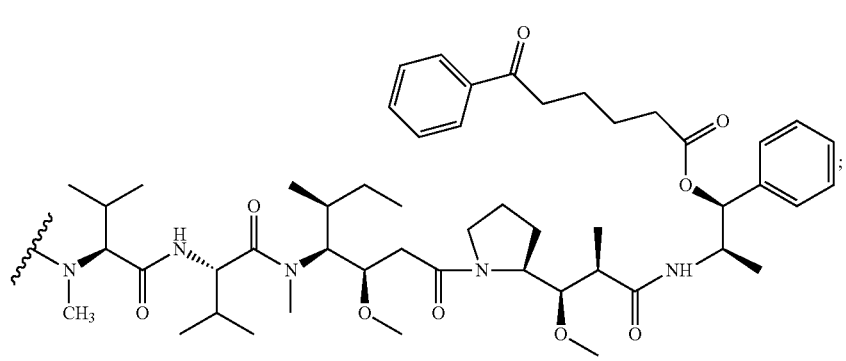

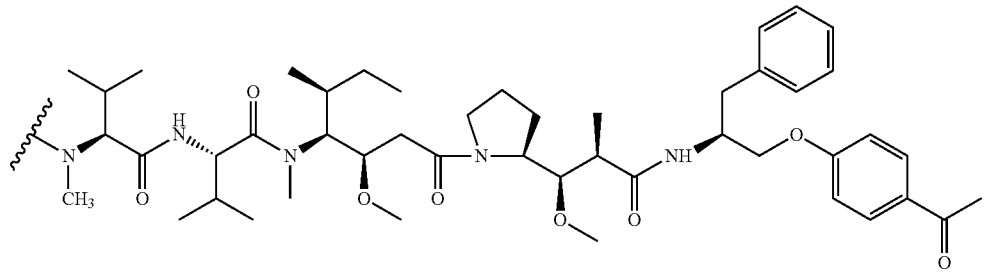

(XIX)

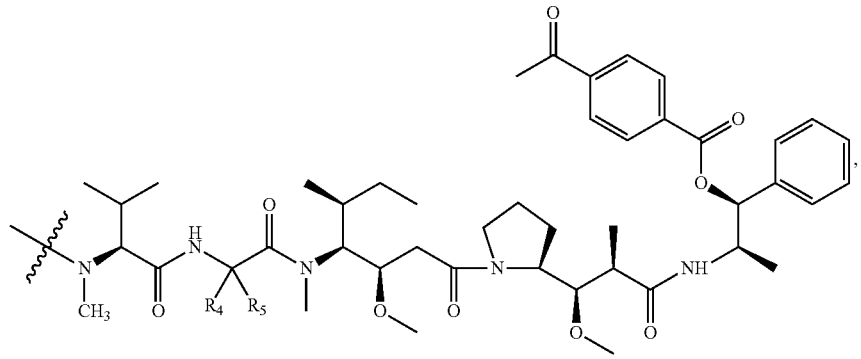

(XX)

wherein R_4 is isopropyl or sec-butyl and R_5 is hydrogen.

For example, D is a compound of Formula (Ii) or a pharmaceutically acceptable salt thereof:

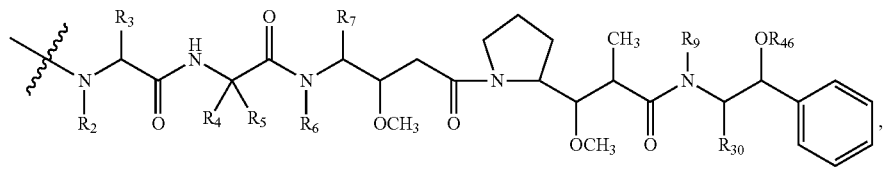

(Ii)

wherein:

$R_2$, $R_6$ and $R_9$ are each independently H or $C_{1-8}$ alkyl; H or $C_{1-8}$ alkyl;

$R_3$ is $C_{1-8}$ alkyl;

$R_4$ is $C_{1-8}$ alkyl, $C_{6-10}$ aryl, $CH_2$—($C_{5-7}$ carbocycle);

$R_5$ is H or methyl; or $R_4$ and $R_5$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;

n is an integer from 2 to 7;

$R_7$ is sec-butyl or iso-butyl;

$R_{30}$ is hydrogen or $C_{1-8}$ alkyl; and $R_{46}$ is hydrogen, a hydroxyl protecting group, or a covalent bond where $OR_{46}$ represents =O.

For example, the compound of Formula (Ii) is a compound of Formula (XXI) or a pharmaceutically acceptable salt thereof:

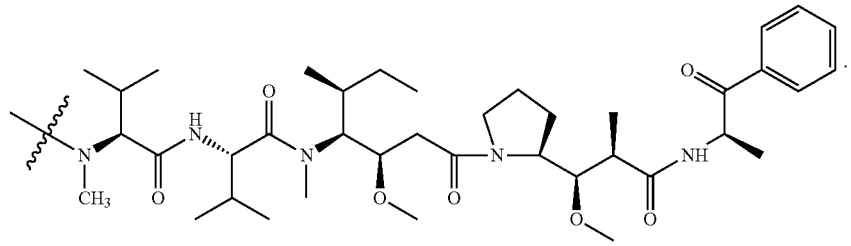

(XXI)

For example, D is a compound of Formula (Ij) or a pharmaceutically acceptable salt thereof:

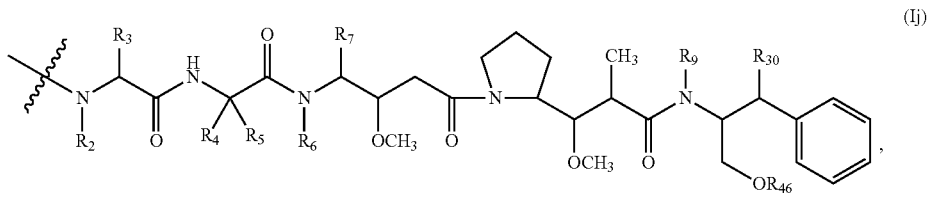

wherein:

$R_2$, $R_6$ and $R_9$ are each independently H or $C_{1-8}$ alkyl;

$R_3$ is $C_{1-8}$ alkyl;

$R_4$ is $C_{1-8}$ alkyl, $C_{6-10}$ aryl, $CH_2$—($C_{5-7}$ carbocycle);

$R_5$ is H or methyl; or $R_4$ and $R_5$ together with the carbon atom to which they are attached Run a carbocyclic ring having the formula —$(CR_aR_b)_n$— wherein each of $R_a$ and $R_b$ independently is H, $C_{1-8}$ alkyl or $C_{3-8}$ carbocycle;

n is an integer from 2 to 7;

$R_7$ is sec-butyl or iso-butyl;

$R_{30}$ is hydrogen or $C_{1-8}$ alkyl; and $R_{46}$ is hydrogen, a hydroxyl protecting group, or a covalent bond where $OR_{46}$ represents =O.

For example, the compounds of Formula (Ij) are compounds of Formula (XXII) or (XXIII):

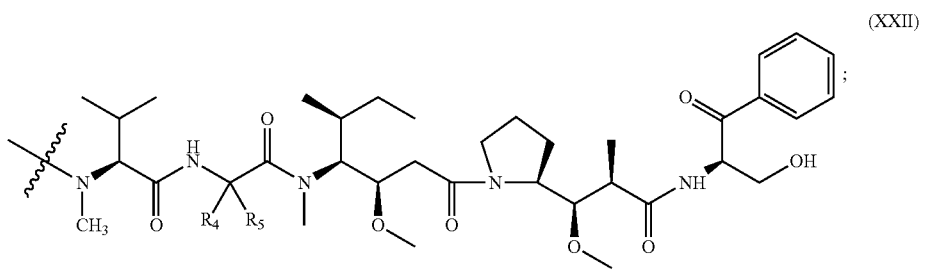

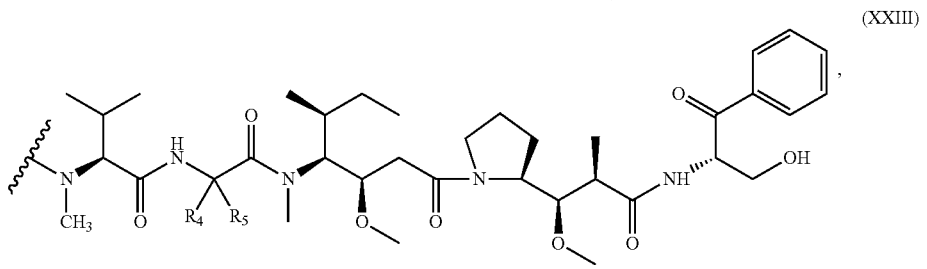

wherein $R_4$ is iso-propyl or sec-butyl and $R_5$ is hydrogen.

For example, D is a compound of Formula (Ik) or a pharmaceutically acceptable salt thereof:

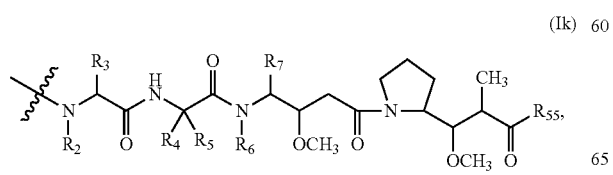

wherein:

$R_2$ and $R_6$ are each independently H or $C_{1-8}$ alkyl;

$R_3$ is $C_{1-8}$ alkyl;

$R_4$ is $C_{1-8}$ alkyl, $C_{6-10}$ aryl, $CH_2$—($C_{5-7}$ carbocycle);

$R_5$ is H or methyl; or $R_4$ and $R_5$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;

n is an integer from 2 to 7;

$R_7$ is sec-butyl or iso-butyl; and $R_{55}$ is:

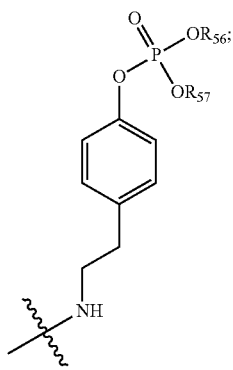

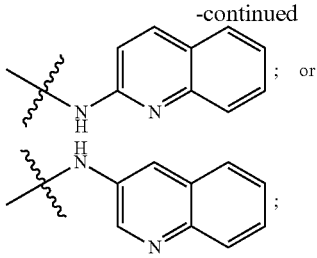

wherein:

$R_{56}$ and $R_{57}$ are independently H, lithium (Li+), sodium (Na+), potassium (K+), morpholine, quinine, tris(hydroxymethyl)aminomethane (TRIS), serine, or nitroarginine;

$R_{58}$ is H, $C_{1-8}$ alkyl, $C_{1-8}$ alkenyl, or $C_{1-8}$ alkynyl.

For example, the compounds of Formula (Ik) are compounds of Formula (XXIV):

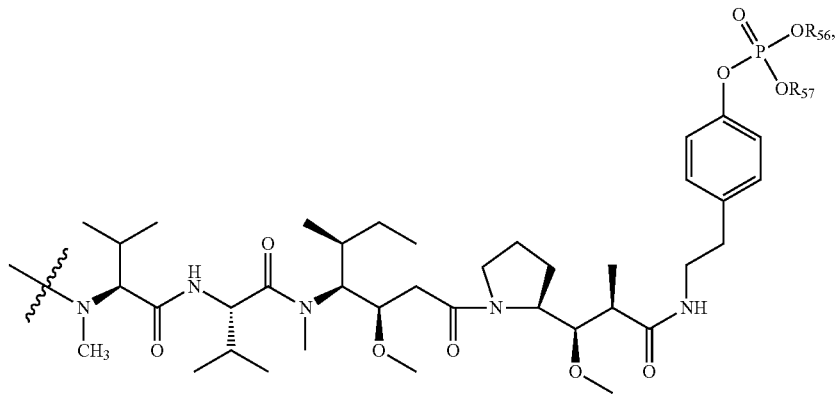

(XXIV)

where $R_{56}$ and $R_{57}$ are as defined herein.

For example, D is a compound of any of Formulae (IIg), (IIh) and (IIi) or a pharmaceutically acceptable salt thereof:

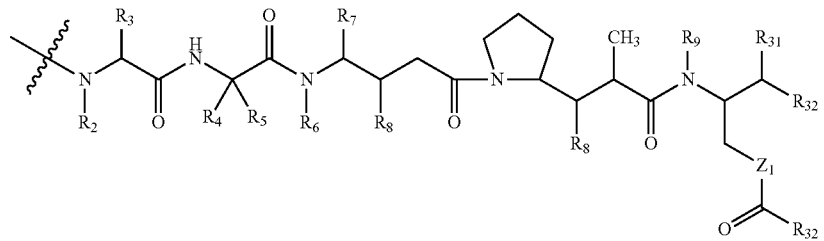

(IIg)

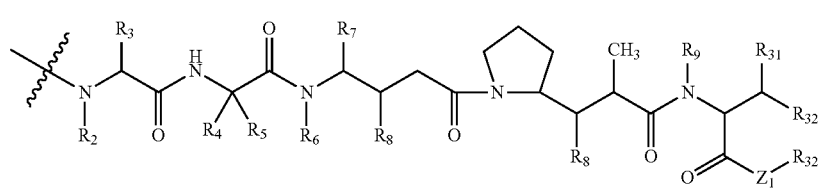

(IIh)

-continued

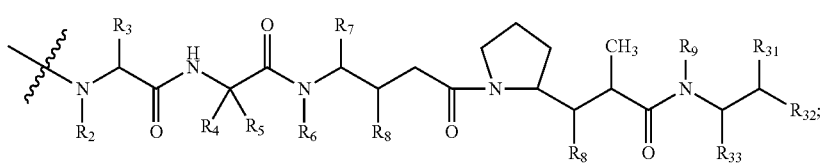

(IIi)

wherein:

$R_2$, $R_6$ and $R_9$ are each independently H or $C_{1-8}$ alkyl;

$R_3$ is H, $C_{1-8}$ alkyl, $C_{3-8}$ carbocycle, $C_{6-10}$ aryl, $C_{1-8}$ alkyl-$C_{6-10}$ aryl, $C_{1-8}$ alkyl-($C_{3-8}$ carbocycle), $C_{3-8}$ heterocycle or $C_{1-8}$ alkyl-($C_{3-8}$ heterocycle);

$R_4$ is H, $C_{1-8}$ alkyl, $C_{3-8}$ carbocycle, $C_{6-10}$ aryl, $C_{1-8}$ alkyl-$C_{6-10}$ aryl, $C_{1-8}$ alkyl-($C_{3-8}$ carbocycle), $C_{3-8}$ heterocycle or $C_{1-8}$ alkyl-($C_{3-8}$ heterocycle);

$R_5$ is H or methyl; or $R_4$ and $R_5$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;

$R_7$ is H, $C_{1-8}$ alkyl, $C_{3-8}$ carbocycle, $C_{6-10}$ aryl, $C_{1-8}$ alkyl-$C_{6-10}$ aryl, $C_{1-8}$ alkyl-($C_{3-8}$ carbocycle), $C_{3-8}$ heterocycle or $C_{1-8}$ alkyl-($C_{3-8}$ heterocycle);

each $R_8$ independently is H, OH, $C_{1-8}$ alkyl, $C_{3-8}$ carbocycle or O—($C_{1-8}$ alkyl);

$Z_1$ is O, S, or $NR_{34}$;

$R_{31}$ is H, OH, $N(R_{34})_2$, $C_{1-8}$ alkyl, $C_{3-8}$ carbocycle, O—($C_{1-8}$ alkyl), $C_{6-10}$ aryl, $X_4$—$C_{6-10}$ aryl, $X_4$—($C_{3-8}$ carbocycle), $C_{3-8}$ heterocycle, $X_4$—($C_{3-8}$ heterocycle), $C_{1-8}$ alkylene-$NH_2$, or $(CH_2)_2SCH_3$; or $R_{31}$ is an oxygen atom which forms a carbonyl unit (C=O) with the carbon atom to which it is attached and one hydrogen atom on this carbon atom is replaced by one of the bonds in the (C=O) double bond;

$X_4$ is $C_{1-10}$ alkylene or $C_{3-10}$ cycloalkylene;

each $R_{32}$ independently is —$C_{6-10}$ aryl or —$C_{3-8}$ heterocycle;

$R_{32}$ is $C_{6-10}$-aryl or $C_{3-8}$ heterocycle;

$R_{33}$ is H, OH, $N(R_{34})_2$, $C_{1-8}$ alkyl, $C_{3-8}$ carbocycle, O—($C_{1-8}$ alkyl), $C_{6-10}$ aryl, $C_{1-8}$ alkyl-$C_{6-10}$ aryl, $C_{1-8}$ alkyl-($C_{3-8}$ carbocycle), $C_{3-8}$ heterocycle, or $C_{1-8}$ alkyl-($C_{3-8}$ heterocycle); and each $R_{34}$ independently is H or $C_{1-8}$ alkyl.

For example, the compound of Formula (IIi) is a compound of Formula (XXV) or a pharmaceutically acceptable salt thereof:

In other embodiments, D is a compound of Formula (Ic) or a pharmaceutically acceptable salt thereof:

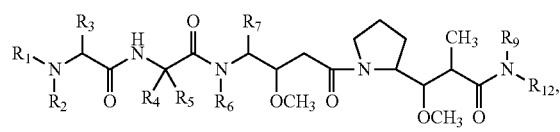

(Ic)

wherein:

$R_1$, $R_2$, $R_6$, and $R_9$ are each independently H or $C_{1-8}$ alkyl;

$R_3$ is $C_{1-8}$ alkyl;

$R_4$ is $C_{1-8}$ alkyl, $C_{6-10}$ aryl, $CH_2$—($C_{5-7}$ carbocycle);

$R_5$ is H or methyl; or $R_4$ and $R_5$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;

n is an integer from 2 to 7;

$R_7$ is sec-butyl or iso-butyl;

$R_{12}$ is any one of the following structures:

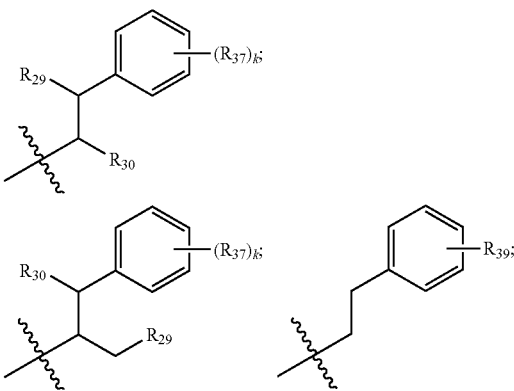

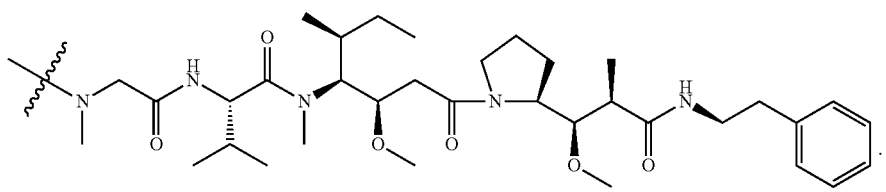

(XXV)

-continued

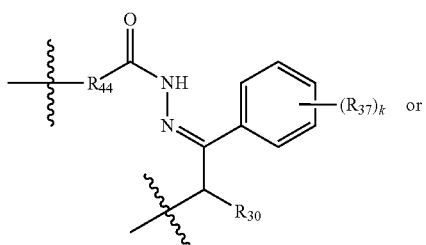

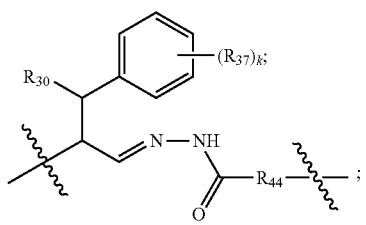

wherein:

R_29 is:

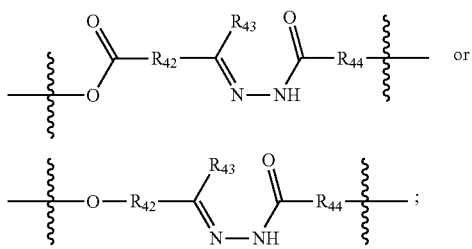

$R_{30}$ is hydrogen or $C_{1-8}$ alkyl;

$R_{37}$ at each occurrence independently is $C_{1-8}$ alkyl, halogen, or methoxy;

k is an integer from 0 to 5;

$R_{39}$ is:

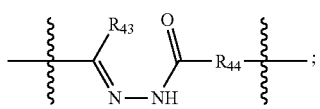

wherein:

$R_{42}$ is a covalent bond, alkylaryl, $C_{1-10}$ alkylene or $C_{6-10}$ arylene;

$R_{43}$ is hydrogen, $C_{1-8}$ alkyl and $C_{6-10}$ aryl;

$R_{44}$ is alkylaryl, $C_{1-10}$ alkylene, $C_{6-10}$ arylene, and —(CH$_2$OCH$_2$)$_p$CH$_2$—; and p is an integer from 1 to 5.

For example, in the compounds of Formula (Ic), $R_1$ is hydrogen; $R_1$ and $R_2$ are methyl; $R_3$ is isopropyl; $R_4$ is $C_{1-8}$ alkyl, $C_{6-10}$ aryl, or —CH$_2$—($C_{5-7}$ carbocycle) and $R_5$ is H or methyl; $R_4$ is $C_{1-8}$ alkyl and $R_5$ is H or methyl; or $R_4$ and $R_5$ together with the carbon atom to which they are attached form a carbocyclic ring having the formula —(CR$_a$R$_b$)$_n$— wherein each of R$_a$ and R$_b$ independently is H or $C_{1-8}$ alkyl; n is an integer from 2 to 7; $R_8$ is H or $C_{1-8}$ alkyl.

For example, in the compounds of Formula (Ic), $R_{12}$ is

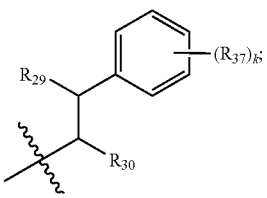

wherein:

$R_{29}$ is

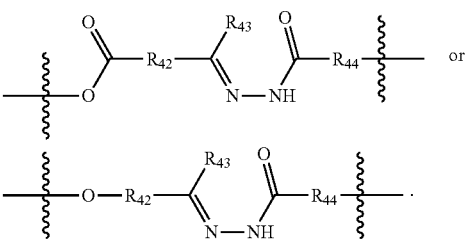

For example, $R_{29}$ is

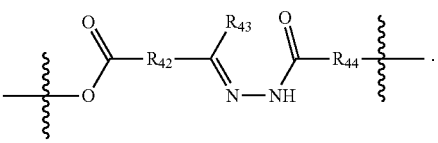

For example, $R_{29}$ is

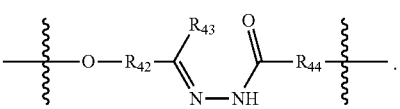

For example, $R_{42}$ is $C_{6-10}$ arylene or $C_{1-10}$ alkylene; $R_{43}$ is $C_{1-8}$ alkyl or $C_{6-10}$ aryl; and $R_{44}$ is $C_{1-10}$ alkylene.

For example, in the compounds of Formula (Ic), $R_{12}$ is

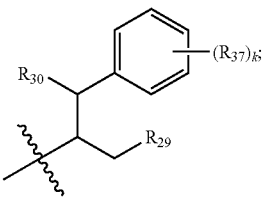

wherein:

$R_{29}$ is

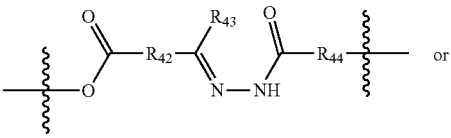

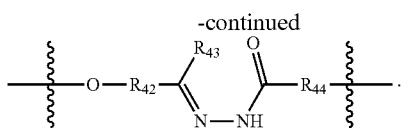

For example, $R_{42}$ is $C_{6-10}$ arylene or $C_{1-10}$ alkylene; $R_{43}$ is lower alkyl or aryl; and $R^{44}$ is $C_{1-10}$ alkylene.

For example, $R_{12}$ is

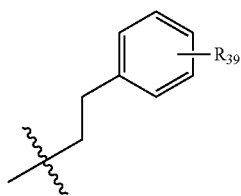

and $R_{39}$ is

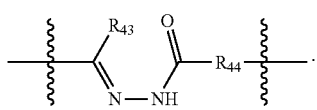

For example, $R_{43}$ is lower alkyl; and $R_{44}$ is $C_{1-10}$ alkylene.

For example, $R_{12}$ is

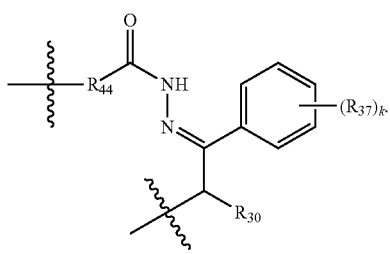

For example, $R_{44}$ is $C_{1-10}$ alkylene.

For example, $R_{12}$ is

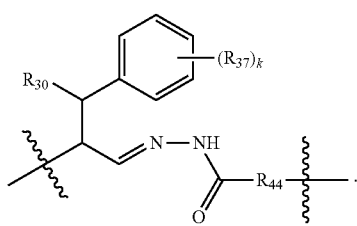

For example, $R_{44}$ is $C_{1-10}$ alkylene or $C_{6-10}$ arylene.

For example, D is a compound of Formula (Ie) or a pharmaceutically acceptable salt thereof:

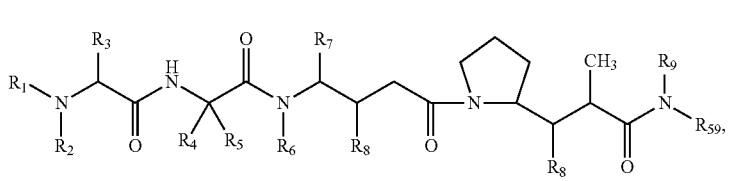

wherein:

$R_1$ is H, $C_{1-8}$ alkyl or $C_{3-8}$ carbocycle;

$R_2$, $R_6$ and $R_9$ are each independently H or $C_{1-8}$ alkyl; or $R_1$ and $R_2$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;

n is an integer from 2 to 7;

$R_3$ is H, $C_{1-8}$ alkyl, $C_{3-8}$ carbocycle, $C_{6-10}$ aryl, $C_{1-8}$ alkyl-$C_{6-10}$ aryl, $C_{1-8}$ alkyl-($C_{3-8}$ carbocycle), $C_{3-8}$ heterocycle or $C_{1-8}$ alkyl-($C_{3-8}$ heterocycle);

$R_4$ is H, $C_{1-8}$ alkyl, $C_{3-8}$ carbocycle, $C_{6-10}$ aryl, $C_{1-8}$ alkyl-$C_{6-10}$ aryl, $C_{1-8}$ alkyl-($C_{3-8}$ carbocycle), $C_{3-8}$ heterocycle or $C_{1-8}$ alkyl-($C_{3-8}$ heterocycle);

$R_5$ is H or methyl; or $R_4$ and $R_5$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;

$R_7$ is H, $C_{1-8}$ alkyl, $C_{3-8}$ carbocycle, $C_{6-10}$ aryl, $C_{1-8}$ alkyl-$C_{6-10}$ aryl, $C_{1-8}$ alkyl-($C_{3-8}$ carbocycle), $C_{3-8}$ heterocycle or $C_{1-8}$ alkyl-($C_{3-8}$ heterocycle);

each $R_8$ independently is H, OH, $C_{1-8}$ alkyl, $C_{3-8}$ carbocycle or O—($C_{1-8}$ alkyl);

$R_{59}$ is:

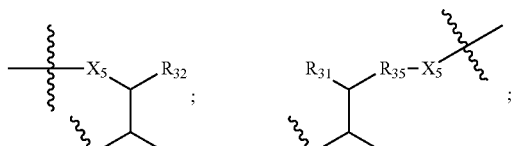

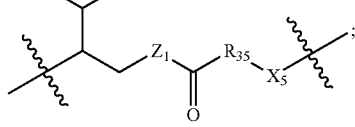

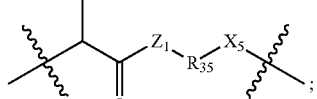

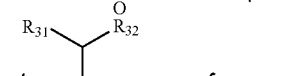

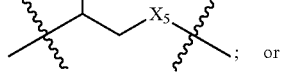 or

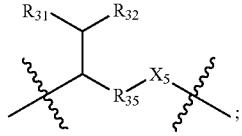

$X_5$ is O, S, or $N(R_{34})$, where $X_5$ can form a bond with Linker unit $L^{D2}$;

$Z_1$ is O, S, or $NR_{34}$;

$R_{31}$ is H, OH, $N(R_{34})_2$, $C_{1-8}$ alkyl, $C_{3-8}$ carbocycle, O—($C_{1-8}$ alkyl), $C_{6-10}$ aryl, $X_4$—$C_{6-10}$ aryl, $X_4$—($C_{3-8}$ carbocycle), $C_{3-8}$ heterocycle, $X_4$—($C_{3-8}$ heterocycle), $C_{1-8}$ alkylene-$NH_2$, or $(CH_2)_2SCH_3$; or $R_{31}$ is an oxygen atom which forms a carbonyl unit (C=O) with the carbon atom to which it is attached and one hydrogen atom on this carbon atom is replaced by one of the bonds in the (C=O) double bond;

$X_4$ is $C_{1-10}$ alkylene or $C_{3-10}$ cycloalkylene;

$R_{32}$ is $C_{6-10}$-aryl or $C_{3-8}$ heterocycle;

$R_{33}$ is H, OH, $N(R_{34})_2$, $C_{1-8}$ alkyl, —$C_{3-8}$ carbocycle, O—($C_{1-8}$ alkyl), $C_{6-10}$ aryl, $C_{1-8}$ alkyl-$C_{6-10}$ aryl, $C_{1-8}$ alkyl-($C_{3-8}$ carbocycle), $C_{3-8}$ heterocycle, or $C_{1-8}$ alkyl-($C_{3-8}$ heterocycle);

each $R_{34}$ independently is H or $C_{1-8}$ alkyl; and $R_{35}$ is arylene, $C_{3-8}$ carbocyclo or $C_{-3-8}$ heterocyclo.

For example, when $R_{31}$ is H, $R_{59}$ is:

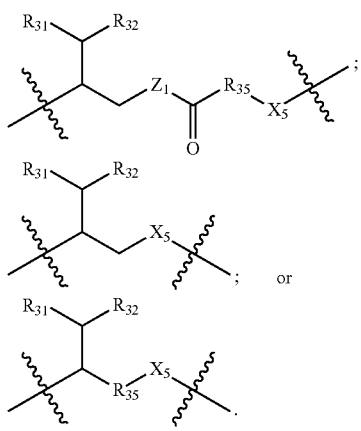

For example, in the compounds of Formula (Ie):

$R_1$, $R_2$, $R_4$ and $R_6$ are each independently H or methyl;

$R_3$ is H, methyl or isopropyl;

$R_5$ is isopropyl, isobutyl, sec-butyl, methyl or t-butyl; or $R_4$ and $R_5$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;

n is an integer from 2 to 7;

$R_8$ is —OH, methoxy or ethoxy; and $R_{59}$ is:

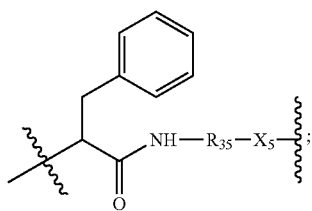

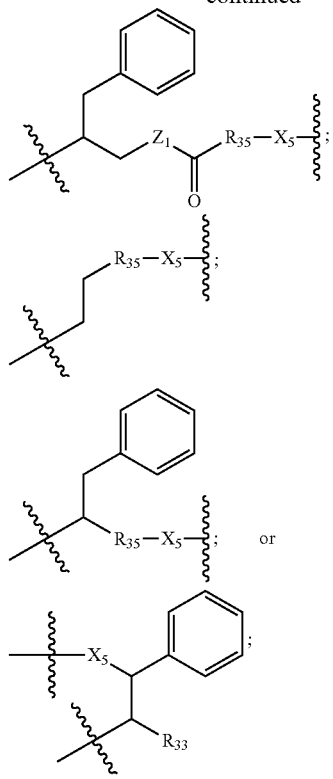

wherein:

$X_5$ is O, S, or $N(R_{34})$, and can form a bond with Y when y is 1 or 2, with W when y is 0, and with A when w and y are both 0;

$Z_1$ is O or $NR_{34}$;

$R_{33}$ is H or methyl;

$R_{34}$ is $C_{1-8}$ alkyl; and $R_{35}$ is arylene, $C_{3-8}$ carbocyclo, or $C_{3-8}$ heterocyclo.

For example, in the compounds of Formula (Ie), when $R_1$ is -methyl, $R_{59}$ is:

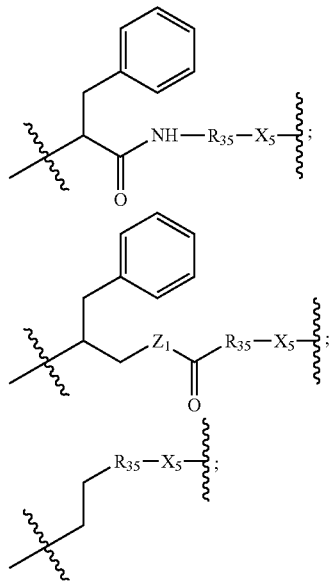

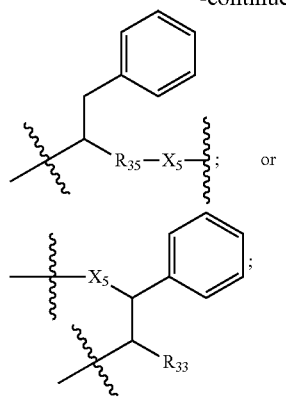 or

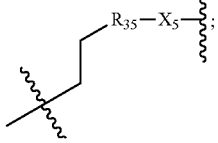

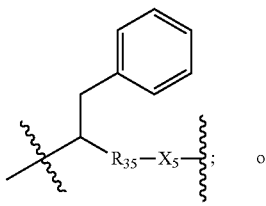

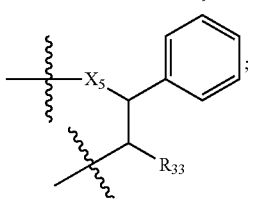 or wherein:
X$_5$ is O, S, or N(R$_{34}$), and can form a bond with Y when y is 1 or 2, with W when y is 0;
Z$_1$ is O, or NR$_{34}$;
R$_{33}$ is H or methyl;
R$_{34}$ is C$_{1-8}$ alkyl; and
R$_{35}$ is arylene, C$_{3-8}$ carbocyclo, or C$_{3-8}$ heterocyclo.

For example, in the compounds of Formula (Ie), when R$_1$ is methyl, R$_{59}$ is:

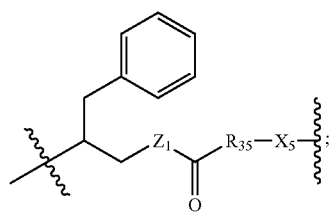

wherein:
X$_5$ is O, S, or N(R$_{34}$), and can form a bond with Y when y is 1 or 2, or with W when y is 0;
Z$_1$ is O or NR$_{34}$;
R$_{33}$ is H or methyl;
R$_{34}$ is C$_{1-8}$ alkyl; and
R$_{35}$ is arylene, C$_{3-8}$ carbocyclo, or C$_{3-8}$ heterocyclo.

For example, the compounds of Formula (Ie) are compounds of any of Formulae (XXVI) and (XXVII) or pharmaceutically acceptable salts thereof:

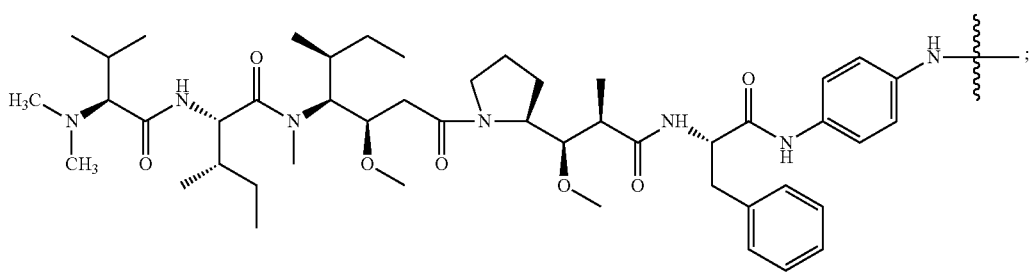

(XXVI)

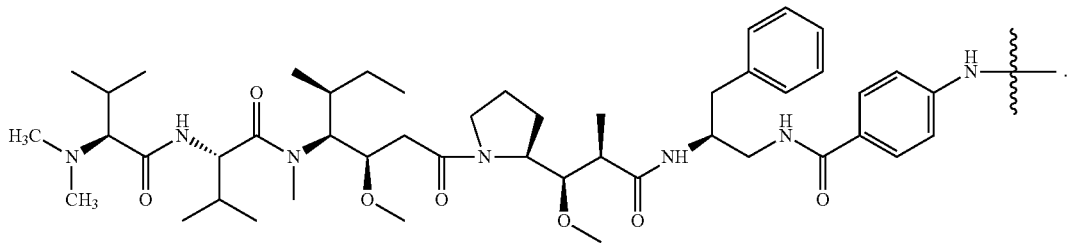

(XXVII)

For example, D is a compound of Formula (IIa) or a pharmaceutically acceptable salt thereof:

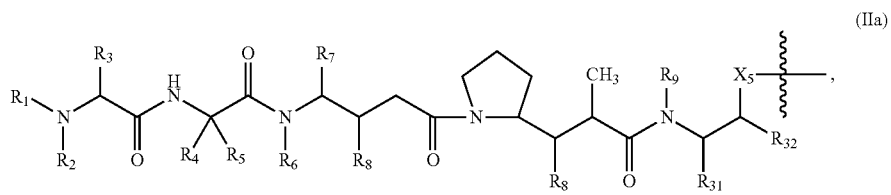

(IIa)

wherein:

$R_1$ is H, $C_{1-8}$ alkyl or $C_{3-8}$ carbocycle;

$R_2$, is H or $C_{1-8}$ alkyl; or $R_1$ and $R_2$ together with the carbon atom to which they are attached foul) a carbocyclic ring having the formula —$(CR_aR_b)_n$— wherein each of $R_a$ and $R_b$ independently is H, $C_{1-8}$ alkyl or $C_{3-8}$ carbocycle;

n is an integer from 2 to 7;

$R_3$ is H, $C_{1-8}$ alkyl, $C_{3-8}$ carbocycle, $C_{6-10}$ aryl, $C_{1-8}$ alkyl-$C_{6-10}$ aryl, $C_{1-8}$ alkyl-($C_{3-8}$ carbocycle), $C_{3-8}$ heterocycle or $C_{1-8}$ alkyl-($C_{3-8}$ heterocycle);

$R_4$ is H, $C_{1-8}$ alkyl, $C_{3-8}$ carbocycle, $C_{6-10}$ aryl, $C_{1-8}$ alkyl-$C_{6-10}$ aryl, $C_{1-8}$ alkyl-($C_{3-8}$ carbocycle), $C_{3-8}$ heterocycle or $C_{1-8}$ alkyl-($C_{3-8}$ heterocycle);

$R_5$ is H or methyl; or $R_4$ and $R_5$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;

$R_6$ and $R_9$ are each independently H or $C_{1-8}$ alkyl;

$R_7$ is H, $C_{1-8}$ alkyl, $C_{3-8}$ carbocycle, $C_{6-10}$ aryl, $C_{1-8}$ alkyl-$C_{6-10}$ aryl, $C_{1-8}$ alkyl-($C_{3-8}$ carbocycle), $C_{3-8}$ heterocycle or $C_{1-8}$ alkyl-($C_{3-8}$ heterocycle);

each $R_8$ independently is H, OH, $C_{1-8}$ alkyl, $C_{3-8}$ carbocycle or O—($C_{1-8}$ alkyl);

$X_5$ is O, S, or $NR_{34}$;

$R_{31}$ is H, OH, $N(R_{34})_2$, $C_{1-8}$ alkyl, $C_{3-8}$ carbocycle, O—($C_{1-8}$ alkyl), $C_{6-10}$ aryl, $X_4$—$C_{6-10}$ aryl, $X_4$—($C_{3-8}$ carbocycle), $C_{3-8}$ heterocycle, $X_4$—($C_{3-8}$ heterocycle), $C_{1-8}$ alkylene-$NH_2$, or $(CH_2)_2SCH_3$; or $R_{31}$ is an oxygen atom which forms a carbonyl unit (C=O) with the carbon atom to which it is attached and one hydrogen atom on this carbon atom is replaced by one of the bonds in the (C=O) double bond;

$X_4$ is $C_{1-10}$ alkylene or $C_{3-10}$ cycloalkylene;

each $R_{32}$ independently is $C_{6-10}$ aryl or $C_{3-8}$ heterocycle; and each $R_{34}$ is independently H or $C_{1-8}$ alkyl.

For example, the compound of Formula (IIa) is a compound of Formula (XXVIII) or a pharmaceutically acceptable salt thereof:

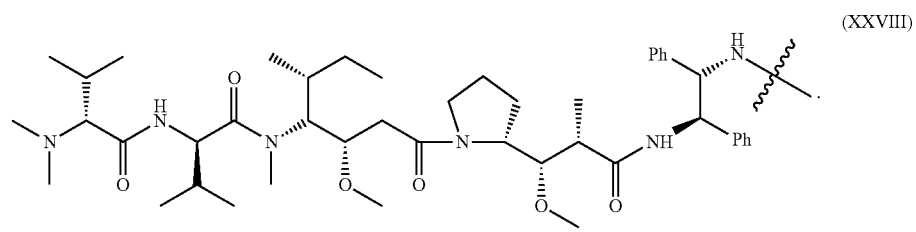

(XXVIII)

For example, D is a compound of any of Formulae (IIb), (IIc), (IId) and (IIe), or a pharmaceutically acceptable salt thereof:

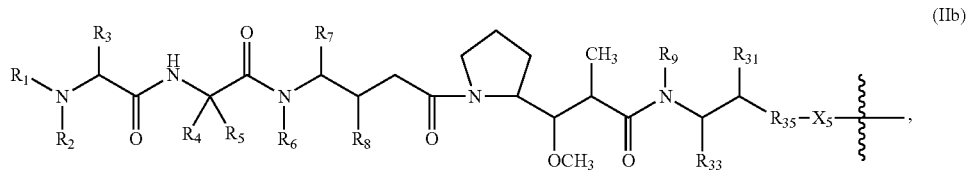

(IIb)

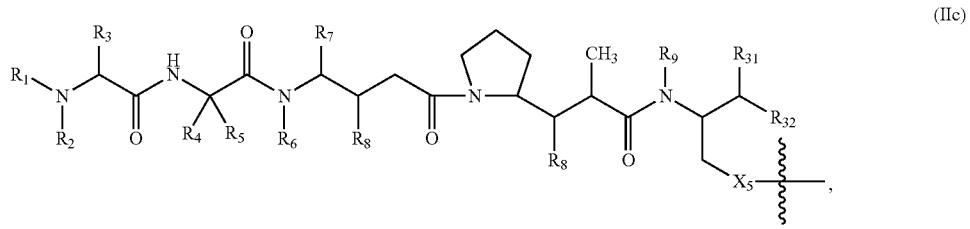

(IIc)

-continued

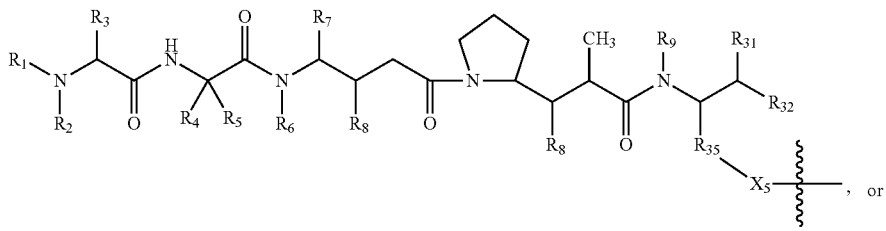
(IId)

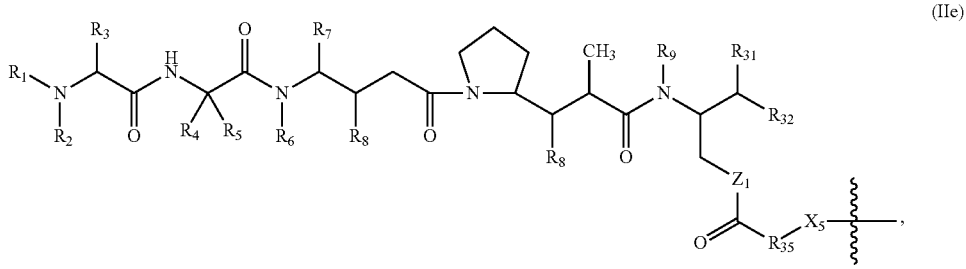
(IIe)

wherein:

$R_1$ is H, $C_{1-8}$ alkyl or $C_{3-8}$ carbocycle;

$R_2$ is H or $C_{1-8}$ alkyl; or $R_1$ and $R_2$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;

n is an integer from 2 to 7;

$R_3$ is H, $C_{1-8}$ alkyl, $C_{3-8}$ carbocycle, $C_{6-10}$ aryl, $C_{1-8}$ alkyl-$C_{6-10}$ aryl, $C_{1-8}$ alkyl-($C_{3-8}$ carbocycle), $C_{3-8}$ heterocycle or $C_{1-8}$ alkyl-($C_{3-8}$ heterocycle);

$R_4$ is H, $C_{1-8}$ alkyl, $C_{3-8}$ carbocycle, $C_{6-10}$ aryl, $C_{1-8}$ alkyl-$C_{6-10}$ aryl, $C_{1-8}$ alkyl-($C_{3-8}$ carbocycle), $C_{3-8}$ heterocycle or $C_{1-8}$ alkyl-($C_{3-8}$ heterocycle);

$R_5$ is H or methyl; or $R_4$ and $R_5$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;

$R_6$ is H or $C_{1-8}$ alkyl;

$R_7$ is H, $C_{1-8}$ alkyl, $C_{3-8}$ carbocycle, $C_{6-10}$ aryl, $C_{1-8}$ alkyl-$C_{6-10}$ aryl, $C_{1-8}$ alkyl-($C_{3-8}$ carbocycle), $C_{3-8}$ heterocycle or $C_{1-8}$ alkyl-($C_{3-8}$ heterocycle);

each $R_8$ independently is H, OH, $C_{1-8}$ alkyl, $C_{3-8}$ carbocycle or O—($C_{1-8}$ alkyl);

$R_9$ is —H or —$C_{1-8}$ alkyl;

$X_5$ is O, S, or $NR_{34}$, where $X_5$ can form a bond with Y when y is 1 or 2, or $X_5$ can form a bond with W when y is 0;

$Z_1$ is O, S, or $NR_{34}$;

$R_{31}$ is H, OH, $N(R_{34})_2$, $C_{1-8}$ alkyl, $C_{3-8}$ carbocycle, O—($C_{1-8}$ alkyl), $C_{6-10}$ aryl, $X_4$—$C_{6-10}$ aryl, $X_4$—($C_{3-8}$ carbocycle), $C_{3-8}$ heterocycle, $X_4$—($C_{3-8}$ heterocycle), $C_{1-8}$ alkylene-$NH_2$, or $(CH_2)_2SCH_3$; or $R_{31}$ is an oxygen atom which forms a carbonyl unit (C=O) with the carbon atom to which it is attached and one hydrogen atom on this carbon atom is replaced by one of the bonds in the (C=O) double bond;

$X_4$ is $C_{1-10}$ alkylene or $C_{3-10}$ cycloalkylene;

$R_{32}$ is $C_{6-10}$-aryl or $C_{3-8}$ heterocycle;

$R_{33}$ is H, OH, $N(R_{34})_2$, $C_{1-8}$ alkyl, $C_{3-8}$ carbocycle, O—($C_{1-8}$ alkyl), $C_{6-10}$ aryl, $C_{1-8}$ alkyl-$C_{6-10}$ aryl, $C_{1-8}$ alkyl-($C_{3-8}$ carbocycle), $C_{3-8}$ heterocycle, or $C_{1-8}$ alkyl-($C_{3-8}$ heterocycle);

each $R_{34}$ independently is H or $C_{1-8}$ alkyl; and $R_{35}$ is arylene, $C_{3-8}$ carbocyclo, or C-$_{3-8}$ heterocyclo.

For example, D is a compound of Formula (IIf) or a pharmaceutically acceptable salt thereof:

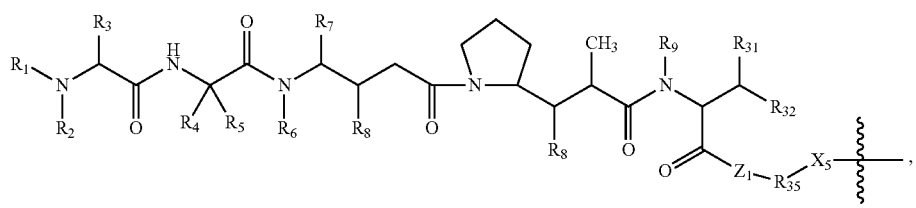
(IIf)

wherein:

$R_1$ is H, $C_{1-8}$ alkyl or $C_{3-8}$ carbocycle;

$R_2$ is H or $C_{1-8}$ alkyl; or $R_1$ and $R_2$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;

n is an integer from 2 to 7;

$R_3$ is H, $C_{1-8}$ alkyl, $C_{3-8}$ carbocycle, $C_{6-10}$ aryl, $C_{1-8}$ alkyl-$C_{6-10}$ aryl, $C_{1-8}$ alkyl-($C_{3-8}$ carbocycle), $C_{3-8}$ heterocycle or $C_{1-8}$ alkyl-($C_{3-8}$ heterocycle);

$R_4$ is H, $C_{1-8}$ alkyl, $C_{3-8}$ carbocycle, $C_{6-10}$ aryl, $C_{1-8}$ alkyl-$C_{6-10}$ aryl, $C_{1-8}$ alkyl-($C_{3-8}$ carbocycle), $C_{3-8}$ heterocycle or $C_{1-8}$ alkyl-($C_{3-8}$ heterocycle);

R$_5$ is H or methyl; or

R$_4$ and R$_5$ together with the carbon atom to which they are attached form a carbocyclic ring having the formula —(CR$_a$R$_b$)$_n$— wherein each of R$_a$ and R$_b$ independently is H, C$_{1-8}$ alkyl or C$_{3-8}$ carbocycle;

R$_6$ is H or C$_{1-8}$ alkyl;

R$_7$ is H, C$_{1-8}$ alkyl, C$_{3-8}$ carbocycle, C$_{6-10}$ aryl, C$_{1-8}$ alkyl-C$_{6-10}$ aryl, C$_{1-8}$ alkyl-(C$_{3-8}$ carbocycle), C$_{3-8}$ heterocycle or C$_{1-8}$ alkyl-(C$_{3-8}$ heterocycle);

each R$_8$ independently is H, OH, C$_{1-8}$ alkyl, C$_{3-8}$ carbocycle or O—(C$_{1-8}$ alkyl);

R$^9$ is —H or —C$_{1-8}$ alkyl;

X$_5$ is O, S, or NR$_{34}$;

Z$_1$ is O, S, or NR$_{34}$;

R$_{31}$ is H, OH, N(R$_{34}$)$_2$, C$_{1-8}$ alkyl, C$_{3-8}$ carbocycle, O—(C$_{1-8}$ alkyl), C$_{6-10}$ aryl, X$_4$—C$_{6-10}$ aryl, X$_4$—(C$_{3-8}$ carbocycle), C$_{3-8}$ heterocycle, X$_4$—(C$_{3-8}$ heterocycle), C$_{1-8}$ alkylene-NH$_2$, or (CH$_2$)$_2$SCH$_3$; or R$_{31}$ is an oxygen atom which forms a carbonyl unit (C=O) with the carbon atom to which it is attached and one hydrogen atom on this carbon atom is replaced by one of the bonds in the (C=O) double bond;

X$_4$ is C$_{1-10}$ alkylene or C$_{3-10}$ cycloalkylene;

R$_{32}$ is C$_{6-10}$-aryl or C$_{3-8}$ heterocycle;

R$_{33}$ is H, OH, N(R$_{34}$)$_2$, C$_{1-8}$ alkyl, C$_{3-8}$ carbocycle, O—(C$_{1-8}$ alkyl), C$_{6-10}$ aryl, C$_{1-8}$ alkyl-C$_{6-10}$ aryl, C$_{1-8}$ alkyl-(C$_{3-8}$ carbocycle), C$_{3-8}$ heterocycle, or C$_{1-8}$ alkyl-(C$_{3-8}$ heterocycle);

each R$_{34}$ independently is H or C$_{1-8}$ alkyl; and

R$_{35}$ is arylene, C$_{3-8}$ carbocyclo, or C$_{3-8}$ heterocyclo.

For example, in the compounds of Formula (IIf), R$_1$ is C$_{1-8}$ alkyl or C$_{3-8}$ carbocycle; R$_2$ is H or C$_{1-8}$ alkyl; or R$_1$ and R$_2$ together with the carbon atom to which they are attached form a carbocyclic ring having the formula —(CR$_a$R$_b$)$_n$— wherein each of R$_a$ and R$_b$ independently is H, C$_{1-8}$ alkyl or C$_{3-8}$ carbocycle; and n is an integer from 2 to 7.

For example, compounds of Formula (IIf) are compounds of Formula (XXIX) or pharmaceutically acceptable salts thereof:

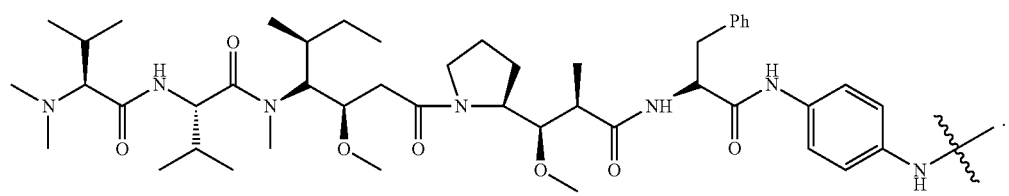

(XXIX)

For example, D is a compound of Formula (Im) or a pharmaceutically acceptable salt thereof:

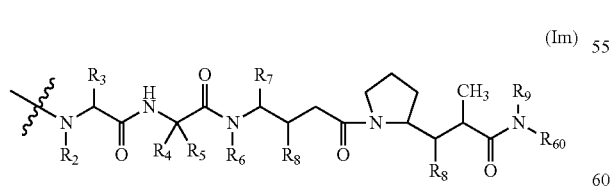

(Im)

wherein:

R$_2$ is H or C$_{1-8}$ alkyl;

R$_3$ is H, C$_{1-8}$ alkyl (optionally substituted with hydroxyl), C$_{3-8}$ carbocycle, X$_4$—C$_{3-8}$ carbocycle, C$_{6-10}$ aryl, X$_4$—C$_{6-10}$ aryl, C$_{3-8}$ heterocycle, or X$_4$—C$_{3-8}$ heterocycle;

R$_4$ is H, C$_{1-8}$ alkyl, C$_{3-8}$ carbocycle, X$_4$—C$_{3-8}$ carbocycle, C$_{6-10}$ aryl, X$_4$—C$_{6-10}$ aryl, C$_{3-8}$ heterocycle, or X$_4$—C$_{3-8}$ heterocycle;

R$_5$ is H or methyl; or

R$_4$ and R$_5$ together with the carbon atom to which they are attached form a carbocyclic ring having the formula —(CR$_a$R$_b$)$_n$— wherein each of R$_a$ and R$_b$ independently is H, C$_{1-8}$ alkyl or C$_{3-8}$ carbocycle;

R$_6$ is H or C$_{1-8}$ alkyl;

R$_7$ is H, C$_{1-8}$ alkyl, C$_{3-8}$ carbocycle, X$_4$—C$_{3-8}$ carbocycle, C$_{6-10}$ aryl, X$_4$—C$_{6-10}$ aryl, C$_{3-8}$ heterocycle, or X$_4$—C$_{3-8}$ heterocycle;

each R$_8$ independently is H, OH, C$_{1-8}$ alkyl, C$_{3-8}$ carbocycle or O—(C$_{1-8}$ alkyl);

each X$_4$ independently is C$_{1-10}$ alkylene or C$_{3-10}$ cycloalkylene;

R$_9$ is H or C$_{1-8}$ alkyl;

R$_{60}$ is:

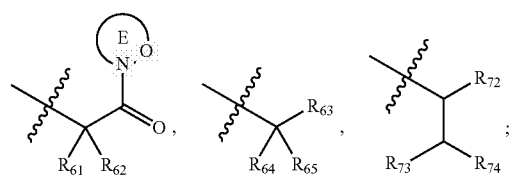

R$_{61}$ is hydrogen or methyl;

R$_{62}$ is isopropyl, isobutyl, sec-butyl, tert-butyl, phenyl, benzyl, 1-hydroxyethyl, 4-hydroxybenzyl, 4-hydroxy-3-nitrobenzyl, 4-hydroxy-3-aminobenzyl, 1-phenylethyl, diphenylmethyl, 1H-imidazol-4-yl methyl or 1H-indol-3-yl methyl, or R$_{61}$ and R$_{62}$ together with the carbon atom to which they are attached form a (1S,2R)-2-phenylcyclopropane-1,1-diyl group of the formula:

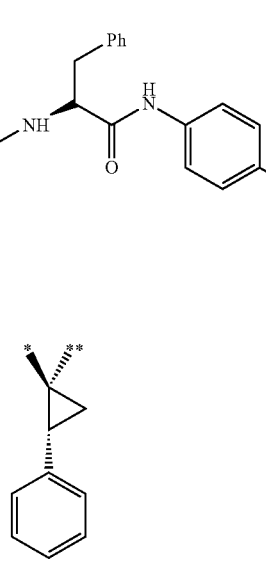

wherein:

* marks the point of attachment with the adjacent nitrogen atom;

** marks the point of attachment with the carbonyl group;

the ring E with the N—O moiety present therein is a mono- or bicyclic, optionally substituted heterocycle of formula:

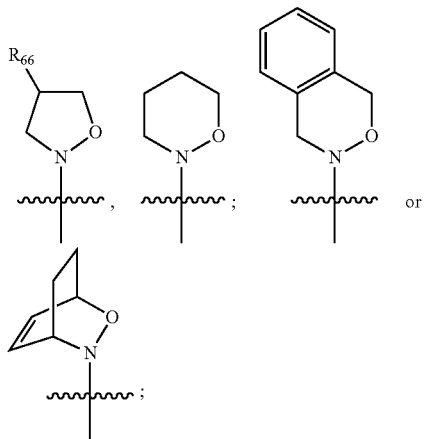

$R_{66}$ is hydrogen, hydroxy or benzyloxy;
$R_{64}$ is hydrogen or methyl,
$R_{65}$ is isopropyl, isobutyl, sec-butyl, tert-butyl, phenyl, benzyl, 1-hydroxyethyl, 4-hydroxybenzyl, 4-hydroxy-3-nitrobenzyl, 4-hydroxy-3-aminobenzyl, 1-phenylethyl, diphenylmethyl, 1H-imidazol-4-yl methyl or 1H-indol-3-yl methyl, or
$R_{64}$ and $R_{65}$ together with the carbon atom to which they are attached form a (1S,2R)-2-phenylcyclopropane-1,1-diyl group of formula:

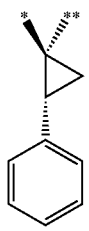

wherein:
* marks the point of attachment with the adjacent nitrogen atom;
** marks the point of attachment with the carbonyl group;
$R_{63}$ is —C(O)—OR$_{67}$, —C(O)—NR$_{68}$R$_{69}$, —C(O)—NH—NH—R$_{70}$ or —CH$_2$—O—R$_{71}$;
$R_{67}$ is hydrogen, methyl, ethyl, n-propyl, tert-butyl, benzyl or adamantylmethyl;
$R_{68}$ is hydrogen or methyl;
$R_{69}$ is hydrogen, methyl, ethyl, n-propyl or benzyl, or
$R_{68}$ and $R_{69}$ together with the nitrogen atom to which they are attached form a 4- to 7-membered heterocycle;
$R_{70}$ is benzoyl;
$R_{71}$ is benzyl, optionally substituted in the phenyl group by methoxycarbonyl or carboxyl,
$R_{72}$ is hydrogen, methyl,

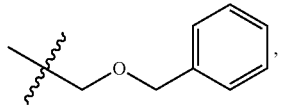

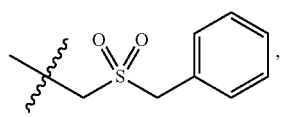

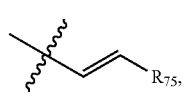

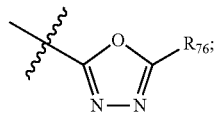

$R_{75}$ is phenyl optionally substituted with methoxycarbonyl, carboxyl or —S(O)$_2$OH;
$R_{76}$ is phenyl optionally substituted with methoxycarbonyl or carboxyl;
$R_{73}$ is hydrogen or hydroxyl; and
$R_{74}$ is phenyl, benzyl, 1H-indol-3-yl or 1H-indol-3-yl methyl.

The compounds of Formula (Im) can include one or more of the following features.

For example, each $X_4$ independently is $C_{1-8}$ alkylene.

For example, $R_3$ is $C(R_{3a})CH_3$ wherein $R_{3a}$ is methyl or hydroxyl.

For example, $R_3$, $R_4$ and $R_7$ are each independently isopropyl or sec-butyl and $R_5$ is H. In an exemplary embodiment, $R_3$ and $R_4$ are each isopropyl, $R_5$ is H, and $R_7$ is sec-butyl.

For example, $R_2$ and $R_6$ are each methyl, and $R_9$ is H.

For example, each occurrence of $R_8$ is OCH$_3$.

For example, $R_3$ and $R_4$ are each isopropyl, $R_2$ and $R_6$ are each methyl, $R_5$ is H, $R_7$ is sec-butyl, each occurrence of $R_8$ is OCH$_3$, and $R_9$ is H.

For example, ring E is:

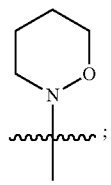

For example, $R_{61}$ is hydrogen;
For example, $R_{62}$ is 4-hydroxybenzyl or 1H-indol-3-yl methyl;
For example, $R_{63}$ is —C(O)—NH$_2$;
For example, $R_{64}$ is hydrogen;
For example, $R_{65}$ is 1H-indol-3-yl methyl.

For example, the compounds of Formula (Im) are compound of any one of Formulae (XXX) to (XXXII) or a pharmaceutically acceptable salt thereof:

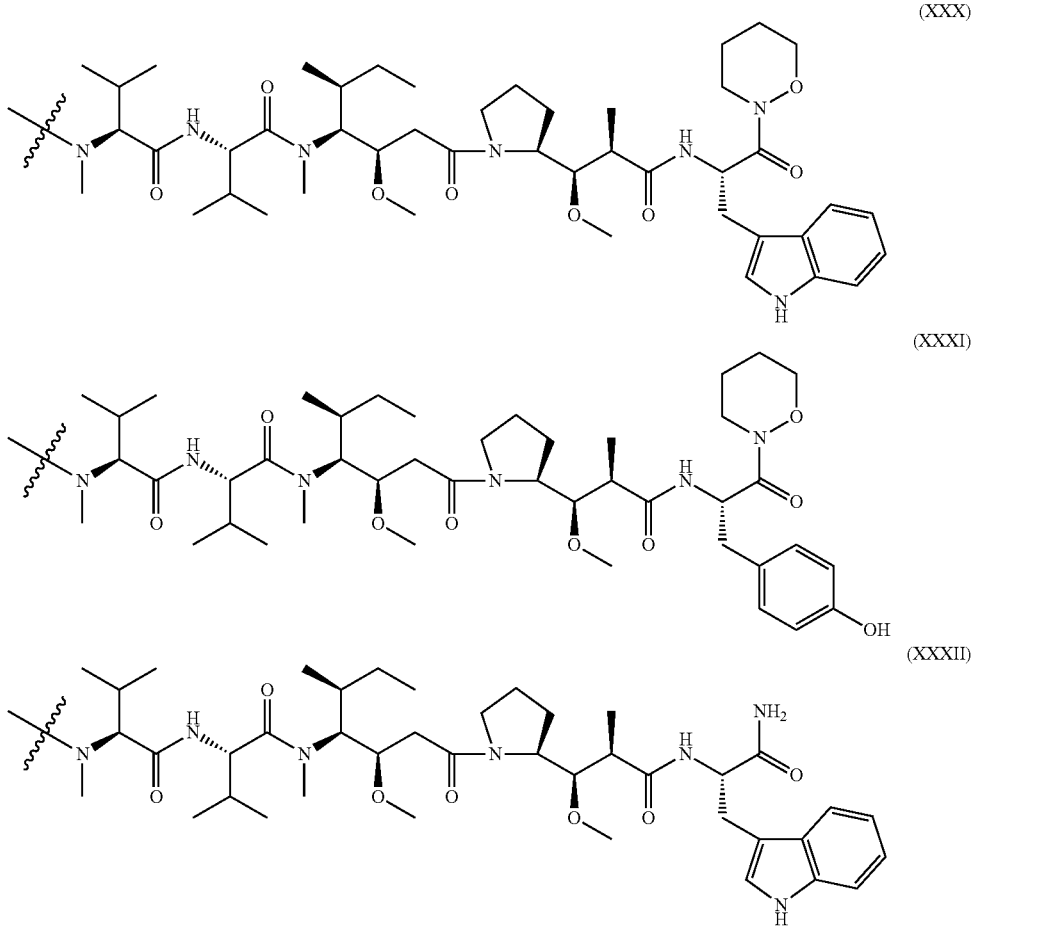

Additional examples of auristatin compounds suitable for use in the present invention are described in US 2012/0003247, US 2012/0003248, US2013/0095123, US 2013/0066055, US2013/0122024, US 2013/0157960, WO 2002/088172, WO 2004/010957, WO 2005/0181711, WO 2007/008603, WO 2009/117531, WO 2012/059882, WO 2012/135440, WO 2012/143499, and U.S. Pat. Nos. 6,884,869, 7,098,308, 7,256,257, 7,423,116, 7,498,298, 7,659,241, 7,829,531, 7,851,437, 7,994,135, 7,965,567, each of which is hereby incorporated by reference in its entirety.

This invention also relates to auristatin compounds having the structure: D-$Y_y$—$W_w$-$A'_a$, in which D, Y, W, A', y, w, and a are as defined herein.

Protein-Based Recognition Molecules (PBRMs)

The protein-based recognition molecule directs the drug-polymer carrier conjugates to specific tissues, cells, or locations in a cell. The protein-based recognition molecule can direct the modified polymer in culture or in a whole organism, or both. In each case, the protein-based recognition molecule has a ligand that is present on the cell surface of the targeted cell(s) to which it binds with an effective specificity, affinity and avidity. In some embodiments, the protein-based recognition molecule targets the modified polymer to tissues other than the liver. In other embodiments the protein-based recognition molecule targets the modified polymer to a specific tissue such as the liver, kidney, lung or pancreas. The protein-based recognition molecule can target the modified polymer to a target cell such as a cancer cell, such as a receptor expressed on a cell such as a cancer cell, a matrix tissue, or a protein associated with cancer such as tumor antigen. Alternatively, cells comprising the tumor vasculature may be targeted. Protein-based recognition molecules can direct the polymer to specific types of cells such as specific targeting to hepatocytes in the liver as opposed to Kupffer cells. In other cases, protein-based recognition molecules can direct the polymer to cells of the reticular endothelial or lymphatic system, or to professional phagocytic cells such as macrophages or eosinophils. (In such cases the polymer itself might also be an effective delivery system, without the need for specific targeting).

In still other embodiments, the protein based recognition molecule can target the modified polymer to a location within the cell, such as the nucleus, the cytoplasm, or the endosome, for example. In specific embodiments, the protein based recognition molecule can enhance cellular binding to receptors, or cytoplasmic transport to the nucleus and nuclear entry or release from endosomes or other intracellular vesicles.

In specific embodiments the protein based recognition molecules include antibodies, proteins and peptides or peptide mimics.

Exemplary antibodies or antibodies derived from Fab, Fab2, scFv or camel antibody heavy-chain fragments specific to the cell surface markers, include, but are not limited to, 5T4, AOC3, ALK, AXL, C242, CA-125, CCL11, CCR 5, CD2, CD3, CD4, CD5, CD15, CA15-3, CD18, CD19, CA19-9, CD20, CD22, CD23, CD25, CD28, CD30, CD31, CD33, CD37, CD38, CD40, CD41, CD44, CD44 v6, CD51, CD52, CD54, CD56, CD62E, CD62P, CD62L, CD70, CD74, CD79-B, CD80, CD125, CD138, CD141, CD147, CD152, CD 154, CD326, CEA, clumping factor, CTLA-4, CXCR2, EGFR, ErbB2, ErbB3, EpCAM, EPHA2, EPHB2, EPHB4, FGFR (i.e. FGFR1, FGFR2, FGFR3, FGFR4), FLT3, folate receptor, FAP, GD2, GD3, GPNMB, HGF, HER2, ICAM, IGF-1 receptor, VEGFR1, EphA2, TRPV1, CFTR, gpNMB, CA9, Cripto, c-KIT, c-MET, ACE, APP, adrenergic receptor-beta2, Claudine 3, Mesothelin, MUC1, RON, ROR1, PD-L1, PD-L2, B7-H3, B7-B4, IL-2 receptor, IL-4 receptor, IL-13 receptor, integrins (including $\alpha_4$, $\alpha_v\beta_3$, $\alpha_v\beta_5$, $\alpha_v\beta_6$, $\alpha_1\beta_4$, $\alpha_4\beta_1$, $\alpha_4\beta_7$, $\alpha_5\beta_1$, $\alpha_6\beta_4$, $\alpha_{IIb}\beta_3$ intergins), IFN-α, IFN-γ, IgE, IgE, IGF-1 receptor, IL-1, IL-12, IL-23, IL-13, IL-22, IL-4, IL-5, IL-6, interferon receptor, ITGB2 (CD18), LFA-1 (CD11a), L-selectin (CD62L), mucin, MUC1, myostatin, NCA-90, NGF, PDGFRα, phosphatidylserine, prostatic carcinoma cell, *Pseudomonas aeruginosa*, rabies, RANKL, respiratory syncytial virus, Rhesus factor, SLAMF7, sphingosine-1-phosphate, TAG-72, T-cell receptor, tenascin C, TGF-1, TGF-β2, TGF-β, TNF-α, TRAIL-R1, TRAIL-R2, tumor antigen CTAA16.88, VEGF-A, VEGFR2, vimentin, and the like.

In one embodiment the antibodies or antibody derived from Fab, Fab2, scFv or camel antibody heavy-chain fragments specific to the cell surface markers include CA-125, C242, CD3, CD19, CD22, CD25, CD30, CD31, CD33, CD37, CD40, CD44, CD51, CD54, CD56, CD62E, CD62P, CD62L, CD70, CD138, CD141, CD326, CEA, CTLA-4, EGFR, ErbB2, ErbB3, FAP, folate receptor, IGF-1 receptor, GD3, GPNMB, HGF, HER2, VEGF-A, VEGFR2, VEGFR1, EphA2, EpCAM, 5T4, TAG-72, tenascin C, TRPV1, CFTR, gpNMB, CA9, Cripto, ACE, APP, PDGFR α, phosphatidylserine, prostatic carcinoma cells, adrenergic receptor-beta2, Claudine 3, mucin, MUC1, Mesothelin, IL-2 receptor, IL-4 receptor, IL-13 receptor and integrins (including $\alpha_v\beta_3$, $\alpha_v\beta_5$, $\alpha_v\beta_6$, $\alpha_1\beta_4$, $\alpha_4\beta_1$, $\alpha_5\beta_1$, $\alpha_6\beta_4$ intergins), tenascin C, TRAIL-R2 and vimentin.

Exemplary antibodies include 3F8, abagovomab, abciximab (REOPRO), adalimumab (HUMIRA), adecatumumab, afelimomab, afutuzumab, alacizumab, ALD518, alemtuzumab (CAMPATH), altumomab, amatuximab, anatumomab, anrukinzumab, apolizumab, arcitumomab (CEA-SCAN), aselizumab, atlizumab (tocilizumab, Actemra, RoActemra), atorolimumab, bapineuzumab, basiliximab (Simulect), bavituximab, bectumomab (LYMPHOSCAN), belimumab (BENLYSTA), benralizumab, bertilimumab, besilesomab (SCINITIMUN), bevacizumab (AVASTIN), biciromab (FIBRISCINT), bivatuzumab, blinatumomab, brentuximab, briakinumab, canakinumab (ILARIS), cantuzumab, capromab, catumaxomab (REMOVAB), CC49, cedelizumab, certolizumab, cetuximab (ERBITUX), citatuzumab, cixutumumab, clenoliximab, clivatuzumab, conatumumab, CR6261, dacetuzumab, daclizumab (ZENAPAX), daratumumab, denosumab (PROLIA), detumomab, dorlimomab, dorlixizumab, ecromeximab, eculizumab (SOURIS), edobacomab, edrecolomab (PANOREX), efalizumab (RAPTIVA), efungumab (MYCOGRAB), elotuzumab, elsilimomab, enlimomab, epitumomab, epratuzumab, erlizumab, ertumaxomab (REXOMUN), etaracizumab (ABEGRIN), exbivirumab, fanolesomab (NEUTROSPEC), faralimomab, farletuzumab, felvizumab, fezakinumab, figitumumab, fontolizumab (HuZAF), foravirumab, fresolimumab, galiximab, gantenerumab, gavilimomab, gemtuzumab girentuximab, glembatumumab, golimumab (SIMPONI), gomiliximab, ibaliximab, ibritumomab, igovomab (INDIMACIS-125), imciromab (MYOSCINT), infliximab (REMICADE), intetumumab, inolimomab, inotuzumab, ipilimumab, iratumumab, keliximab, labetuzumab (CEA-CIDE), lebrikizumab, lemalesomab, lerdelimumab, lexatumumab, libivirumab, lintuzumab, lucatumumab, lumiliximab, mapatumumab, maslimomab, matuzumab, mepolizumab (BOSATRIA), metelimumab, milatuzumab, minretumomab, mitumomab, morolimumab, motavizumab (NUMAX), muromonab-CD3 (ORTHOCLONE OKT3), nacolomab, naptumomab, natalizumab (TYSABRI), nebacumab, necitumumab, nerelimomab, nimotuzumab (THERACIM), nofetumomab, ocrelizumab, odulimomab, ofatumumab (ARZERRA), olaratumab, omalizumab (XOLAIR), ontecizumab, oportuzumab, oregovomab (OVAREX), otelixizumab, pagibaximab, palivizumab (SYNAGIS), panitumumab (VECTIBIX), panobacumab, pascolizumab, pemtumomab (THERAGYN), pertuzumab (OMNITARG), pexelizumab, pintumomab, priliximab, pritumumab, PRO 140, rafivirumab, ramucirumab, ranibizumab (LUCENTIS), raxibacumab, regavirumab, reslizumab, rilotumumab, rituximab (RITUXAN), robatumumab, rontalizumab, rovelizumab (LEUKARREST), ruplizumab (ANTOVA), satumomab pendetide, sevirumab, sibrotuzumab, sifalimumab, siltuximab, siplizumab, solanezumab, sonepcizumab, sontuzumab, stamulumab, sulesomab (LEUKOSCAN), tacatuzumab (AFP-CIDE), tetraxetan, tadocizumab, talizumab, tanezumab, taplitumomab paptox, tefibazumab (AUREXIS), telimomab, tenatumomab, teneliximab, teplizumab, TGN1412, ticilimumab (tremelimumab), tigatuzumab, TNX-650, tocilizumab (atlizumab, ACTEMRA), toralizumab, tositumomab (BEXXAR), trastuzumab (HERCEPTIN), tremelimumab, tucotuzumab, tuvirumab, urtoxazumab, ustekinumab (STELERA), vapaliximab, vedolizumab, veltuzumab, vepalimomab, visilizumab (NUVION), volociximab (HUMASPECT), votumumab, zalutumumab (HuMEX-EGFr), zanolimumab (HuMAX-CD4), ziralimumab and zolimomab.

In some embodiments the antibodies are directed to cell surface markers for 5T4, CA-125, CEA, CD3, CD19, CD20, CD22, CD30, CD33, CD40, CD44, CD51, CTLA-4, EpCAM, HER2, EGFR, FAP, folate receptor, HGF, integrin $\alpha_v\beta_3$, integrin $\alpha_5\beta_1$, IGF-1 receptor, GD3, GPNMB, mucin, MUC1, phosphatidylserine, prostatic carcinoma cells, PDGFR α, TAG-72, tenascin C, TRAIL-R2, VEGF-A and VEGFR2. In this embodiment the antibodies are abagovomab, adecatumumab, alacizumab, altumomab, anatumomab, arcitumomab, bavituximab, bevacizumab (AVASTIN), bivatuzumab, blinatumomab, brentuximab, cantuzumab, catumaxomab, capromab, cetuximab, citatuzumab, clivatuzumab, conatumumab, dacetuzumab, edrecolomab, epratuzumab, ertumaxomab, etaracizumab, farletuzumab, figitumumab, gemtuzumab, glembatumumab, ibritumomab, igovomab, intetumumab, inotuzumab, labetuzumab, lexatumumab, lintuzumab, lucatumumab, matuzumab, mitumomab, naptumomab estafenatox, necitumumab, oportuzumab, oregovomab, panitumumab, pemtumomab, pertuzumab, pritumumab, rituximab (RITUXAN), rilotumumab, robatumumab, satumomab sibrotuzumab, taplitumomab, tenatumomab, tenatumomab, ticilimumab (tremelimumab), tigatuzumab, trastuzumab (HERCEPTIN), tositumomab, tremelimumab, tucotuzumab celmoleukin, volociximab and zalutumumab.

In specific embodiments the antibodies directed to cell surface markers for HER2 are pertuzumab or trastuzumab and for EGFR the antibody is cetuximab and for CD20 the antibody is rituximab and for VEGF-A is bevacizumab and for CD-22 the antibody is epratuzumab or veltuzumab and for CEA the antibody is labetuzumab.

Exemplary peptides or peptide mimics include integrin targeting peptides (RGD peptides), LHRH receptor targeting peptides, ErbB2 (HER2) receptor targeting peptides, prostate specific membrane bound antigen (PSMA) targeting peptides, lipoprotein receptor LRP1 targeting, ApoE protein derived peptides, ApoA protein peptides, somatostatin receptor targeting peptides, chlorotoxin derived peptides, and bombesin.

In specific embodiments the peptides or peptide mimics are LHRH receptor targeting peptides and ErbB2 (HER2) receptor targeting peptides.

Exemplary proteins comprise insulin, transferrin, fibrinogen-gamma fragment, thrombospondin, claudin, apolipoprotein E, Affibody molecules such as, for example, ABY-025, Ankyrin repeat proteins, ankyrin-like repeats proteins and synthetic peptides.

In some embodiments of the invention the protein drug polymer conjugates comprise broad spectrum cytotoxins in combination with cell surface markers for HER2 such as pertuzumab or trastuzumab; for EGFR such as cetuximab; for CEA such as labetuzumab; for CD20 such as rituximab; for VEGF-A such as bevacizumab; or for CD-22 such as epratuzumab or veltuzumab.

In other embodiments of the invention the protein-drug-polymer conjugates or protein-polymer conjugates used in the invention comprise combinations of two or more protein based recognition molecules, such as, for example, combination of bispecific antibodies directed to the EGF receptor (EGFR) on tumor cells and to CD3 and CD28 on T cells; combination of antibodies or antibody derived from Fab, Fab2, scFv or camel antibody heavy-chain fragments and peptides or peptide mimetics; combination of antibodies or antibody derived from Fab, Fab2, scFv or camel antibody heavy-chain fragments and proteins; combination of two bispecific antibodies such as CD3 x CD19 plus CD28 x CD22 bispecific antibodies.

In other embodiments of the invention the protein-drug-polymer conjugates or protein-polymer conjugates used in the invention comprise protein based recognition molecules which are antibodies against antigens, such as, for example B7-H4, B7-H3, CA125, CD33, CXCR2, EGFR, FGFR1, FGFR2, FGFR3, FGFR4, HER2, PD-L1 and 5T4.

Table D below provides more examples of the PBRM described hereof, which are suitable for conjugation to form the polymer-drug-protein conjugates or polymer-PBRM scaffolds of the invention.

TABLE D

| Ref # | PBRM |
|---|---|
| Ex 9 | 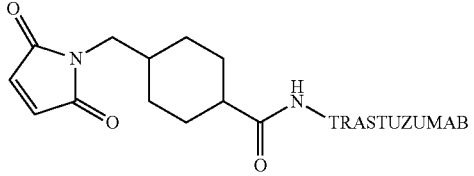 |
| Ex 11 | 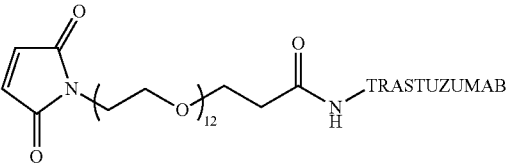 |
| | 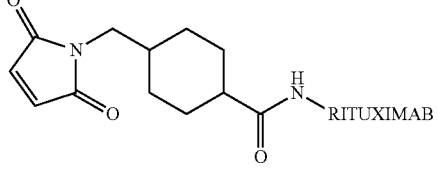 |

TRASTUZUMAB-Fab'-SH

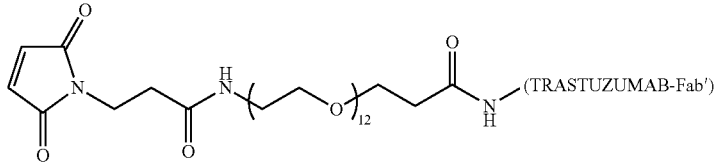

| Ref # | PBRM |
|---|---|
| | 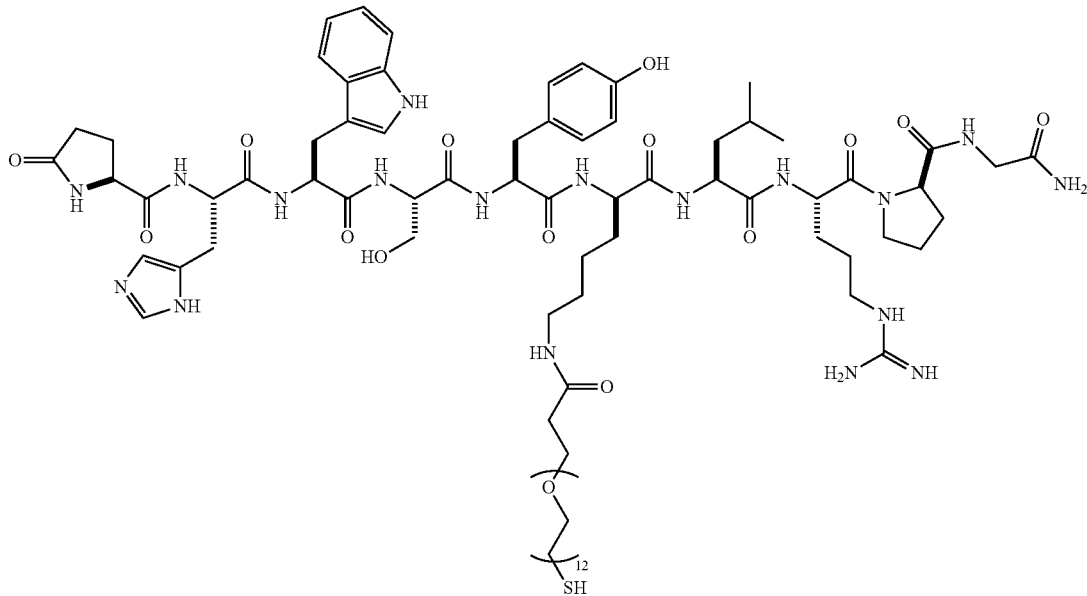 |
| | 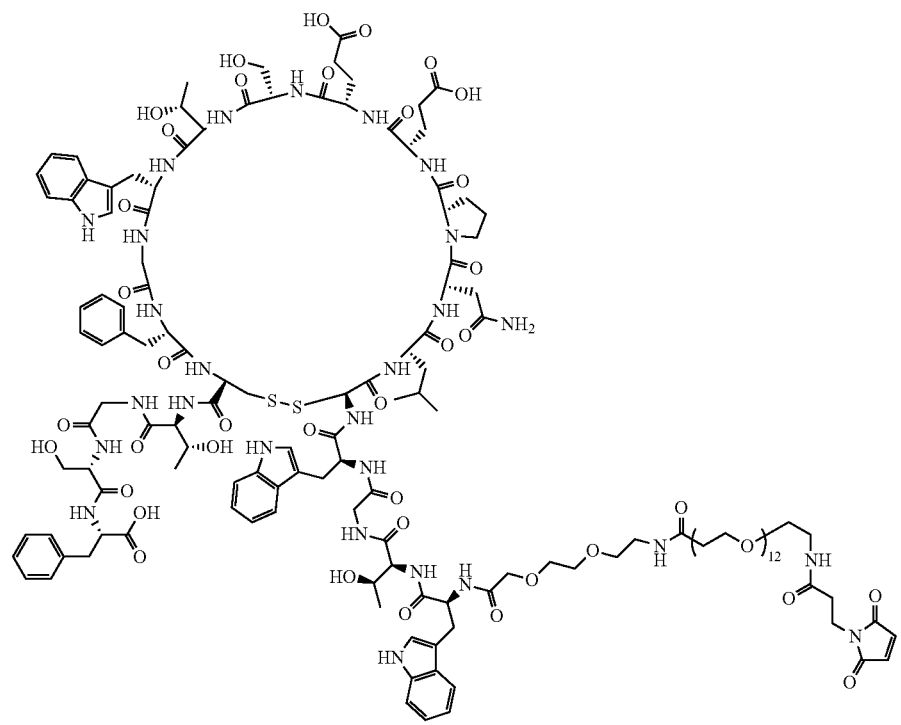 |

TABLE D-continued

| Ref # | PBRM |
|---|---|
| | 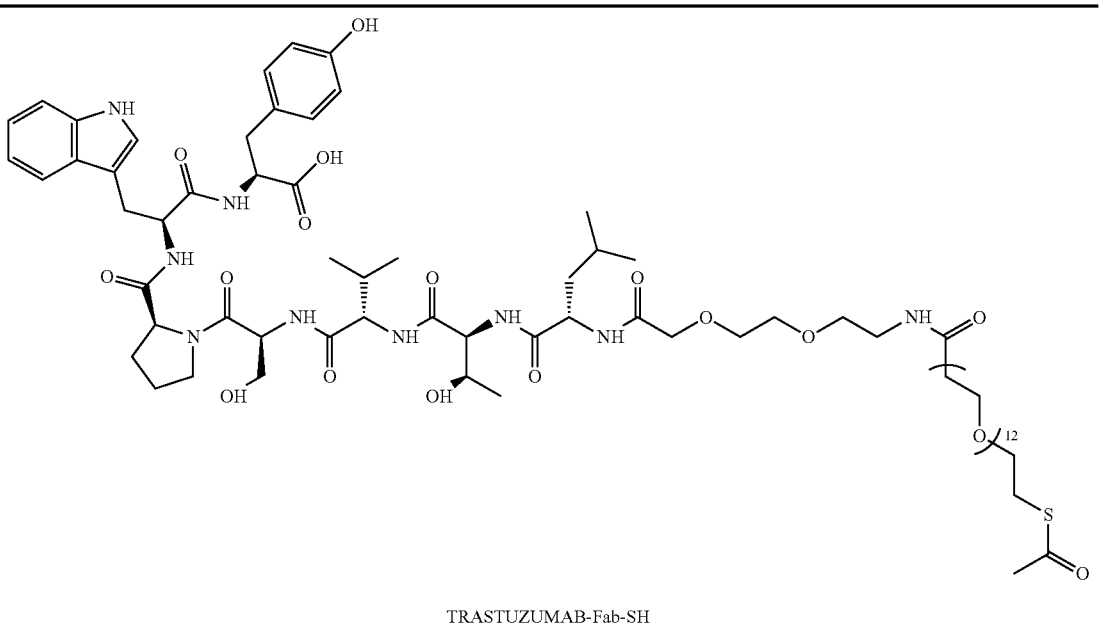<br>TRASTUZUMAB-Fab-SH |

Linkers ($L^D$ and $L^P$)

As described above, the drug or PBRM is connected to the polymeric carrier via a linker $L^D$ or $L^P$. In some embodiments, the linker is biocleavable/biodegradable under intracellular conditions, such that the cleavage of the linker releases the drug (i.e., auristatin compound) or PBRM from the polymer unit in the intracellular environment.

A linker is any chemical moiety that is capable of linking a drug or a PBRM to a polymer backbone through chemical bonds such that the drug or PBRM and the polymer are chemically coupled (e.g., covalently bonded) to each other. In some embodiments, the linker comprises a biodegradable linker moiety (e.g., a biodegradable bond such as an ester or amide bond).

In other embodiments, the linker $L^D$ or $L^P$ is biodegradable under mild conditions, i.e., conditions within a cell under which the activity of the drug is not affected. Examples of suitable biodegradable linker moiety include disulfide linkers, acid labile linkers, photolabile linkers, peptidase labile linkers, and esterase labile linkers.

In some embodiments, the linker $L^D$ or $L^P$ is biocleavable under reducing conditions (e.g., a disulfide linker). In this embodiment the drug or PBRM moiety is linked to the polymer through a disulfide bond. The linker molecule comprises a reactive chemical group that can react with the drug. Preferred reactive chemical groups for reaction with the drug or PBRM moiety are N-succinimidyl esters and N-sulfosuccinimidyl esters. Additionally the linker molecule comprises a reactive chemical group, preferably a dithiopyridyl group that can react with the drug to form a disulfide bond. In some embodiments the linker molecules include, for example, N-succinimidyl 3-(2-pyridyldithio)propionate (SPDP), N-succinimidyl 4-(2-pyridyldithio)butanoate (SPDB), N-succinimidyl 4-(2-pyridyldithio)pentanoate (SPP), N-succinimidyl-S-acetylthioacetate (SATA) and N-succinimidyl-oxycarbonyl-alpha-methyl-alpha-(2-pyridyl-dithio)toluene or 2,5-dioxopyrrolidin-1-yl 4-(1-(pyridin-2-yldisulfanyl)ethyl)benzoate (SMPT).

In other embodiments, the biocleavable linker $L^D$ or $L^P$ is pH-sensitive, i.e., sensitive to hydrolysis at certain pH values. Typically, the pH-sensitive linker is hydrolysable under acidic conditions. For example, an acid-labile linker that is hydrolysable in the lysosome or endosome (e.g., a hydrazone, semicarbazone, thiosemicarbazone, cis-aconitic amide, orthoester, acetal, ketal, or the like) can be used. Such linkers are relatively stable under neutral pH conditions, such as those in the blood, but are unstable at below pH 5.5 or 5.0, the approximate pH of the lysosome. In certain embodiments, the hydrolysable linker is a thioether linker (such as, e.g., a thioether attached to the auristatin compound via an acylhydrazone bond.

In other embodiments the linker $L^D$ or $L^P$ is photo-labile and is useful at the body surface and in many body cavities that are accessible to light. Furthermore, $L^D$ or $L^P$ is biocleavable by infrared light which can penetrate tissue. Accordingly, $L^D$ or $L^P$ is useful for both applications on the body surface and in the tissue.

In some embodiments, the linker $L^D$ or $L^P$ is biocleavable by a cleaving agent that is present in the intracellular environment (e.g., within a lysosome or endosome or caveolea). The linker can be, for example, a peptidyl linker that is cleaved by an intracellular peptidase or protease enzyme, including, but not limited to, a lysosomal or endosomal protease.

In some embodiments the linker $L^D$ or $L^P$ is cleaved by esterases. Only certain esters can be cleaved by esterases present inside or outside cells. Esters are formed by the condensation of a carboxylic acid and an alcohol. Simple esters are esters produced with simple alcohols, such as aliphatic alcohols, and small cyclic and small aromatic alcohols.

In yet other embodiments, the linker $L^D$ or $L^P$ is not biocleavable and the drug is released by antibody degradation. See, for example, U.S. Pat. No. 7,498,298, which is incorporated by reference herein in its entirety and for all purposes.

Typically, the linker $L^D$ or $L^P$ is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of Polymer Drug Conjugate, are cleaved when the Polymer Drug Conjugate presents in an extracellular environment (e.g., in plasma) for 24 hours. Whether a linker is not substantially sensitive to the extracellular environment can be determined, for example, by incubating the Polymer Drug Conjugate with plasma for a predetermined time period (e.g., 2, 4, 8, 16, or 24 hours) and then quantitating the amount of free drug present in the plasma.

In embodiments, the linker $L^D$ has the structure: —$R^{L1}$—C(=O)—$X^D$—$M^{D1}$—$Y^D$—$M^{D2}$—//—$L^{D2}$—, with $R^{L1}$ connected to an oxygen atom of the polymeric carrier and $L^{D2}$ connected to the drug molecule to be delivered, in which the bond "—//—" between $M^{D2}$ and $L^{D2}$ denotes direct or indirect attachment of $L^{D2}$ to $M^{D2}$.

In embodiments, the linker $L^P$ has the structure: —$R^{L2}$—C(=O)—$X^P$—$M^{P1}$—$Y^P$—$M^{P2}$—$Z^P$—$M^{P3}$—$Q^P$—$M^{P4}$—, with $R^{L2}$ connected to an oxygen atom of the polymeric carrier and $M^{P4}$ connected to the PBRM.

For example, each of $R^{L1}$ and $R^{L2}$ independently is absent, alkyl, alkenyl, alkynyl, cycloalkyl, heteroalkyl, heteroalkenyl, heteroalkynyl, heterocycloalkyl, aryl, or heteroaryl.

For example, each of $R^{L1}$ and $R^{L2}$ independently is absent, alkyl, cycloalkyl, heteroalkyl, or heterocycloalkyl.

For example, $R^{L1}$ is absent.

For example, $R^{L2}$ is absent.

For example, each of $X^D$ and $X^P$, independently is —O—, —S—, —N($R^1$)—, or absent, in which $R^1$ is hydrogen, an aliphatic, heteroaliphatic, carbocyclic, or heterocycloalkyl moiety, —C(=O)$R^{1B}$, —C(=O)O$R^{1B}$, —SO$_2R^{1B}$ or —N($R^1$)— is a heterocycloalkyl moiety, wherein $R^{1B}$ is hydrogen, an aliphatic, heteroaliphatic, carbocyclic, or heterocycloalkyl moiety.

For example, each of $Y^D$, $Y^P$, $Z^P$, and $Q^P$, independently, is absent or a biodegradable linker moiety selected from the group consisting of —S—S—, —C(=O)O—, —C(=O)NR$^2$—, —OC(=O)—, —NR$^2$C(=O)—, —OC(=O)O—, —OC(=O)NR$^2$—, —NR$^2$C(=O)O—, —NR$^2$C(=O)NR$^3$—, —C(OR$^2$)O—, —C(OR$^2$)S—, —C(OR$^2$)NR$^3$—, —C(SR$^2$)O—, —C(SR$^2$)S—, —C(SR$^2$)NR$^3$—, —C(NR$^2$R$^3$)O—, —C(NR$^2$R$^3$)S—, —C(NR$^2$R$^3$)NR$^4$—, —C(=O)S—, —SC(=O)—, —SC(=O)S—, —OC(=O)S—, —SC(=O)O—, —C(=S)S—, —SC(=S)—, —OC(=S)—, —C(=S)O—, —SC(=S)O—, —OC(=S)S—, —OC(=S)O—, —SC(=S)S—, —C(=NR$^2$)O, —C(=NR$^2$)S—, —C(=NR$^2$)NR$^3$—, —OC(=NR$^2$)—, —SC(=NR$^2$)—, —NR$^3$C(=NR$^2$)—, —NR$^2$SO$_2$—, —NR$^2$NR$^3$—, —C(=O)NR$^2$NR$^3$—, —NR$^2$NR$^3$C(=O)—, —OC(=O)NR$^2$NR$^3$—, —NR$^2$NR$^3$C(=O)O, —C(=S) NR$^2$NR$^3$—, —NR$^2$NR$^3$C(=S)—, —C(=NR$^4$)NR$^2$NR$^3$—, —NR$^2$NR$^3$C(=NR$^4$)—, —O(N=CR$^3$)—, —(CR$^3$=N) O—, —C(=O)NR$^2$—(N=CR$^3$)—, —(CR$^3$=N)—NR$^2$C (=O)—, —SO$_3$—, —NR$^2$SO$_2$NR$^3$—, —SO$_2$NR$^2$—, and polyamide, wherein each occurrence of R$^2$, R$^3$, and R$^4$ independently is hydrogen or an aliphatic, heteroaliphatic, carbocyclic, or heterocyclic moiety, or each occurrence of —NR$^2$— or —NR$^2$NR$^3$— is a heterocycloalkyl moiety.

For example, each of $M^{D1}$, $M^{D2}$, $M^{P1}$, $M^{P2}$, $M^{P3}$ and $M^{P4}$, independently, is absent or a non-biodegradable linker moiety selected from the group consisting of alkyl, alkenyl, alkynyl, cycloalkyl, heteroalkyl, heteroalkenyl, heteroalkynyl, heterocycloalkyl, aryl, heteroaryl, and a combination thereof and each of $M^{D1}$, $M^{D2}$, $M^{P1}$, $M^{P2}$, and $M^{P3}$ optionally contains one or more —(C=O)— but does not contain any of the biodegradable linker moieties mentioned above.

For example, each of $M^{D1}$, $M^{D2}$, $M^{P1}$, $M^{P2}$, $M^{P3}$ and $M^{P4}$, independently is $C_{1-6}$ alkyl, $C_{1-6}$ alkyl-C(O)—$C_{0-6}$ alkyl, $C_{1-6}$ alkyl-NH—$C_{0-6}$ alkyl, $C_{1-6}$ alkyl-O—$C_{0-6}$ alkyl, $C_{1-6}$ alkyl-S—$C_{0-6}$ alkyl, $C_{1-6}$ alkyl-C(O)—$C_{1-6}$ alkyl-NH, $C_{1-6}$ alkyl-C(O)—$C_{1-6}$ alkyl-O, $C_{1-6}$ alkyl-C(O)—$C_{1-6}$ alkyl-S, $C_{3-10}$ cycloalkyl-C(O)—$C_{0-6}$ alkyl, 3-19 membered heterocycloalkyl-C(O)—$C_{0-6}$ alkyl, aryl-C(O)—$C_{0-6}$ alkyl, (CH$_2$CH$_2$O)$_{1-12}$, and the like.

For example, for each $L^D$, $M^{D1}$ is not absent when $X^D$ is absent.

For example, for each $L^P$, $M^{P1}$ is not absent when $X^P$ is absent.

For example, for each $L^D$, at least one of $X^D$ and $Y^D$ is not absent.

For example, for each $L^P$, at least one of $X^P$, $Y^P$, $Z^P$, and $Q^P$ is not absent.

For example, each of $M^{D1}$ and $M^{P1}$ independently is $C_{1-6}$ alkyl or $C_{1-6}$ heteroalkyl.

For example, each of $M^{D2}$, $M^{P2}$, $M^{P3}$, and $M^{P4}$, independently is absent, $C_{1-6}$ alkyl, cycloalkyl, heteroalkyl, heterocycloalkyl, or a combination thereof.

For example, for each $L^D$, $M^{D2}$ is absent.

For example, for each $L^P$, at most two of $M^{P2}$, $M^{P3}$, and $M^{P4}$ are absent.

For example, for each $L^D$, $M^{D2}$ has one of the following structures:

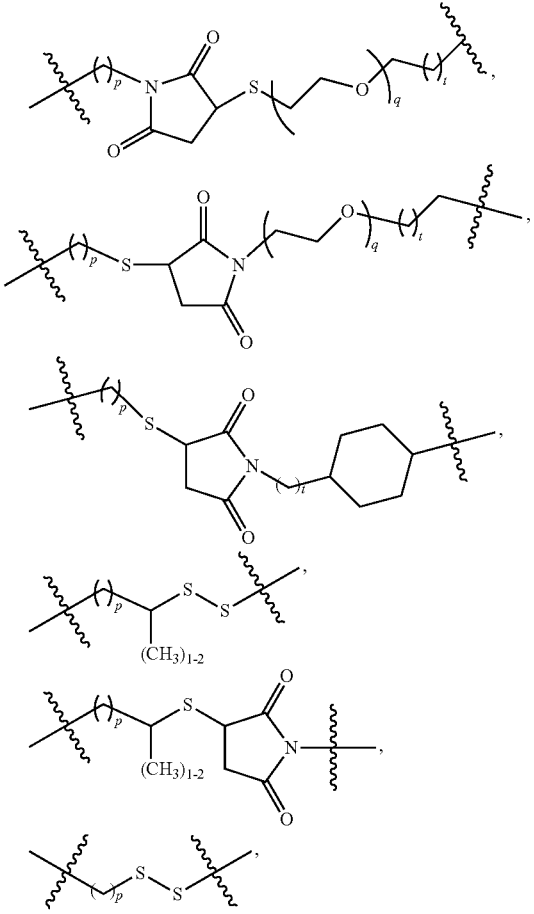

-continued

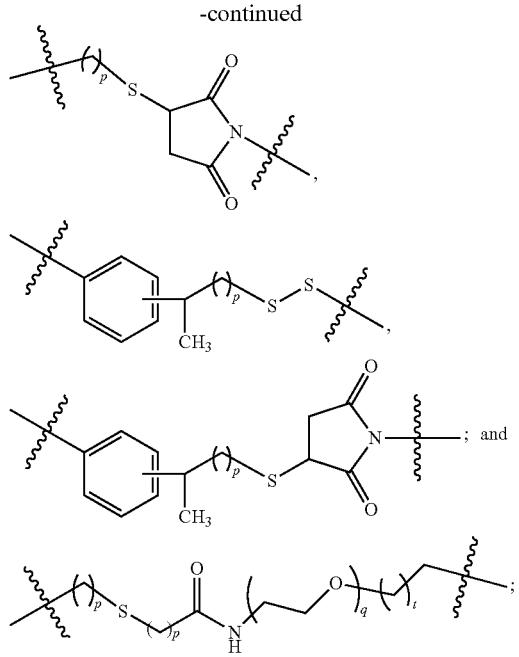

in which q is an integer from 0 to 12 and each of p and t independently is an integer from 0 to 3, and the other of $M^{D2}$ is either absent or a moiety different from the above, such as $C_{1-6}$ alkyl.

For example, for each $L^P$, one of $M^{P2}$ and $M^{P3}$ has one of the following structures:

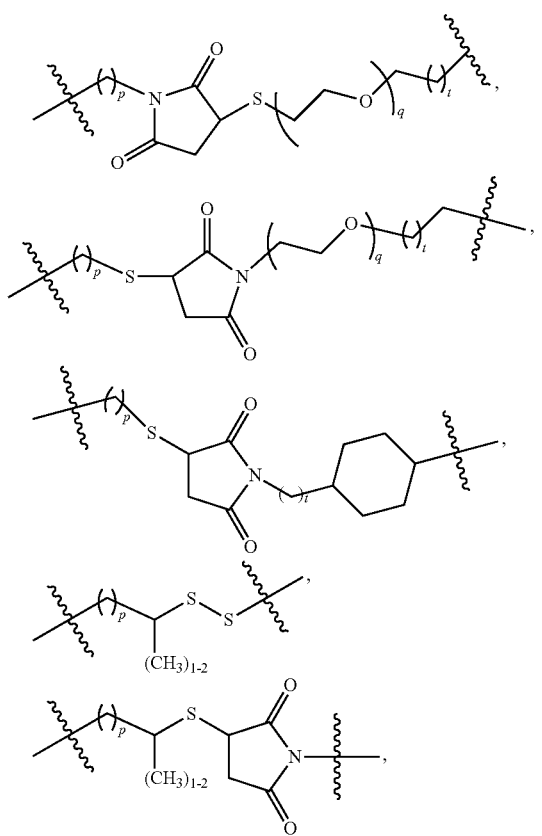

-continued

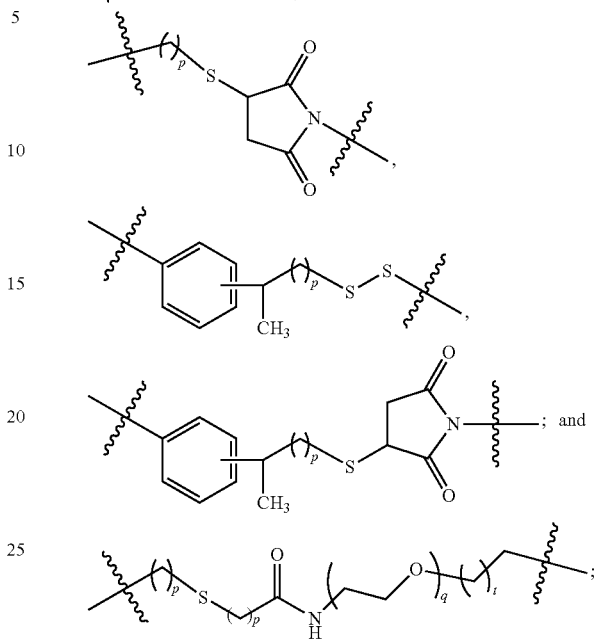

in which q is an integer from 0 to 12 and each of p and t independently is an integer from 0 to 3, and the other of $M^{P2}$ or $M^{P3}$ is either absent or a moiety different from the above, such as $C_{1-6}$ alkyl.

For example, p is 2.

For example, q is 0 or 12.

For example, t is 0 or 1.

For example, each of -$M^{D2}$-//-$L^{D2}$- or -$L^{D2}$-//-$M^{D2}$-, independently has one of the following structures:

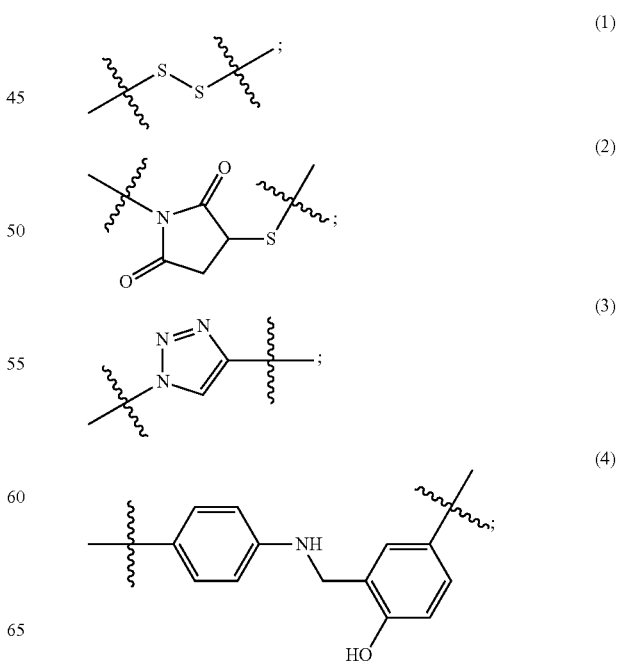

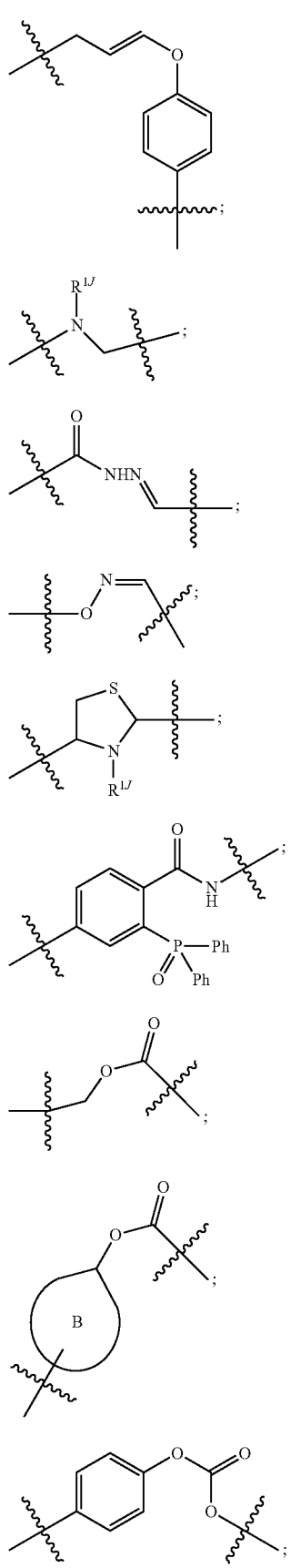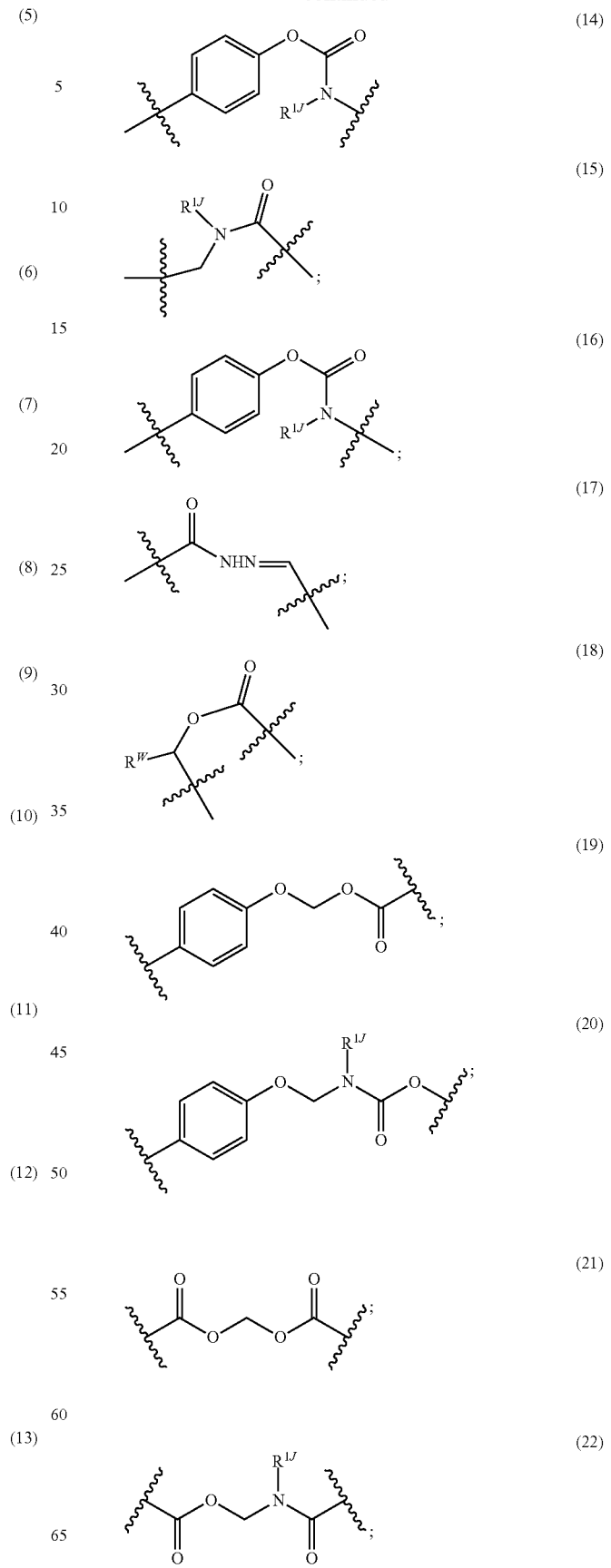

(23)
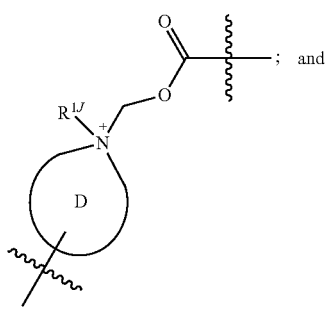 ; and

(24)
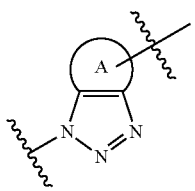

in which ring A or B independently is cycloalkyl or heterocycloalkyl; $R^W$ is an aliphatic, heteroaliphatic, carbocyclic, or heterocycloalkyl moiety; $R^{1J}$ is hydrogen, an aliphatic, heteroaliphatic, carbocyclic, or heterocycloalkyl moiety; and ring D is heterocycloalkyl.

For example, each of $-M^{P2}-Z^P-$, $-Z^P-M^{P3}-$, $-Z^P-M^{P2}-$, and $-M^{P3}-Z^P-$ independently, has one of the following structures:

(1)
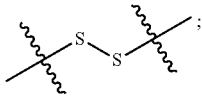

(2)
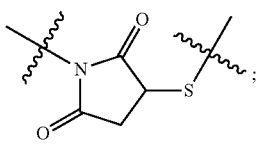

(3)
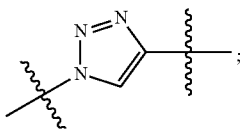

(4)
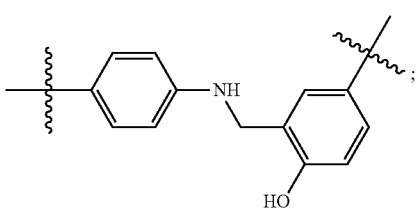

(5)
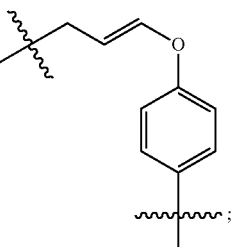

(6)
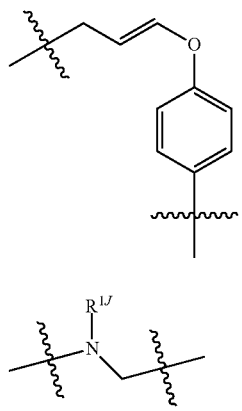

(7)
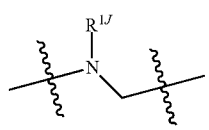

(8)
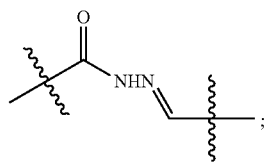

(9)
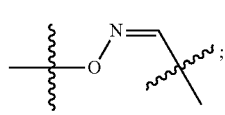

(10)
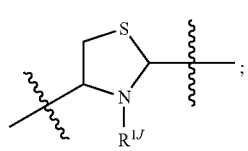

(11)
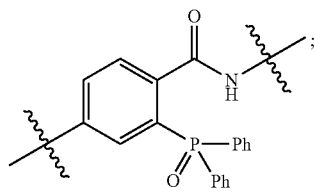 ; and

(12)
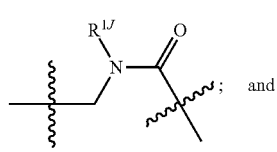

in which ring A is cycloalkyl or heterocycloalkyl and $R^{1J}$ is hydrogen, an aliphatic, heteroaliphatic, carbocyclic, or heterocycloalkyl moiety.

For example, ring A is 5-19 membered heterocycloalkyl, e.g.,

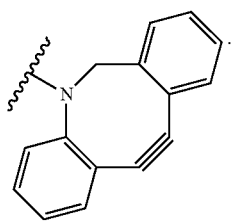 [SMILES: *N1Cc2ccccc2C#Cc2ccccc21]

For example, ring A is $C_{3-8}$ cycloalkyl.
For example, ring D is piperazinyl or piperidinyl.
For example, $R^W$ is $C_{1-6}$ alkyl.
For example, $R^{1J}$ is hydrogen or $C_{1-6}$ alkyl.
For example, $Z^P$ is

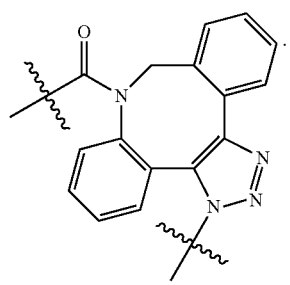 [SMILES: *C(=O)N1Cc2ccccc2-c2nnn(*)c2-c2ccccc21]

For example, $X^D$ is absent, O or NH.
For example, $X^P$ is absent, O or NH.
For example, each of $X^D$ and $X^P$, independently is

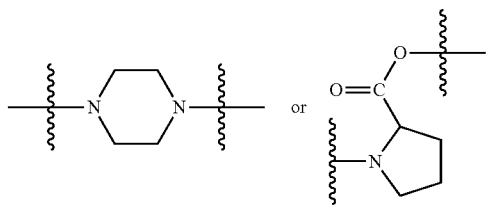

For example, each of $Y^D$ and $Y^P$ independently is —S—S—, —OCO—, —COO—, —CONH— or —NHCO—.
For example, each $Q^P$ independently is absent, —S—S—, —OCO—, —COO—, —CONH—, —NHCO—, —OCONHNH—, or —NHNHCOO—.
For example, polymeric carrier-$L^P$-PBRM can have one of the following structures below:

(1)

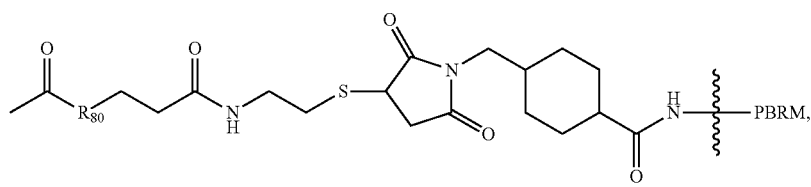

(2)

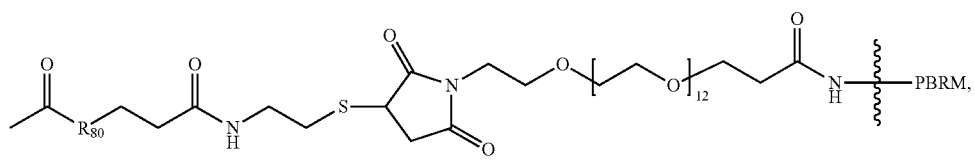

(3)

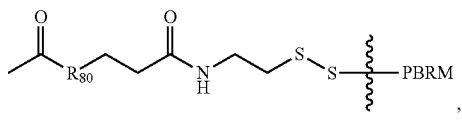

(4)

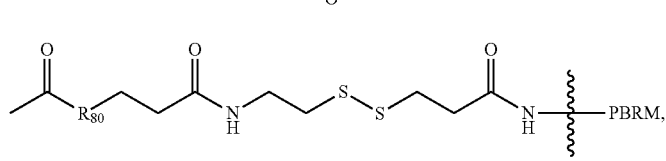

(5)

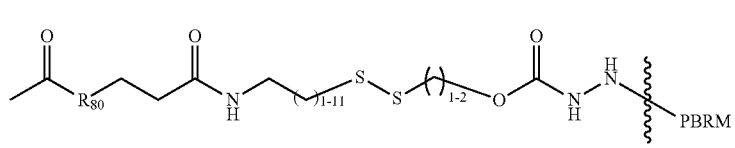

(6)

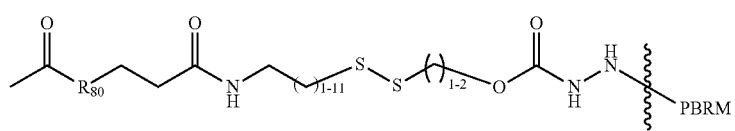

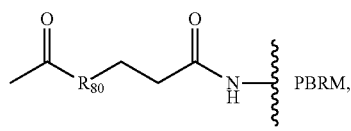(7)
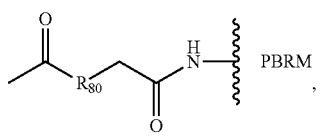(8)
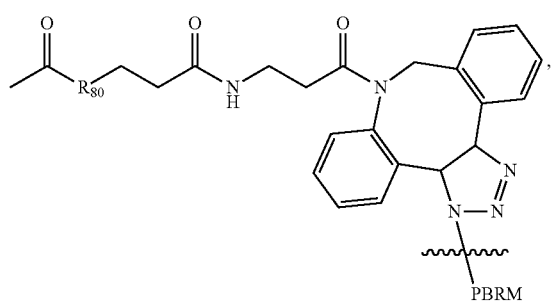(9)
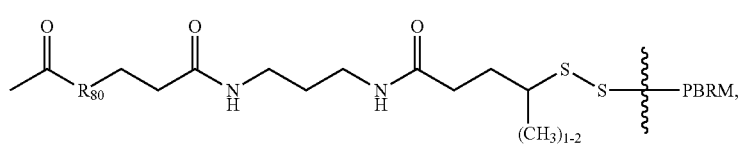(10)
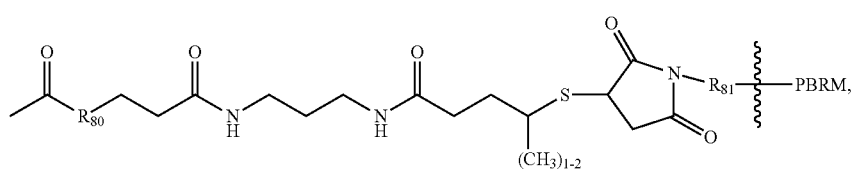(11)
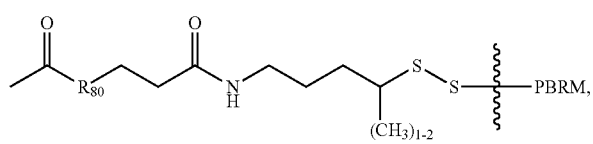(12)
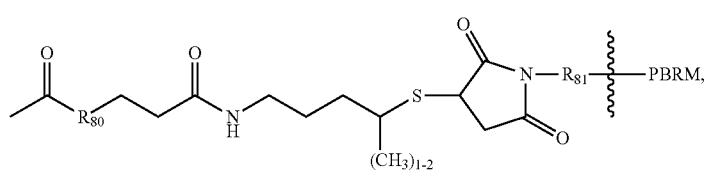(13)
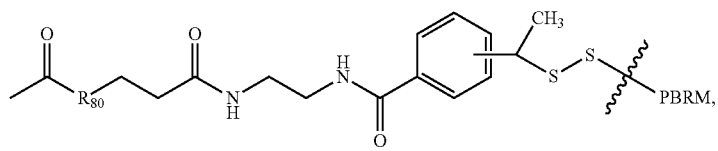(14)
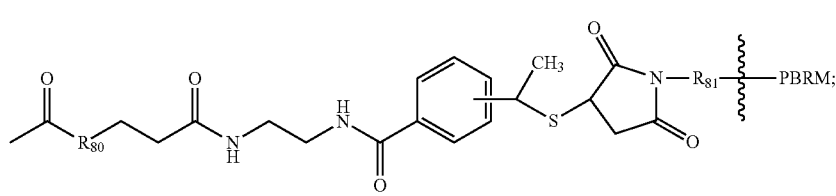(15)
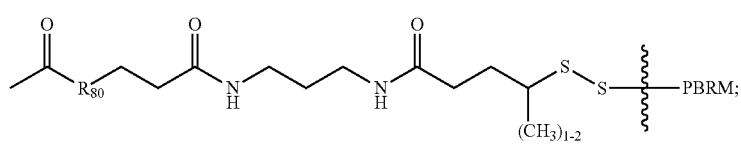(16)

-continued

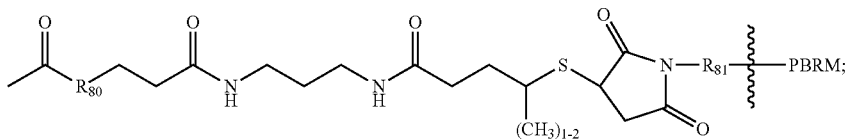
(17)

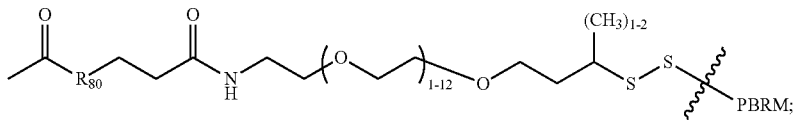
(18)

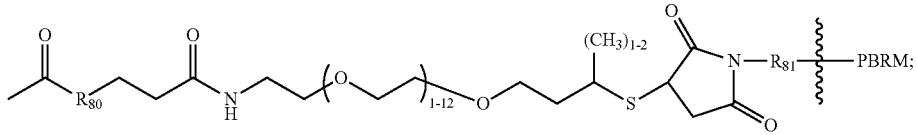
(19)

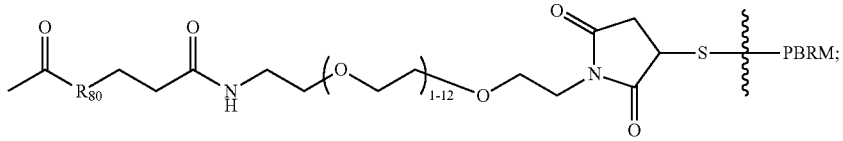
(20)

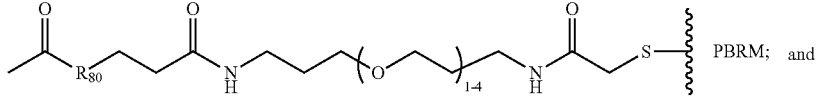
(21)

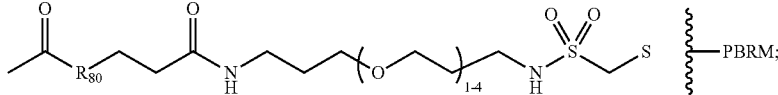
(22)

wherein:

$R_{80}$ is $CH_2$, NH or oxygen; and $R_{81}$ is

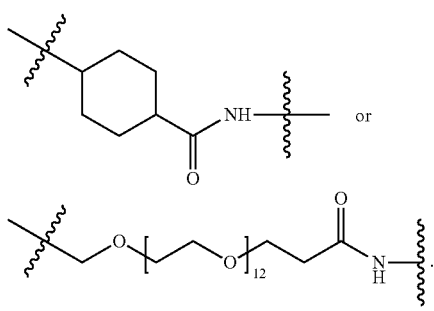

Additional examples of linker $L^D$ and $L^P$ which are suitable for use in the present invention are described in US 2012/0321583 and US 2013/0101546, each of which is hereby incorporated by reference in its entirety.

A "Linker unit" ($L^{D2}$) is a bifunctional compound which can be used to link a Drug unit to the polymer to form Drug-Linker-Polymer Conjugates, or which are useful in the formation of protein-drug-polymer conjugates directed against tumor associated antigens. Such protein-drug-polymer conjugates allow the selective delivery of toxic drugs to tumor cells.

In one embodiment, the Linker unit $L^{D2}$ is a moiety of Formula (Iaa):

$$-A_a-W_w-Y_y-$$  (Iaa)

in which

-A- is a Stretcher unit and is proximal to the polymeric carrier;

a is an integer 0 or 1;

each —W— is independently an amino acid unit;

w is an integer from 0 to 12;

—Y— is a self-immolative or non-self-immolative Spacer unit and is proximal to D; and y is an integer from 0 to 2.

The Linker unit $L^{D2}$ can have one or more of the following features.

For example, at least one of a, w, and y is not 0.

For example, $L^{D2}$ has the Formula: —$W_w$—$Y_y$—, wherein W and Y are as defined herein, neither of w and y is 0, the Spacer unit Y is directly connect to the drug, and the amino acid unit W is directly connect to the polymer.

For example, $L^{D2}$ has the Formula: -$A_a$-$W_w$—, wherein A and W are as defined herein, and neither of w and a is 0.

For example, the $L^{D2}$ linker is any one of the following structures:

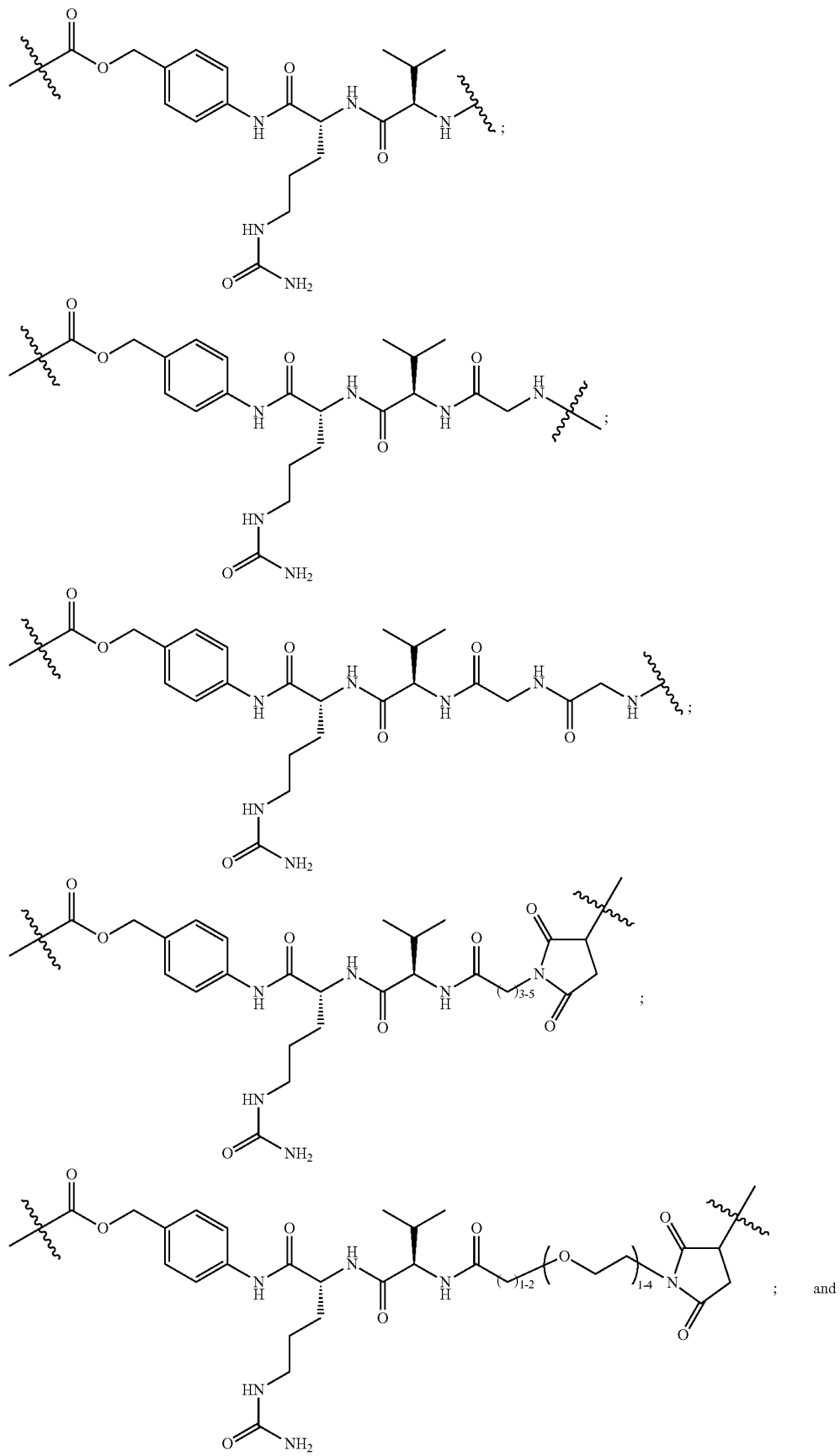

-continued

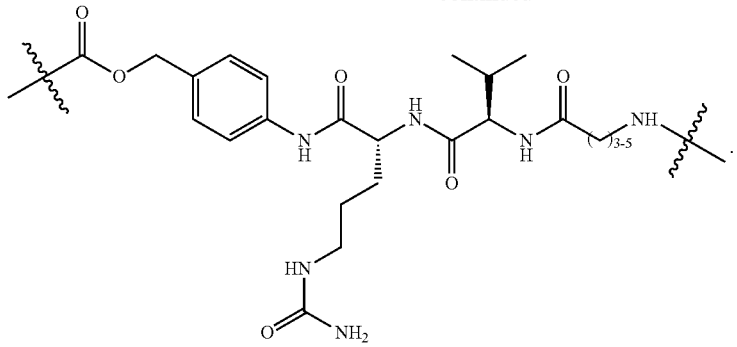

For example, the $L^{D2}$ linker is converted from $L^{D3}$ which has the formula $A'_a$—$W_w$—$Y_y$—
in which
-A' is a moiety capable of converting to a Stretcher unit -A-;
a is an integer 0 or 1;
each —W— is independently an amino acid unit;
w is an integer from 0 to 12;
—Y— is a self-immolative or non-self-immolative Spacer unit and is proximal to D; and
y is an integer from 0 to 2.

For example, $L^{D3}$ is any one of the following structures:

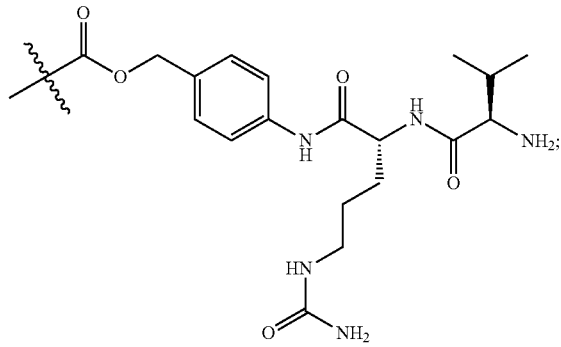

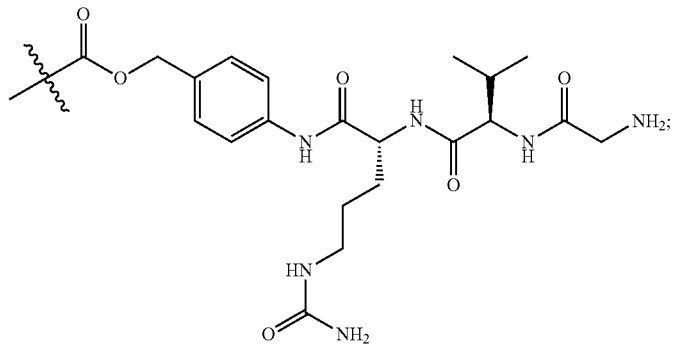

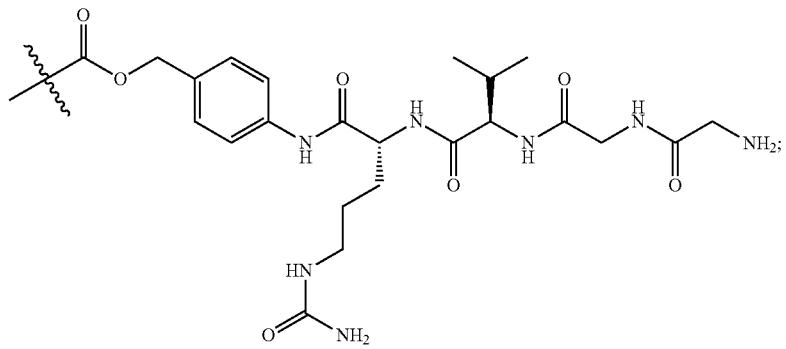

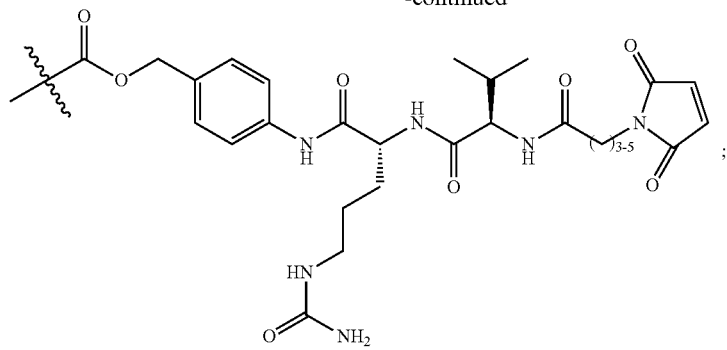

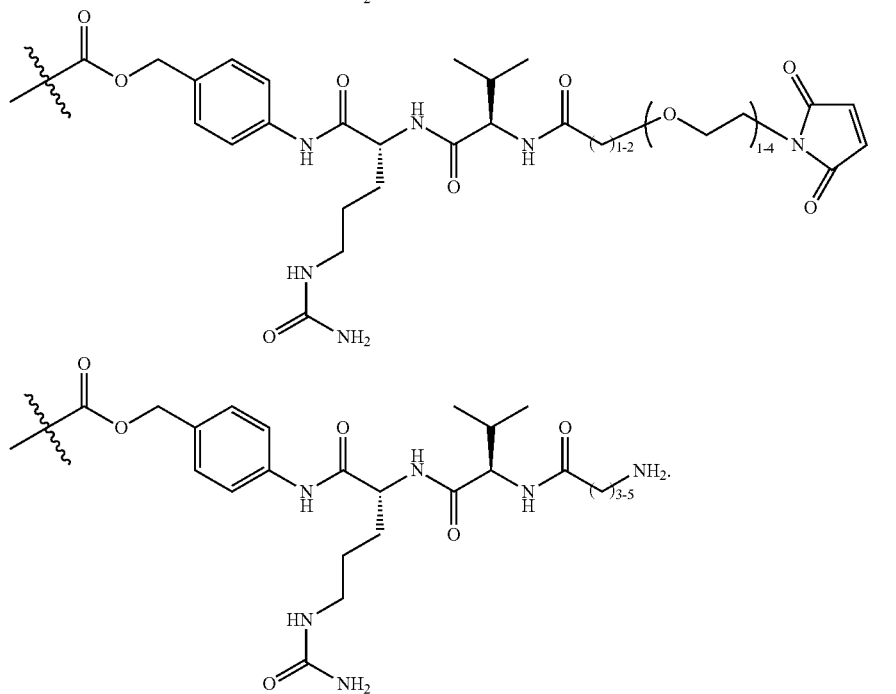

For example, the Drug-Linker-Polymer Conjugates of this invention are formed by reacting $D\text{-}L^{D3}$ or $D\text{-}Y_y\text{-}W_w\text{-}A'_a$ with $L^{D1}$ moiety of the polymer.

While biocleavable linkers preferably are used in the invention, a non-biocleavable linker also can be used to generate the above-described conjugate. A non-biocleavable linker is any chemical moiety that is capable of linking a drug or PBRM, to a polymer in a stable, covalent manner. Thus, non-biocleavable linkers are substantially resistant to acid-induced cleavage, light-induced cleavage, peptidase-induced cleavage, esterase-induced cleavage, and/or disulfide bond cleavage, at conditions under which the drug or polymer remains active.

In one embodiment, a substantial amount of the drug moiety is not cleaved from the conjugate until the protein-polymer-drug conjugate enters a cell with a cell-surface receptor specific for the PBRM of the protein-polymer-drug conjugate, and the drug moiety is cleaved from the protein-polymer-drug conjugate when the protein-polymer-drug conjugate does enter the cell.

In another embodiment, the bioavailability of the protein-polymer-drug conjugate or an intracellular metabolite of the protein-polymer-drug conjugate in a subject is improved when compared to a drug compound or conjugate compris-ing the drug moiety of the protein-polymer-drug conjugate, or when compared to an analog of the compound not having the drug moiety.

In another embodiment, the drug moiety is intracellularly cleaved in a subject from the protein-polymer-drug conjugate, or an intracellular metabolite of the protein-polymer-drug conjugate.

The Stretcher Unit

The Stretcher unit (-A-), when present, is capable of linking a polymer to an amino acid unit (—W—). In this regard the polymer has a linker $-L^{D1}$ that can form a bond with a functional group of a Stretcher unit. Useful functional groups that can be present on a polymer, include, but are not limited to, sulfhydryl (—SH), primary or secondary amine, hydroxyl, aldehyde, ketone, carboxyl, and the like.

In one embodiment, when a is 1, the Stretcher unit forms a single or double bond with an oxygen atom, sulfur atom, carbon atom, or nitrogen atom of the polymer.

For example, the Stretcher unit -A- is

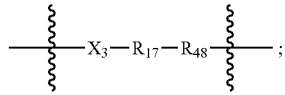

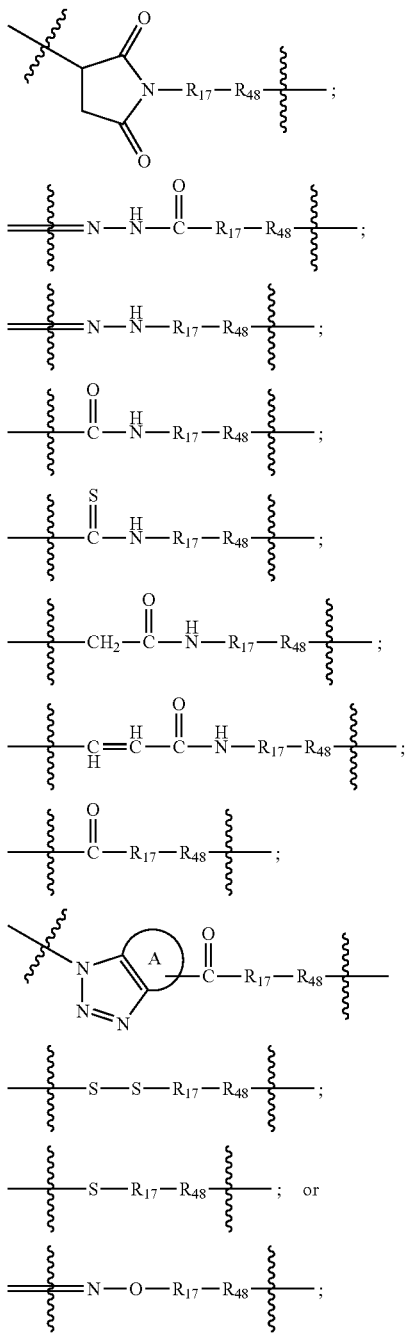

wherein $R_{48}$ is proximal to D and is —C(O), NH or O;

$X_3$ is —O— or —NH;

$R_{17}$ is —$C_{1-10}$ alkylene-, —$C_{3-8}$ carbocyclo-, $C_{1-30}$ heteroalkylene, —O—($C_{1-8}$ alkyl)-, -arylene-, —$C_{1-10}$ alkylene-arylene-, -arylene-$C_{1-10}$ alkylene-, —$C_{1-10}$ alkylene-($C_{3-8}$ carbocyclo)-, —($C_{3-8}$ carbocyclo)-$C_{1-10}$ alkylene-, —$C_{3-8}$ heterocyclo-, —$C_{1-10}$ alkylene-($C_{3-8}$ heterocyclo)-, —($C_{3-8}$ heterocyclo)-$C_{1-10}$ alkylene-, and —$(CH_2CH_2O)_h$—$(CH_2)_c$, in which c is an integer from 0 to 3 and h is an integer from 1 to 12; and ring A is cycloalkyl or heterocycloalkyl.

For example, -A- is

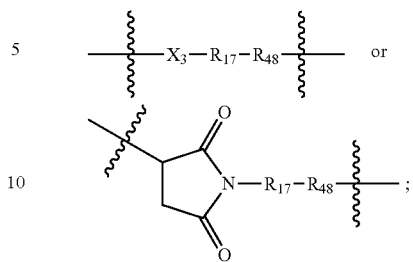

For example, in -A-, —C(O)—$R_{17}$— is —C(O)—$C_{1-10}$ alkylene-, —C(O)—$C_{1-10}$ alkylene-NH—C(O)—$C_{1-10}$ alkylene-, —C(O)—$C_{1-10}$ alkylene-C(O)—NH—$C_{1-10}$ alkylene-, —C(O)—$(CH_2CH_2O)_h$—, —C(O)—$(CH_2CH_2O)_h$—$(CH_2)_{1-3}$, —C(O)—$(CH_2CH_2NH)_h$—$(CH_2)_{1-3}$, —C(O)—$(CH_2CH_2NH)_h$—$(CH_2)_h$—NH—C(O)—$(CH_2)_h$—, —C(O)—($C_{3-8}$ carbocyclo)-, —C(O)-(arylene)-, or —C(O)—($C_{3-8}$ heterocyclo-)-, wherein each h independently is an integer from 1 to 12.

For example, in -A-, —NH—$R_{17}$— is —NH—$C_{1-10}$ alkylene-, —NH—$C_{1-10}$ alkylene-NH—C(O)—$C_{1-10}$ alkylene-, —NH—$C_{1-10}$ alkylene-C(O)—NH—$C_{1-10}$ alkylene-, —NH—$(CH_2CH_2O)h$-, —NH—$(CH_2CH_2O)h$-$(CH_2)_{1-3}$, —NH—$(CH_2CH_2NH)_h$—$(CH_2)_{1-3}$, —NH—$(CH_2CH_2NH)_h$—$(CH_2)_{1-3}$—NH—C(O)—$(CH_2)_h$-, —NH—($C_{3-8}$ carbocyclo)-, —NH-(arylene)-, or —NH—($C_{3-8}$ heterocyclo-)-, wherein each h independently is an integer from 1 to 10.

For example, in -A-, —O—$R_{17}$— is selected from —O—$C_{1-10}$ alkylene-, —O—$C_{1-10}$ alkylene-NH—C(O)—$C_{1-10}$ alkylene-, —O—$C_{1-10}$ alkylene-C(O)—NH—$C_{1-10}$ alkylene-, —O—$(CH_2CH_2O)_h$—, O—$(CH_2CH_2O)h$-$(CH_2)_{1-3}$, —O—($C_{3-8}$ carbocyclo)-, —O-(arylene)-, and —O—($C_{3-8}$ heterocyclo-)-, each h independently is an integer from 1 to 10.

For example, -A- is formed by reacting -A' with a functional group of $L^{D1}$ in the polymeric scaffolds and -A' is:

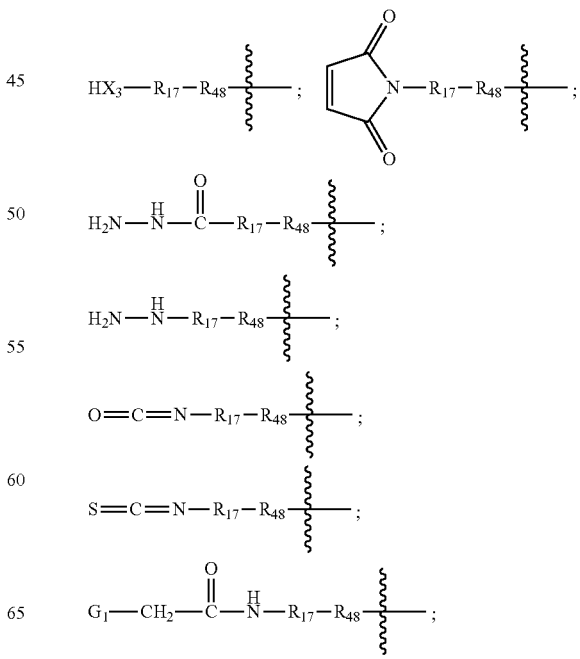

-continued

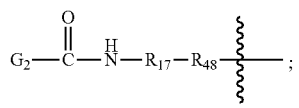

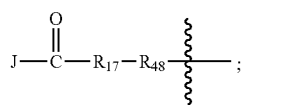

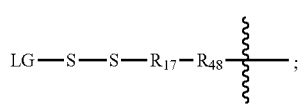

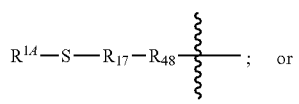

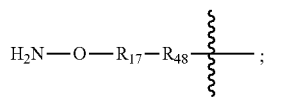

wherein
$X_3$ is —O— or —NH;
G is —Cl, —Br, —I, —OH, —O-mesyl, or —O-tosyl,
$G_2$ is

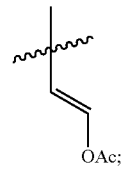

J is —Cl, —Br, —I—, —F, —OH, —O—N-succinimide, —O-(4-nitrophenyl), —O-pentafluorophenyl, —O-tetrafluorophenyl, —O—C(O)—OR$_{38}$, or

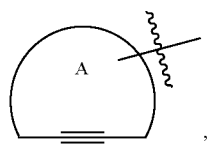

in which $R_{38}$ is $C_{1-8}$ alkyl or $C_{6-10}$ aryl and ring A is cycloalkyl or heterocycloalkyl;

LG is a leaving group;

$R_{17}$ is —$C_{1-10}$ alkylene-, —$C_{3-8}$ carbocyclo-, $C_{1-30}$ heteroalkylene, —O—($C_{1-8}$ alkyl)-, -arylene-, —$C_{1-10}$ alkylene-arylene-, -arylene-$C_{1-10}$ alkylene-, —$C_{1-10}$ alkylene-($C_{3-8}$ carbocyclo)-, —($C_{3-8}$ carbocyclo)-$C_{1-10}$ alkylene-, —$C_{3-8}$ heterocyclo-, —$C_{1-10}$ alkylene-($C_{3-8}$ heterocyclo)-, —($C_{3-8}$heterocyclo)-$C_{1-10}$ alkylene-, and —(CH$_2$CH$_2$O)$_h$—(CH$_2$)$_c$, in which c is an integer from 0 to 3 and h is an integer from 1 to 12;

$R_{48}$ is —C(O), NH or O; and $R^{14}$ is H or a sulfur protecting group.

For example, -A' is

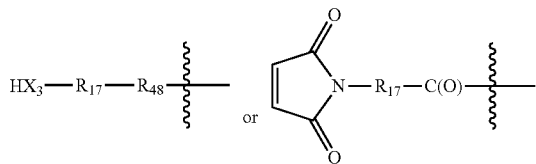

Examples of -A', include, but are not limited to:

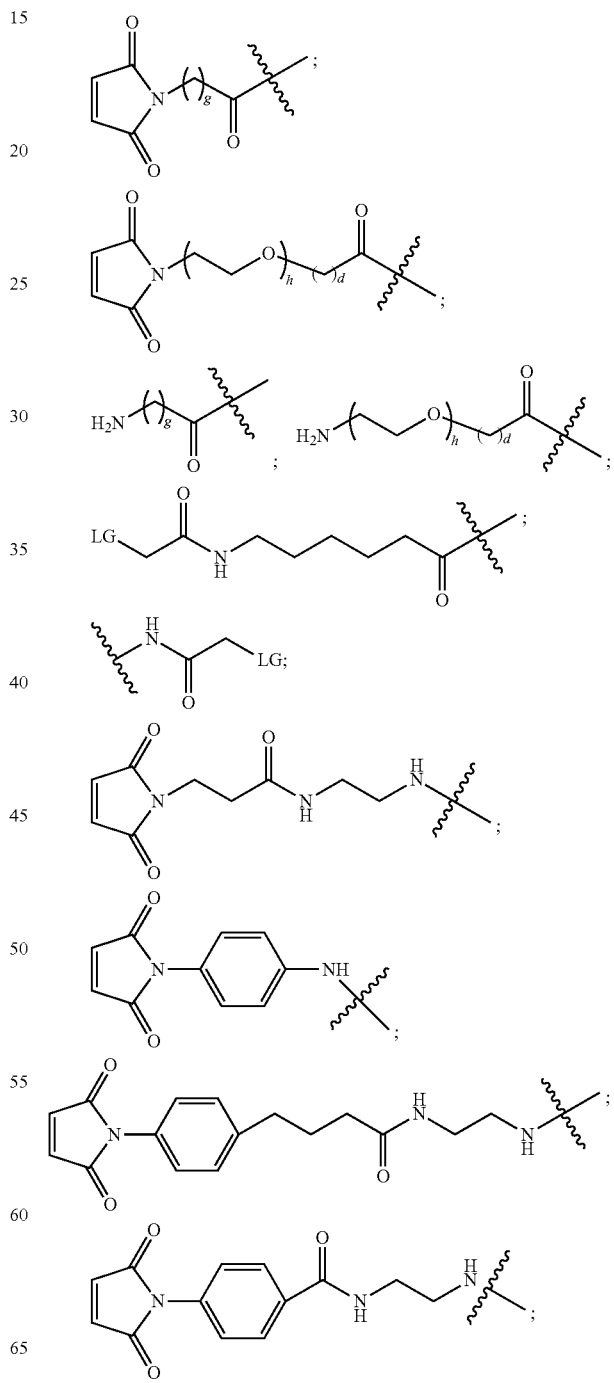

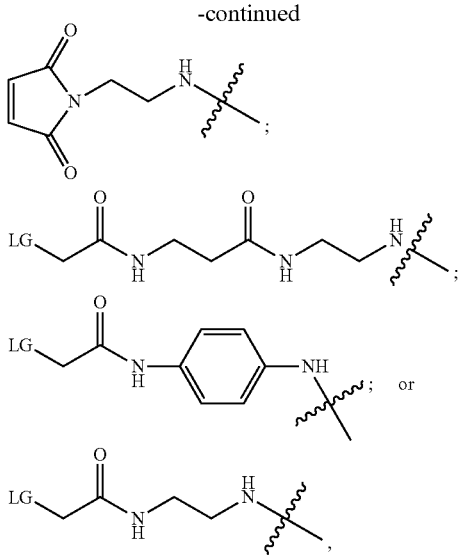

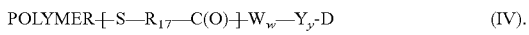

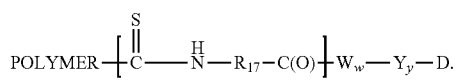

wherein:
  h is an integer from 1 to 12;
  g is an integer from 2 to 6;
  d is an integer from 1 to 3; and
  LG is a leaving group.

In another embodiment, the Stretcher unit is proximal to the polymer via a disulfide bond between a sulfur atom of the polymer unit and a sulfur atom of the Stretcher unit. A representative Stretcher unit of this embodiment is depicted within the square brackets of Formula (IV), wherein $R_{17}$, POLYMER, —W—, —Y—, D, w and y are as defined herein.

$$\text{POLYMER}{-}[{-}S{-}R_{17}{-}C(O){-}]{-}W_w{-}Y_y{-}D \qquad (IV).$$

In yet another embodiment, the reactive group of the Stretcher contains a reactive site that can form a bond with a primary or secondary amino group of a polymer. Example of these reactive sites include, but are not limited to, activated esters such as succinimide esters, 4-nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas (Va) and (Vb), wherein —$R_{17}$—, POLYMER, —W—, —Y—, -D, w and y are as defined herein.

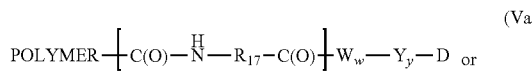

In yet another embodiment of the invention, the reactive group of the Stretcher contains a reactive moiety that is reactive to an aldehyde (—CHO) group that can be present on a polymer. For example, a (—CHO) unit of the polymer can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko, T. et al. Bioconjugate Chem 1991, 2, 133-41. Representative Stretcher units of this embodiment are depicted within the square brackets of Formulas (VIa)-(VIc), wherein —$R_{17}$—, POLYMER, —W—, —Y—, -D, w and y are as defined herein.

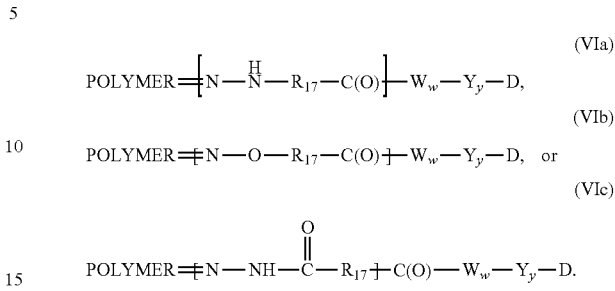

In another embodiment, the Stretcher unit is absent.

The Amino Acid Unit

The Amino Acid unit (—W—), when present, links the Stretcher unit (-A-) to the Spacer unit (—Y—) if the Spacer unit is present, links the Stretcher unit (-A-) to the Drug moiety (D) if the Spacer unit is absent, and links the polymer to the Drug unit if the Stretcher unit and Spacer unit are absent.

—$W_w$— is an amino acid or a dipeptide, tripeptide, tetrapeptide, pentapeptide, hexapeptide, heptapeptide, octapeptide, nonapeptide, decapeptide, undecapeptide or dodecapeptide unit. In some embodiments $W_w$ is a dipeptide.

Each amino acid W can be a natural or unnatural amino acid. Similarly, each amino acid can be a D- or L-isomer. In some embodiments, each W— unit independently has the Formula denoted below in the square brackets, and w is an integer from 0 to 12:

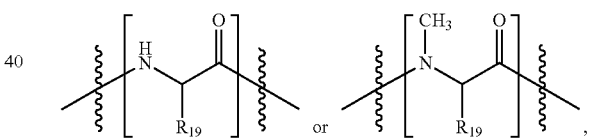

wherein the —C=O is proximal to the Drug moiety (D); and the —NH or —N(CH$_3$) is proximal to the polymer; and $R_{19}$ is hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl, or any one of the following structures:

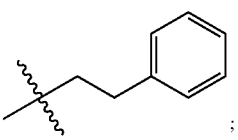

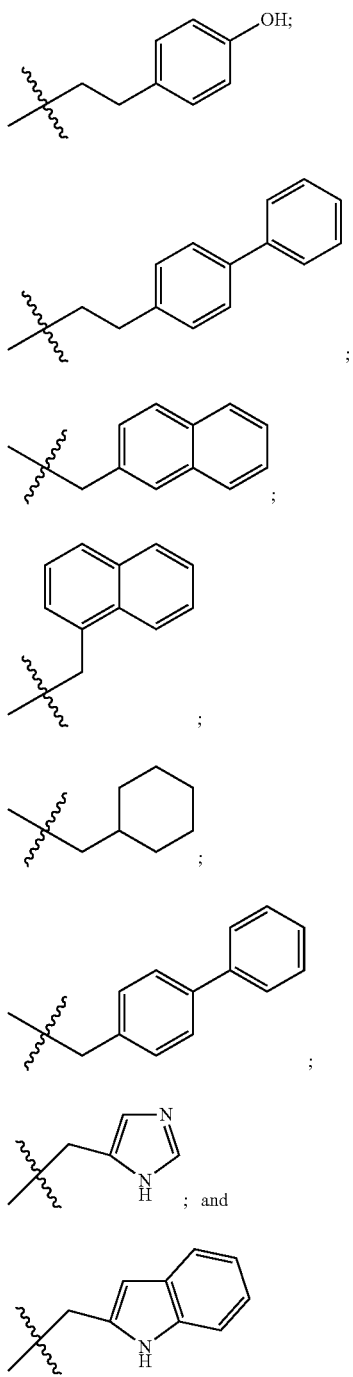

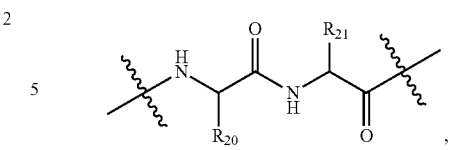

wherein $R_{20}$ and $R_{21}$ are as follows:

| $R_{20}$ | $R_{21}$ |
|---|---|
| benzyl | $-(CH_2)_4NH_2$; |
| methyl | $-(CH_2)_4NH_2$; |
| isopropyl | $-(CH_2)_4NH_2$; |
| isopropyl | $-(CH_2)_3NHCONH_2$; |
| benzyl | $-(CH_2)_3NHCONH_2$; |
| isobenztyl | $-(CH_2)_3NHCONH_2$; |
| sec-butyl | $-(CH_2)_3NHCONH_2$; |
| (indole structure) | $-(CH_2)_3NHCONH_2$; |
| benzyl | methyl; and |
| benzyl | $-(CH_2)_3NHC(=NH)NH_2$; |

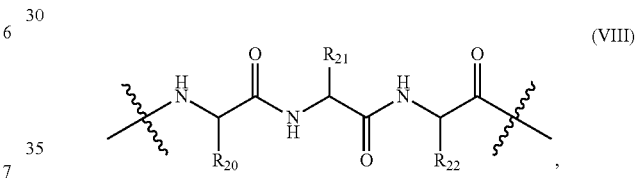

wherein $R_{20}$, $R_{21}$ and $R_{22}$ are as follows:

| $R_{20}$ | $R_{21}$ | $R_{22}$ |
|---|---|---|
| benzyl | benzyl | $-(CH_2)_4NH_2$; |
| isopropyl | benzyl | $-(CH_2)_4NH_2$; and |
| H | benzyl | $-(CH_2)_4NH_2$; |

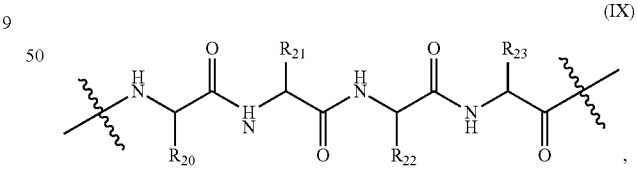

wherein $R_{20}$, $R_{21}$, $R_{22}$ and $R_{23}$ are as follows:

| $R_{20}$ | $R_{21}$ | $R_{22}$ | $R_{23}$ |
|---|---|---|---|
| H | benzyl | isobutyl | H; and |
| methyl | isobutyl | methyl | isobutyl. |

In some embodiments, the linkage between the Amino Acid unit and the Drug unit can be enzymatically cleaved by one or more enzymes, including a tumor-associated protease, to liberate the Drug unit (-D), which in one embodiment is protonated in vivo upon release to provide a Drug (D). Examples of Ww units are represented by Formulas (VII)-(IX):

Exemplary Amino Acid units include, but are not limited to, units of formula (VII) wherein $R_{20}$ is benzyl and $R_{21}$ is $-(CH_2)_4NH_2$; $R_{20}$ is isopropyl and $R_{21}$ is $-(CH_2)_4NH_2$; $R_{20}$ is isopropyl and $R_{21}$ is $-(CH_2)_3NHCONH_2$. Another exemplary Amino Acid unit is a unit of Formula (VIII) wherein $R_{20}$ is benzyl, $R_{21}$ is benzyl, and $R_{22}$ is —$(CH_2)_4NH_2$.

In one embodiment, —$W_w$— is a dipeptide, tripeptide, tetrapeptide or pentapeptide.

When $R_{19}$, $R_{20}$, $R_{21}$, $R_{22}$ or $R_{23}$ is a moiety other than hydrogen, the carbon atom to which $R_{19}$, $R_{20}$, $R_{21}$, $R_{22}$ or $R_{23}$ is attached is chiral.

Each carbon atom to which $R_{19}$, $R_{20}$, $R_{21}$, $R_{22}$ or $R_{23}$ is attached independently is in the (S) or (R) configuration.

In another embodiment, each —W— unit independently is selected from the group consisting of the following amino acids: alanine, arginine, aspartic acid, asparagine, histidine, glycine, glutamic acid, glutamine, phenylalanine, lysine, leucine, serine, tyrosine, threonine, isoleucine, proline, tryptophan, valine, ornithine, penicillamine, β-alanine, aminoalkanoic acid, aminoalkyrioic acid, aminoalkanedioic acid, aminobenzoic acid, amino-heterocyclo-alkanoic acid, heterocyclo-carboxylic acid, citrulline, statine, diaminoalkanoic acid, and derivatives thereof.

In another embodiment, each —W— unit independently is selected from the group consisting of the following L-(natural) amino acids: alanine, arginine, aspartic acid, asparagine, histidine, glycine, glutamic acid, glutamine, phenylalanine, lysine, leucine, serine, tyrosine, threonine, isoleucine, tryptophan and valine.

In another embodiment, each —W— unit independently is selected from the group consisting of the following D-isomers of these natural amino acids: alanine, arginine, aspartic acid, asparagine, histidine, glycine, glutamic acid, glutamine, phenylalanine, lysine, leucine, serine, tyrosine, threonine, isoleucine, tryptophan and valine. In some embodiments, the amino acid unit (—$W_1$—) proximal to the Drug unit (D) is not a D amino acid.

Exemplary alanine and derivatives thereof include, but are not limited to, alanine (Ala), N-alkyl-alanine, dehydroalanine, 4-thiazolylalanine, 2-pyridylalanine, 3-pyridylalanine, 4-pyridylalanine, β-(1-naphthyl)-alanine, β-(2-naphthyl)-alanine, α-aminobutyric acid, β-chloro-alanine, β-cyano-alanine, β-cyclopentyl-alanine, β-cyclohexyl-alanine, β-iodo-alanine, β-cyclopentenyl-alanine, β-tBu-alanine, β-cyclopropyl-alanine, β-diphenyl-alanine, β-fluoroalanine, β-piperazinyl-alanine with the piperazine ring protected or not, β-(2-quinolyl)-alanine, β-(1,2,4-triazol-1-yl)-alanine, β-ureido-alanine, H-β-(3-benzothienyl)-Ala-OH, and H-β-(2-thienyl)-Ala-OH.

Exemplary arginine and derivatives thereof include, but are not limited to, arginine (Arg), N-alkyl-arginine, H-Arg (Me)-OH, H-Arg($NH_2$)—OH, H-Arg($NO_2$)—OH, H-Arg (Ac)$_2$-OH, H-Arg(Me)$_2$-OH (asymmetrical), H-Arg(Me)$_2$-OH (symmetrical), 2-amino-4-(2'-hydroxyguanidino)-butyric acid (N-ω-hydroxy-nor-arginine) and homoarginine.

Exemplary aspartic acid and derivatives thereof include, but are not limited to, aspartic acid (Asp), N-alkyl-aspartic acid, and H-Asp(OtBu)-OH.

Exemplary asparagine and derivatives thereof include, but are not limited to, asparagine (Asn), N-alkyl-asparagine, and isoasparagine (H-Asp-$NH_2$).

Exemplary cysteine (Cys) derivatives (containing no free SH group) thereof include, but are not limited to, H-Cys (Acm)-OH, H-Cys(Trt)-OH, H-Cys(tBu)-OH, H-Cys(Bzl)-OH, H-Cys(Et)-OH, H-Cys(SO3H)—OH, H-Cys(aminoethyl)-OH, H-Cys(carbamoyl)-OH, H-Cys(phenyl)-OH, H-Cys(Boc)-OH, and H-Cys(hydroxyethyl)-OH.

Exemplary histidine and derivatives thereof include, but are not limited to, histidine (His), N-alkyl-histidine, H-His (Boc)-OH, H-His(Bzl)-OH, H-His(1-Me)-OH, H-His(1-Tos)-OH, H-2,5-diiodo-His-OH, and H-His(3-Me)-OH.

Exemplary glycine and derivatives thereof include, but are not limited to, glycine (Gly), N-alkyl-glycine, H-propargylglycine,

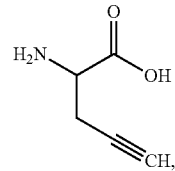

α-aminoglycine (protected or not), β-cyclopropyl-glycine, cyclopentyl-glycine, cyclohexyl-glycine, α-allylglycine, t-Butyl-glycine, neopentylglycine, and phenylglycine.

Exemplary glutamic acid and derivatives thereof include, but are not limited to, glutamic acid (Glu), N-alkyl-glutamic acid, H-Glu(OtBu)-OH, H-γ-hydroxy-Glu-OH, H-γ-methylene-Glu-OH, H-γ-carboxy-Glu(OtBu)$_2$-OH, and pyroglutamic acid.

Exemplary glutamine and derivatives thereof include, but are not limited to, glutamine (Gln), N-alkyl-glutamine, isoglutamine (H-Glu-$NH_2$), H-Gln(Trt)-OH, and H-Gln(isopropyl)-OH.

Exemplary phenylalanine and derivatives thereof include, but are not limited to, phenylalanine (Phe), N-alkyl-phenylalanine, H-p-amino-Phe-OH, H-p-amino-Phe(Z)—OH, H-p-bromo-Phe-OH, H-p-Benzyl-Phe-OH, H-p-tBu-Phe-OH, H-p-carboxy-Phe(OtBu)-OH, H-p-carboxy-Phe-OH, H-p-cyano-Phe-OH, H-p-fluoro-Phe-OH, H-3,4-dichloro-Phe-OH, H-p-iodo-Phe-OH, H-p-nitro-Phe-OH, H-p-methyl-Phe-OH, H-pentafluoro-Phe-OH, H-m-fluoro-Phe-OH, H-α-Me-Phe-OH, H-4-phenyl-Phe-OH, homopenylalanine, chloro-phenylalanine and β-homophenylalanine.

Exemplary lysine and derivatives thereof include, but are not limited to, lysine (Lys), N-alkyl-lysine, H-Lys(Boc)-OH, H-Lys(Ac)-OH, H-Lys(Formyl)-OH, H-Lys(Me)2-OH, H-Lys(nicotinoyl)-OH, H-Lys(Me)3-OH, H-trans-4,5-dehydro-Lys-OH, H-Lys(Aloc)-OH, H-s-hydroxy-Lys-OH, H-δ-hydroxy-Lys(Boc)-OH, H-Lys(acetamidoyl)-OH, and H-Lys(isopropyl)-OH.

Exemplary leucine and derivatives thereof include, but are not limited to, leucine (Leu), N-alkyl-leucine, 4,5-dehydroleucine, H-α-Me-Leu-OH, homoleucine, norleucine, and t-leucine.

Exemplary methionine and derivatives thereof include, but are not limited to, methionine (Met), H-Met(O)—OH, and H-Met(O)$_2$—OH.

Exemplary serine and derivatives thereof include, but are not limited to, serine (Ser), N-alkyl-serine, H-Ser(Ac)-OH, H-Ser(tBu)-OH, H-Ser(Bzl)-OH, H-Ser(p-chloro-Bzl)-OH, H-β-(3,4-dihydroxyphenyl)-Ser-OH, H-β-(2-thienyl)-Ser-OH, isoserine N-alkyl-isoserine, and 3-phenylisoserine.

Exemplary tyrosine and derivatives thereof include, but are not limited to, tyrosine (Tyr), N-alkyl-tyrosine, H-3,5-dinitro-Tyr-OH, H-3-amino-Tyr-OH, H-3,5-dibromo-Tyr-OH, H-3,5-diiodo-Tyr-OH, H-Tyr(Me)-OH, H-Tyr(tBu)-OH, H-Tyr(Boc)-OH, H-Tyr(Bzl)-OH, H-Tyr(Et)-OH, H-3-iodo-Tyr-OH, and H-3-nitro-Tyr-OH.

Exemplary threonine and derivatives thereof include, but are not limited to, threonine (Thr), N-alkyl-threonine, allo-threonine, H-Thr(Ac)-OH, H-Thr(tBu)-OH, and H-Thr (Bzl)-OH.

Exemplary isoleucine and derivatives thereof include, but are not limited to, isoleucine (Ile), N-alkyl-isoleucine, allo-isoleucine, and norleucine.

Exemplary tryptophan and derivatives thereof include, but are not limited to, tryptophan (Trp), N-alkyl-tryptophan, H-5-Me-Trp-OH, H-5-hydroxy-Trp-OH, H-4-Me-Trp-OH, H-α-Me-Trp-OH, H-Trp(Boc)-OH, H-Trp(Formyl)-OH, and H-Trp(Mesitylene-2-sulfonyl)-OH.

Exemplary proline and derivatives thereof include, but are not limited to, praline (Pro), N-alkyl-proline, homoproline, thioproline, hydroxyproline (H-Hyp-OH), H-Hyp(tBu)-OH, H-Hyp(Bzl)-OH, H-3,4-dehydro-Pro-OH, 4-keto-proline, α-Me-Pro-OH, and H-4-fluoro-Pro-OH.

Exemplary valine and derivatives thereof include, but are not limited to, valine (Val), N-alkyl-valine, H-α-Me-Val-OH, and norvaline.

Exemplary ornithine and derivatives thereof include, but are not limited to, ornithine, N-alkyl-ornithine, H-Orn(Boc)-OH, H-Orn(Z)—OH, H-α-difluoro-Me-Orn-OH (Eflornitine), and H-Orn(Aloc)-OH.

Exemplary penicillamine and derivatives thereof include, but are not limited to, penicillamine, H-penicillamine(Acm)-OH (H-β,β-dimethylcys(Acm)-OH) and N-alkyl-penicillamine.

Exemplary β-alanine and derivatives thereof include, but are not limited to, β-alanine, N-alkyl-β-alanine, and dehydro-alanine.

Exemplary aminoalkynoic acid and derivatives thereof include, but are not limited to, N-alkylaminoalkanoic acid, aminobutyric acid, 4-(neopentyloxysulfonyl)-aminobutyric acid, ε-aminocaproic acid, α-aminoisobutyric acid, piperidylacetic acid, 3-aminopropionic acid, 3-amino-3-(3-pyridye-propionic acid, 5-aminopentanioic acid (aminovaleric acid), 6-amino-4-hexynoic acid, and 6-(Boc-amino)-4-hexynoic acid.

Exemplary aminoalkanedioic acid and derivatives thereof include, but are not limited to, N-alkylaminoalkanedioic acid, 2-aminohexanedioic acid, 2-aminoheptanedioic acid, 2-aminooctanedioic acid (H-Asu-OH).

Exemplary aminobenzoic acid and derivatives thereof include, but are not limited to, N-alkylaminobenzoic acid, 2-aminobenzoic acid, 3-aminobenzoic acid, and 4-aminobenzoic acid.

Exemplary amino-heterocyclo-alkanoic acid and derivatives thereof include, but are not limited to, N-alkylamino-heterocyclo-alkanoic acids, 4-amino-1-methyl-1H-imidazol-2-carboxylic acid, 4-amino-1-methyl-1H-pyrrole-2-carboxylic acid, 4-amino-piperidine-4-carboxylic acid (H-Pip-OH; 1-protected or not), 3-amino-3-(3-pyridyl)-propionic acid.

Exemplary heterocyclo-carboxylic acid and derivatives thereof include, but are not limited to, azetidine-2-carboxylic acid, azetidine-3-carboxylic acid, piperidine-4-carboxylic acid, and thiazolidine-4-carboxylic acid.

Exemplary citrulline and derivatives thereof include, but are not limited to, citrulline (cit), N-alkyl-citrulline, thiocitrulline, S-methyl-thiocitrulline, and homocitrulline.

Exemplary statine and derivatives thereof include, but are not limited to, statine, N-alkyl-statine, cyclohexylstatine, and phenylstatine.

Exemplary diaminoalkanoic acid (Dab) and derivatives thereof include, but are not limited to, N-alkyl-diaminoalkanoic acids, N,N-dialkylamino-alkanoic acids, α,γ-diaminobutyric acid (H-Dab-OH), H-Dab(Aloc)-OH, H-Dab(Boc)-OH, H-Dab(Z)—OH, α,β-diaminopropionic acid and its side-chain protected versions.

Useful -Ww- units-Drug unit can be designed and optimized in their selectivity for enzymatic cleavage by a particular enzyme, for example, a tumor-associated protease. In one embodiment, a linkage between the -Ww- unit and the Drug unit is that which cleavage is catalyzed by cathepsin B, C and D, or a plasmin protease.

In another embodiment, $W_1$, the first W unit attached to the carboxyl-terminus of the Drug unit of formula D, cannot form a secondary amide with the C-terminal amino acid of the Drug unit of formula D.

In one embodiment, w is 1. In certain embodiments, w is an integer ranging from 2 to 12. In one embodiment, -Ww- is a dipeptide, tripeptide, tetrapeptide or pentapeptide. In another embodiment, w is 2.

In certain embodiments, the Amino Acid unit can comprise only natural amino acids. In other embodiments, the Amino Acid unit can comprise only non-natural amino acids. In some embodiments, the Amino Acid unit can comprise a natural amino acid linked to a non-natural amino acid. In some embodiments, the Amino Acid unit can comprise a natural amino acid linked to a D-isomer of a natural amino acid.

In another embodiment, at least one W is an L-amino acid. In another group of embodiments, at least one W is a D-amino acid. In some embodiments, at least one W has a chiral center in the S-configuration. In some embodiments, at least one W has a chiral center in the R-configuration.

In one embodiment, the Amino Acid unit, Ww, is citrulline-valine; lysine-phenylalanine; citrulline-phenylalanine; citrulline-leucine; citrulline-valine-glycine-glycine; glycine-phenylalanine-glycine-glycine; valine; proline; leucine or isoleucine. In another embodiment, the Amino Acid unit is phenylalanine-lysine (i.e., fk). In yet another embodiment, the Amino Acid unit is N-methylvaline-citrulline. In some embodiments the Amino acid unit is selected from the group consisting of -Methionine-(L)Lysine-, and -Asparagine-(L)Lysine-. In one embodiment of the Amino Acid unit, Ww is selected from the group consisting of -Tyrosine-(D)Aspartic Acid-, -Norvaline-(D)Aspartic Acid-, -Phenylglycine-(D)Lysine-, -Methionine-(D)Lysine-, and -Asparagine-(D)Lysine-. In yet another embodiment, the Amino Acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

In one embodiment, the Amino Acid unit, $—W_w—$, is citrulline-valine.

The Spacer Unit

The Spacer unit (—Y—), when present, links an Amino Acid unit to the Drug moiety when an Amino Acid unit is present. Alternately, the Spacer unit links the Stretcher unit to the Drug moiety when the Amino Acid unit is absent. The Spacer unit also links the Drug moiety to the polymer when both the Amino Acid unit and Stretcher unit are absent.

Spacer units are of two general types: self-immolative and non-self-immolative. A non-self-immolative Spacer unit is one in which part or all of the Spacer unit remains bound to the Drug moiety after cleavage, particularly enzymatic, of an Amino Acid unit from the Drug-Linker-Polymer Conjugate or the Drug-Linker Compound. Examples of a non-self-immolative Spacer unit include, but are not limited to a (glycine-glycine) Spacer unit and a glycine Spacer unit (both depicted in FIG. 1) (infra). When an exemplary compound containing a glycine-glycine Spacer unit or a glycine Spacer unit undergoes enzymatic cleavage via a tumor-cell associated-protease, a cancer-cell-associated protease or a lymphocyte-associated protease, a glycine-glycine-Drug moiety or a glycine-Drug moiety is cleaved from

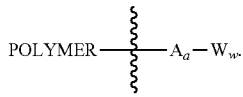

In one embodiment, an independent hydrolysis reaction takes place within the target cell, cleaving the glycine-Drug moiety bond and liberating the Drug.

In another embodiment, —$Y_y$— is a p-aminobenzyl alcohol (PAB) unit (see FIGS. 2 and 3) whose phenylene portion is substituted with $Q_q$, wherein Q is —$C_{1-8}$ alkyl, —O—($C_{1-8}$ alkyl), -halogen, -nitro or -cyano; and q is an integer from 0 to 4.

In one embodiment, a non-self-immolative Spacer unit (—Y—) is -Gly-Gly-. In another embodiment, a non-self-immolative the Spacer unit (—Y—) is -Gly-.

In one embodiment, a Drug-Linker Compound or a Drug-Linker Polymer Conjugate is provided in which the Spacer unit is absent (y is 0), or a pharmaceutically acceptable salt or solvate thereof.

Figure 2:
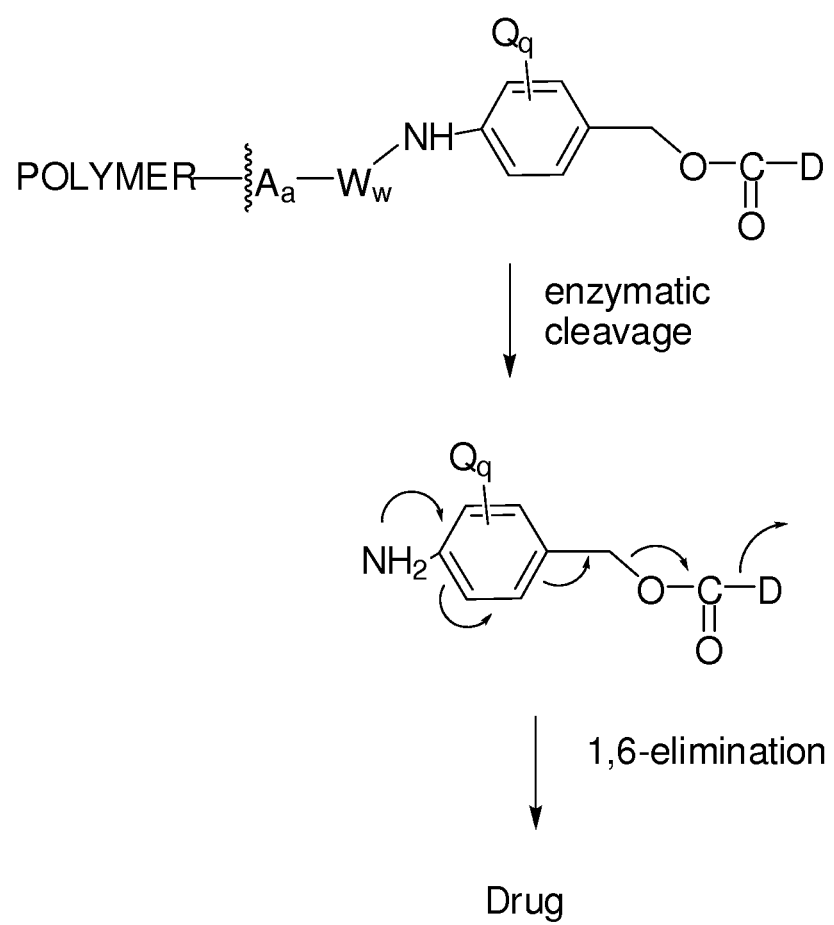
FIG. 2 shows a scheme of a possible mechanism of Drug release from a PAB group which is attached directly to -D via a carbamate or carbonate group.

Alternatively, an Exemplary Compound containing a self-immolative Spacer unit can release -D without the need for a separate hydrolysis step. In this embodiment, —Y— is a PAB group that is proximal to —$W_w$— via the amino nitrogen atom of the PAB group, and connected directly to -D via a carbonate, carbamate or ether group. Without being bound by any particular theory or mechanism, FIG. 2 depicts a possible mechanism of Drug release of a PAB group which is attached directly to -D via a carbamate or carbonate group as described in Toki et al. (2002) J. Org. Chem. 67:1866-1872.

In FIG. 2 Q is —$C_{1-8}$ alkyl, —O—($C_{1-8}$ alkyl), -halogen, -nitro or -cyano; q is an integer from 0 to 4.

Figure 3:
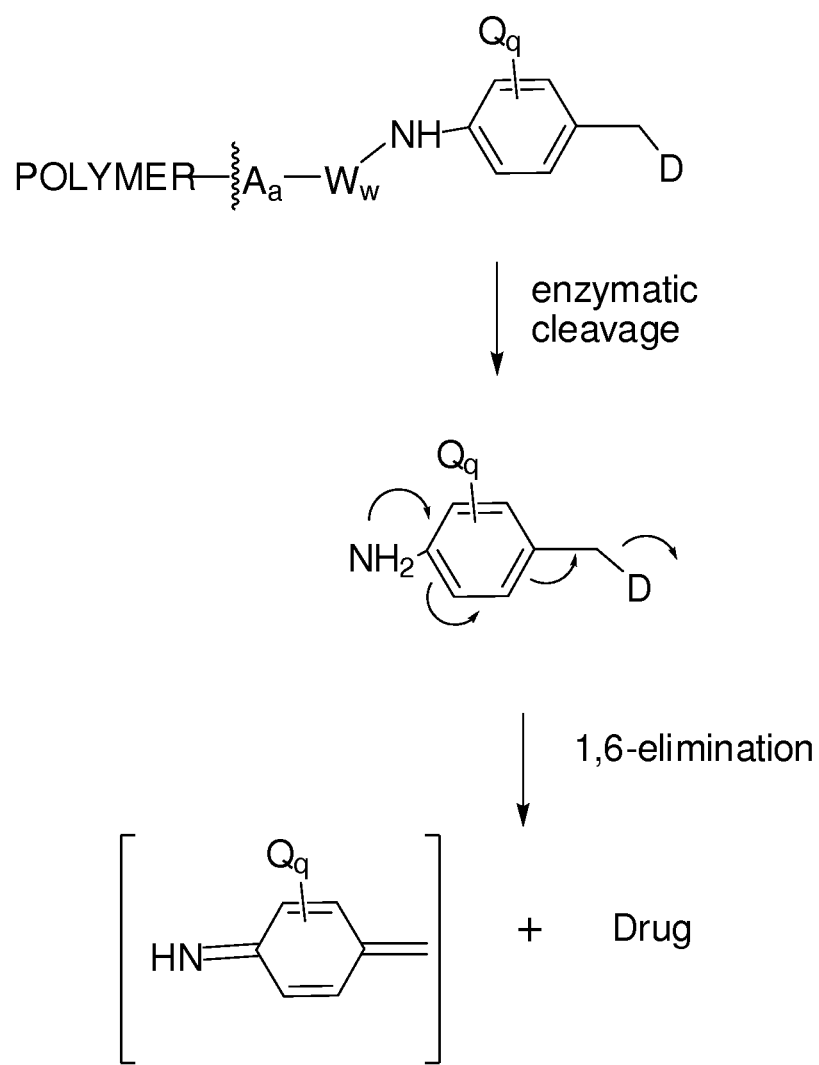
FIG. 3 shows a scheme of a possible mechanism of Drug release from a PAB group which is attached directly to -D via an ether or amine linkage.

Without being bound by any particular theory or mechanism, FIG. 3 depicts a possible mechanism of Drug release of a PAB group which is attached directly to -D via an ether or amine linkage.

In FIG. 3 Q is —$C_{1-8}$ alkyl, —O—($C_{1-8}$), -halogen, -nitro or -cyano; q is an integer from 0 to 4.

Other examples of self-immolative spacers include, but are not limited to, aromatic compounds that are electronically similar to the PAB group such as 2-aminoimidazol-5-methanol derivatives (Hay et al. (1999) Bioorg. Med. Chem. Lett. 9:2237) and ortho or para-aminobenzylacetals. Spacers can be used that undergo cyclization upon amide bond hydrolysis, such as substituted and unsubstituted 4-aminobutyric acid amides (Rodrigues et al., Chemistry Biology, 1995, 2, 223), appropriately substituted bicyclo[2.2.1] and bicyclo[2.2.2] ring systems (Storm, et al., J. Amer. Chem. Soc., 1972, 94, 5815) and 2-aminophenylpropionic acid amides (Amsberry, et al., J. Org. Chem., 1990, 55, 5867). Elimination of amine-containing drugs that are substituted at the a-position of glycine (Kingsbury, et al., J. Med. Chem., 1984, 27, 1447) are also examples of self-immolative spacer useful in Exemplary Compounds.

In one embodiment, Spacer units (—$Y_y$—) are represented by Formulas (X)-(XII):

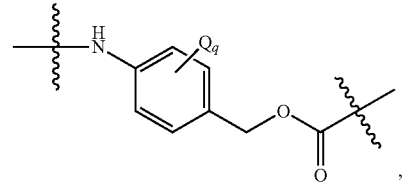
(X)

wherein Q is —$C_{1-8}$ alkyl, —O—($C_{1-8}$ alkyl), -halogen, -nitro or -cyano; and q is an integer from 0 to 4;

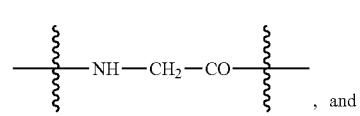
(XI)

, and

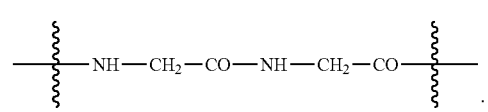
(XII)

In another embodiment the Spacer unit is:

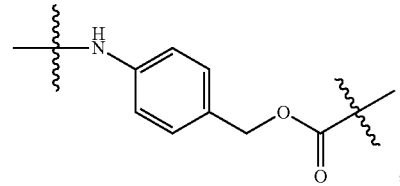

wherein the C=O is proximal to the drug moiety.

Conjugates or Polymeric Scaffolds

Conjugates of the invention comprise one or more occurrences of D, where D is an auristatin compound, wherein the one or more occurrences of D may be the same or different.

In certain other embodiments, one or more occurrences of PBRM is attached to the polymeric carrier, wherein the one or more occurrences of PBRM may be the same or different. In certain other embodiments, one or more polymer carriers that contains one or more occurrences of D are connected to a PBRM (e.g., an antibody).

As discussed more generally above, in certain embodiments, each polymeric carrier independently, has about 0.1 to about 25% monomers comprising a D, more preferably about 0.5 to about 20%, more preferably about 1 to about 15%, and even more preferably about 2 to about 10%.

In certain embodiments, the conjugate of this invention is of Formula (I):

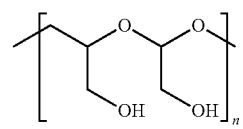
(I)

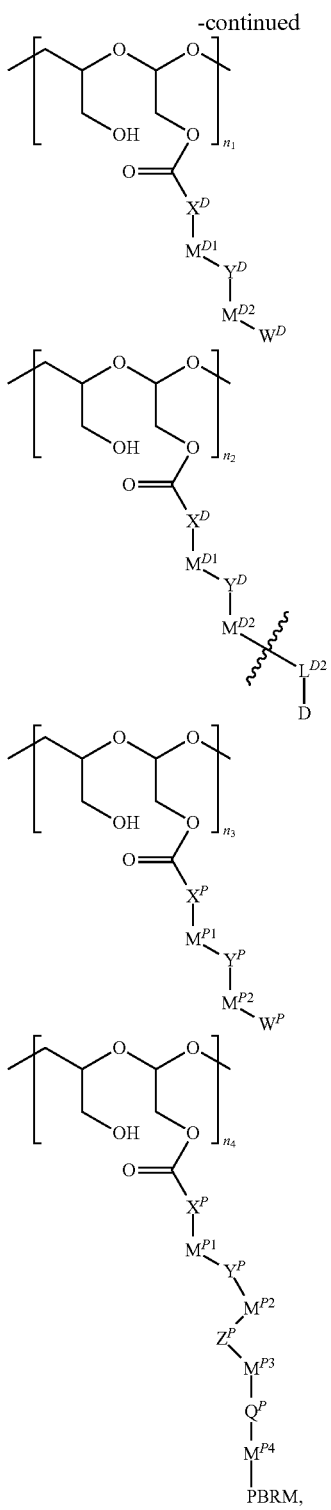

wherein:

each of n, $n_1$, $n_2$, $n_3$, and $n_4$, is the molar fraction of the corresponding polymer unit ranging between 0 and 1; $n+n_1+n_2+n_3+n_4=1$; provided that none of n, $n_2$, and $n_4$ is 0.

For example, the ratio between $n_2$ and $n_4$ is greater than 1:1 and ≤200:1.

For example, the ratio between $n_2$ and $n_4$ is between 10:1 and 50:1.

For example, the ratio between $n_2$ and $n_4$ is between 30:1 and 50:1.

For example, the ratio between $n_2$ and $n_4$ is about 50:1, 25:1, 10:1, 5:1 or 2:1.

In certain embodiments, the conjugates are formed in several steps. These steps include (1) modifying a polymer so that it contains a functional group that can react with a functional group of the drug or its derivative; (2) reacting the modified polymer with the drug or its derivative so that the drug is linked to the polymer; (3) modifying the polymer-drug conjugate so that the polymer contains a functional group that can react with a functional group of the PBRM or its derivative; and (4) reacting the modified polymer-drug conjugate with the PBRM or its derivative to form the conjugate of this invention. Step (3) may be omitted if the modified polymer produced by step (1) contains a functional group that can react with a functional group of the PBRM or its derivative.

In another embodiment the conjugates are formed in several steps: (1) modifying a polymer so that it contains a functional group that can react with a functional group of a first drug or its derivative; (2) reacting the modified polymer with the first drug or its derivative so that the first drug is linked to the polymer; (3) modifying the polymer-drug conjugate so that it contains a different functional group that can react with a functional group of a second drug or its derivative (4) reacting the modified polymer-drug conjugate with the second drug or its derivative so that the second drug is linked to the polymer-drug conjugate; (5) modifying the polymer-drug conjugate containing two different drugs so that the polymer contains a functional group that can react with a functional group of the PBRM or its derivative; and (6) reacting the modified polymer-drug conjugate of step (5) with the PBRM or its derivative to form the conjugate of this invention. Steps (5) and (6) may be repeated if two different PBRM or their derivatives are to be conjugated to form a polymer-drug conjugate comprising two different drugs and two different PBRMs.

In yet another embodiment, the conjugates are formed in several steps. These steps include (1) modifying a polymer so that it contains a functional group that can react with a functional group of the drug or its derivative; (2) further modifying the polymer so that it also contains a functional group that can react with a functional group of the PBRM or its derivative; (3) reacting the modified polymer with the drug or its derivative so that the drug is linked to the polymer; and (4) reacting the modified polymer-drug conjugate with the PBRM or its derivative to form the conjugate of this invention. The sequence of steps (1) and (2) or that of steps (3) and (4) can be reversed. Further either step (1) or (2) may be omitted if the modified polymer contains a functional group that can react with both a functional group of the drug or its derivatives and a functional group of the PBRM or its derivative.

In another embodiment the conjugates are formed in several steps: (1) modifying a polymer so that it contains a functional group that can react with a functional group of a first drug or its derivative; (2) further modifying a polymer so that it contains a functional group that can react with a functional group of the PBRM or its derivative; (3) reacting the modified polymer with the first drug or its derivative so that the first drug is linked to the polymer; (4) modifying the polymer-drug conjugate so that it contains a different functional group that can react with a functional group of a second drug or its derivative (5) reacting the modified polymer-drug conjugate with the second drug or its derivative so that the second drug is linked to the polymer-drug conjugate; (6) reacting the modified polymer-drug conjugate containing two different drugs so that the polymer with the PBRM or its derivative to form the conjugate of this invention. Step (6) may be repeated if two different PBRM or their derivatives are to be conjugated to form a polymer-drug conjugate comprising two different drugs and two different PBRMs. Step (4) may be carried out after step (1) so that the modified polymer contains two different functional groups that can react with two different drugs or their derivatives. In this embodiment, the modified polymer containing two different functional group that can react with two different drugs or their derivatives can be further modified so that it contains a functional group that can react with a functional group of the PBRM or its derivative; prior to the reaction of the modified polymer with either the two different drugs (step (3) and step (5) or PBRM (step (6)).

The biodegradable biocompatible conjugates of the invention can be prepared to meet desired requirements of biodegradability and hydrophilicity. For example, under physiological conditions, a balance between biodegradability and stability can be reached. For instance, it is known that molecules with molecular weights beyond a certain threshold (generally, above 40-100 kDa, depending on the physical shape of the molecule) are not excreted through kidneys, as small molecules are, and can be cleared from the body only through uptake by cells and degradation in intracellular compartments, most notably lysosomes. This observation exemplifies how functionally stable yet biodegradable materials may be designed by modulating their stability under general physiological conditions (pH=7.5±0.5) and at lysosomal pH (pH near 5). For example, hydrolysis of acetal and ketal groups is known to be catalyzed by acids, therefore polyals will be in general less stable in acidic lysosomal environment than, for example, in blood plasma. One can design a test to compare polymer degradation profile at, for example, pH=5 and pH=7.5 at 37° C. in aqueous media, and thus to determine the expected balance of polymer stability in normal physiological environment and in the "digestive" lysosomal compartment after uptake by cells. Polymer integrity in such tests can be measured, for example, by size exclusion HPLC. One skilled on the art can select other suitable methods for studying various fragments of the degraded conjugates of this invention.

In many cases, it will be preferable that at pH=7.5 the effective size of the polymer will not detectably change over 1 to 7 days, and remain within 50% from the original for at least several weeks. At pH=5, on the other hand, the polymer should preferably detectably degrade over 1 to 5 days, and be completely transformed into low molecular weight fragments within a two-week to several-month time frame. Although faster degradation may be in some cases preferable, in general it may be more desirable that the polymer degrades in cells with the rate that does not exceed the rate of metabolization or excretion of polymer fragments by the cells. Accordingly, in certain embodiments, the conjugates of the present invention are expected to be biodegradable, in particular upon uptake by cells, and relatively "inert" in relation to biological systems. The products of carrier degradation are preferably uncharged and do not significantly shift the pH of the environment. It is proposed that the abundance of alcohol groups may provide low rate of polymer recognition by cell receptors, particularly of phagocytes. The polymer backbones of the present invention generally contain few, if any, antigenic determinants (characteristic, for example, for some polysaccharides and polypeptides) and generally do not comprise rigid structures capable of engaging in "key-and-lock" type interactions in vivo unless the latter are desirable. Thus, the soluble, crosslinked and solid conjugates of this invention are predicted to have low toxicity and bioadhesivity, which makes them suitable for several biomedical applications.

In certain embodiments of the present invention, the biodegradable biocompatible conjugates can form linear or branched structures. For example, the biodegradable biocompatible polyal conjugates of the present invention can be chiral (optically active). Optionally, the biodegradable biocompatible polyal conjugates of the present invention can be scalemic.

In certain embodiments, the conjugates of the invention are water-soluble. In certain embodiments, the conjugates of the invention are water-insoluble. In certain embodiments, the inventive conjugate is in a solid form. In certain embodiments, the conjugates of the invention are colloids. In certain embodiments, the conjugates of the invention are in particle form. In certain embodiments, the conjugates of the invention are in gel form.

This invention also features a polymeric scaffold useful for conjugating with a PBRM to form a polymer-drug-PBRM conjugate described herein. The scaffold comprises a polymeric carrier, one or more $L^D$-D connected to the polymeric carrier, and one or more $L^P$ connected to the polymeric carrier which is suitable for connecting a PBRM to the polymeric carrier, wherein:

each occurrence of D is independently an auristatin compound;

the polymeric carrier is a polyacetal or a polyketal, $L^D$ is a first linker having the structure:

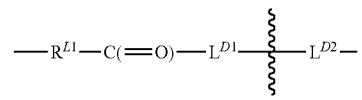

with $R^{L1}$ connected to an oxygen atom of the polymeric carrier and $L^{D1}$ connected to D, and

in

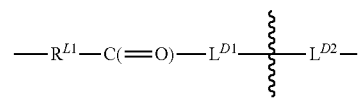

denotes direct or indirect attachment of $L^{D2}$ to $L^{D1}$, and $L^D$ contains a biodegradable bond so that when the bond is broken, D is released in an active form for its intended therapeutic effect;

$L^{D1}$ is a carbonyl-containing moiety;

$L^{D2}$ is a moiety of Formula (Iaa) as defined herein;

$L^P$ is a second linker having the structure: $-R^{L2}-C(=O)-L^{P1}$ with $R^{L2}$ connected to an oxygen atom of the polymeric carrier and $L^{P1}$ suitable for connecting and not yet connected directly or indirectly to a PBRM, and each occurrence of the second linker is distinct from each occurrence of the first linker;

each of $R^{L1}$ and $R^{L2}$ independently is absent, alkyl, heteroalkyl, cycloalkyl, or heterocycloalkyl; and $L^{P1}$ is a moiety containing a functional group that is capable of forming and not yet formed a covalent bond with a functional group of a PBRM.

For example, $L^P$ is a linker having the structure:

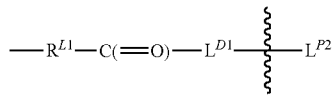

in which $L^{P2}$ is a moiety containing a functional group that is capable of forming and not yet formed a covalent bond with a functional group of a PBRM, and

in

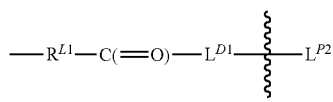

denotes direct or indirect attachment of $L^{P2}$ to $L^{D1}$.

For example, the functional group of $L^{P1}$ or $L^{P2}$ is selected from —$SR^P$, —S—S-LG, maleimido, and halo, in which LG is a leaving group and $R^P$ is H or a sulfur protecting group.

For example, $L^{D1}$ comprises —X—$(CH_2)_v$—C(=O)— with X directly connected to the carbonyl group of $R^{L1}$—C(=O), in which X is $CH_2$, O, or NH, and v is an integer from 1 to 6.

For example, $L^{P1}$ or $L^{P2}$ contains a biodegradable bond.

For example, each of $R^{L1}$ and $R^{L2}$ is absent.

For example, the polymeric carrier of the scaffold of the invention is a polyacetal, e.g., a PHF having a molecular weight (i.e., MW of the unmodified PHF) ranging from about 2 kDa to about 300 kDa. The selection of a polymeric carrier with a specific MW range may depend on the size of the PBRM to be conjugated with. For example, for conjugating a PBRM having a molecular weight of 40 kDa or greater (e.g., 60 kDa or greater, 80 kDa or greater, 100 kDa or greater, 120 kDa or greater, 140 kDa or greater, 160 kDa or greater, or 180 kDa or greater; or 200 kDa or greater, or about 40-200 kDa, 40-180 kDa, 40-140 kDa, 60-200 kDa, 60-180 kDa, 60-140 kDa, 80-200 kDa, 80-180 kDa, 80-140 kDa, 100-200 kDa, 100-180 kDa, or 100-140 kDa), the polymeric carrier of the scaffold of the invention is a polyacetal, e.g., a PHF having a molecular weight (i.e., MW of the unmodified PHF) ranging from about 2 kDa to about 40 kDa (e.g., about 6-20 kDa or about 8-15 kDa).

For example, for conjugating a PBRM having a molecular weight of 60 kDa to 120 kDa, the polymeric carrier of the scaffold of the invention is a polyacetal, e.g., a PHF having a molecular weight (i.e., MW of the unmodified PHF) ranging from about 8 kDa to about 40 kDa (e.g., about 8-30 kDa, about 8-20 kDa or about 8-15 kDa). For example the PHF has a molecular weight of about 10 kDa, 20 kDa, 30 kDa or 40 kDa.

PBRMs in this molecular weight range, include but are not limited to, for example, camelids, scFvFc, Fab2, and the like.

For example, for conjugating a PBRM having a molecular weight of 140 kDa to 180 kDa, the polymeric carrier of the scaffold of the invention is a polyacetal, e.g., a PHF having a molecular weight (i.e., MW of the unmodified PHF) ranging from about 2 kDa to about 40 kDa (e.g., about 6-20 kDa or about 8-15 kDa). For example the PHF has a molecular weight of about 8 kDa, 10 kDa or 15 kDa.

PBRMs in this molecular weight range, include but are not limited to, for example, full length antibodies, such as, IgG and IgM.

For example, for conjugating a PBRM having a molecular weight of 200 kDa or less (e.g., 120 kDa or less, 80 kDa or less, 60 kDa or less, 40 kDa or less, 20 kDa or less or 10 kDa or less), the polymeric carrier of the scaffold of the invention is a polyacetal, e.g., a PHF having a molecular weight (i.e., MW of the unmodified PHF) ranging from about 20 kDa to about 300 kDa (e.g., about 20-150 kDa, about 30-150 kDa, about 50-150 kDa, about 30-100 kDa, or about 50-100 kDa).

For example, for conjugating a PBRM having a molecular weight of 4 kDa to 80 kDa (e.g., 4-20 kDa, 20-30 kDa, or 30-70 kDa), the polymeric carrier of the scaffold of the invention is a polyacetal, e.g., a PHF having a molecular weight (i.e., MW of the unmodified PHF) ranging from about 20 kDa to about 300 kDa (e.g., about 20-150 kDa, about 30-150 kDa, about 50-150 kDa, about 30-100 kDa, or about 50-100 kDa).

For example, for conjugating a PBRM having a molecular weight of 80 kDa or less (e.g., 70 kDa or less, 60 kDa or less, 50 kDa or less or 40 kDa or less), the polymeric carrier of the scaffold of the invention is a polyacetal, e.g., a PHF having a molecular weight (i.e., MW of the unmodified PHF) ranging from about 20 kDa to about 300 kDa (e.g., about 20-150 kDa, about 30-150 kDa, about 50-150 kDa, about 30-100 kDa, or about 50-100 kDa). For example the PHF has a molecular weight of about 50 kDa, 70 kDa or 100 kDa.

PBRMs in this molecular weight range, include but are not limited to, for example, antibody fragments such as, for example Fabs.

For example, for conjugating a PBRM having a molecular weight of 30 kDa or less (e.g., about 20 kDa or less), the polymeric carrier of the scaffold of the invention is a polyacetal, e.g., a PHF having a molecular weight (i.e., MW of the unmodified PHF) ranging from about 20 kDa to about 300 kDa (e.g., about 20-150 kDa, about 30-150 kDa, about 50-150 kDa, about 30-100 kDa, or about 50-100 kDa). For example the PHF has a molecular weight of about 30 kDa, 40 kDa, 50 kDa, 70 kDa, 100 kDa, 120 kDa or 150 kDa.

PBRMs in this molecular weight range, include but are not limited to, for example, antibody fragments, such as, scFv.

For example, for conjugating a PBRM having a molecular weight of 20 kDa or less (e.g., 10 kDa or less), the polymeric carrier of the scaffold of the invention is a polyacetal, e.g., a PHF having a molecular weight (i.e., MW of the unmodified PHF) ranging from about 20 kDa to about 300 kDa (e.g., about 20-150 kDa, about 30-150 kDa, about 50-150 kDa, about 30-100 kDa, or about 50-100 kDa). For example the PHF has a molecular weight of about 30 kDa, 40 kDa, 50 kDa, 70 kDa, 100 kDa, 120 kDa or 150 kDa.

PBRMs in this molecular weight range, include but are not limited to, for example, small proteins and peptides.

For example, the scaffold is of Formula (Ibb):

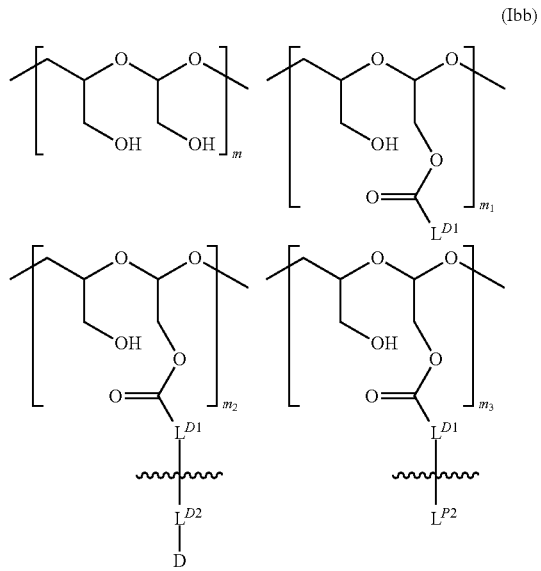

wherein:
m is an integer from 1 to about 2200,
$m_1$ is an integer from 1 to about 660,
$m_2$ is an integer from 1 to about 300,
$m_3$ is an integer from 1 to about 110, and
the sum of m, $m_1$, $m_2$ and $m_3$ ranges from about 15 to about 2200.

For example, when the PHF in Formula (Ibb) has a molecular weight ranging from about 2 kDa to about 40 kDa (i.e., the sum of m, $m_1$, $m_2$, and $m_3$ ranging from about 15 to about 300), $m_2$ is an integer from 1 to about 40, $m_3$ is an integer from 1 to about 18, and/or $m_1$ is an integer from 1 to about 140 (e.g., $m_1$ being about 1-90).

For example, when the PHF in Formula (Ibb) has a molecular weight ranging from about 6 kDa to about 20 kDa (i.e., the sum of m, $m_1$, $m_2$, and $m_3$ ranging from about 45 to about 150), $m_2$ is an integer from 2 to about 20, $m_3$ is an integer from 1 to about 9, and/or $m_1$ is an integer from 1 to about 75 (e.g., $m_1$ being about 4-45).

For example, when the PHF in Formula (Ibb) has a molecular weight ranging from about 8 kDa to about 15 kDa (i.e., the sum of m, $m_1$, $m_2$, and $m_3$ ranging from about 60 to about 110), $m_2$ is an integer from 2 to about 15, $m_3$ is an integer from 1 to about 7, and/or $m_1$ is an integer from 1 to about 55 (e.g., $m_1$ being about 4-30).

For example, when the PHF in Formula (Ibb) has a molecular weight ranging from 20 kDa to 300 kDa (i.e., the sum of m, $m_1$, $m_2$, and $m_3$ ranging from about 150 to about 2200), $m_2$ is an integer from 3 to about 300, $m_3$ is an integer from 1 to about 110, and/or $m_1$ is an integer from 1 to about 660 (e.g., $m_1$ being about 10-250).

For example, when the PHF in Formula (Ibb) has a molecular weight ranging from 20 kDa to 150 kDa (i.e., the sum of m, $m_1$, $m_2$, and $m_3$, ranging from about 150 to about 1100), $m_2$ is an integer from 3 to about 150, $m_3$ is an integer from 1 to about 55, and/or $m_1$ is an integer from 1 to about 330 (e.g., $m_1$ being about 10-330 or about 15-100). This scaffold can be used, for example, for conjugating a PBRM having a molecular weight of about 4 kDa to about 80 kDa.

For example, when the PHF in Formula (Ibb) has a molecular weight ranging from 40 kDa to 150 kDa (i.e., the sum of m, $m_1$, $m_2$, and $m_3$ ranging from about 300 to about 1100), $m_2$ is an integer from 4 to about 150, $m_3$ is an integer from 1 to about 75 (e.g., from 1 to about 55), and/or $m_1$ is an integer from 1 to about 330 (e.g., $m_1$ being about 15-100).

For example, when the PHF in Formula (Ibb) has a molecular weight ranging from 30 kDa to 100 kDa (i.e., the sum of m, $m_1$, $m_2$, and $m_3$ ranging from about 220 to about 740), $m_2$ is an integer from 3 to 100 (e.g., 5-100), $m_3$ is an integer from 1 to about 40, and/or $m_1$ is an integer from 1 to about 220 (e.g., $m_1$ being about 15-80).

Drug-Linker-Polymer Conjugates

For example, the scaffold further comprises a PBRM connected to the polymeric carrier via $L^P$.

For example, when the PHF has a molecular weight ranging from 20 kDa to 300 kDa, (e.g., about 20-150 kDa, about 30-150 kDa, about 50-150 kDa, about 30-100 kDa, or about 50-100 kDa), the number of drugs per PHF (e.g., $m_2$) is an integer from about 3 to about 300, (e.g., about 3 to about 150 or about 3 to about 100). This scaffold can be used, for example, for conjugating a PBRM having a molecular weight of 200 kDa or less (e.g., 80 kDa or less, 60 kDa or less, 40 kDa or less, 20 kDa or less or 10 kDa or less). In this embodiment the ratio of PBRM per PHF is between about 1:1 and about 60:1, for example, between about 1:1 and about 30:1; between about 1:1 and about 20:1, between about 1:1 and about 10:1, between about 1:1 and about 9:1, between about 1:1 and about 8:1, between about 1:1 and about 7:1, between about 1:1 and about 6:1, between about 1:1 and about 5:1, between about 1:1 and about 4:1, between about 1:1 and about 3:1, or between about 1:1 and about 2:1. See, for example, Formula (Icc).

For example, the scaffold further comprises a PBRM connected to the polymeric carrier via $L^P$. For example, one or more PBRMs are connected to one drug-carrying polymeric carrier.

For example, the scaffold (e.g., a PBRM-polymer-drug conjugate) is of Formula (Icc):

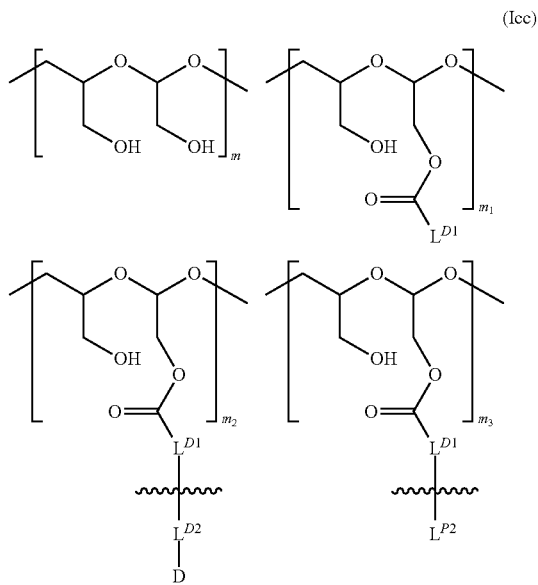

-continued

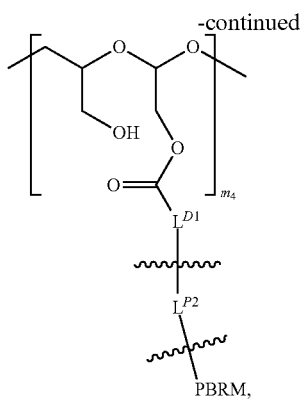

wherein:

between $L^{P2}$ and PBRM in

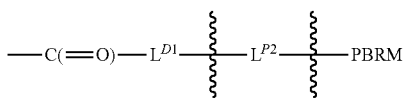

denotes direct or indirect attachment of PBRM to $L^{P2}$, each occurrence of PBRM independently has a molecular weight of less than 200 kDa (e.g., less than 80 kDa), m is an integer from 1 to about 2200,
$m_1$ is an integer from 1 to about 660,
$m_2$ is an integer from 3 to about 300,
$m_3$ is an integer from 0 to about 110,
$m_4$ is an integer from 1 to about 60; and
the sum of m, $m_1$, $m_2$, $m_3$ and $m_4$ ranges from about 150 to about 2200

For example, in Formula (Icc), $m_1$ is an integer from about 10 to about 660 (e.g., about 10-250).

For example, when the PHF in Formula (Icc) has a molecular weight ranging from 20 kDa to 150 kDa (i.e., the sum of m, $m_1$, $m_2$, $m_3$, and $m_4$ ranging from about 150 to about 1100), $m_2$ is an integer from 3 to about 150, $m_3$ is an integer from 1 to about 55, $m_4$ is an integer from 1 to about 30, and/or $m_1$ is an integer from 1 to about 330 (e.g., $m_1$ being about 10-330 or about 15-100). The PBRM in Formula (Icc), can have, for example, a molecular weight of about 4 kDa to about 70 kDa.

For example, when the PHF in Formula (Icc) has a molecular weight ranging from about 30 kDa to about 100 kDa (i.e., the sum of m, $m_1$, $m_2$, $m_3$, and $m_4$ ranging from about 225 to about 740), $m_2$ is an integer from 3 to about 100, $m_3$ is an integer from 1 to about 40, $m_4$ is an integer from 1 to about 20, and/or $m_1$ is an integer from 1 to about 220 (e.g., $m_1$ being about 15-80). In this embodiment the ratio of PBRM per PHF is between about 1:1 to 10:1, between about 1:1 and about 9:1, between about 1:1 and about 8:1, between about 1:1 and about 7:1, between about 1:1 and about 6:1, between about 1:1 and about 5:1, between about 1:1 and about 4:1, between about 1:1 and about 3:1, or between about 1:1 and about 2:1.

PBRMs in this molecular weight range, include but are not limited to, for example, small proteins and peptides.

For example, when the PHF has a molecular weight ranging from 20 kDa to 150 kDa, (e.g., 50-100 kDa), the number of drugs per PHF (e.g., $m_2$) is an integer from about 3 to about 150 (e.g., about 3 to about 100). This scaffold can be used, for example, for conjugating a PBRM having a molecular weight of about 30 kDa to about 70 kDa In this embodiment the ratio of PBRM per PHF is between about 1:1 and about 30:1, between about 1:1 and about 10:1, between about 1:1 and about 9:1, between about 1:1 and about 8:1, between about 1:1 and about 7:1, between about 1:1 and about 6:1, between about 1:1 and about 5:1, between about 1:1 and about 4:1, between about 1:1 and about 3:1, or between about 1:1 and about 2:1.

PBRMs in this molecular weight range, include but are not limited to, for example, antibody fragments such as, for example Fab.

Alternatively or additionally, one or more drug-carrying polymeric carriers are connected to one PBRM. For example, the scaffold (e.g., a PBRM-polymer-drug conjugate) comprises a PBRM with a molecular weight of greater than 40 kDa and one or more D-carrying polymeric carriers connected to the PBRM, in which each of the D-carrying polymeric carrier independently is of Formula (Idd):

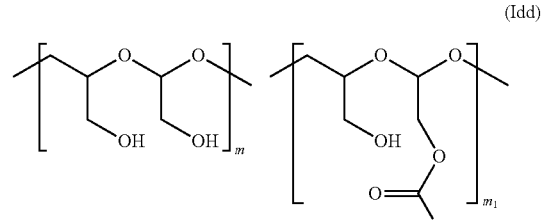

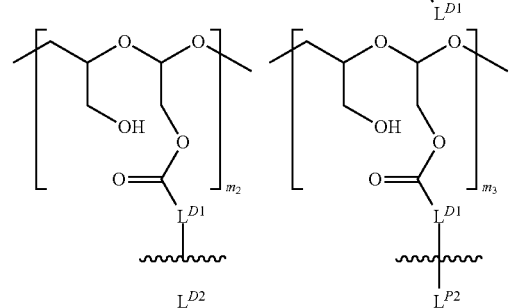

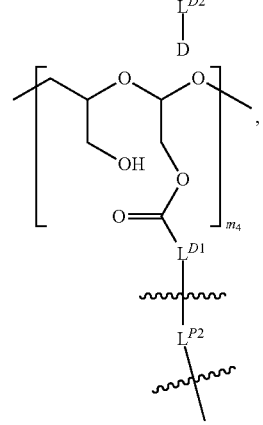

wherein:
terminal

in

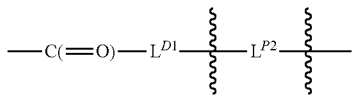

denotes direct or indirect attachment of $L^{P2}$ to PBRM such that the $L^{P2}$-D carrying polymeric carrier is connected to the PBRM, m is an integer from 1 to 300,
$m_1$ is an integer from 1 to 140,
$m_2$ is an integer from 1 to 40,
$m_3$ is an integer from 0 to 18,
$m_4$ is an integer from 1 to 10; and
the sum of m, $m_1$, $m_2$, $m_3$, and $m_4$ ranges from 15 to 300; provided that the total number of $L^{P2}$ attached to the PBRM is 10 or less.

For example, in Formula (Idd), $m_1$ is an integer from 1 to about 120 (e.g., about 1-90) and/or $m_3$ is an integer from 1 to about 10 (e.g., about 1-8).

For example, when the PHF in Formula (Idd) has a molecular weight ranging from about 6 kDa to about 20 kDa (i.e., the sum of m, $m_1$, $m_2$, $m_3$, and $m_4$ ranging from about 45 to about 150), $m_2$ is an integer from 2 to about 20, $m_3$ is an integer from 1 to about 9, and/or $m_1$ is an integer from 1 to about 75 (e.g., $m_1$ being about 4-45).

For example, when the PHF in Formula (Idd) has a molecular weight ranging from about 8 kDa to about 15 kDa (i.e., the sum of m, $m_1$, $m_2$, $m_3$, and $m_4$ ranging from about 60 to about 110), $m_2$ is an integer from 2 to about 15, $m_3$ is an integer from 1 to about 7, and/or $m_1$ is an integer from 1 to about 55 (e.g., $m_1$ being about 4-30).

For example, when the PHF has a molecular weight ranging from 2 kDa to 40 kDa, (e.g., about 6-20 kDa or about 8-15 kDa), the number of drugs per PHF (e.g., m2) is an integer from 1 to about 40, (e.g., about 2-20 or about 2-15). This scaffold can be used, for example, for conjugating a PBRM having a molecular weight of 40 kDa or greater (e.g., 60 kDa or greater; 80 kDa or greater; or 100 kDa or greater; 120 kDa or greater; 140 kDa or greater; 160 kDa or greater or 180 kDa or greater). In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, or between about 1:1 and about 1:2.

For example, when the PHF has a molecular weight ranging from 2 kDa to 40 kDa, (e.g., about 6-20 kDa or about 8-15 kDa), the number of drugs per PHF (e.g., m2) is an integer from 1 to about 40 (e.g., about 1:10 or about 1-15). This scaffold can be used, for example, for conjugating a PBRM having a molecular weight of 140 kDa to 180 kDa. In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, or between about 1:1 and about 1:2.

PBRMs in this molecular weight range, include but are not limited to, for example, full length antibodies, such as, IgG and IgM.

For example, when the PHF has a molecular weight ranging from 2 kDa to 40 kDa, the number of drugs per PHF (e.g., m2) is an integer from 1 to about 40, (e.g., about 1:20 or about 1:15). This scaffold can be used, for example, for conjugating a PBRM having a molecular weight of 60 kDa to 120 kDa. In this embodiment the ratio of PBRM per PHF is between about 1:1 and about 1:10, between about 1:1 and about 1:9, between about 1:1 and about 1:8, between about 1:1 and about 1:7, between about 1:1 and about 1:6, between about 1:1 and about 1:5, between about 1:1 and about 1:4, between about 1:1 and about 1:3, or between about 1:1 and about 1:2.

PBRMs in this molecular weight range, include but are not limited to, for example, antibody fragments such as, for example Fab2 and camelids.

In one embodiment the protein-polymer auristatin compound conjugate comprises a PBRM having a molecular weight of about 140 kDa to about 180 kDa (e.g., an antibody), the PHF has a molecular weight of about 8 to 15 kDa, and a load range of about 1 to about 15 of an auristatin compound.

In one embodiment the protein-polymer auristatin compound conjugate comprises a PBRM having a molecular weight of about 60 kDa to about 120 kDa (e.g., $Fab_2$, camelids), the PHF has a molecular weight of about 8 to 40 kDa, and a load range of about 1 to about 20 of an auristatin compound.

In one embodiment the protein-polymer auristatin compound conjugate comprises a PBRM having a molecular weight of about 30 kDa to about 70 kDa (e.g., Fab), the PHF has a molecular weight of about 50 to 100 kDa, and a load range of about 5 to about 100 of an auristatin compound.

In one embodiment the protein-polymer auristatin compound conjugate comprises a PBRM having a molecular weight of about 20 kDa to about 30 kDa (e.g., scFv), the PHF has a molecular weight of about 50 to 150 kDa, and a load range of about 5 to about 150 of an auristatin compound.

In one embodiment the protein-polymer auristatin compound conjugate comprises a PBRM having a molecular weight of about 4 kDa to about 20 kDa (e.g., a small protein), the PHF has a molecular weight of about 50 to 150 kDa, and a load range of about 5 to about 150 of an auristatin compound.

In some embodiments, the protein-polymer auristatin compound conjugate is one of those characterized by Table 1 of FIG. 4.

In some embodiment, the protein-polymer auristatin compound conjugate is one of those characterized by Table 2 of FIG. 4.

In some embodiments, the protein-polymer auristatin compound conjugate includes PHF having a MW of up to 60 kDa (e.g., up to 50 kDa) and a drug to PHF ratio of up to 50:1 (e.g., about 45:1, 40:1, or 35:1).

In certain embodiments, the conjugate of this invention is of Formula (Ia) or (Iaaa):

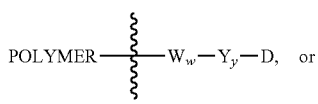
(Ia)

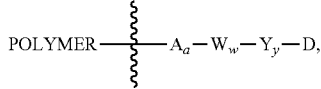
(Iaaa)

wherein, POLYMER is a polyal or polyketal, and —W—, w, —Y—, y, -A-, a, and D are as defined herein.

The conjugate of this invention is of Formula (Ia) or (Iaaa) can include one or more of the following features.

For example, the conjugates of Formula (Ia) or (Iaaa) include the following compounds:

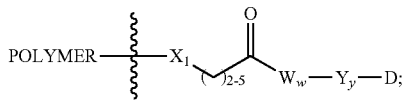

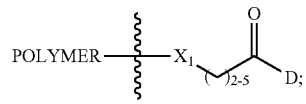

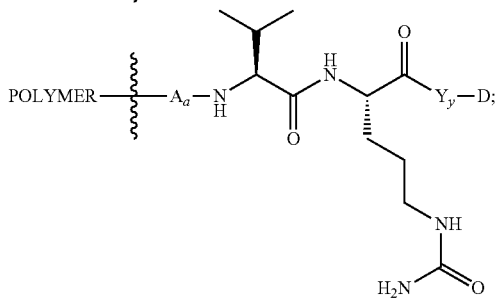

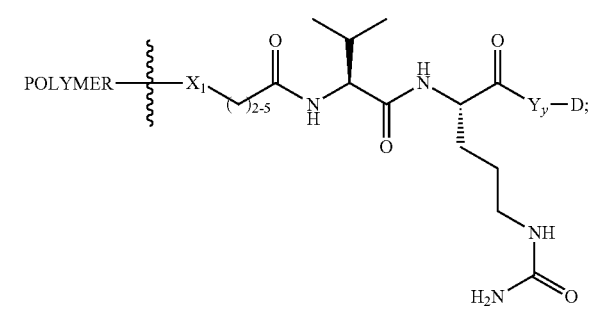

and

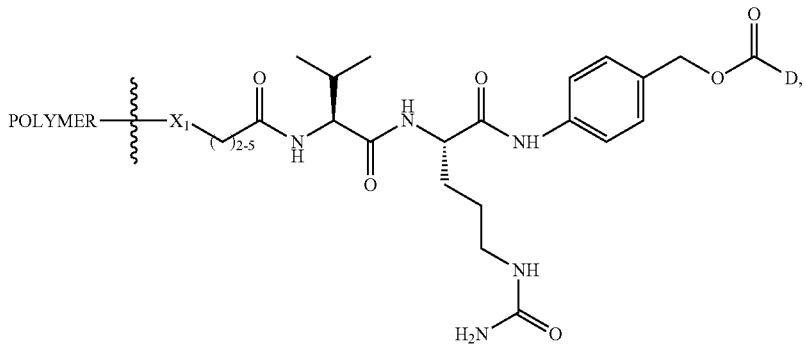

in which $X_1$ is NH, O or

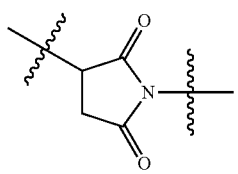

wherein N— is distal to the POLYMER; and —W—, w, —Y—, y, -A-, a, and D are as defined herein.

For example, —$W_w$— is -Val-Cit- where Val is valine and Cit is citrulline, and Cit is proximal to D.

For example, w is an integer from 2 to 12.

For example, —$Y_y$— is a compound of Formula (X) to (XII):

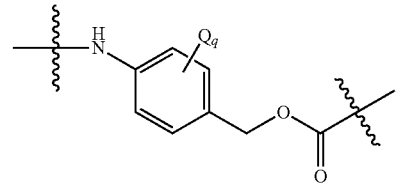
(X)

wherein Q is —$C_{1-8}$ alkyl, —O—($C_{1-8}$ alkyl), -halogen, -nitro or -cyano; and q is an integer from 0 to 4;

(XI)
$$\text{—NH—CH}_2\text{—CO—}$$
and (XII)
$$\text{—NH—CH}_2\text{—CO—NH—CH}_2\text{—CO—}$$

For example, —Y$_y$— is:

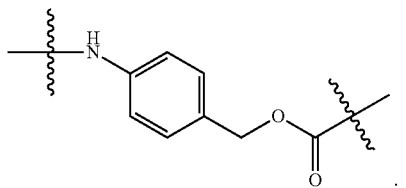 [SMILES: *Nc1ccc(COC(*)=O)cc1]

For example, the conjugate of Formula (Ia) is of Formula (V1) or (V2):

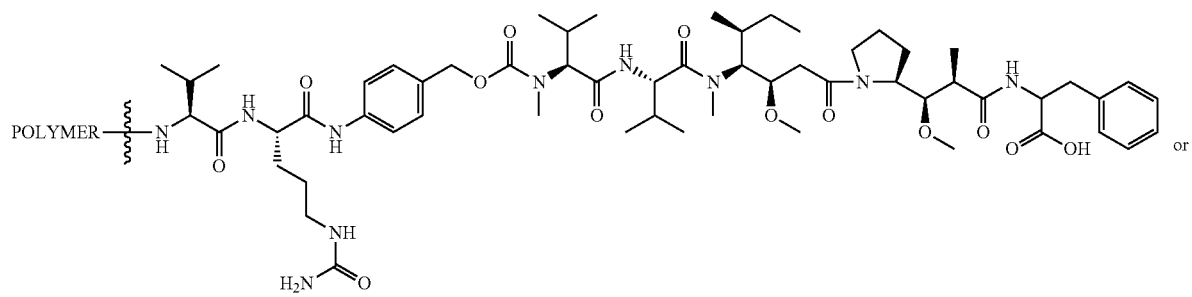

(V1)

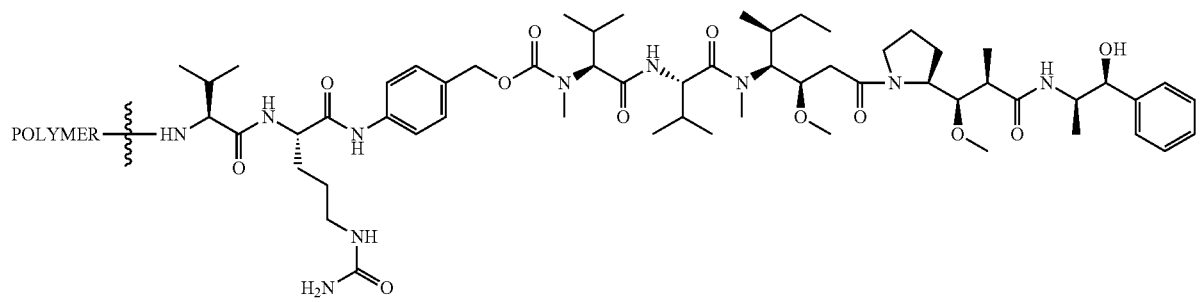

(V2)

For example, in the conjugates of Formula (Iaaa), -A- is a moiety of Formula (IIIa), (IIIb) or (IIIc):

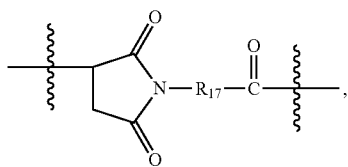

(IIIa)

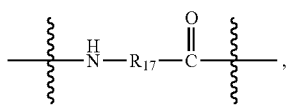

(IIIb)

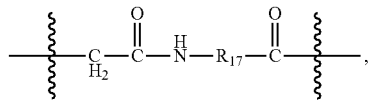

(IIIc)

wherein $R_{17}$ is —$(CH_2)_{2-5}$ or —$(CH_2)_{1-2}$—$(OCH_2CH_2)_{1-12}$ and the carbonyl group next $R_{17}$ to is proximal to D.

For example, D is an auristatin compound of Formula (Ib) described herein.

For example, the conjugates of Formula (Iaaa) are selected from:

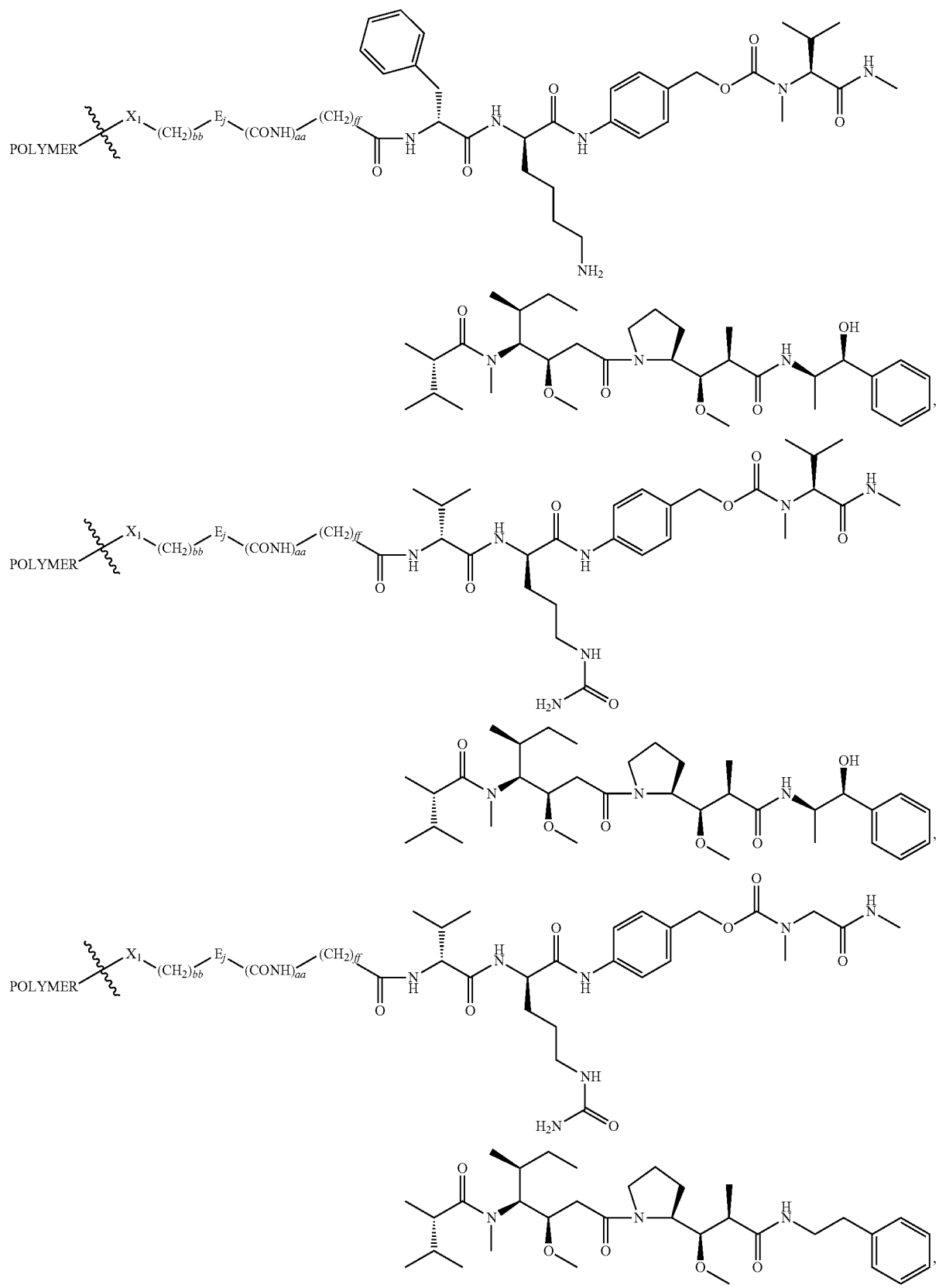

-continued
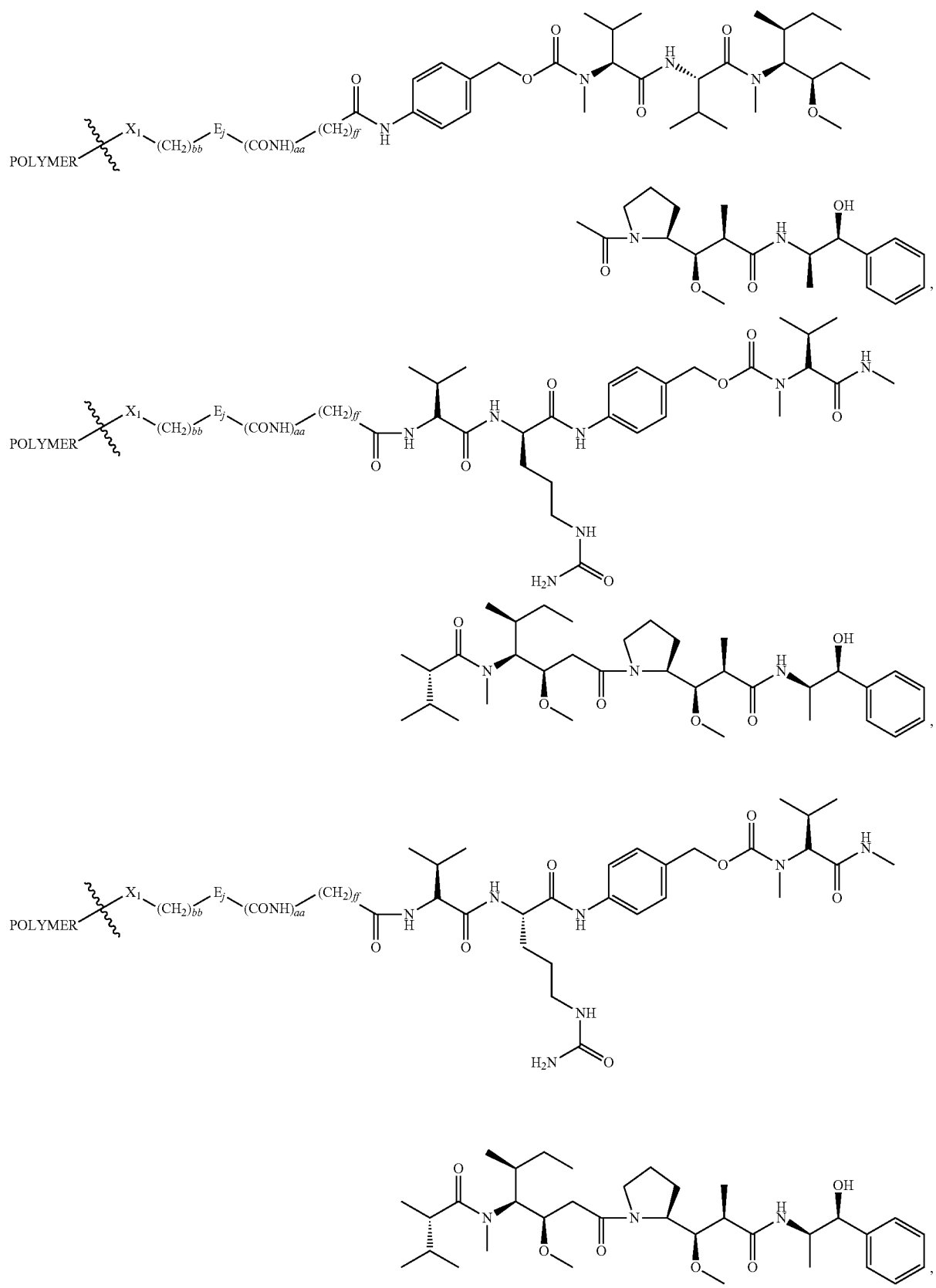

-continued

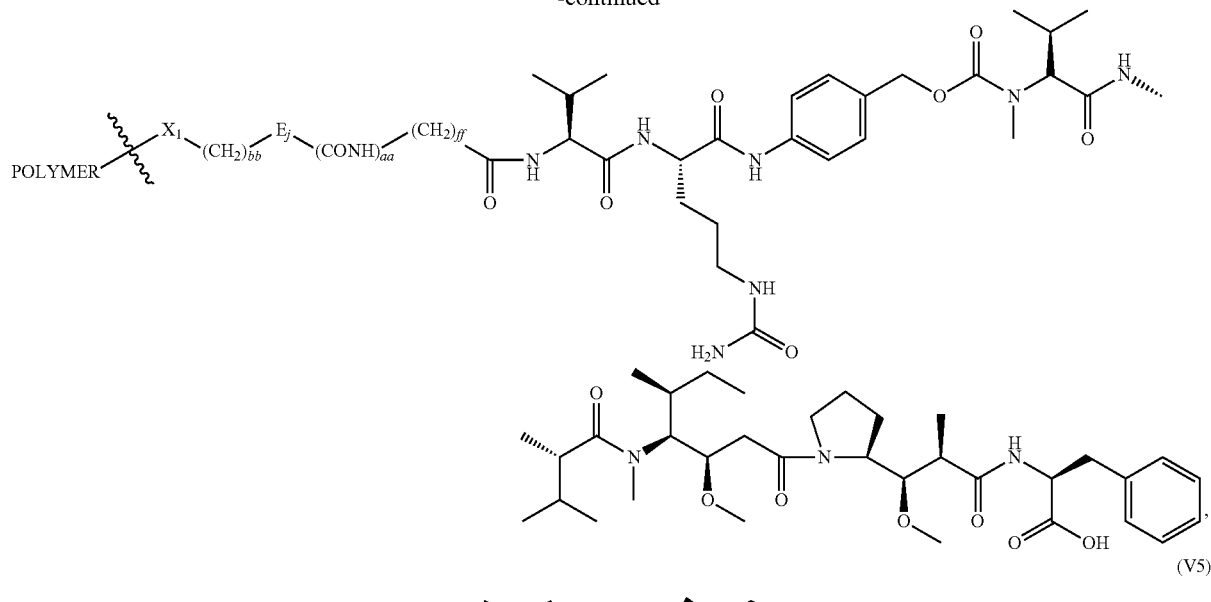

(V5)

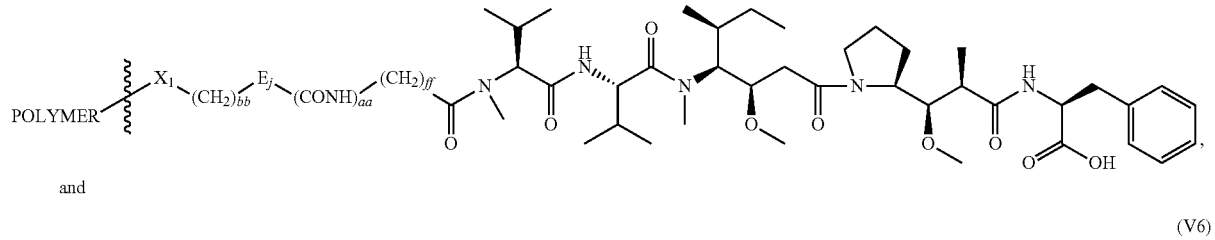

and (V6)

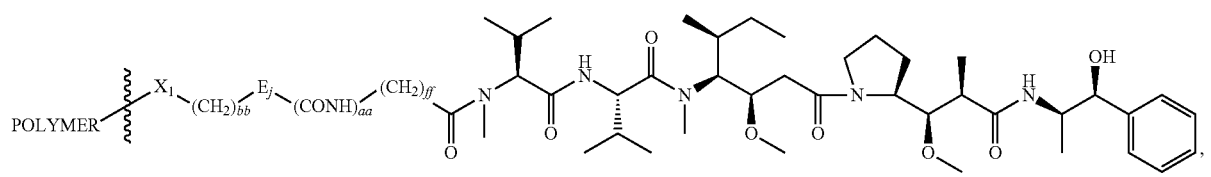

and pharmaceutically acceptable salts and solvates thereof, wherein:

E is —CH$_2$— or —OCH$_2$CH$_2$—;
aa is an integer 0 or 1;
bb is an integer 0 or 2;
ff is an integer from 0 to 10;
j is an integer from 0 to 12; and
when E is —CH$_2$—, bb is 0 and j is an integer from 0 to 10; and when E is —CH$_2$CH$_2$—O—, bb is 2 and j is an integer from 1 to 12;
X$_1$ is NH, O or

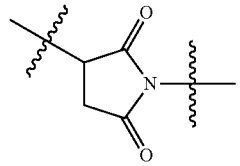

wherein N— is distal to the POLYMER.
For example, aa is 0.
For example, bb is 0.
For example, both aa and bb are 0.
For example, D is a drug unit of Formula (Ie) described herein.
For example, conjugates of Formula (Iaaa) are selected from:

165
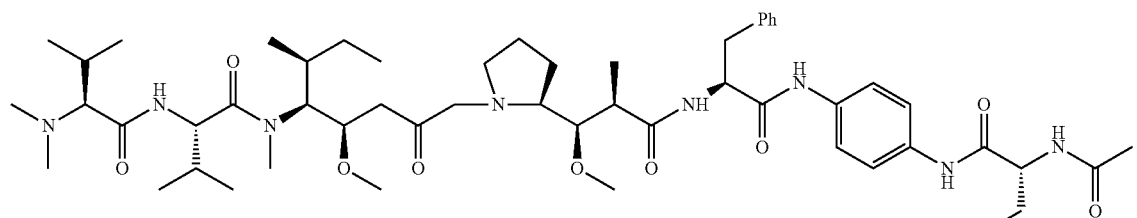
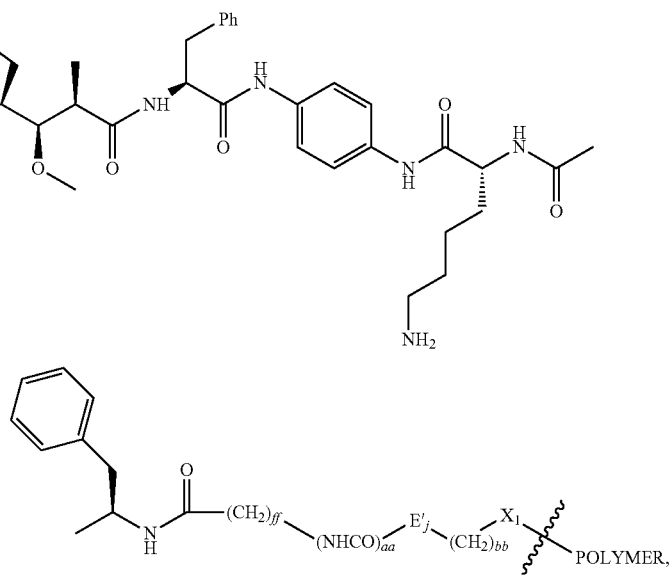
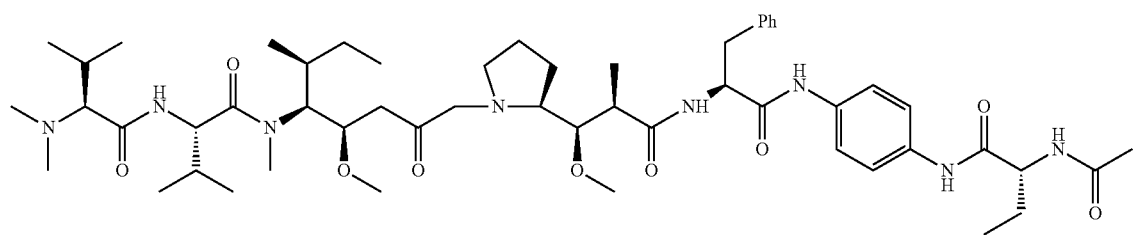
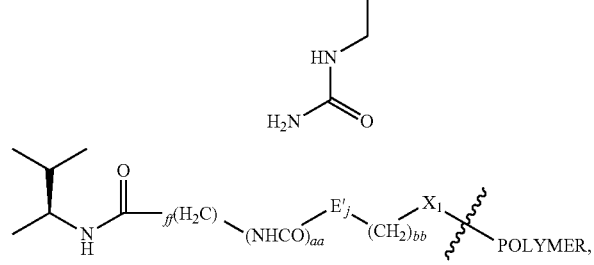
166
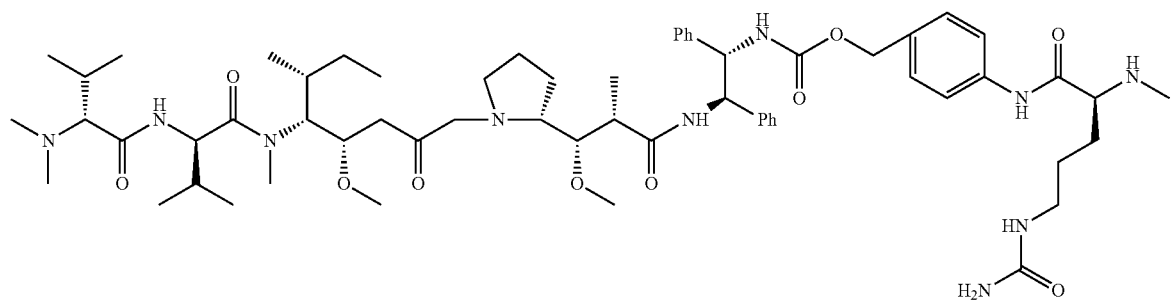
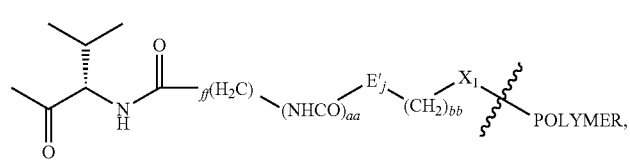

-continued

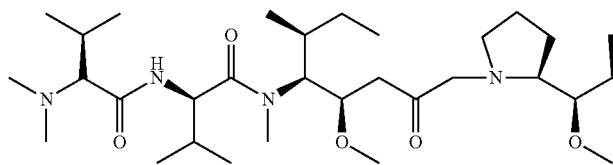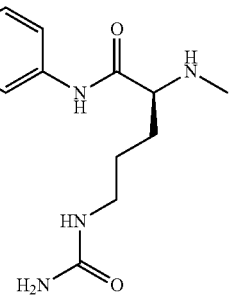

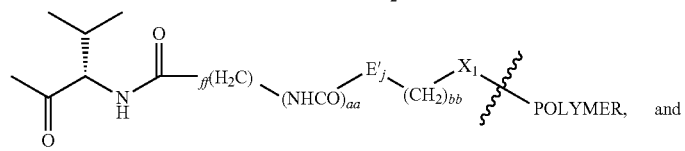POLYMER, and

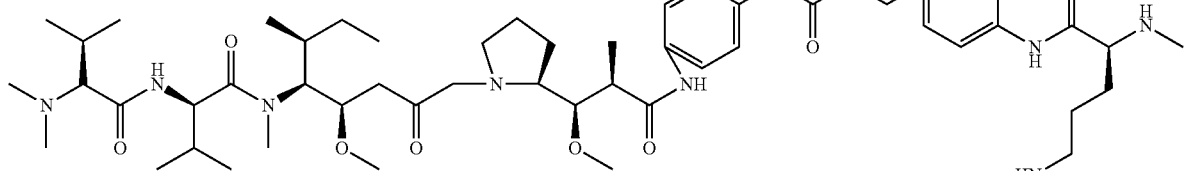

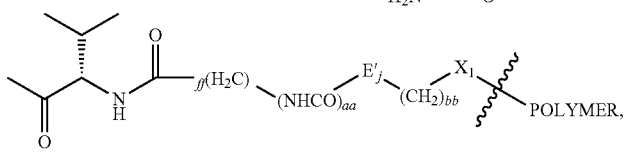POLYMER, and pharmaceutically acceptable salts and solvates thereof, wherein:

E' is —CH$_2$— or —CH$_2$CH$_2$O—;
aa is an integer 0 or 1;
bb is an integer 0 or 2;
ff is an integer from 0 to 10;
j is an integer from 0 to 12; and
when E is —CH$_2$—, bb is 0 and j is an integer from 0 to 10; and when E is —CH$_2$CH$_2$—O—, bb is 2 and j is an integer from 1 to 12;
X$_1$ is NH, O or

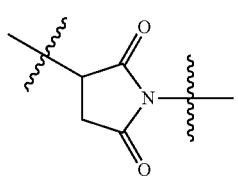

wherein N— is distal to the POLYMER.
For example, aa is 0.
For example, bb is 0.
For example, both aa and bb are 0.
For example, D is a drug unit of Formula (IIa) as described herein.

For example, the conjugate of Formula (Iaaa) is:
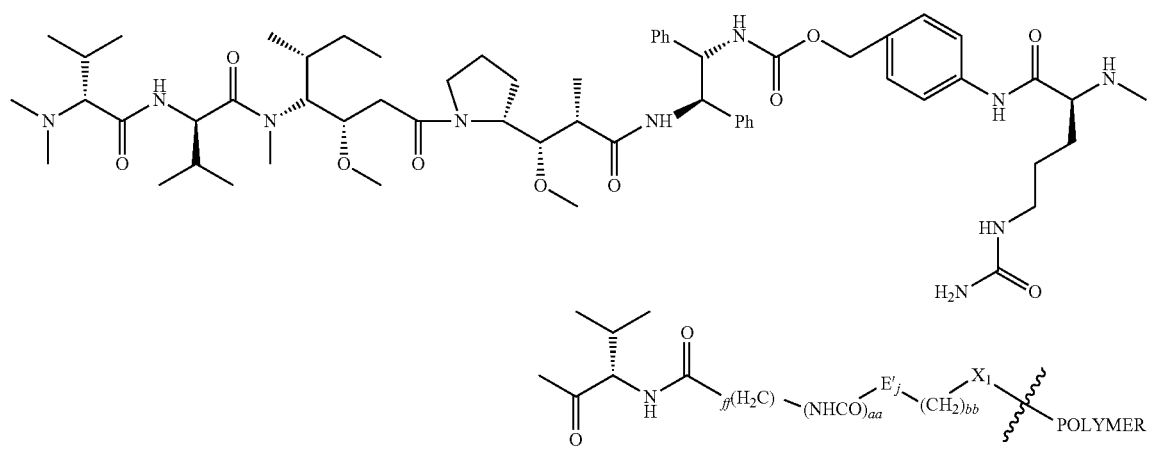
wherein E', $X_1$, aa, bb, and ff are as defined herein.
For example, D is a compound of Formula (IIf) described herein.
For example, the conjugates of Formula (Iaaa) are selected from:

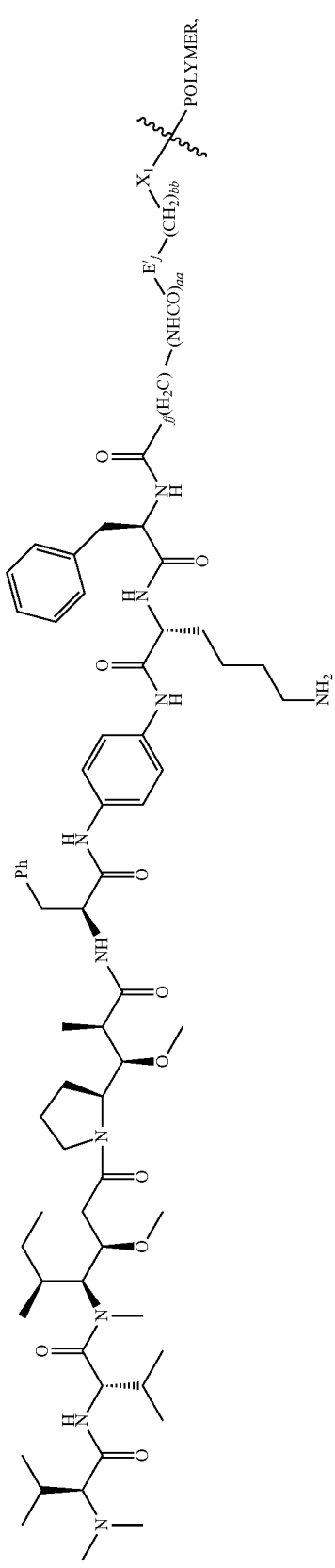
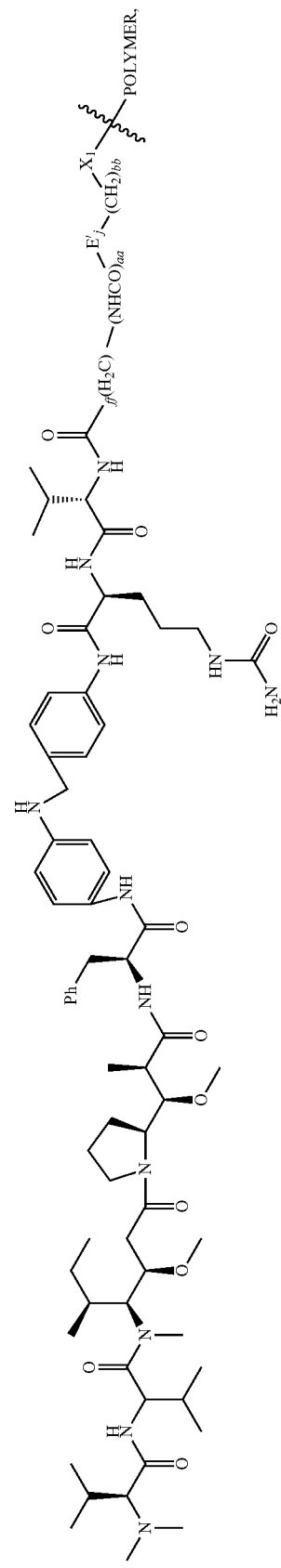

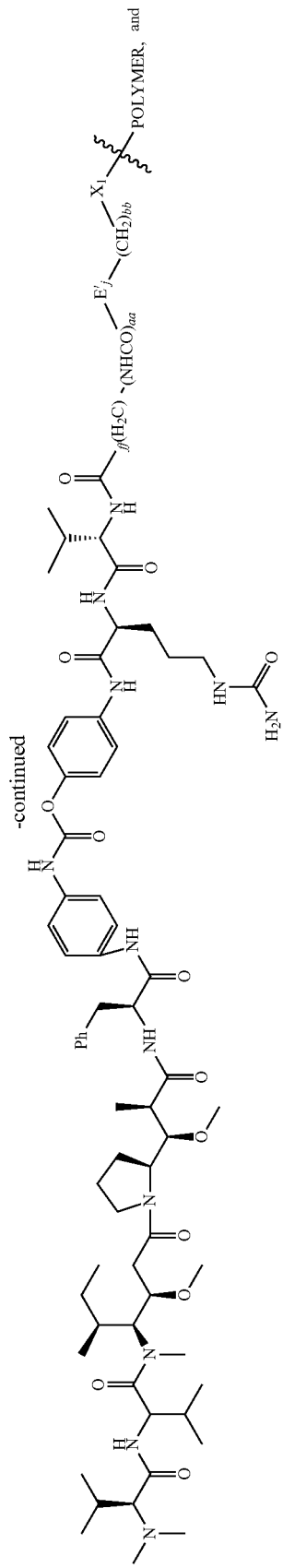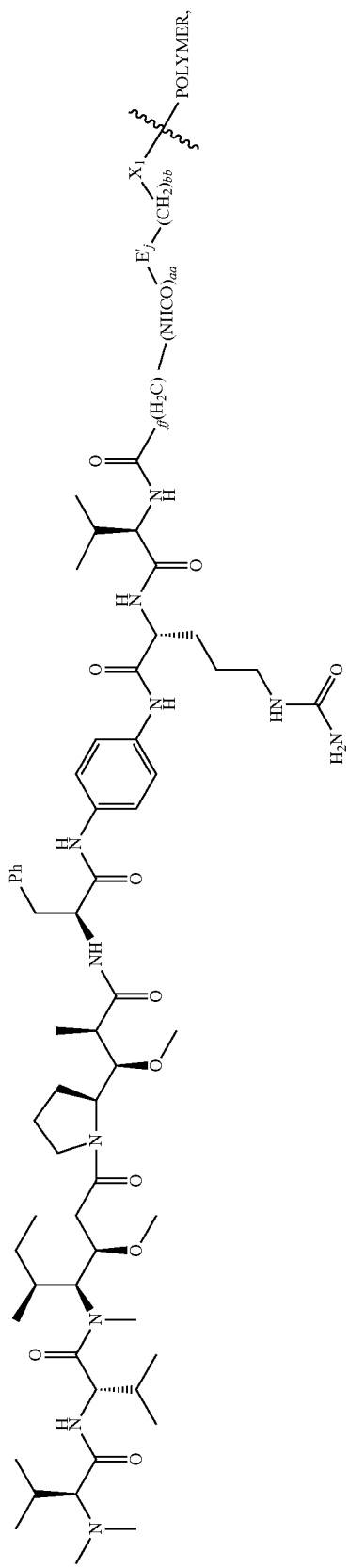

and pharmaceutically acceptable salts and solvates thereof, wherein E', $X_1$, aa, bb, and ff are as defined herein.

For example, the POLYMER is PHF.

For example, the POLYMER is of the structure:

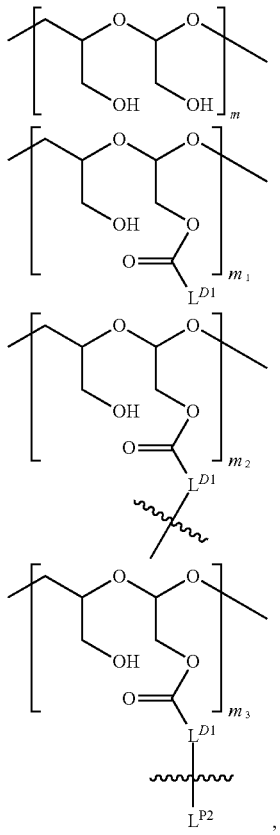

and the wavy

line between the POLYMER and $X_1$ denotes direct or indirect attachment. $L^{D1}$, $L^{P2}$, m, $m_1$, $m_2$, and $m_3$ are as defined herein.

In some embodiments, the polymeric scaffold (e.g., a polyacetal polymer such as PHF) is conjugated with PBRMs by utilizing random lysine modification. In other embodiments, the polymeric scaffold (e.g., a polyacetal polymer such as PHF) is conjugated with PBRMs by utilizing cysteine-based bioconjugation strategy. See, e.g., WO2010100430 and U.S. Pat. No. 7,595,292, the contents of which are hereby incorporated by reference in their entireties. In one embodiment, the polymeric scaffold (e.g., a polyacetal polymer such as PHF) conjugates with a PBRM (e.g., an antibody) via cysteines in the antibody hinge region. Without wishing to be bound by the theory, the resulting conjugate is stabilized through the formation of inter-chain bridge structures.

Accordingly, the invention also relates to a polymeric scaffold comprising at least two -$G^X$ moieties connected to the polymeric scaffold, in which each -$G^X$ is capable of conjugation to a thiol group from an amino acid (e.g., cysteine) in a PBRM so as to form a protein-polymer conjugate. In embodiments, -$G^X$ is a maleimide group, a disulfide group, a thiol group, a triflate group, a tosylate group, an aziridine group, a 5-pydriyl functional group, a vinylsulfone group, a vinyl pyridine group, an alkyl halide group, an acrylate group or a methacrylate group.

In embodiments, one or more free thiol groups of a PBRM are produced by reducing a protein. The one or more free thiol groups of the PBRM then react with the at least two -$G^X$ moieties contained in the polymer scaffold so as to conjugate the PBRM with the polymer scaffold.

In embodiments, the free thiol groups of the PBRM that are used for the conjugation are derived from a disulfide bridge of a native protein or a disulfide bridge of a protein complex consisting of two or more protein chains connected by the disulfide bridge. A disulfide bridge may be intrachain or interchain bridge. Alternatively, the free thiol groups of the PBRM are from cysteines or the unpaired thiol groups of the native protein that are not involved in inter or intra disulfide bridge formation.

Disulfide bonds can be reduced, for example, with dithiothreitol, mercaptoethanol, tris-carboxyethylphosphine, dehydroascorbic acid, copper sulfate, using conventional methods. A protein can contain one or more disulfide bridges. Reduction to give free thiol groups can be controlled to reduce one or more specific disulfide bridges in a protein. Depending on the extent of disulfide reduction and the stoichiometry of the -$G^X$ moieties on the polymeric scaffold polymeric, it is possible to conjugate one or more polymer scaffolds to the protein. Immobilized reducing agents may be used if it is desired to reduce less than the total number of disulfides, as can partial reduction using different reaction conditions or the addition of denaturants.

Advantages of conjugating a polymer to a protein via a thiol include, but are not limited to optimized efficacy, improved dose to dose consistency and homogeneity (as the number of conjugated polymer molecules per protein is the substantially the same for each protein molecule), specific conjugation directed to a specific residue or residues on each protein, and easier purification. Also, the protein-polymer conjugates via the thiol conjugation exhibits substantially improved half-life, mean residence time, and/or clearance rate in circulation as compared to the unconjugated protein.

In one embodiment, the scaffold for conjugating to thiol groups in a PBRM is of Formula (IIIaa):

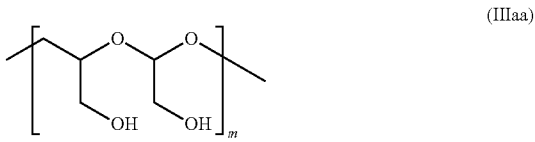

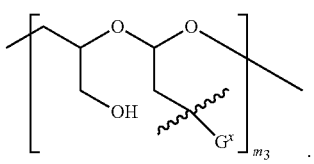

(IIIaa)

The wavy line

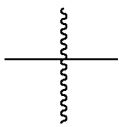

in Formula (IIIaa) above denotes direct or indirect attachment of -$G^X$ to the backbone of PHF. m and $m_3$ are as defined herein. For example, -$G^X$ is connected to the polymeric scaffold by a linker -$L^S$ having the structure:

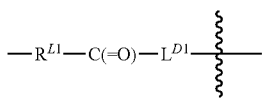

with $R^{L1}$ and $L^{D1}$ defined as herein and

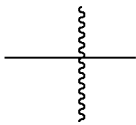

in

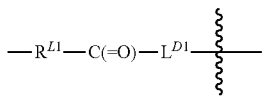

denoting direct or indirect attachment of $L^{D1}$ to $G^X$.

For example, m is an integer from 1 to 2200.

For example, $m_3$ is an integer from 2 to 20 (e.g., an integer from 2 to 10, or an integer from 2 to 6).

In another embodiment, the scaffold for conjugating to thiol groups in a PBRM is of Formula (IIIbb):

(IIIbb)

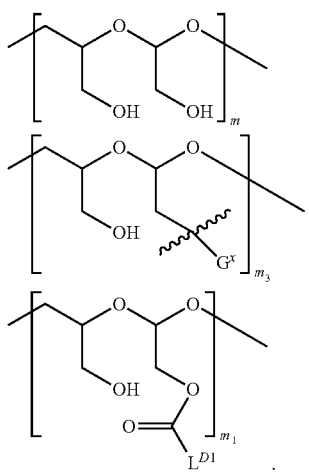

The wavy line

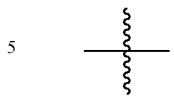

in Formula (IIIbb) above denotes direct or indirect attachment of -$G^X$ to the backbone of PHF. For example, -$G^X$ is connected to the polymeric scaffold by a linker -$L^S$ having the structure:

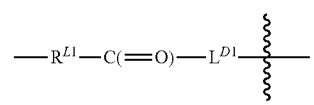

with $R^{L1}$ and $L^{D1}$ defined as herein and

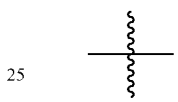

in

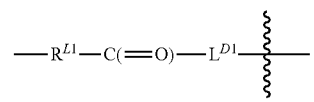

denoting direct or indirect attachment of $L^{D1}$ to $G^X$; and m, $m_1$, and $m_3$ are as defined herein.

For example, m is an integer from 1 to 2200.

For example, $m_3$ is an integer from 2 to 20 (e.g., an integer from 2 to 10, or an integer from 2 to 6).

For example, $m_1$ is an integer from 1 to 660.

In yet another embodiment, the scaffold for conjugating to thiol groups in a PBRM is of Formula (IIIcc):

(IIIcc)

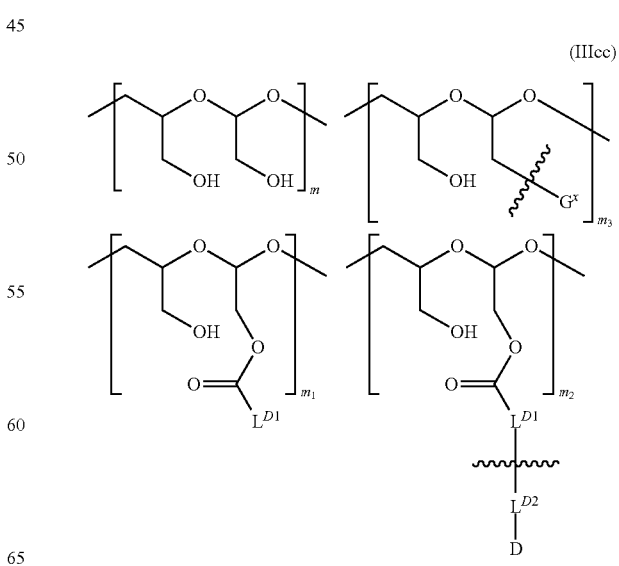

The wavy line

in Formula (IIIcc) above denotes direct or indirect attachment of -$G^X$ to the backbone of PHF. For example, -$G^X$ is connected to the polymeric scaffold by a linker -$L^S$ having the structure:

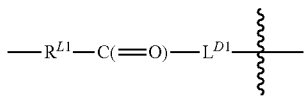

with $R^{L1}$ and $L^{D1}$ as defined herein and

in

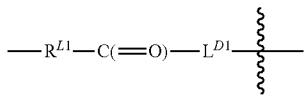

denoting direct or indirect attachment of $L^{D1}$ to $G^X$; and $L^{D2}$, D, m, $m_1$, $m_2$, and $m_3$ are as defined herein.

For example, m is an integer from 1 to 2200.

For example, $m_3$ is an integer from 2 to 20 (e.g., an integer from 2 to 10, or an integer from 2 to 6).

For example, $m_1$ is an integer from 1 to 660.

For example, $m_2$ is an integer from 1 to 300.

In some embodiments, the auristatin compound-polymer-PBRM conjugates, auristatin compound-polymer conjugates, auristatin compound carrying-polymeric scaffolds, or PBRM-carrying polymer scaffolds described herein each have a polydispersity index (PDI) of less than 1.5.

PBRM-auristatin compound -polymer conjugates, auristatin compound carrying-polymeric scaffolds, or PBRM-carrying polymer scaffolds can be purified (i.e., removal of residual unreacted auristatin compound, PBRM, or polymeric starting materials) by extensive diafiltration. If necessary, additional purification by size exclusion chromatography can be conducted to remove any aggregated PBRM-auristatin compound polymer conjugates. In general, the PBRM-drug polymer conjugates as purified typically contain <5% aggregated PBRM-auristatin compound polymer conjugates as determined by SEC or SDS-PAGE; <1% polymer-drug conjugate as determined by SEC and <2% unconjugated PBRM as determined by HPLC.

Tables E and F below provide examples of the drug-carrying polymeric scaffolds and the polymer-drug-protein conjugates of the invention respectively.

TABLE E

| Ref # | Drug:PHF Ratio | Structure |
|---|---|---|
| Ex 4 | ND | 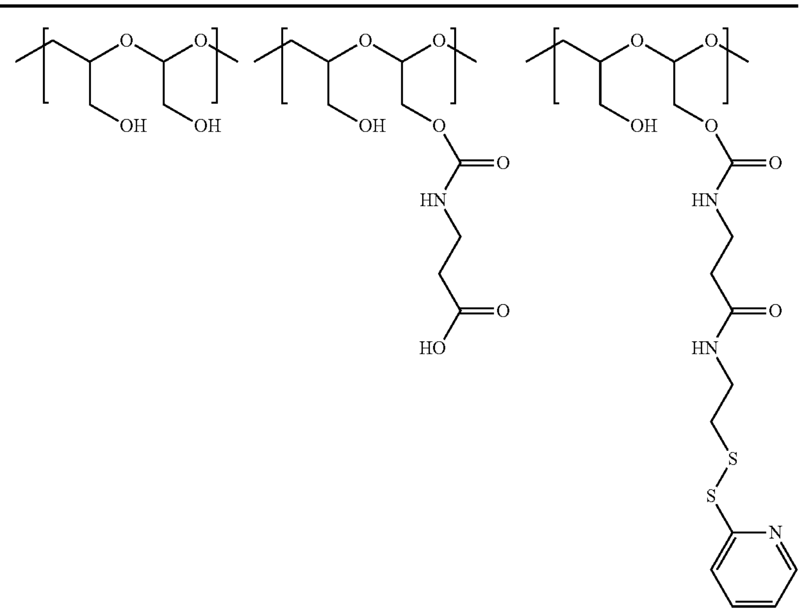 |

TABLE E-continued
| Ref # | Drug: PHF Ratio | Structure |
|---|---|---|
|  |  | 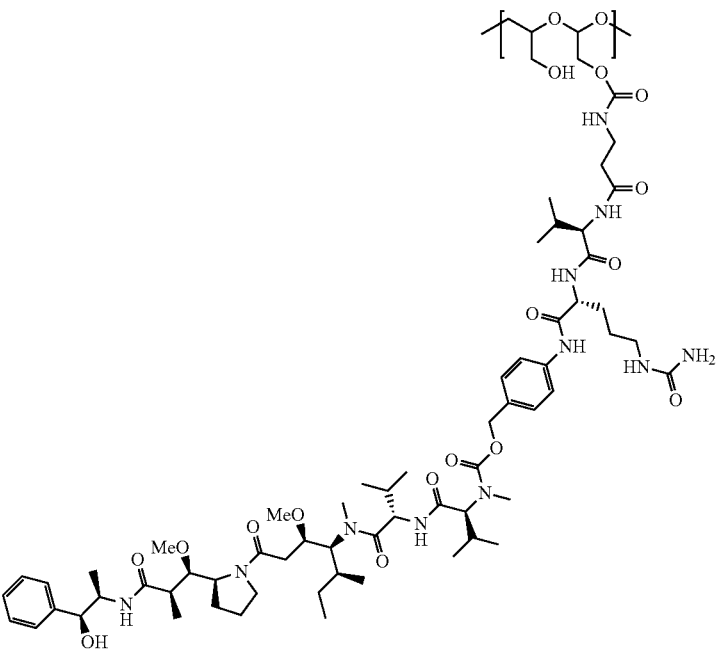 |
| Ex 8 | ND | 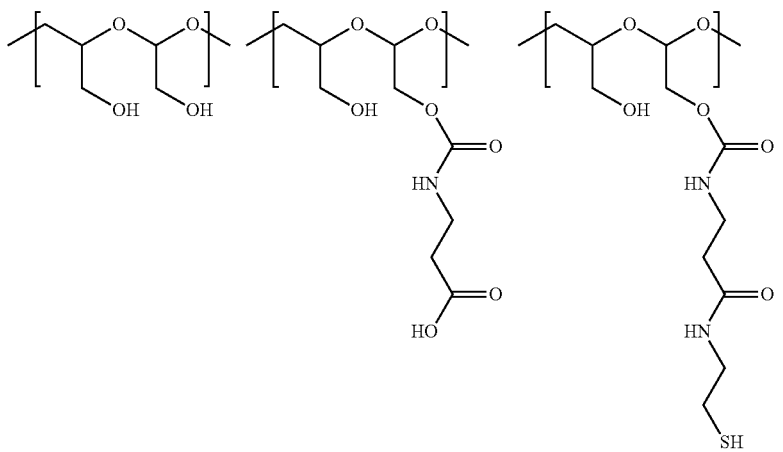 |

TABLE E-continued
| Ref # | Drug: PHF Ratio | Structure |
|---|---|---|
| | | 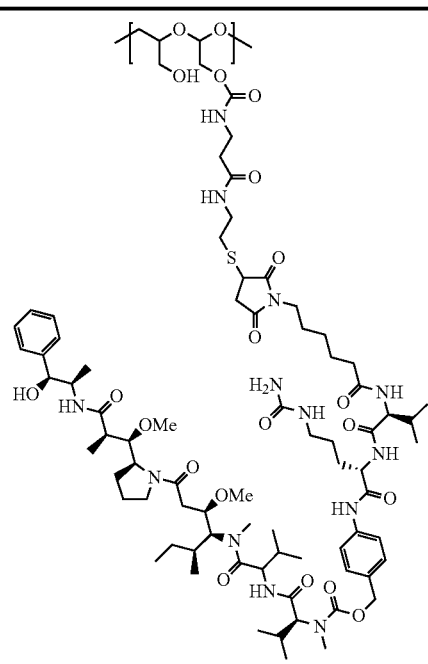 |
TABLE F
| Ref # | Drug: PBRM Ratio | Structure |
|---|---|---|
| Ex 5 | 6:1 to 10:1 | 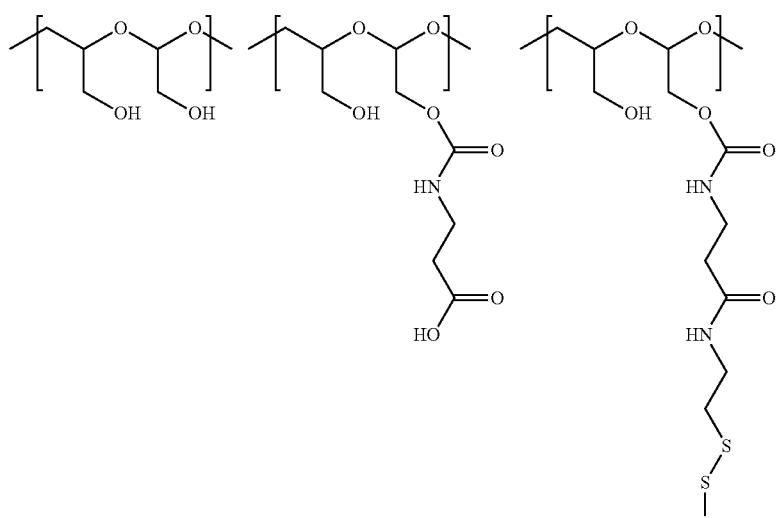 |

TABLE F-continued
| Ref # | Drug: PBRM Ratio | Structure |
|---|---|---|
| Ex 10 | ND |  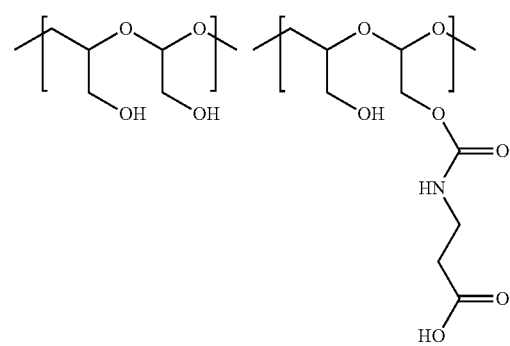 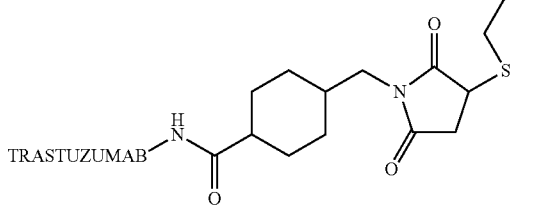 |

TABLE F-continued
| Ref # | Drug: PBRM Ratio | Structure |
|---|---|---|
| | | 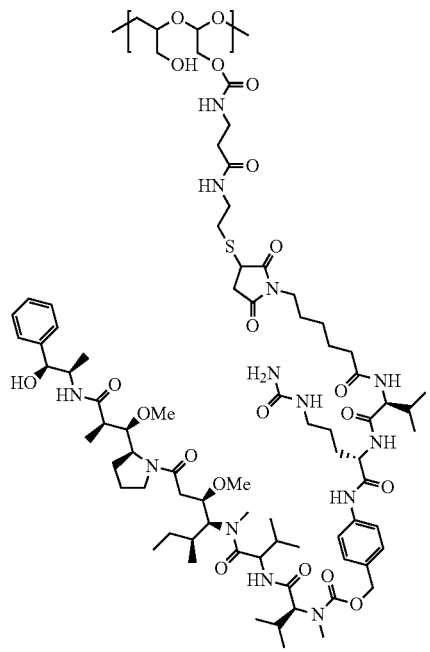 |
| Ex 12 | ND | 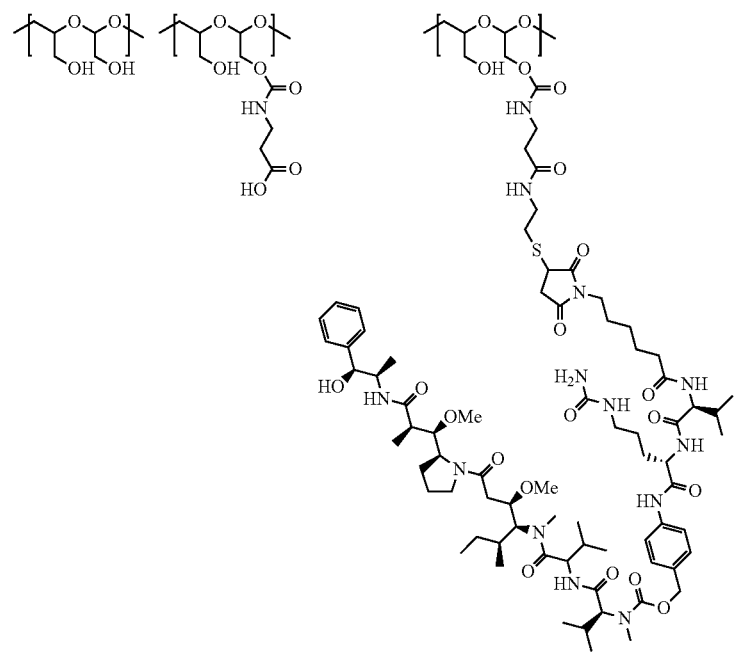 |

TABLE F-continued

Drug:
Ref PBRM
Ratio   Structure

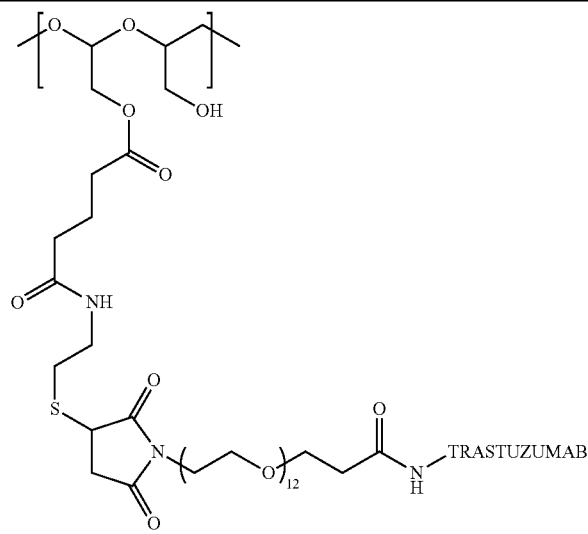

Synthetic Methods

According to the present invention, any available techniques can be used to make the inventive conjugates or compositions including them, and intermediates and components (e.g., carriers and modifiers) useful for making them. For example, semi-synthetic and fully synthetic methods such as those discussed in detail below may be used.

Carriers

Methods for preparing polymer carriers (e.g., biocompatible, biodegradable polymer carriers) suitable for conjugation to modifiers are known in the art. For example, synthetic guidance can be found in U.S. Pat. Nos. 5,811,510; 5,863,990; 5,958,398; 7,838,619; and 7,790,150; and U.S. Publication No. 2012/0321583 and 2013/0101546. The skilled practitioner will know how to adapt these methods to make polymer carriers for use in the practice of the invention.

For example, semi-synthetic polyals may be prepared from polyaldoses and polyketoses via complete lateral cleavage of carbohydrate rings with periodate in aqueous solutions, with subsequent conversion into hydrophilic moieties (e.g., via borohydride reduction) for conjugation of hydroxyl groups with one or more drug molecules or PBRMs, via a dicarboxylic acid linker (e.g., glutaric acid or β-alanine linker). In an exemplary embodiment, the carbohydrate rings of a suitable polysaccharide can be oxidized by glycol-specific reagents, resulting in the cleavage of carbon-carbon bonds between carbon atoms that are each connected to a hydroxyl group. An example of application of this methodology to dextran B-512 is illustrated below:

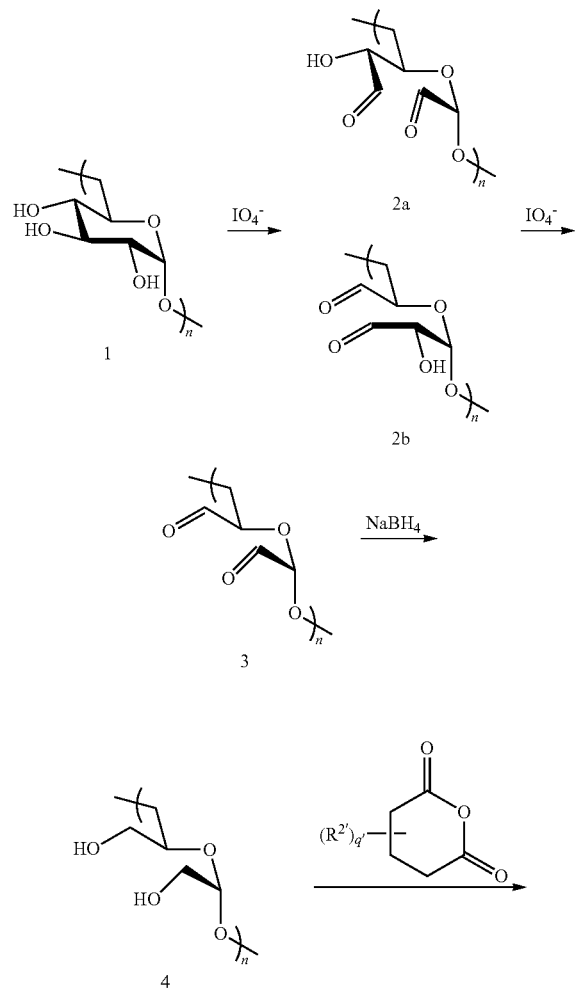

191
-continued

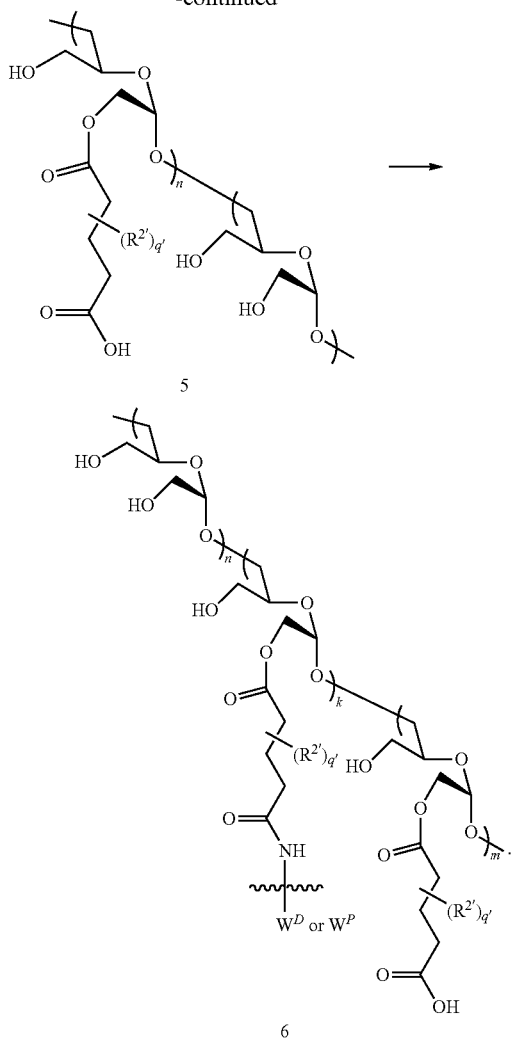

5

6

A similar approach may be used with Levan:

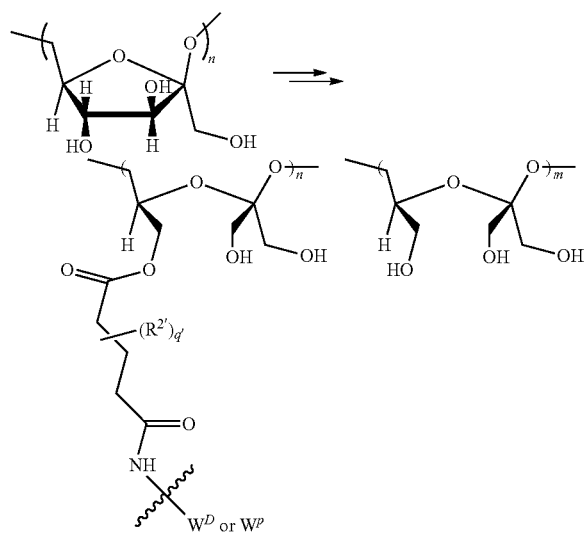

192
and Inulin:

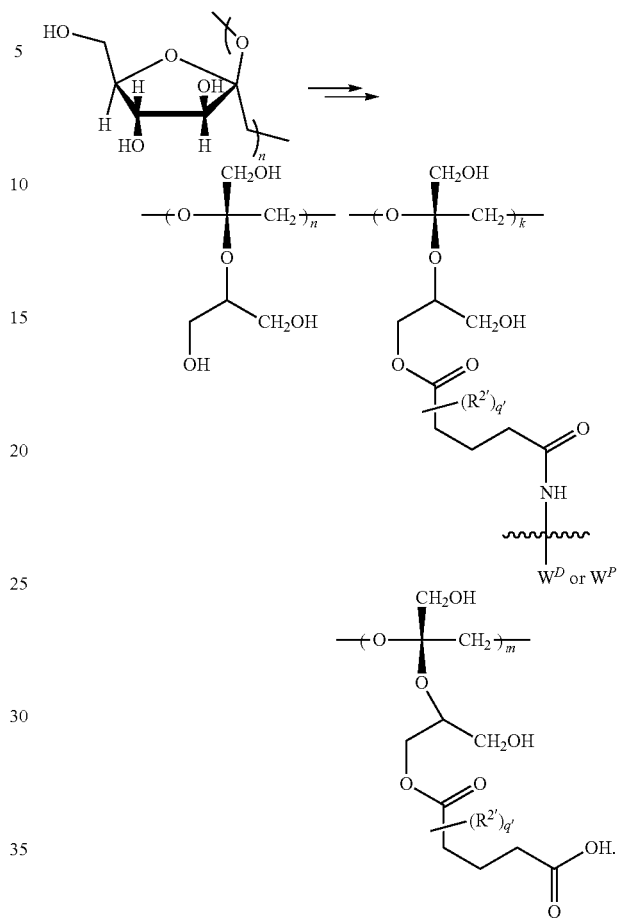

In the above schemes, the wavy bond indicates that $W^D$ or $W^P$ are connected directly as shown or via another moiety such as $M^{D2}$ or $M^{P2}$ respectively.

In the above schemes, q' is an integer from 0 to 4; and each occurrence of $R^{2'}$ is independently hydrogen, halogen, —CN, $NO_2$, an aliphatic, heteroaliphatic, carbocyclic, or heterocycloalkyl moiety, or -$GR^{G1}$ wherein G is —O—, —S—, —$NR^{G2}$—, —C(=O)—, —S(=O)—, —$SO_2$—, —C(=O)O—, —C(=O)$NR^{G2}$—, —OC(=O)—, —$NR^{G2}$C(=O)—, —OC(=O)O—, —OC(=O)$NR^{G2}$—, —$NR^{G2}$C(=O)O—, —$NR^{G2}$C(=O)$NR^{G2}$—, —C(=S)—, —C(=S)S—, —SC(=S)—, —SC(=S)S—, —C(=$NR^{G2}$)—, —C(=$NR^{G2}$)O—, —C(=$NR^{G2}$)$NR^{G3}$—, —OC(=$NR^{G2}$)—, —$NR^{G2}$C(=$NR^{G3}$)—, —$NR^{G2}SO_2$—, —$NR^{G2}SO_2NR^{G3}$—, or —$SO_2NR^{G2}$—, wherein each occurrence of $R^{G1}$, $R^{G2}$ and $R^{G3}$ is independently hydrogen, halogen, or an aliphatic, heteroaliphatic, carbocyclic, or heterocycloalkyl moiety, each of which is optionally substituted.

In certain embodiments, each occurrence of $R^{2'}$ is independently hydrogen, alkyl, alkenyl, alkynyl, cycloalkyl, heteroalkyl, heteroalkenyl, heteroalkynyl, heterocycloalkyl, aryl, heteroaryl, —C(=O)$R^{2A}$ or —$ZR^{2A}$, wherein Z is O, S, $NR^{2B}$, wherein each occurrence of $R^{2A}$ and $R^{2B}$ is independently hydrogen, or an alkyl, alkenyl, alkynyl, cycloalkyl, heteroalkyl, heteroalkenyl, heteroalkynyl, heterocycloalkyl, aryl or heteroaryl moiety. In certain embodiments, each occurrence of $R^{2'}$ is hydrogen. In certain embodiments, one or more occurrences of $R^{2'}$ is a $C_{1-10}$ alkyl moiety. In certain embodiments, one or more occurrences of $R^{2'}$ is lower alkyl. In certain embodiments, one or more occurrences of $R^{2'}$ is a hydrophobic group. In certain embodiments, one or more occurrences of $R^{2'}$ is a hydrophilic group. In certain embodiments, one or more occurrences of $R^2$ is an anionic group. In certain embodiments, one or more occurrences of $R^{2'}$ is a cationic group. In certain embodiments, one or more occurrences of $R^{2'}$ is a receptor ligand.

In one embodiment, a method for forming the biodegradable biocompatible polyal conjugates of the present invention comprises a process by which a suitable polysaccharide is combined with an efficient amount of a glycol-specific oxidizing agent to form an aldehyde intermediate. The aldehyde intermediate, which is a polyal itself, may then be reduced to the corresponding polyol, succinylated, and coupled with one or more suitable modifiers to form a biodegradable biocompatible polyal conjugate comprising succinamide-containing linkages.

In another preferred embodiment, fully synthetic biodegradable biocompatible polyals for used in the present invention can be prepared by reacting a suitable initiator with a suitable precursor compound.

For example, fully synthetic polyals may be prepared by condensation of vinyl ethers with protected substituted diols. Other methods, such as cycle opening polymerization, may be used, in which the method efficacy may depend on the degree of substitution and bulkiness of the protective groups.

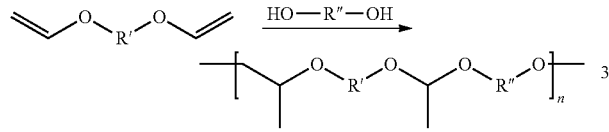

One of ordinary skill in the art will appreciate that solvent systems, catalysts and other factors may be optimized to obtain high molecular weight products.

In certain embodiments, the carrier is PHF.

In embodiments, the polymer carrier is PHF having a polydispersity index (PDI) of less than 1.5.

Auristatin Compounds

The Drug Linker compounds D-$L^{D2}$ can be made using the synthetic procedures outlined in, for example US Patent Application No. 2009/0111756, 2011/0020343.

The auristatin compounds may be prepared according to the general methods of: U.S. Pat. Nos. 5,635,483; and 5,780,588; Pettit et al., 1989, J. Am. Chem. Soc. 111:5463-5465; Pettit et al., 1998, Anti-Cancer Drug Design 13:243-277; and Pettit et al., 1996, J. Chem. Soc. Perkin Trans. 1 5:859-863.

Stretcher units may be synthesized according to known procedures. Aminooxy Stretchers can be prepared by treating alkyl halides with N-Boc-hydroxylamine according to procedures described in Jones et al., 2000, Tetrahedron Letters 41(10):1531-1533; and Gilon et al., 1967, Tetrahedron 23(11):4441-4447. The aminooxy group reacts with a reactive group on the Ligand unit. Useful Stretcher units can also be obtained via commercial sources, such as Molecular Biosciences Inc. (Boulder, Colo.).

Conjugates or Polymeric Scaffolds

The general methods of producing the conjugates or polymeric scaffolds of this invention have been described above. Schemes 1-7 below exemplify how the conjugates or polymeric scaffolds are synthesized. The variables (e.g., $X^D$, $X^P$, $L^{D1}$, $L^{P2}$, X, etc) in these schemes have the same definitions as described herein unless otherwise specified. Each $L^{D3}$ comprises a function moiety that is capable of reacting with $W^D$ to form $L^{D2}$ and each $W^{P1}$ is a function moiety that is capable of reacting with $W^P$ to form $Z^P$-$M^{P3}$. —$X^D$-$M^{D1}$-$Y^D$-$M^{D2}$-$W^D$ and —$X^P$-$M^{P1}$-$Y^P$-$M^{P2}$-$W^P$ may be different (such as in Schemes 1 and 1A) or the same (such as in Scheme 2). In some embodiments —$X^P$-$M^{P1}$-$Y^P$-$M^{P2}$-$W^P$ is formed by further modification of —$X^D$-$M^{D1}$-$Y^D$-$M^{D2}$-$W^D$.

Scheme 1

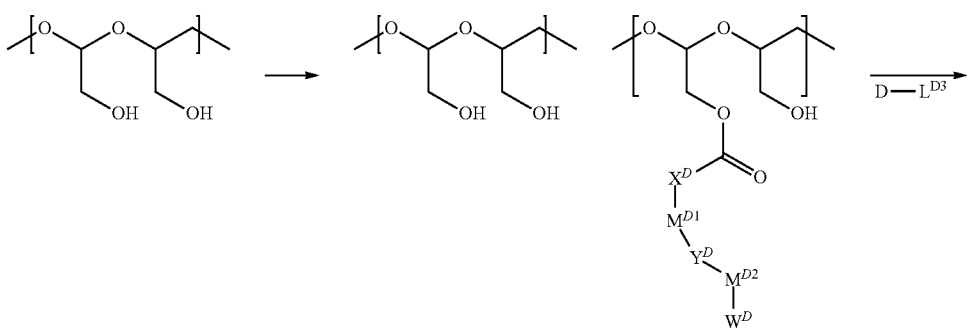

195     196
-continued
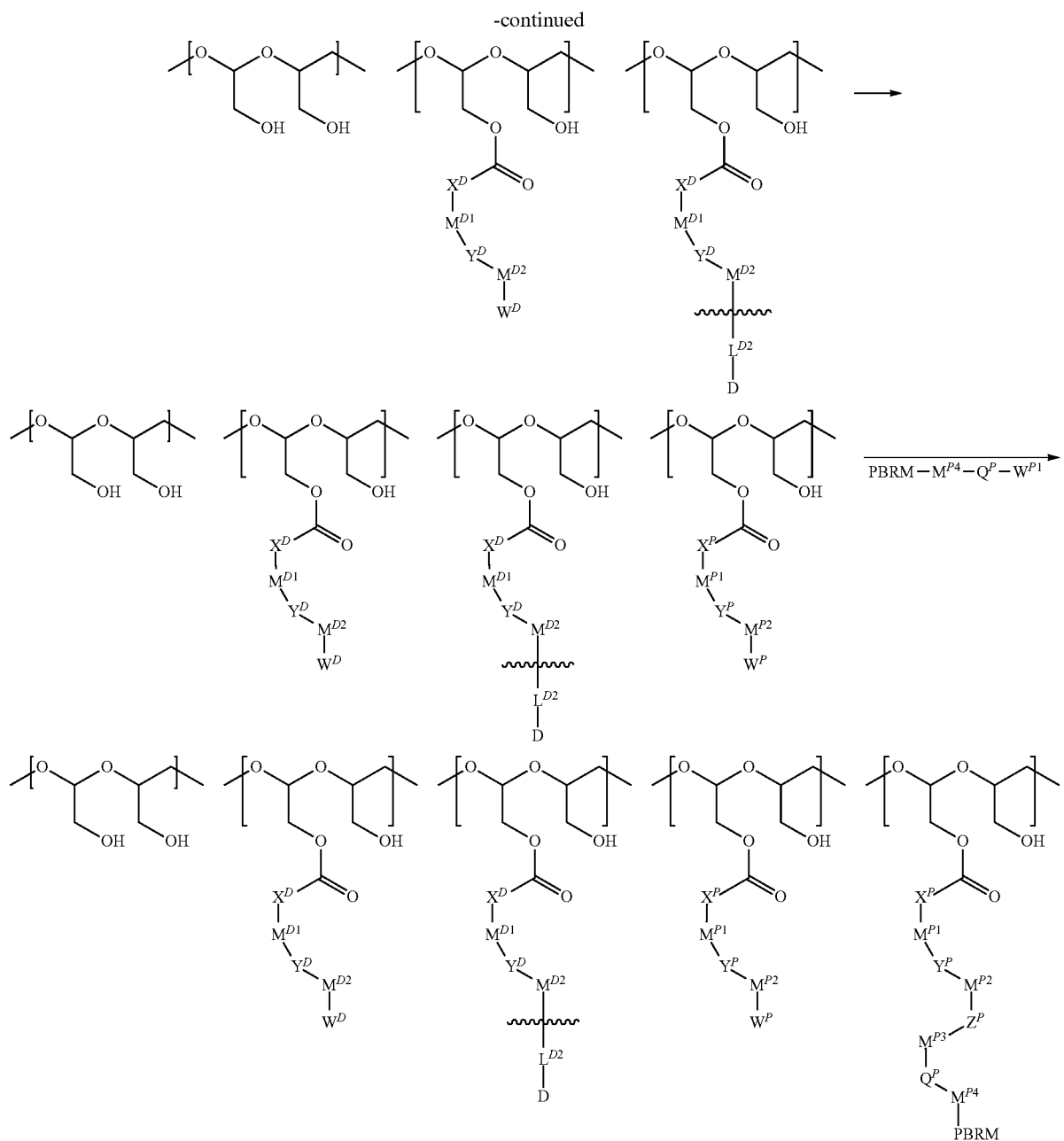
Scheme 1A
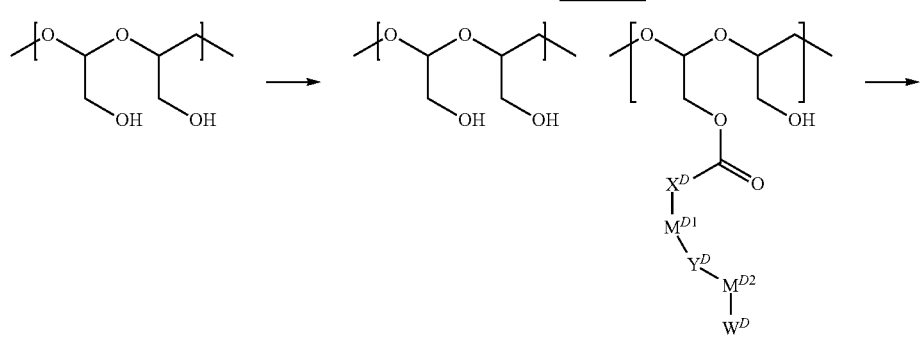

197 198
-continued
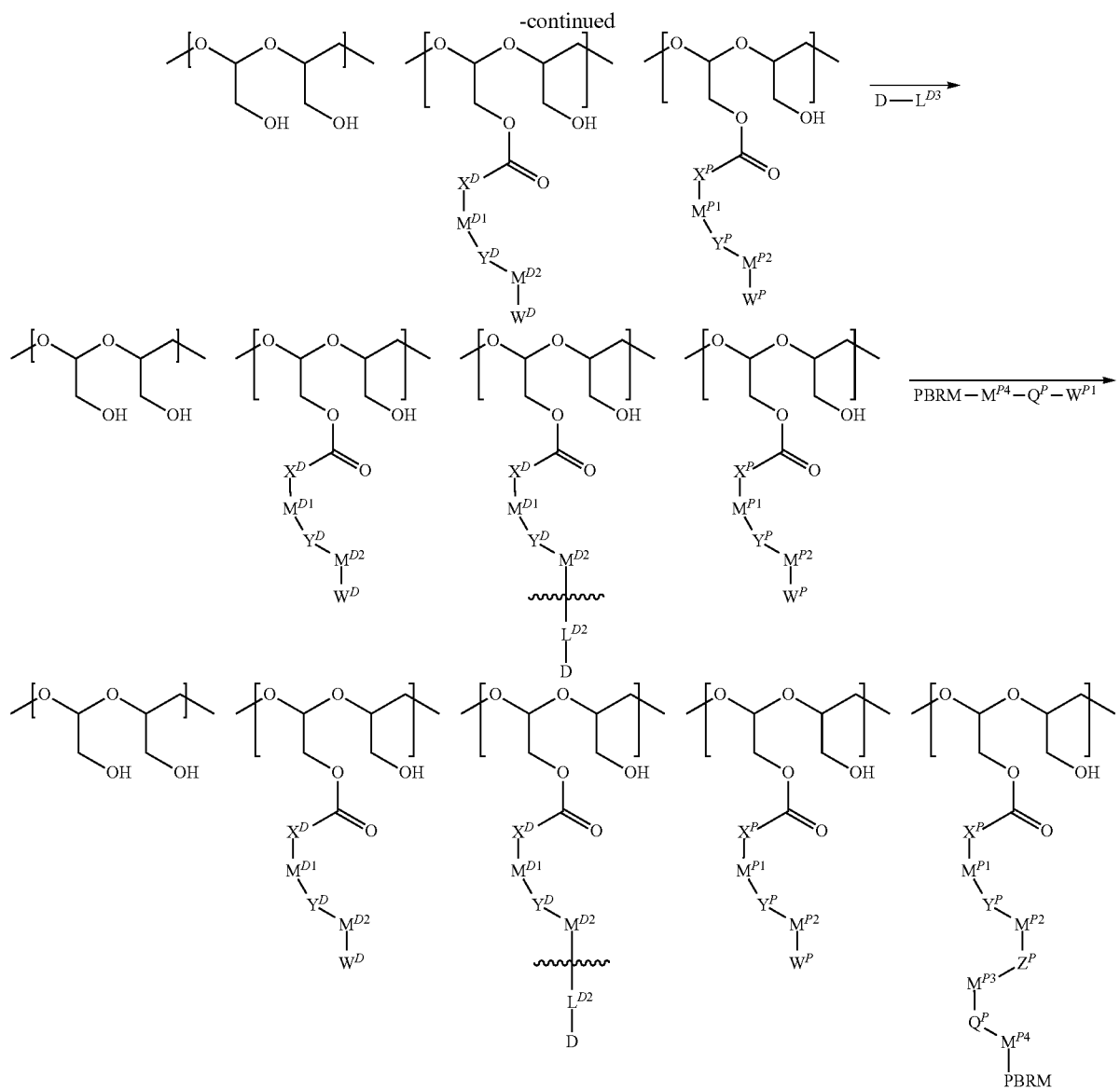
Scheme 2
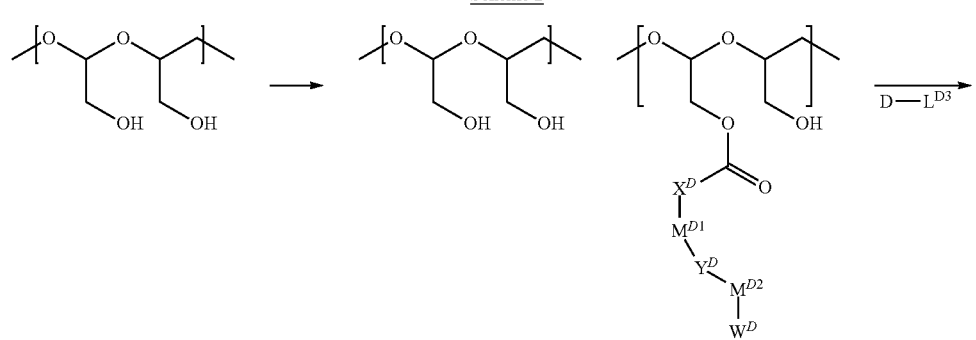

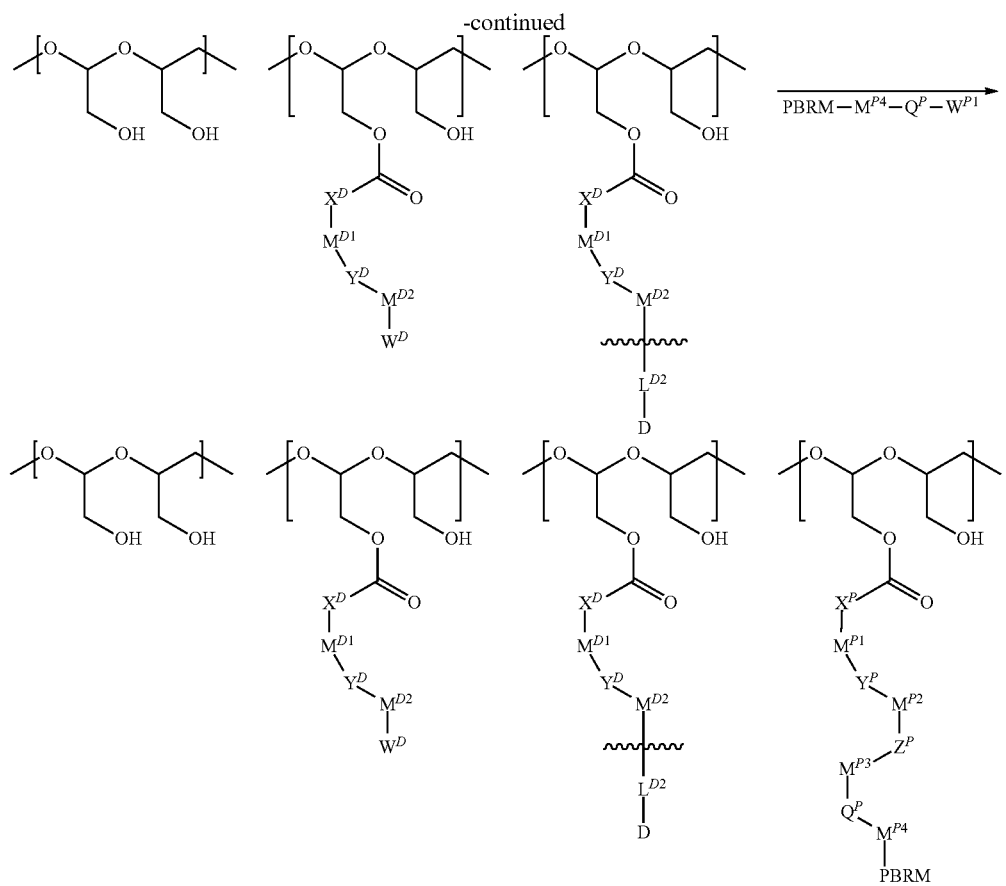

The PBRM can be linked to the drug-polymer conjugate to form the protein-drug polymer conjugate using standard synthetic methods for protein conjugation, including, but not limited to, reactions based on reductive amination, Staudinger ligation, oxime formation, thiazolidine formation and the methods and reactions described herein.

Scheme 3 below shows the synthesis of a PBRM-drug-polymer conjugate in which the PBRM is linked to the drug polymer conjugate using click chemistry.

Scheme 3

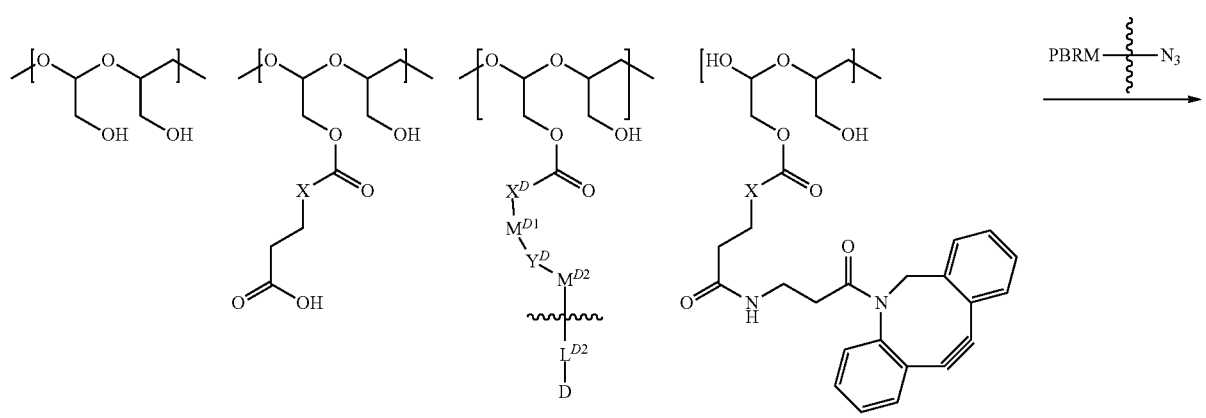

201
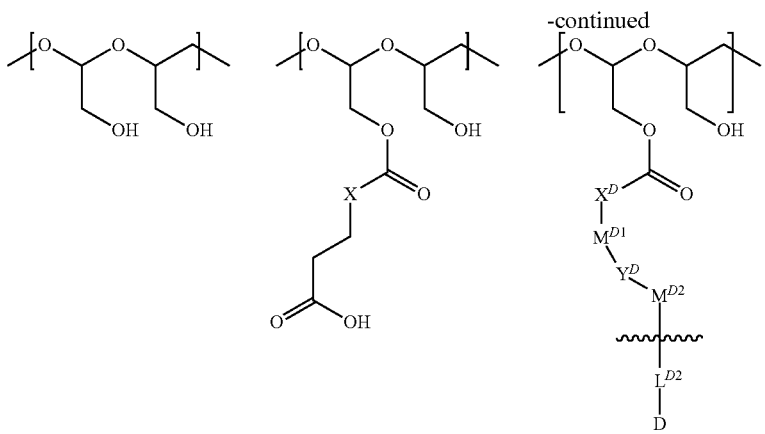
202
-continued
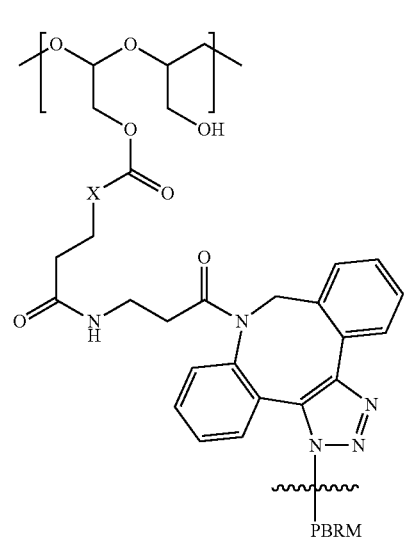
Scheme 4 below shows the synthesis of a PBRM-drug-polymer conjugate is which the PBRM is linked to the drug polymer conjugate by a Mannich reaction.
Scheme 5 below shows the synthesis of a PBRM-drug-polymer conjugate is which the PBRM is linked to the drug polymer conjugate by palladium catalyzed cross coupling.
Scheme 4
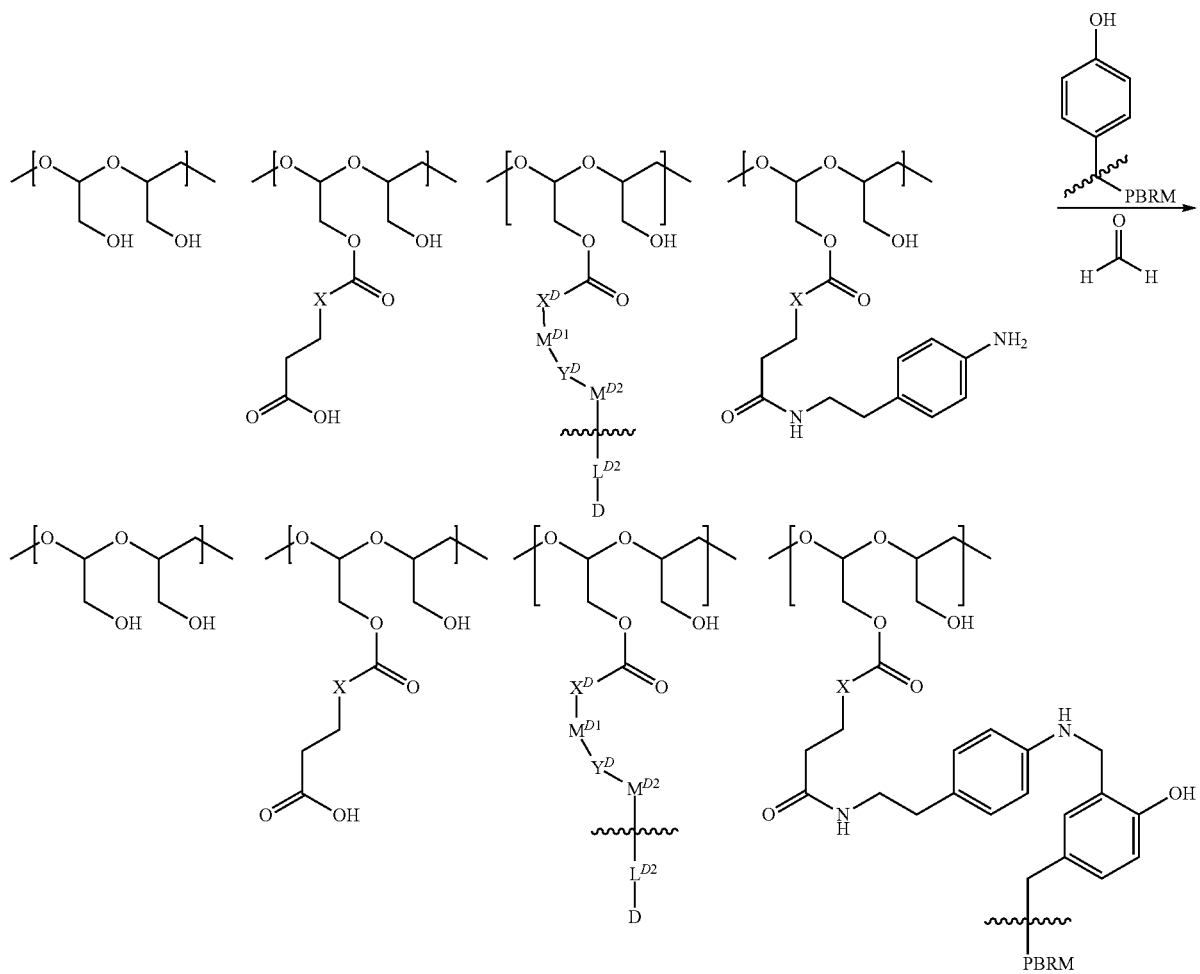

Scheme 5

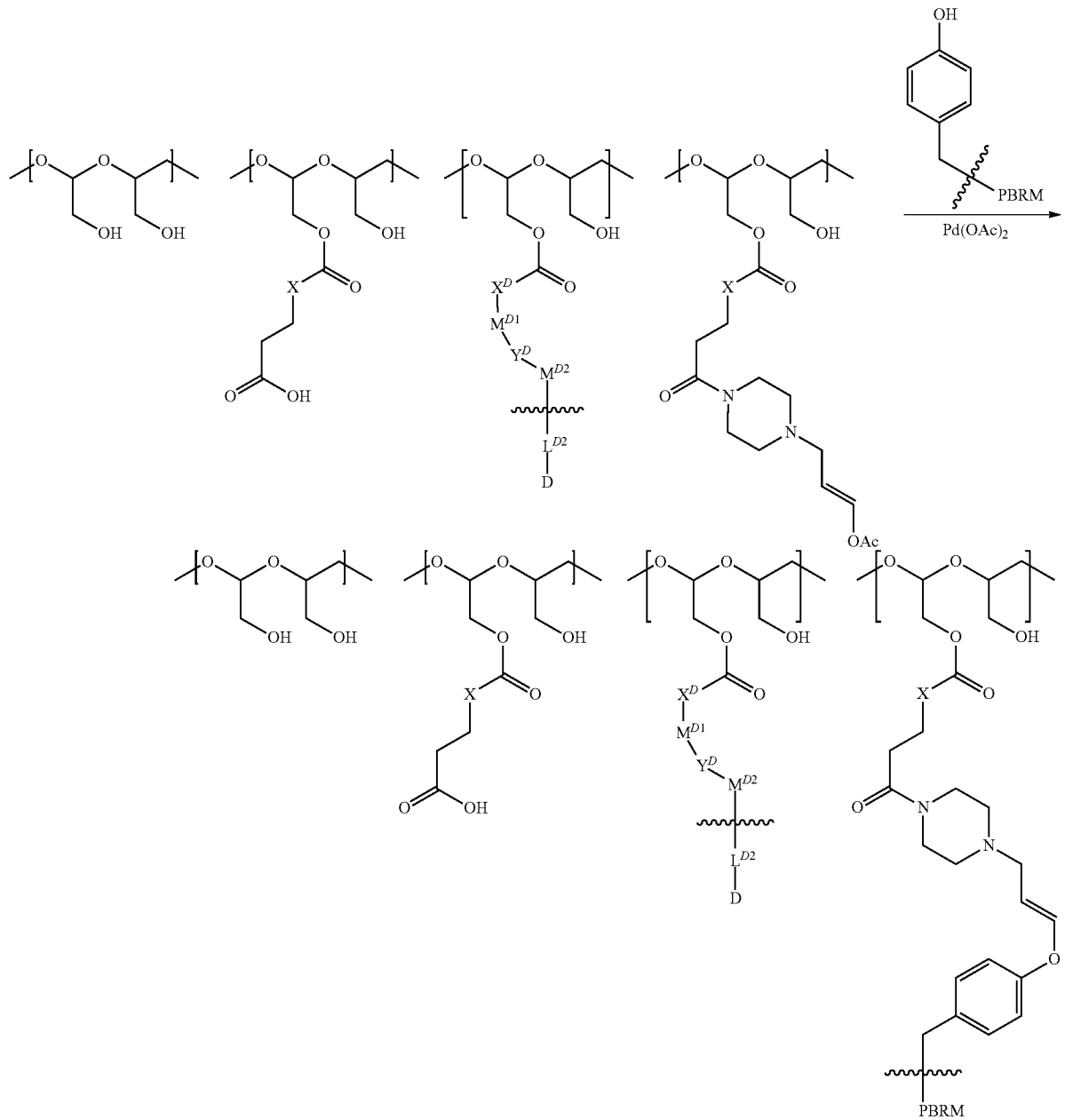

In Schemes 3-5 above, the wavy bond

indicates that PBRM is either connected to the functional modifier directly or via another moiety such as alkyl, cycloalkyl, aryl, etc.

Scheme 6 below shows a general synthetic scheme of making the polymeric scaffolds of the invention. The wavy bond

indicates direct or indirect connection between $L^{D1}$ and $L^{D2}$ or $L^{P2}$. The conjugates are formed in several steps: (1) the polymer, PHF is modified to contain a —O—CO-$L^{D1}$ moiety; (2) the polymer is then further modified so that it contains a $L^{P2}$ moiety that is capable of forming a covalent bond with a functional group of a PBRM; (3) the modified polymer, containing two different functional groups, is reacted with a functional group of a drug or its derivative (e.g., $L^{D3}$-D) to form a polymer-drug conjugate; (4) the PBRM is then reacted with the polymer-drug conjugate to form the protein-polymer-drug conjugate as depicted in the right side route in Scheme 6 below. In another embodiment the order of steps (2) and (3) can be reversed as depicted in the left side route in Scheme 6 below The PBRM can be linked to the drug-polymer conjugate to form the protein-drug polymer conjugate using standard synthetic methods for protein conjugation, including, but not limited to, reactions based on reductive amination, Staudinger ligation, oxime formation, thiazolidine formation and the methods and reactions described herein.

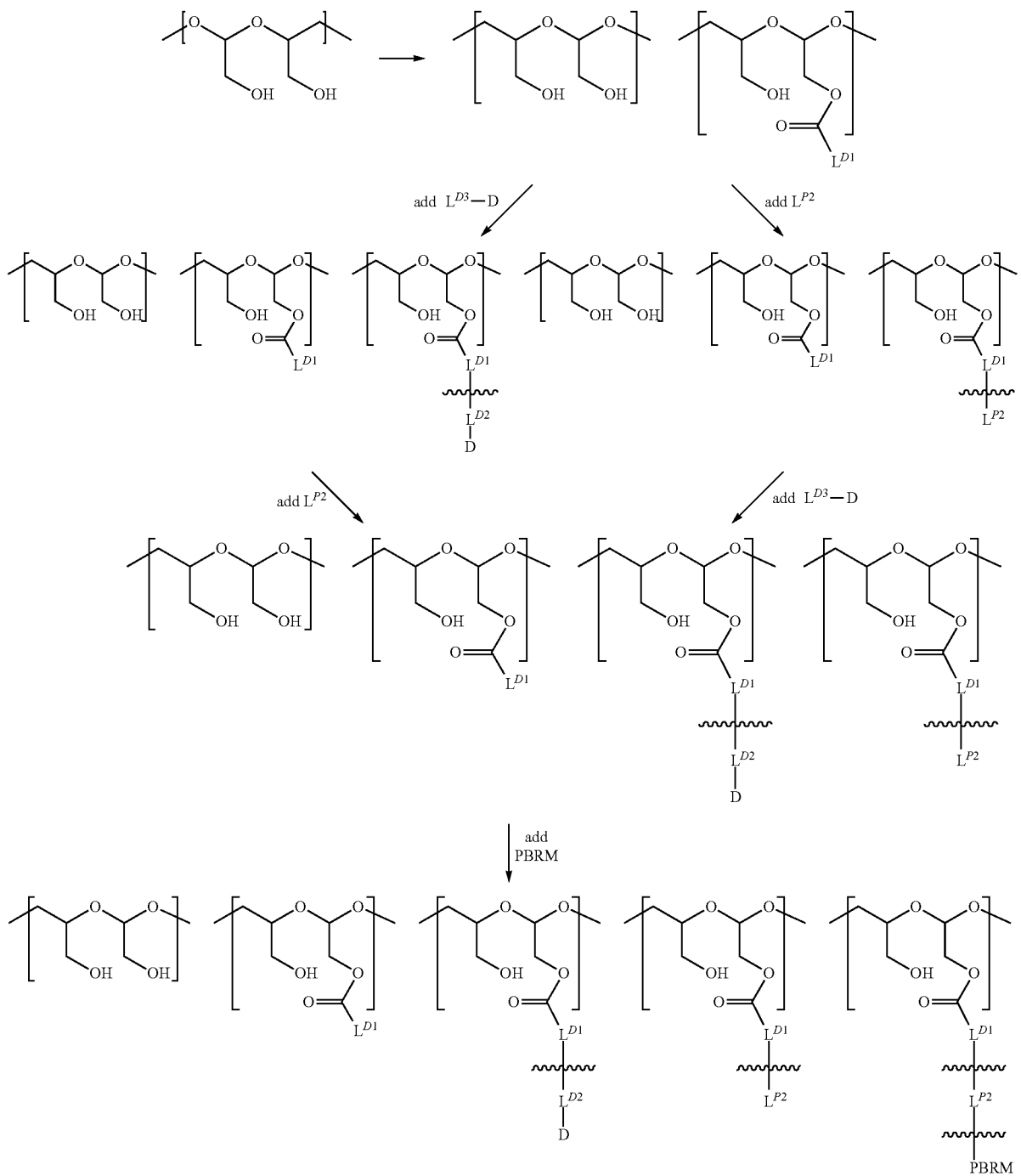

Scheme 6

In yet another embodiment, steps (2) and (3) above are carried out simultaneously as depicted in Scheme 7 below.

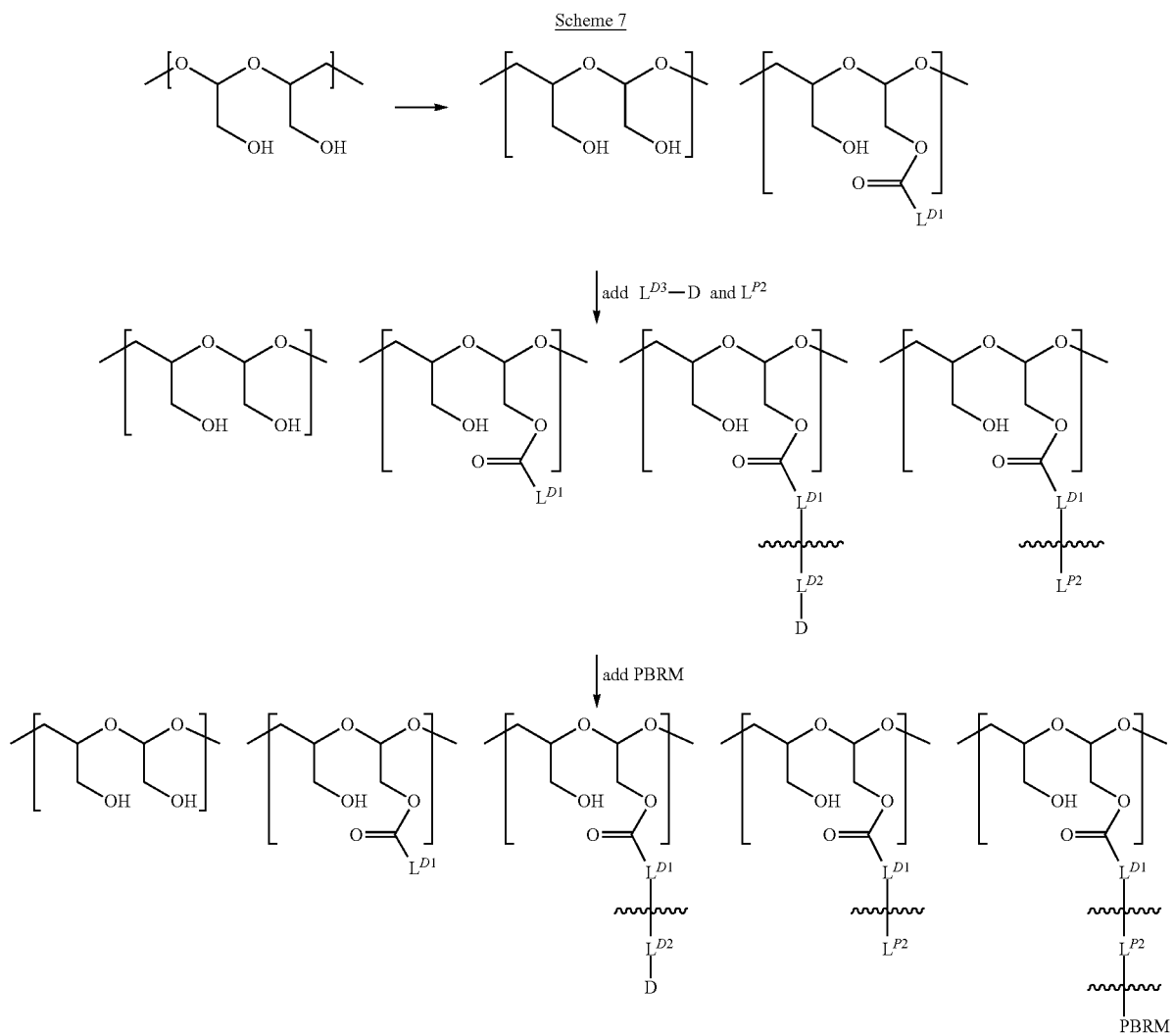

Pharmaceutical Compositions

Also included are pharmaceutical compositions comprising one or more protein-polymer-drug conjugates as disclosed herein in an acceptable carrier, such as a stabilizer, buffer, and the like. The conjugates can be administered and introduced into a subject by standard means, with or without stabilizers, buffers, and the like, to form a pharmaceutical composition. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal, oral or parenteral administration including intravenous, intraarterial, subcutaneous, intraperitoneal or intramuscular injection or infusion or intracranial, e.g., intrathecal or intraventricular, administration. The conjugates can be formulated and used as sterile solutions and/or suspensions for injectable administration; lyophilized powders for reconstitution prior to injection/infusion; topical compositions; as tablets, capsules, or elixirs for oral administration; or suppositories for rectal administration, and the other compositions known in the art.

A pharmacological composition or formulation refers to a composition or formulation in a form suitable for administration, e.g., systemic administration, into a cell or subject, including for example a human. Suitable forms, in part, depend upon the use or the route of entry, for example oral, inhaled, transdermal, or by injection/infusion. Such forms should not prevent the composition or formulation from reaching a target cell (i.e., a cell to which the drug is desirable for delivery). For example, pharmacological compositions injected into the blood stream should be soluble. Other factors are known in the art, and include considerations such as toxicity and forms that prevent the composition or formulation from exerting its effect.

By "systemic administration" is meant in vivo systemic absorption or accumulation of the modified polymer in the blood stream followed by distribution throughout the entire body. Administration routes that lead to systemic absorption include, without limitation: intravenous, subcutaneous, intraperitoneal, inhalation, oral, intrapulmonary, and intramuscular. Each of these administration routes exposes the modified polymers to an accessible diseased tissue. The rate of entry of an active agent into the circulation has been shown to be a function of molecular weight or size. The use of a conjugate of this invention can localize the drug delivery in certain cells, such as cancer cells via the specificity of PBRMs.

A "pharmaceutically acceptable formulation" means a composition or formulation that allows for the effective distribution of the conjugates in the physical location most suitable for their desired activity. In one embodiment, effective delivery occurs before clearance by the reticuloendothelial system or the production of off-target binding which can result in reduced efficacy or toxicity. Non-limiting examples of agents suitable for formulation with the conjugates include: P-glycoprotein inhibitors (such as Pluronic P85), which can enhance entry of active agents into the CNS; biodegradable polymers, such as poly(DL-lactide-coglycolide) microspheres for sustained release delivery after intracerebral implantation; and loaded nanoparticles, such as those made of polybutylcyanoacrylate, which can deliver active agents across the blood brain barrier and can alter neuronal uptake mechanisms.

Also included herein are pharmaceutical compositions prepared for storage or administration, which include a pharmaceutically effective amount of the desired conjugates in a pharmaceutically acceptable carrier or diluent. Acceptable carriers, diluents, and/or excipients for therapeutic use are well known in the pharmaceutical art. For example, buffers, preservatives, bulking agents, dispersants, stabilizers, dyes, can be provided. In addition, antioxidants and suspending agents can be used Examples of suitable carriers, diluents and/or excipients include, but are not limited to: (1) Dulbecco's phosphate buffered saline, pH about 6.5, which would contain about 1 mg/ml to 25 mg/ml human serum albumin, (2) 0.9% saline (0.9% w/v NaCl), and (3) 5% (w/v) dextrose.

The term "pharmaceutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Pharmaceutically effective amounts for a given situation can be determined by routine experimentation that is within the skill and judgment of the clinician. In a preferred aspect, the disease or condition to can be treated via gene silencing.

For any conjugate, the pharmaceutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

For example, a drug or its derivatives, drug-polymer conjugates or PBRM-drug-polymer conjugates can be evaluated for their ability to inhibit tumor growth in several cell lines using Cell titer Glo. Dose response curves can be generated using SoftMax Pro software and $IC_{50}$ values can be determined from four-parameter curve fitting. Cell lines employed can include those which are the targets of the PBRM and a control cell line that is not the target of the PBRM contained in the test conjugates.

In one embodiment, the conjugates are formulated for parenteral administration by injection including using conventional catheterization techniques or infusion. Formulations for injection may be presented in unit dosage form, e.g., in ampules or in multi-dose containers, with an added preservative. The conjugates can be administered parenterally in a sterile medium. The conjugate, depending on the vehicle and concentration used, can either be suspended or dissolved in the vehicle. Advantageously, adjuvants such as local anesthetics, preservatives, and buffering agents can be dissolved in the vehicle. The term "parenteral" as used herein includes percutaneous, subcutaneous, intravascular (e.g., intravenous), intramuscular, or intrathecal injection or infusion techniques and the like. In addition, there is provided a pharmaceutical formulation comprising conjugates and a pharmaceutically acceptable carrier. One or more of the conjugates can be present in association with one or more non-toxic pharmaceutically acceptable carriers and/or diluents and/or adjuvants, and if desired other active ingredients.

The sterile injectable preparation can also be a sterile injectable solution or suspension in a non-toxic parentally acceptable diluent or solvent, for example as a solution in 1,3-butanediol. Among the acceptable vehicles and solvents that can be employed are water, Ringer's solution, and isotonic sodium chloride solution. In addition, sterile, fixed oils are conventionally employed as a solvent or suspending medium. For this purpose, a bland fixed oil can be employed including synthetic mono- or diglycerides. In addition, fatty acids such as oleic acid find use in the preparation of injectables.

The conjugates and compositions described herein may be administered in appropriate form, preferably parenterally, more preferably intravenously. For parenteral administration, the conjugates or compositions can be aqueous or nonaqueous sterile solutions, suspensions or emulsions. Propylene glycol, vegetable oils and injectable organic esters, such as ethyl oleate, can be used as the solvent or vehicle. The compositions can also contain adjuvants, emulsifiers or dispersants.

Dosage levels of the order of from between about 0.01 mg and about 140 mg per kilogram of body weight per day are useful in the treatment of the above-indicated conditions (between about 0.05 mg and about 7 g per subject per day). In some embodiments, the dosage administered to a patient is between about 0.01 mg/kg to about 100 mg/kg of the subject's body weight. In some embodiments, the dosage administered to a patient is between about 0.01 mg/kg to about 15 mg/kg of the subjects body weight. In some embodiments, the dosage administered to a patient is between about 0.1 mg/kg and about 15 mg/kg of the subject's body weight. In some embodiments, the dosage administered to a patient is between about 0.1 mg/kg and about 20 mg/kg of the subject's body weight. In some embodiments, the dosage administered is between about 0.1 mg/kg to about 5 mg/kg or about 0.1 mg/kg to about 10 mg/kg of the subject's body weight. In some embodiments, the dosage administered is between about 1 mg/kg to about 15 mg/kg of the subject's body weight. In some embodiments, the dosage administered is between about 1 mg/kg to about 10 mg/kg of the subject's body weight. The amount of conjugate that can be combined with the carrier materials to produce a single dosage form varies depending upon the host treated and the particular mode of administration. Dosage unit forms can generally contain from between about 0.01 mg and about 100 mg; between about 0.01 mg and about 75 mg; or between about 0.01 mg and about 50 mg; or between about 0.01 mg and about 25 mg; of a conjugate.

For intravenous administration, the dosage levels can comprise from about 0.01 to about 200 mg of a conjugate per kg of the animal's body weight. In one aspect, the composition can include from about 1 to about 100 mg of a conjugate per kg of the animal's body weight. In another aspect, the amount administered will be in the range from about 0.1 to about 25 mg/kg of body weight of a compound.

In some embodiments, the conjugates can be administered are as follows. The conjugates can be given daily for about 5 days either as an i.v., bolus each day for about 5 days, or as a continuous infusion for about 5 days.

Alternatively, the conjugates can be administered once a week for six weeks or longer. As another alternative, the conjugates can be administered once every two or three weeks. Bolus doses are given in about 50 to about 400 ml of normal saline to which about 5 to about 10 ml of human serum albumin can be added. Continuous infusions are given in about 250 to about 500 ml of normal saline, to which about 25 to about 50 ml of human serum albumin can be added, per 24 hour period.

In some embodiments about one to about four weeks after treatment, the patient can receive a second course of treatment. Specific clinical protocols with regard to route of administration, excipients, diluents, dosages, and times can be determined by the skilled artisan as the clinical situation warrants.

It is understood that the specific dose level for a particular subject depends upon a variety of factors including the activity of the specific conjugate, the age, body Weight, general health, sex, diet, time of administration, route of administration, and rate of excretion, combination with other active agents, and the severity of the particular disease undergoing therapy.

For administration to non-human animals, the conjugates can also be added to the animal feed or drinking water. It can be convenient to formulate the animal feed and drinking water so that the animal takes in a therapeutically appropriate quantity of the conjugates along with its diet. It can also be convenient to present the conjugates as a premix for addition to the feed or drinking water.

The conjugates can also be administered to a subject in combination with other therapeutic compounds to increase the overall therapeutic effect. The use of multiple compounds to treat an indication can increase the beneficial effects while reducing the presence of side effects. In some embodiment the conjugates are used in combination with chemotherapeutic agents, such as those disclosed in U.S. Pat. No. 7,303,749. In other embodiments the chemotherapeutic agents, include, but are not limited to letrozole, oxaliplatin, docetaxel, 5-FU, lapatinib, capecitabine, leucovorin, erlotinib, pertuzumab, bevacizumab, and gemcitabine.

The present invention also provides pharmaceutical kits comprising one or more containers filled with one or more of the conjugates and/or compositions of the present invention, including, one or more chemotherapeutic agents. Such kits can also include, for example, other compounds and/or compositions, a device(s) for administering the compounds and/or compositions, and written instructions in a form prescribed by a governmental agency regulating the manufacture, use or sale of pharmaceuticals or biological products.

Methods of Use
Methods of Treating

In certain preferred embodiments of the invention, the protein-polymer-drug conjugate of the invention are used in methods of treating animals (preferably mammals, most preferably humans and includes males, females, infants, children and adults). In one embodiment, the conjugates of the present invention may be used in a method of treating animals which comprises administering to the animal a biodegradable biocompatible conjugate of the invention. For example, conjugates in accordance with the invention can be administered in the form of soluble linear polymers, copolymers, conjugates, colloids, particles, gels, solid items, fibers, films, etc. Biodegradable biocompatible conjugates of this invention can be used as drug carriers and drug carrier components, in systems of controlled drug release, preparations for low-invasive surgical procedures, etc. Pharmaceutical formulations can be injectable, implantable, etc.

In yet another aspect, the invention provides a method of treating a disease or disorder in a subject in need thereof, comprising administering to the subject an efficient amount of at least one conjugate of the invention; wherein said conjugate releases one or more auristatin compounds upon biodegradation.

In another embodiment the conjugates can be administered in vitro, in vivo and/or ex vivo to treat patients and/or to modulate the growth of selected cell populations including, for example, cancer. In some embodiments, the particular types of cancers that can be treated with the conjugates include, but are not limited to: (1) solid tumors, including but not limited to fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophogeal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma, multiforme astrocytoma, medulloblastoma, craniopharyngioma, ependymoma, pinealoma, hemangioblastoma, acoustic neuroma, oligodendroglioma, meningioma, skin cancer, melanoma, neuroblastoma, and retinoblastoma; (2) blood-borne cancers, including but not limited to acute lymphoblastic leukemia "ALL", acute lymphoblastic B-cell leukemia, acute lymphoblastic T-cell leukemia, acute myeloblastic leukemia "AML", acute promyelocytic leukemia "APL", acute monoblastic leukemia, acute erythroleukemic leukemia, acute megakaryoblastic leukemia, acute myelomonocytic leukemia, acute nonlymphocyctic leukemia, acute undifferentiated leukemia, chronic myelocytic leukemia "CML", chronic lymphocytic leukemia "CLL", hairy cell leukemia, multiple myeloma, acute and chronic leukemias, e.g., lymphoblastic myelogenous and lymphocytic myelocytic leukemias; and (3) lymphomas such as Hodgkin's disease, non-Hodgkin's Lymphoma, Multiple myeloma, Waldenstrom's macroglobulinemia, Heavy chain disease, and Polycythemia vera.

In another embodiment the conjugates can be administered in vitro, in vivo and/or ex vivo to treat autoimmune diseases, such as systemic lupus, rheumatoid arthritis, psoriasis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, and AIDS; and parasite infections, such as giardiasis, amoebiasis, schistosomiasis, and the like.

In certain embodiments the conjugates can also be used for the manufacture of a medicament useful for treating or lessening the severity of disorders, such as, characterized by abnormal growth of cells (e.g., cancer).

In certain embodiments, the auristatin compound is locally delivered to a specific target cell, tissue, or organ.

In certain embodiments, in practicing the method of the invention, the conjugate further comprises or is associated with a diagnostic label. In certain exemplary embodiments, the diagnostic label is selected from the group consisting of: radiopharmaceutical or radioactive isotopes for gamma scintigraphy and PET, contrast agent for Magnetic Resonance Imaging (MRI), contrast agent for computed tomography, contrast agent for X-ray imaging method, agent for ultrasound diagnostic method, agent for neutron activation, moiety which can reflect, scatter or affect X-rays, ultrasounds, radiowaves and microwaves and fluorophores. In certain exemplary embodiments, the conjugate is further monitored in vivo.

Examples of diagnostic labels include, but are not limited to, diagnostic radiopharmaceutical or radioactive isotopes for gamma scintigraphy and PET, contrast agent for Magnetic Resonance Imaging (MRI) (for example paramagnetic atoms and superparamagnetic nanocrystals), contrast agent for computed tomography, contrast agent for X-ray imaging method, agent for ultrasound diagnostic method, agent for neutron activation, and moiety which can reflect, scatter or affect X-rays, ultrasounds, radiowaves and microwaves, fluorophores in various optical procedures, etc. Diagnostic radiopharmaceuticals include γ-emitting radionuclides, e.g., indium-111, technetium-99m and iodine-131, etc. Contrast agents for MRI (Magnetic Resonance Imaging) include magnetic compounds, e.g., paramagnetic ions, iron, manganese, gadolinium, lanthanides, organic paramagnetic moieties and superparamagnetic, ferromagnetic and antiferromagnetic compounds, e.g., iron oxide colloids, ferrite colloids, etc. Contrast agents for computed tomography and other X-ray based imaging methods include compounds absorbing X-rays, e.g., iodine, barium, etc. Contrast agents for ultrasound based methods include compounds which can absorb, reflect and scatter ultrasound waves; e.g., emulsions, crystals, gas bubbles, etc. Still other examples include substances useful for neutron activation, such as boron and gadolinium. Further, labels can be employed which can reflect, refract, scatter, or otherwise affect X-rays, ultrasound, radiowaves, microwaves and other rays useful in diagnostic procedures. Fluorescent labels can be used for photoimaging. In certain embodiments a modifier comprises a paramagnetic ion or group.

In another aspect, the invention provides a method of treating a disease or disorder in a subject, comprising preparing an aqueous formulation of at least one conjugate of the invention and parenterally injecting said formulation in the subject.

In another aspect, the invention provides a method of treating a disease or disorder in a subject, comprising preparing an implant comprising at least one conjugate of the invention, and implanting said implant into the subject. In certain exemplary embodiments, the implant is a biodegradable gel matrix.

In another aspect, the invention provides a method for treating of an animal in need thereof, comprising administering a conjugate according to the methods described above.

In another aspect, the invention provides a method for eliciting an immune response in an animal, comprising administering a conjugate as in the methods described above.

In another aspect, the invention provides a method of diagnosing a disease in an animal, comprising steps of:
administering a conjugate as in the methods described above, wherein said conjugate comprises a detectable molecule; and detecting the detectable molecule.

In certain exemplary embodiments, the step of detecting the detectable molecule is performed non-invasively. In certain exemplary embodiments, the step of detecting the detectable molecule is performed using suitable imaging equipment.

In one embodiment, a method for treating an animal comprises administering to the animal a biodegradable biocompatible conjugate of the invention as a packing for a surgical wound from which a tumor or growth has been removed. The biodegradable biocompatible conjugate packing will replace the tumor site during recovery and degrade and dissipate as the wound heals.

In certain embodiments, the conjugate is associated with a diagnostic label for in vivo monitoring.

The conjugates described above can be used for therapeutic, preventative, and analytical (diagnostic) treatment of animals. The conjugates are intended, generally, for parenteral administration, but in some cases may be administered by other routes.

In one embodiment, soluble or colloidal conjugates are administered intravenously. In another embodiment, soluble or colloidal conjugates are administered via local (e.g., subcutaneous, intramuscular) injection. In another embodiment, solid conjugates (e.g., particles, implants, drug delivery systems) are administered via implantation or injection.

In another embodiment, conjugates comprising a detectable label are administered to study the patterns and dynamics of label distribution in animal body.

In certain embodiments, any one or more of the conjugates disclosed herein may be used in practicing any of the methods described above. In certain exemplary embodiments, the conjugate is a Trastuzumab-PHF-, Rituximab-PHF-, Lintuzumab-PHF, anti-5T4-PHF, anti-mesothelin-PHF or LHRH-PHF-drug conjugate.

Throughout the description, where compositions are described as having, including, or comprising specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the invention remains operable. Moreover, two or more steps or actions can be conducted simultaneously.

The synthetic processes of the invention can tolerate a wide variety of functional groups; therefore various substituted starting materials can be used. The processes generally provide the desired final compound at or near the end of the overall process, although it may be desirable in certain instances to further convert the compound to a pharmaceutically acceptable salt, ester or prodrug thereof.

Drug compounds used for the conjugates of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations can be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; and Greene, T. W., Wuts, P. G. M., *Protective Groups in Organic Synthesis*, $3^{rd}$ edition, John Wiley & Sons: New York, 1999, incorporated by reference herein, are useful and recognized reference textbooks of organic synthesis known to those in the art. The following descriptions of synthetic methods are designed to illustrate, but not to limit, general procedures for the preparation of compounds of the present invention.

Conjugates of the present invention and the drug compounds included therein can be conveniently prepared by a variety of methods familiar to those skilled in the art. The conjugates or compounds of this invention with each of the formulae described herein may be prepared according to the following procedures from commercially available starting materials or starting materials which can be prepared using literature procedures. These procedures show the preparation of representative conjugates of this invention.

Conjugates designed, selected and/or optimized by methods described above, once produced, can be characterized using a variety of assays known to those skilled in the art to determine whether the conjugates have biological activity. For example, the conjugates can be characterized by conventional assays, including but not limited to those assays described below, to determine whether they have a predicted activity, binding activity and/or binding specificity.

Furthermore, high-throughput screening can be used to speed up analysis using such assays. As a result, it can be possible to rapidly screen the conjugate molecules described herein for activity, using techniques known in the art. General methodologies for performing high-throughput screening are described, for example, in Devlin (1998) High Throughput Screening, Marcel Dekker; and U.S. Pat. No. 5,763,263. High-throughput assays can use one or more different assay techniques including, but not limited to, those described below.

All publications and patent documents cited herein are incorporated herein by reference as if each such publication or document was specifically and individually indicated to be incorporated herein by reference. Citation of publications and patent documents is not intended as an admission that any is pertinent prior art, nor does it constitute any admission as to the contents or date of the same. The invention having now been described by way of written description, those of skill in the art will recognize that the invention can be practiced in a variety of embodiments and that the foregoing description and examples below are for purposes of illustration and not limitation of the claims that follow.

EXAMPLES

Conjugates described herein can be prepared by the schemes generally outlined above and by methods described in the Examples below. The term "content" as used in certain examples below, unless otherwise specified, means the molar fraction of the polymer units that are substituted with the intended moiety, such as the linker, the drug molecule (i.e., auristatin compound), or PBRM.

Abbreviations

The following abbreviations are used in the reaction schemes and synthetic examples, which follow. This list is not meant to be an all-inclusive list of abbreviations used in the application as additional standard abbreviations, which are readily understood by those skilled in the art of organic synthesis, can also be used in the synthetic schemes and examples.

| | |
|---|---|
| AE | Auristatin E |
| AF | Auristatin F |
| BA | β-Alanine |
| BOC | tert-Butyloxycarbonyl |
| DIC | N,N'-Diisopropylcarbodiimide |
| DMA | Dimethylacetami |
| DMF | Dimethylfoimamide |
| DMAP | 4-Dimethylaminopyridine |
| DMSO | Dimethylsulfoxide |
| DTT | (2S,3S)-1,4-dimercaptobutane-2,3-diol |
| EDC | 1-Ethyl-3-[3-dimethylaminopropyl]carbodiimide hydrochloride |
| GA | Glutaric acid |
| HOBt | Hydroxybenzotriazole |
| HPLC | High pressure liquid chromatography |
| HPSEC | High perfoil lance size exclusion chromatography |
| MCC | (N-maleimidomethyl) 1,4-cyclohexyl carbamate |
| MI | Maleimido |
| MMAE | Monomethyl auristatin E |
| MMAF | Monomethyl auristatin F |
| M-(PEG)$_{12}$ | N-maleimido-PEG$_{12}$-propionamide |
| MWCO | Molecular Weight Cut-Off |
| NHS | 1-Hydroxypyrrolidine-2,5-dione |
| NMP | N-methyl-2-pyrrolidone |
| PABA | p-Amino benzoic acid |
| PBS | Phosphate buffered saline, 0.9 % NaCl |
| PHF | poly(1-hydroxymethylethylene hydroxylmethylformal), or FLEXIMER ® |
| PNP | p-Nitrophenoxide |
| SATA | N-Succinimidyl-S-acetylthioacetate |
| SEC | Size exclusion chromatography |
| SMCC | Succinimidy1-4-(N-maleimidomethyl)cyclohexane-1-carboxylate |
| SM(PEG)$_{12}$ | Succinimidyl-([N-maleimidopropionamideFPEG$_{12}$)-ester |
| -SS- | Indicates a covalently bound disulfide group |
| SSPy | 2-(pyridine-2-yldisulfanyl) |
| TCEP | Tris[2-carboxyethyl] phosphine |
| TEA | Triethylamine |
| TFA | Trifluoroacetic acid |

General Information

Fmoc-Val-Cit-PABA-PNP, auristatin E and auristatin F were purchased from Concortis Biosystems.

6-Maleimidohexanoic acid N-hydroxysuccinimide ester was purchased from Aldrich Chemicals.

N-Boc-D-valine was purchased from Alfa Aesar.

N-Boc-L-Val-OH was purchased from Novabiochem.

Anti-Her2 affibody, 14 K, was purchased from Affibody AB.

HPLC purification was performed on a Phenomenex Gemini 5 μm 110 Å, 250×10 mm, 5 micron, semi-preparation column using the following solvent system: Solvent A: water (0.1% TFA); Solvent B: CH$_3$CN (0.1% TFA).

Whenever possible the drug content of the conjugates was determined. spectrophotometrically otherwise LC/MS was performed for quantitative determination of the drug content.

Protein content of the conjugates was determined spectrophotometrically at 280 nm.

Disulfide content in —SSPy conjugates was determined spectrophotometrically at 340 nm after pyridinethione release (10 mM DTT, 10 min, ambient temperature).

The molecular weights of the polymer conjugates were determined by SEC with either polysaccharide or protein molecular weight standards. More specifically, for the polymer or polymer drug conjugates, polysaccharide molecular weights standard are used, and for protein-drug polymer conjugates, protein standards are used. Unless specifically indicated the reported polymer carrier molecular weight is the weight average molecular weight of PHF. The polymer and polymer conjugates synthesized/measured all had a polydispersity <2.

PBRM-drug polymer conjugates were isolated from residual unreacted drug polymer conjugates by extensive diafiltration. If necessary, additional purification by size exclusion chromatography was conducted to remove any aggregated PBRM-drug polymer conjugates. In general, the PBRM-drug polymer conjugates typically contained <5% aggregated PBRM-drug polymer conjugates as determined by SEC or SDS-PAGE; <1% free (unconjugated) drug as determined by SEC and <2% unconjugated PBRM as determined by HPLC.

Reduced or partially reduced antibodies were prepared using procedures described in the literature, see, for example, Francisco et al., Blood 102 (4): 1458-1465 (2003).

Example 1

Synthesis of 13 kDa PHF-β-Alanine

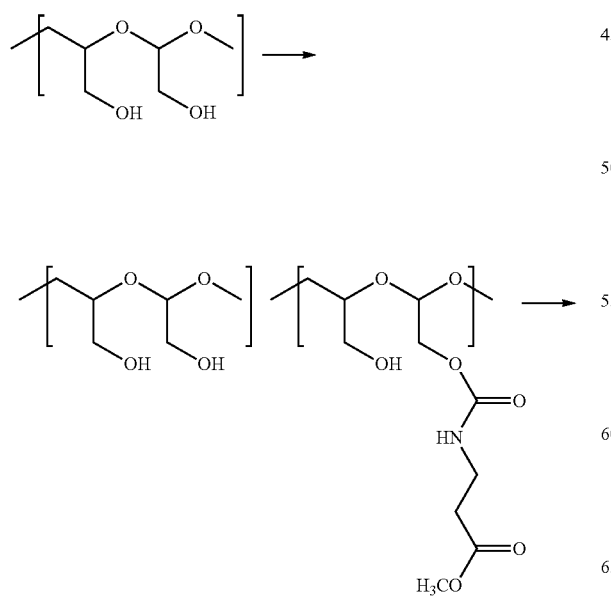

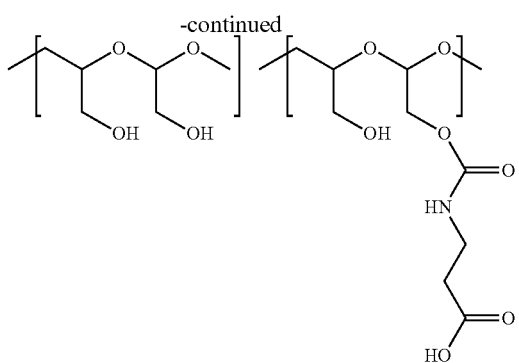

PHF (12 g), DMA (100 g) and pyridine (7.4 g) were stirred at 40° C. for ~3 hours. To the clear solution was added methyl-3-isocyanatopropanoate (3.8 g, 0.33 mole % to PHF) over a period of 5 minutes and the stirring continued for an additional 24 hours at 45° C. The reaction mixture was then diluted with water (320 g) and 5N NaOH (32 g) at 25° C. was added over 2 minutes, final pH 13. The mixture was stirred at 25° C. for 18 h, the pH of the reaction mixture was adjusted to 7 with 1N HCl, followed by dilution to ~3.5 L with water and concentrated by diafiltration using a membrane filter, 3 kDa MWCO followed by purification on a Sephadex G-25 column. (BA ~31%, 14 g, yield 90%). MW ~13 kDa.

Example 2

Synthesis of 13 kDa PHF-BA-SSpy

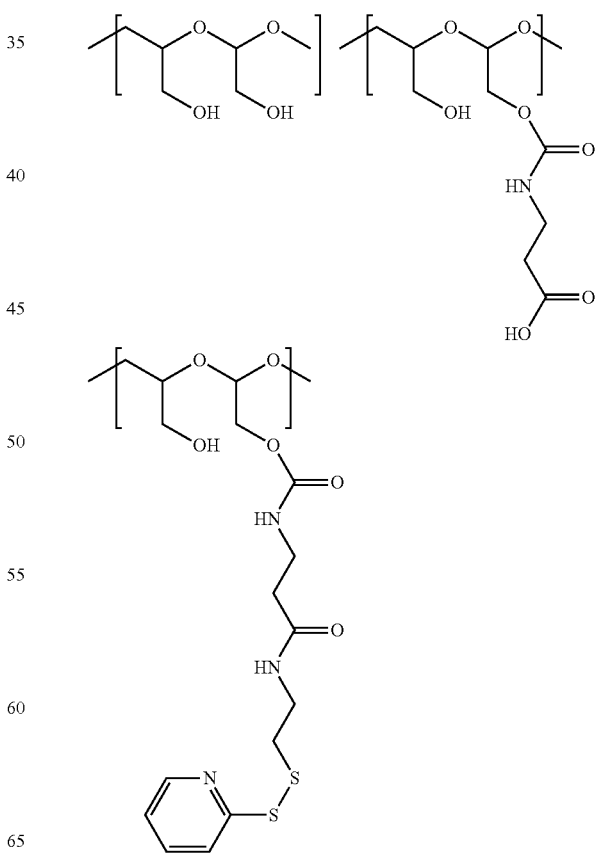

PHF-BA (2.5 g, prepared using the procedure described in Example 1, MW ~13 kDa), NHS (0.103 g) and 2-(pyridine-2-yldisulfanyl)ethaneamine hydrochloride (0.2 g) were dissolved in water (50 mL). The mixture was cooled to 5-10° C. and then an aqueous solution of EDC (0.344 g) was added. The pH of the resulting mixture was adjusted to 5.5-6.0 then stirred at 23° C. for 18 h, followed by purification using a membrane filter, 3 kDa MWCO, and lyophilization to give the title compound (1.9 g, 75% yield) as a white solid. The SSPy content was 5.9%.

Example 3

Synthesis of MMAE-PABA-Val-Cit-NH$_2$

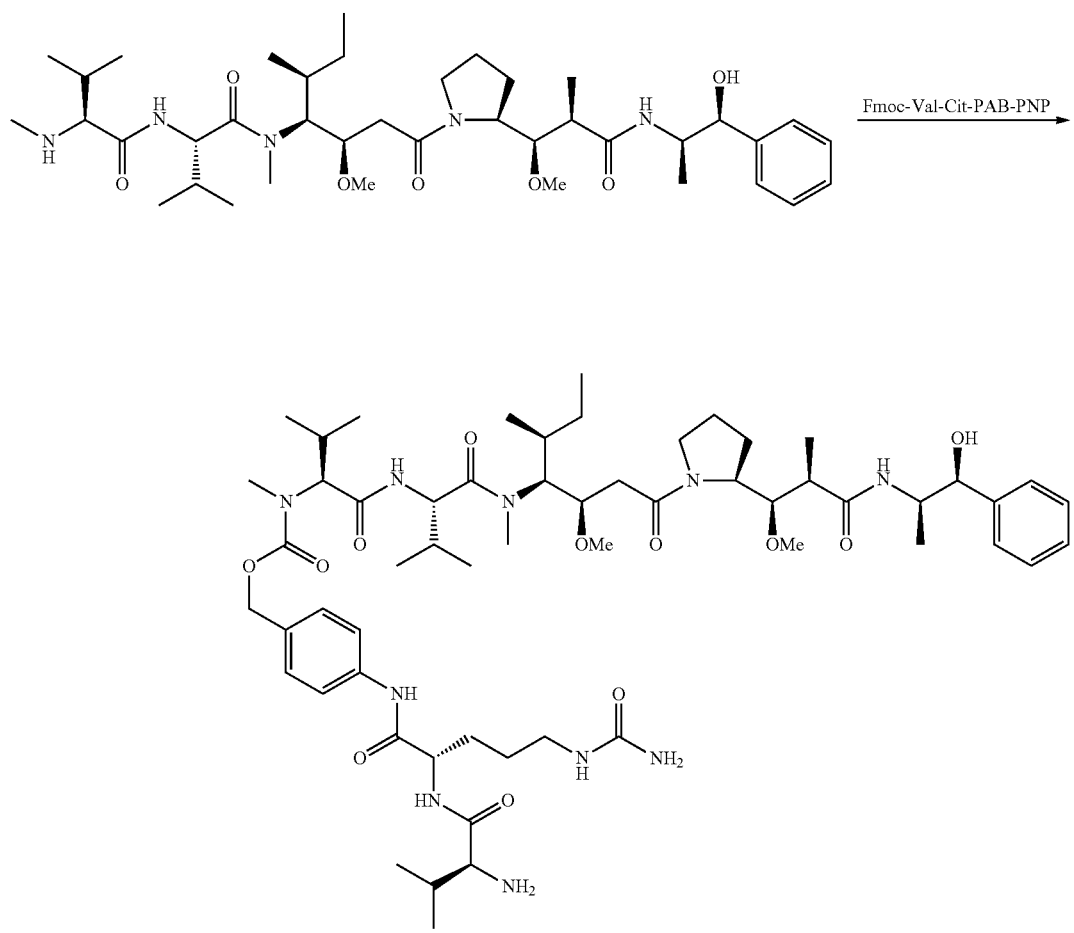

Fmoc-Val-Cit-PABA-PNP (101 mg, 0.132 mmol), MMAE (100 mg, 0.120 mmol) and HOBt (22.1 mg, 0.144 mmol) in DMF (4 mL) were stirred for 5 min until homogeneous. To the reaction mixture was added triethylamine (0.084 ml, 0.601 mmol). After 4 h additional HOBt (10 mg) and Fmoc-Val-Cit-PABA-PNP (20 mg) were added and the mixture stirred overnight at 35° C. The crude reaction mixture was purified to give the title compound as to a white amorphous solid (42.6 mg, 29% yield). M/z=1123.7.

Example 4

Synthesis of 13 kDa PHF BA-(SS-Py)-MMAE-PABA-Val-Cit

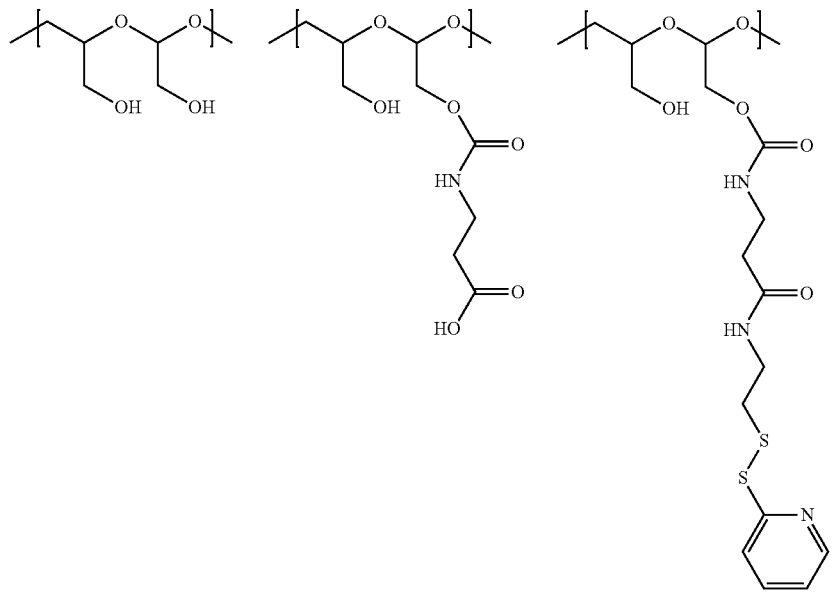

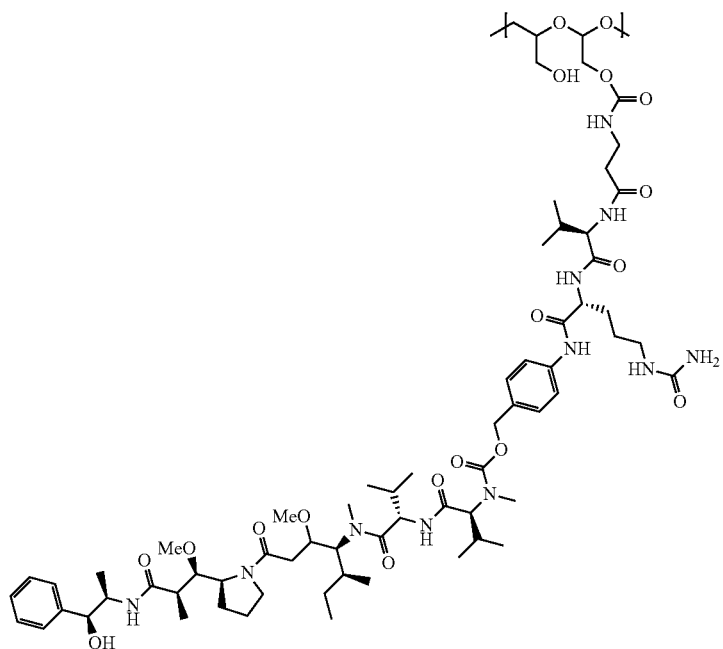

13K PHF-BA(31%)-S—S-pyr (5.9%) (31.1 mg, 2.47 µmol), prepared using the procedure described in Example 2 was dissolved in NMP (2.0 mL). To the reaction mixture HOAt (8.41 mg, 0.062 mmol) in NMP (0.2 mL), and EDC (11.84 mg, 0.062 mmol) in NMP (0.5 mL) were added. The mixture was stirred for 10 minutes and a solution of DIPEA (6.79 µl, 0.04; mmol) and MMAE-PABA-Val-Cit (5.90 mg, 5.90 prepared as described in Example 3) in NMP (0.300 mL) were added. After stirring at room temperature for 18 h the mixture was diluted to 5% organics with deionized water, concentrated via dialysis using a Regenerated cellulose membrane (3K) to give the title compound.

Example 5

Synthesis of 13 kDa PHF BA-MMAE-PABA-Val-Cit-SS-Trastuzumab

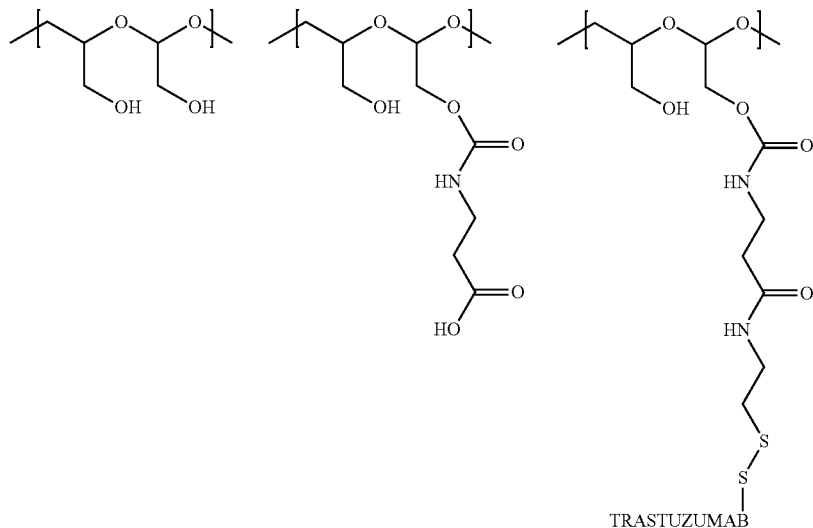

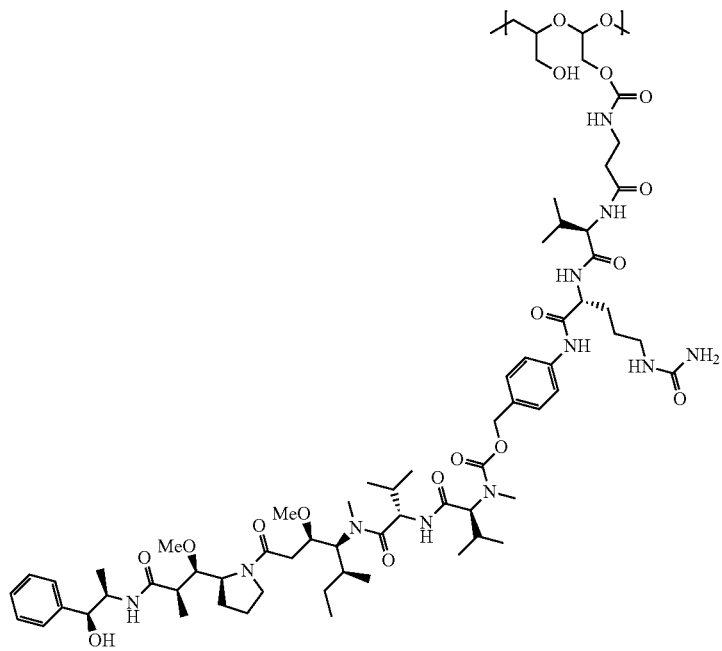

To reduced trastuzumab (5 mg, prepared by treatment with TCEP) in triethylamine acetate buffer (1 mL, 50 mM, containing 1 mM EDTA, pH=7.0) was added 13 kDa PHF BA-SS-Py MMAE-PABA-Val-Cit (1.73 mg, prepared as described in Example 4). After 18 h at room temperature the resulting conjugate was isolated and purified by diafitration (30% yield). The MMAE to Trastuzumab ratio was about 6:1 to about 10:1.

Other protein-auristatin compound-polymer conjugates are synthesized with methods similar to the procedure described above, involving other PBRM derivatives, such as, for example, reduced form of cetuximab, rituximab, bevacizumab, nimotuzumab, gemtuzumab, alemtuzumab, lintuzumab, anti-5T4 or anti-mesothelin antibodies as described above. Also PBRM-drug polymer conjugates with varying ratios of drug to PBRM are obtained by varying the amount of PBRM and drug-polymer scaffold used in the Examples above.

Example 6

Synthesis of MMAE-PABA-Val-Cit-MI

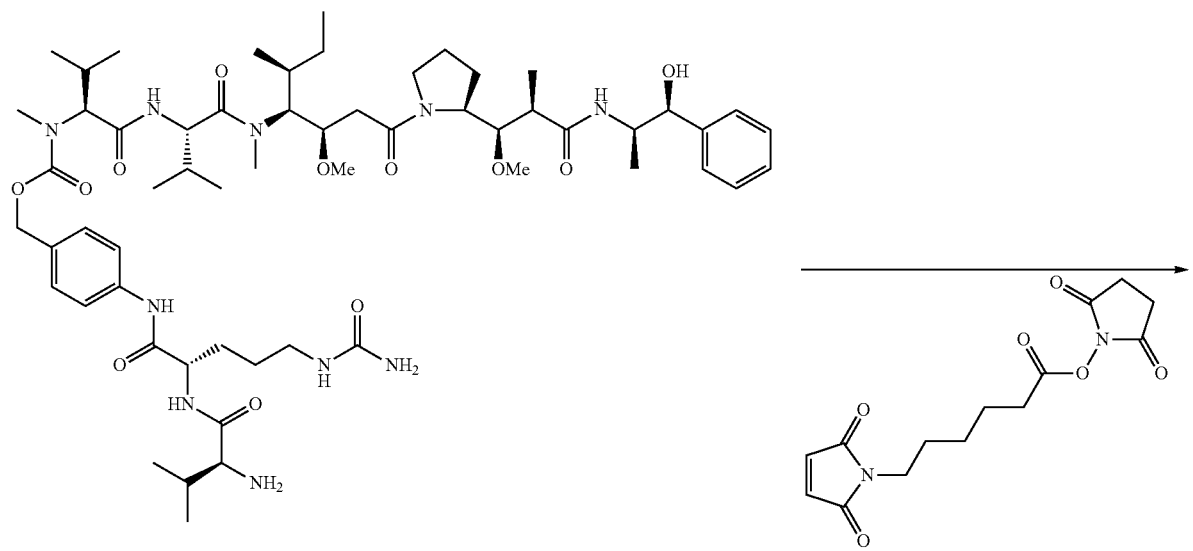

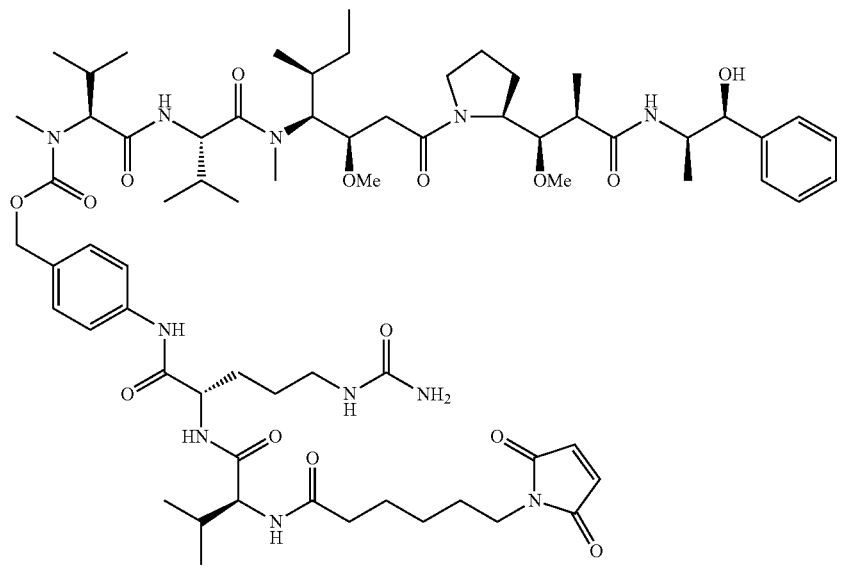

MMAE-PABA-Val-Cit-NH$_2$ (11.2 mg, 9.05 μmol, prepared as described in Example 3), 2,5-dioxopyrrolidin-1-yl 6-(2,5-dioxo-2,5-dihydro-1H-pyrrol-1-yl)hexanoate (5.58 mg, 0.018 mmol) and HOBt (2.77 mg, 0.018 mmol) in DMF (1 mL) were stirred at room temperature, followed by the addition of triethylamine (0.013 ml, 0.091 mmol). After 4 h the reaction mixture was purified to give the title compound as a white amorphous solid (6 mg, 46% yield). M/z=1316.7.

Example 7

Synthesis of MMAE-MI

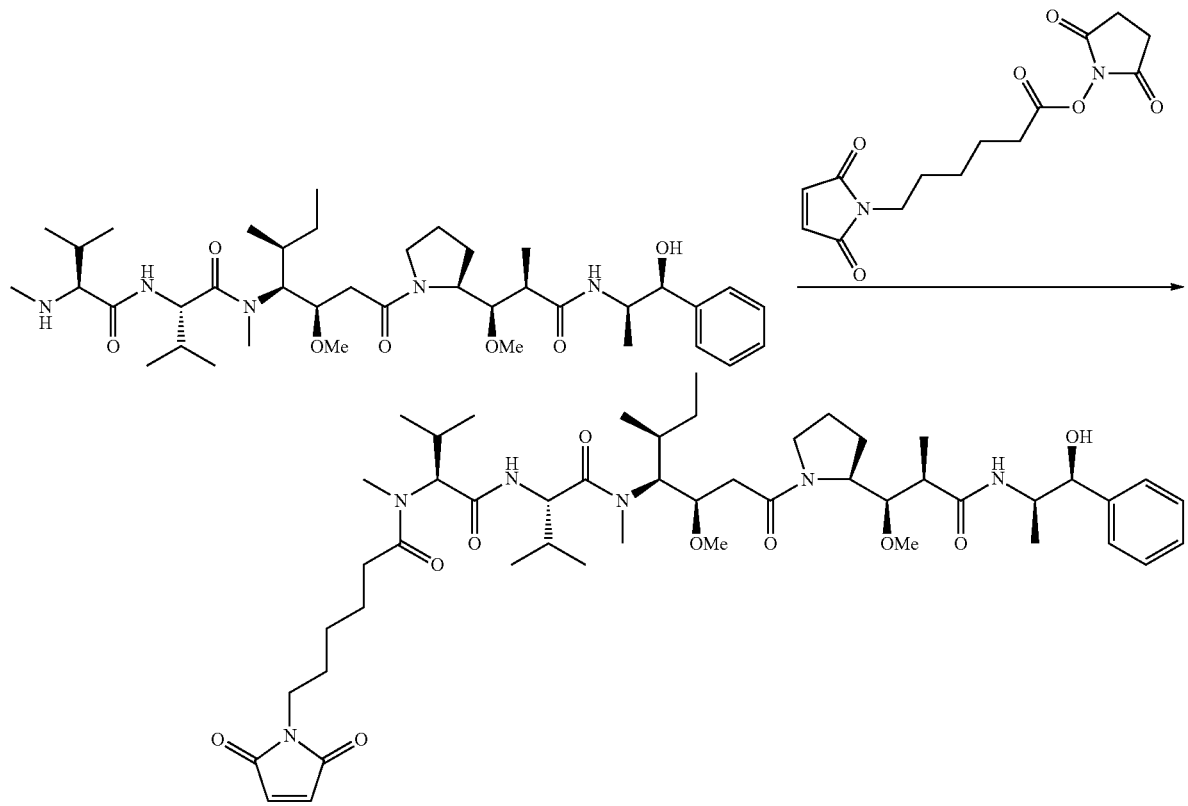

MMAE (25 mg, 0.35 mmol), 2,5-dioxopyrrolidin-1-yl 6-(2,5-dioxo-2,5-dihydro-1H-pyrrol-1-yl)hexanoate (12.88 mg, 0.042 mmol) and HOBt (10.66 mg, 0.070 mmol) in DMA (1.5 mL) were stirred at room temperature, followed by the addition of triethylamine (0.019 ml, 0.139 mmol). After 4 h the reaction mixture was purified to give the title compound as a white amorphous solid (4 mg, 12% yield). M/z=911.6.

Example 8

Synthesis of 13 kDa PHF BA-MMAE-MI-SH

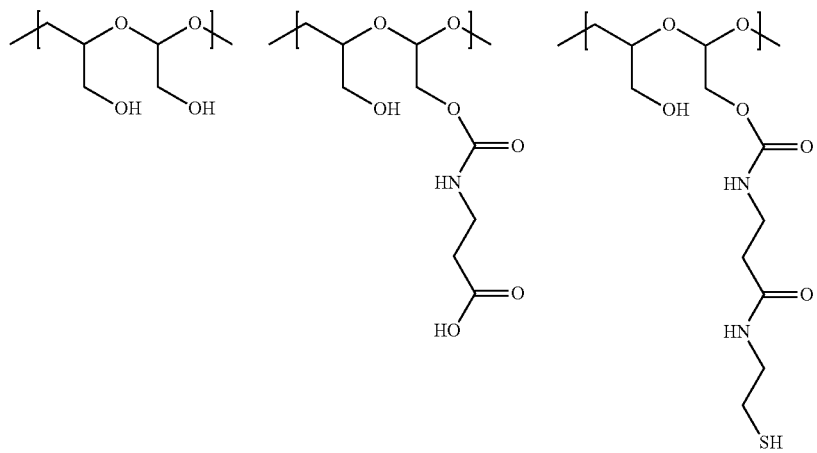

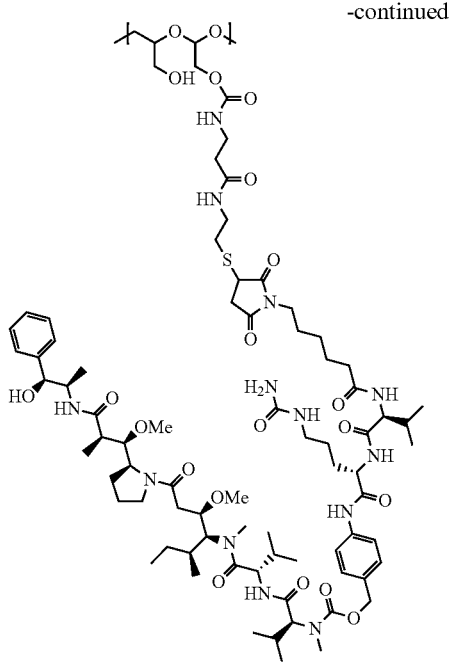

13K PHF-BA(31%)-S—S-pyr(5.9%) (prepared using the procedure described in Example 2 with PHF-BA (31%) (MW ~13 kDa) is taken up in a mixture of water (8 mL) and acetonitrile (4 mL). The pH is adjusted to 7.5 with 1M $NaHCO_3$ and DTT (37.8 mg, 0.245 mmol) is added. The reaction mixture is stirred at 23° C. for 30 min then MMAE-MI prepared as described in Example 7) is added and the resulting mixture is stirred at room temperature for 4 h, pH 7.0. The conjugate is purified by diafiltration to give the title compound.

Example 9

Synthesis of Trastuzumab-MCC Derivative

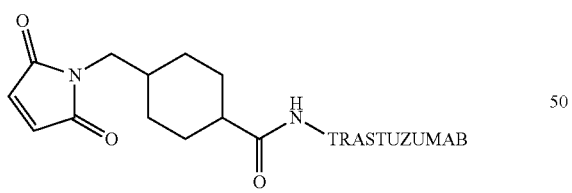

Trastuzumab (10 mg) was dissolved in PBS buffer (1 ml, pH 7.0), then a solution of SMCC in DMSO (5 μL, 30 mg/ml) was added. The resulting solution was stirred at room temperature for 2 h. The trastuzumab-MCC was purified by gel filtration using a PBS equilibrated PD-10 column (90% yield). Analysis showed that on average 5 to 6 MCC groups were linked to one trastuzumab.

Other PBRM-MCC derivatives, such as, MCC derivatives of cetuximab, rituximab, bevacizumab, nimotuzumab, gemtuzumab, alemtuzumab, lintuzumab, anti-5T4 or anti-mesothelin antibodies are synthesized with methods similar to the procedure described above.

Example 10

Synthesis of 13 kDa PHF BA
MMAE-MI-Trastuzumab-MCC

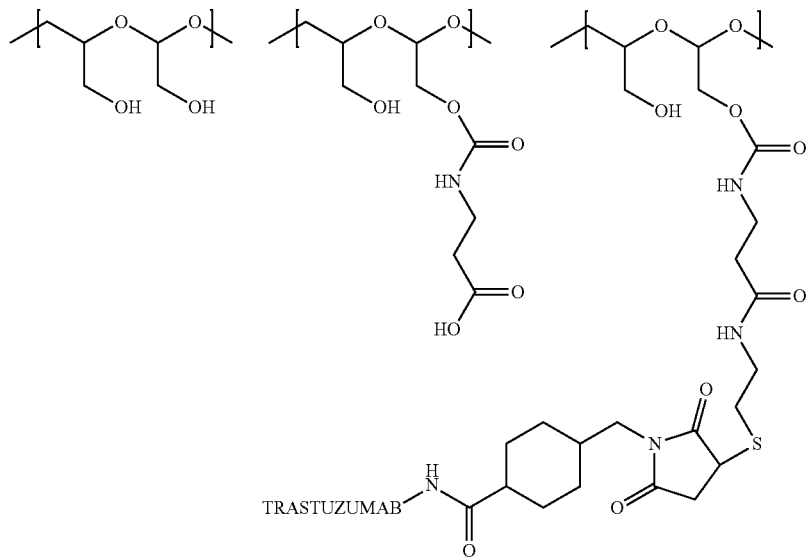

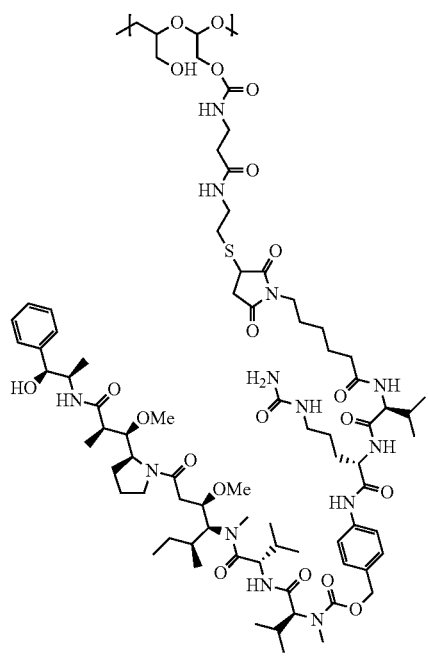

To Trastuzumab-MCC (20 mg, prepared as described in Example 9) in PBS (2 mL, pH 7.0) is added 13 kDa PHF BA -MMAE-MI-SH (11.2 mg, prepared as described in Example 8) in water (0.5 mL). The solution was stirred at room temperature for 4 h at pH 7.0. The resulting conjugate is purified to give the title compound.

Other protein-drug-polymer conjugates are synthesized with methods similar to the procedure described above, involving other PBRM derivatives, such as, for example, MCC derivatives of cetuximab, rituximab, bevacizumab, nimotuzumab, gemtuzumab, alemtuzumab, lintuzumab, anti-5T4 or anti-mesothelin antibodies as described in Example 9 above. Also PBRM-drug polymer conjugates with varying ratios of drug to PBRM are obtained by varying the amount of PBRM and drug-polymer scaffold used in the Examples above.

Example 11

Synthesis of Trastuzumab-M-(PEG)$_{12}$ Derivative

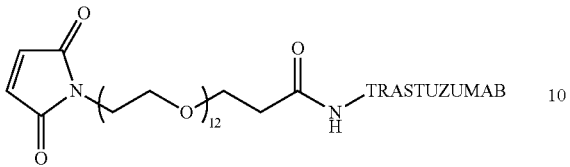

Trastuzumab (10 mg) was dissolved in PBS buffer (1 ml, pH 7.0), then a solution of SM-(PEG)$_{12}$ in DMSO (4 μL, 100 mg/ml) was added. The resulting solution was stirred at room temperature for 2 h. Trastuzumab-M-(PEG)$_{12}$ was purified by gel filtration using a PBS equilibrated PD-10 column (~90% yield). Analysis showed that on average 5 to 6 polyethylene groups were linked to one trastuzumab.

Other PBRM-M-(PEG)$_{12}$ derivatives, such as, M-(PEG)$_{12}$ derivatives of cetuximab, rituximab, bevacizumab, nimotuzumab, gemtuzumab alemtuzumab, lintuzumab, anti-5T4 or anti-mesothelin antibodies are synthesized with methods similar to the procedure described above.

Example 12

Synthesis of 13 kDa PHF BA
MMAE-MI-(Trastuzumab-M-(PEG)$_{12}$)

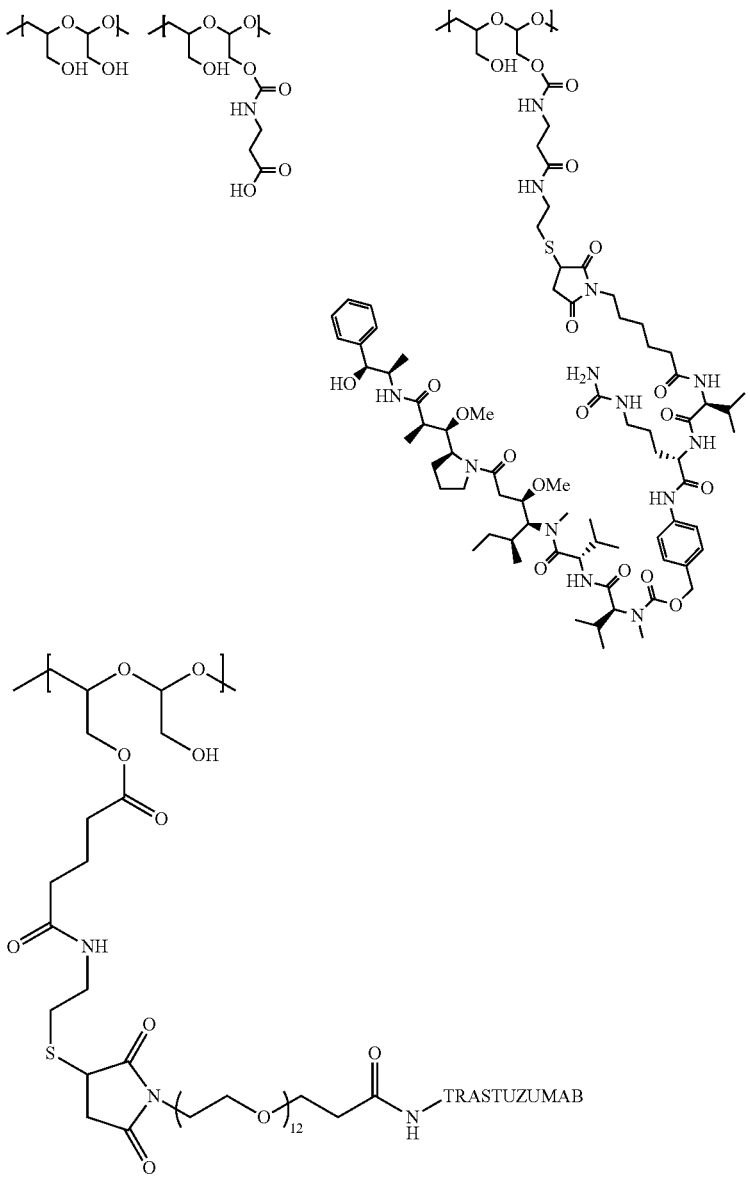

The title compound is prepared as described in Example 10 except Trastuzumab-MCC is replaced by Trastuzumab-M-(PEG)$_{12}$ (prepared as described in Example 11). The molecular weight of the resulting PHF BA MMAE-MI-(Trastuzumab-M-(PEG)$_{12}$) conjugate is determined by SEC.

Other protein-auristatin compound-polymer conjugates are synthesized with methods similar to the procedure described above, involving other PBRM derivatives, such as, for example, M-(PEG)$_{12}$ derivatives cetuximab, rituximab, bevacizumab, nimotuzumab, gemtuzumab, alemtuzumab, lintuzumab, anti-5T4 or anti-mesothelia antibodies as described in Example 11 above. Also PBRM-drug polymer conjugates with varying ratios of drug to PBRM are obtained by varying the amount of PBRM and drug-polymer scaffold used in the Examples above.

Example 13

Cell Viability Assay for PBRM-Drug Polymer Conjugates

PBRM-auristatin compound polymer conjugates are evaluated for their tumor viability using Cell Titer-Glo (Promega Corp). Cells are plated in black walled 96-well plate and allowed to adhere overnight at 37° C. in a humidified atmosphere of 5% CO$_2$. HER2 expressing cells SKBR3, BT474, NCI-N87 and cells expressing low levels of HER2-MCF7 are plated at a density of 5,000 cells per well. The next day the medium is replaced with 50 μL fresh medium and 50 μL of 2× stocks of PBRM-drug polymer conjugate, auristatin compound polymer conjugate or auristatin compound is added to appropriate wells, mixed and incubated for 72 h. Cell Titer-Glo reagent is added to the wells at room temperature and the luminescent signal is measured after 10 min using a SpectraMax M5 plate reader (Molecular Devices). Dose response curves are generated using SoftMax Pro software. IC$_{50}$ values are determined from four-parameter curve fitting.

Example 14

In vivo Efficacy, Pharmacokinetic and Biodistribution Studies

In order to evaluate the efficacy and pharmacokinetics of the protein drug conjugate mouse and rat subcutaneous and orthotopic xenograft models are used.

Test articles, along with appropriate controls are administered intravenously (IV) via tail-vein injection or intraperitoneally. To assess circulating levels of test article blood sample is collected at designated times via terminal cardiac-puncture. Samples are kept at room temperature for 30 min to coagulate, then centrifuged for 10 min at 1,000×g at 4° C. and immediately frozen at −80° C. Total PBRM concentrations in serum samples are measured using ELISA. Circulating auristatin compound concentration (conjugated and free) is determined by LC/MS methods.

To assess efficacy of the PBRM-auristatin compound polymer conjugates the tumor size are measured using digital calipers. Tumor volume is calculated and used to determine the delay in tumor growth.

For the determination of drug biodistribution, tumor, and major organs such as, for example, liver, kidney, spleen, lung, heart, muscles, and brain are harvested, immediately frozen in liquid nitrogen, stored at −80° C. PBRM and/or auristatin compound levels are determined in tissue homogenates by standard methods, such as, for example, ELISA or LC/MS/MS methods respectively.

Example 15

Tumor Growth Response to Administration of PBRM-drug Polymer Conjugates

Female CB-17 SCID mice are inoculated subcutaneously with NCI-N87 cells (n=10 for each group) or BT474 tumors (n=12 or n=10 for each group). Test compounds or vehicle are dosed IV as a single dose on day 1; once every week for 3 weeks on day 1, day 8 and day 15 respectively; or once every week for 3 weeks on day 17, day 24 and day respectively. The auristatin compound polymer conjugate dose is determined such that it delivered the same amount of auristatin compound as that present in the highest dose of the corresponding PBRM-auristatin compound polymer conjugate is administered Tumor size is measured at several different time points using digital calipers. Tumor volume is calculated and are used to determine the delay in tumor growth. Mice are sacrificed when tumors reach a size of 1000 mm$^3$, 800 mm$^3$, or 700 mm$^3$. Tumor volumes are reported as the mean±SEM for each group.

Example 16

In Vitro Stability of PBRM-auristatin Compound Polymer Conjugates

The in vitro stability of PBRM-auristatin compound polymer conjugates are evaluated by incubation of the PBRM-auristatin compound polymer conjugate in physiological saline or animal plasma at 37° C., pH 7.4. The rate of PBRM-auristatin compound polymer conjugate degradation is determined by monitoring the amount of drug released into the matrix by LC/MS analysis after isolation of released drug from the PBRM-auristatin compound polymer conjugate by liquid-liquid extraction.

Example 17

Ligand Binding Studies by BIAcore Surface Plasmon Resonance (SPR)

The kinetic binding of the PBRM-auristatin compound polymer conjugate to an immobilized receptor is determined by BIAcore SPR. The binding constants for the PBRM in the PBRM-auristatin compound-conjugate and PBRM alone is determined using standard BIAcore procedures.

Example 18

Mouse Plasma PK and Tissue Distribution after Administration of PBRM-auristatin Compound Polymer Conjugates The plasma PK stability and the tissue distribution of PBRM-auristatin compound-conjugate is determined after administration of PBRM-auristatin compound-conjugate in female CB-17 SCID mice with NCI-N87 tumors (n=3). The conjugated auristatin compound concentrations is determined by LC/MS analysis. The concentration of the auristatin compound-PBRM-conjugate is estimated from the conjugated auristatin compound data. Total PBRM concentration is determined by ELISA.

INCORPORATION BY REFERENCE

The entire disclosure of each of the patent documents and scientific articles referred to herein is incorporated by reference for all purposes.

EQUIVALENTS

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

What is claimed is:

1. A polymeric scaffold of Formula (Ibb) useful to conjugate with a protein based recognition-molecule (PBRM):

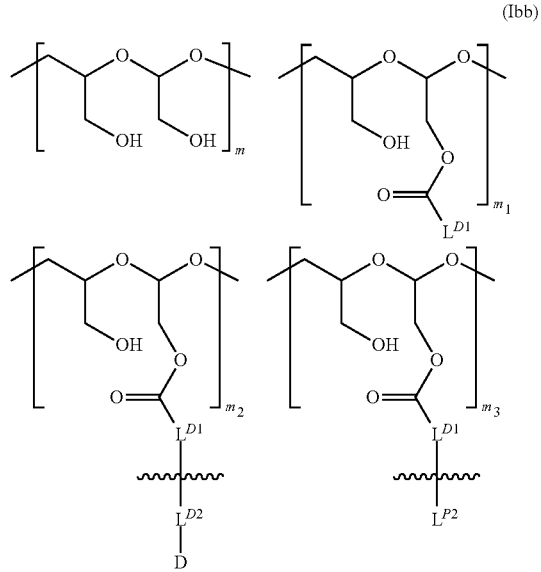

(Ibb)

wherein:
the scaffold comprises poly(1-hydroxymethylethylene hydroxymethyl-formal) (PHF) having a molecular weight ranging from 2 kDa to 40 kDa when the PBRM to be conjugated has a molecular weight of greater than 40 kDa, or the scaffold comprises PHF having a molecular weight ranging from 20 kDa to 300 kDa when the PBRM to be conjugated has a molecular weight of less than 80 kDa;
each occurrence of D is independently an auristatin compound of Formula (Ib):

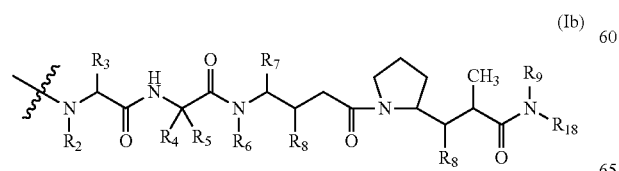

(Ib)

wherein:
$R_2$ is H or $C_{1-8}$ alkyl;
$R_3$ is H, $C_{1-8}$ alkyl, $C_{3-8}$ carbocycle, $X_4$—$C_{3-8}$ carbocycle, $C_{6-10}$ aryl, $X_4$—$C_{6-10}$ aryl, $C_{3-8}$ heterocycle, or $X_4$—$C_{3-8}$ heterocycle;
$R_4$ is H, $C_{1-8}$ alkyl, $C_{3-8}$ carbocycle, $X_4$—$C_{3-8}$ carbocycle, $C_{6-10}$ aryl, $X_4$—$C_{6-10}$ aryl, $C_{3-8}$ heterocycle, or $X_4$—$C_{3-8}$ heterocycle;
$R_5$ is H or methyl; or
$R_4$ and $R_5$ together with the carbon atom to which they are attached form a carbocyclic ring having the formula —$(CR_aR_b)_n$— wherein each of $R_a$ and $R_b$ independently is H, $C_{1-8}$ alkyl or $C_{3-8}$ carbocycle;
$R_6$ is H or $C_{1-8}$ alkyl;
$R_7$ is H, $C_{1-8}$ alkyl, $C_{3-8}$ carbocycle, $X_4$—$C_{3-8}$ carbocycle, $C_{6-10}$ aryl, $X_4$—$C_{6-10}$ aryl, $C_{3-8}$ heterocycle, or $X_4$—$C_{3-8}$ heterocycle;
each $R_8$ independently is H, OH, $C_{1-8}$ alkyl, $C_{3-8}$ carbocycle or O—($C_{1-8}$ alkyl);
each $X_4$ independently is $C_{1-10}$ alkylene or $C_{3-10}$ cycloalkylene;
$R_9$ is H or $C_{1-8}$ alkyl;
$R_{18}$ is —$C(R_8)_2$—$C(R_8)_2$—$C_{6-10}$ aryl, —$C(R_8)_2$—$C(R_8)_2$—($C_{3-8}$ heterocycle), —$C(R_8)_2$—$C(R_8)_2$—($C_{3-8}$ carbocycle), or selected from

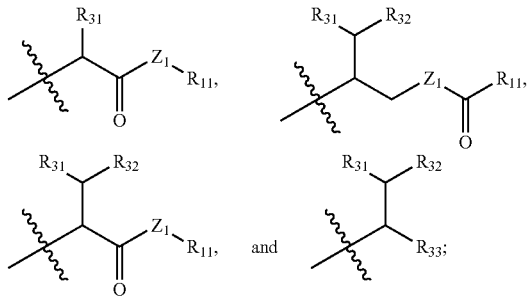

$Z_1$ is O, S, or $NR_{34}$;
$R_{31}$ is H, OH, $N(R_{34})_2$, $C_{1-8}$ alkyl, $C_{3-8}$ carbocycle, O—($C_{1-8}$ alkyl), $C_{6-10}$ aryl, $X_4$—$C_{6-10}$ aryl, $X_4$—($C_{3-8}$ carbocycle), $C_{3-8}$ heterocycle, $X_4$—($C_{3-8}$ heterocycle), $C_{1-8}$ alkylene-$NH_2$, or $(CH_2)_2SCH_3$; or $R_{31}$ is an oxygen atom which forms a carbonyl unit (C=O) with the carbon atom to which it is attached and one hydrogen atom on this carbon atom is replaced by one of the bonds in the (C=O) double bond;
$R_{32}$ is $C_{6-10}$-aryl or $C_{3-8}$ heterocycle;
$R_{33}$ is H, OH, $N(R_{34})_2$, $C_{1-8}$ alkyl, $C_{3-8}$ carbocycle, O—($C_{1-8}$ alkyl), $C_{6-10}$ aryl, $C_{1-8}$ alkyl-$C_{6-10}$ aryl, $C_{1-8}$ alkyl-($C_{3-8}$ carbocycle), $C_{3-8}$ heterocycle, or $C_{1-8}$ alkyl-($C_{3-8}$ heterocycle);
each $R_{34}$ independently is H or $C_{1-8}$ alkyl;
$R_{11}$ is H, OH, $N(R_{34})_2$, $C_{1-20}$ alkyl, $C_{6-10}$ aryl, $C_{3-8}$ heterocycle, —$(R_{13}O)_s$—$R_{14}$, —$(R_{13}O)s$—$CH(R_{15})_2$ or —$[C(R_{50}R_{51})]_b$—$R_{52}$;
$R_{13}$ is $C_{2-8}$ alkyl;
$R_{14}$ is H or $C_{1-8}$ alkyl;
$R_{15}$ is H, COOH, —$(CH_2)_o$—$N(R_{16})_2$, —$(CH_2)_o$—$SO_3H$, or —$(CH_2)_o$—$SO_3$—$C_{1-8}$ alkyl;
$R_{16}$ is H, $C_{1-8}$ alkyl, or —$(CH_2)_o$—COOH;
each of $R_{50}$ and $R_{51}$ independently is hydrogen, $C_{1-6}$ alkyl, $C_{6-10}$ aryl, hydroxylated $C_{6-10}$ aryl, polyhydroxylated $C_{6-10}$ aryl, 5 to 12-membered heterocycle, $C_{3-8}$ cycloalkyl, hydroxylated $C_{3-8}$ cycloalkyl, polyhydroxylated $C_{3-8}$ cycloalkyl or a side chain of a natural or unnatural amino acid;

$R_{52}$ is OH, $NHR_{53}$, COOH, $R_{82}$—C(O)(CH$_2$)$_c$—C(H)($R_{53}$)—N(H)($R_{53}$), $R_{82}$—C(O)(CH$_2$)$_d$—(O—CH$_2$—CH$_2$)$_h$—N(H)($R_{53}$) or $R_{82}$—(C(O)—CH($X_2$)—NH)$_d$—$R_{77}$;

each $R_{53}$ independently is hydrogen, $C_{1-6}$ alkyl, $C_{6-10}$ aryl, $C_{3-8}$ cycloalkyl, COOH, or COO—$C_{1-6}$ alkyl;

$X_2$ is a side chain of a natural or unnatural amino acid;

$R_{77}$ is hydrogen or $X_2$ and $NR_{77}$ form a nitrogen containing cyclic compound;

$R_{82}$ is NH or oxygen;

n is an integer from 2 to 7;
s is an integer from 0 to 1000;
o is an integer from 0 to 6;
b is an integer from 1 to 6;
c is an integer from 0 to 3;
d is an integer from 1 to 3; and
h is an integer from 1 to 12;

$L^{D1}$ is a carbonyl-containing moiety;
$L^{D2}$ is a moiety of Formula (Iaa):

$$-A_a\text{-}W_w\text{—}Y_y\text{—} \quad (Iaa)$$

in which
-A- is a Stretcher unit and is proximal to the polymeric carrier;
a is an integer 0 or 1;
each —W— is independently an amino acid unit;
w is an integer from 0 to 12;
—Y— is a self-immolative or non-self-immolative Spacer unit and is proximal to D; and
y is an integer from 0 to 2;
wherein at least one of a, w, and y is not 0;

each occurrence of

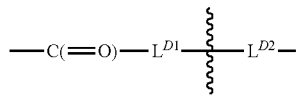

in

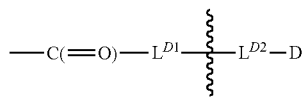

is independently a first linker that contains a biodegradable bond so that when the bond is broken, D is released in an active form for its intended therapeutic effect; in which the

in

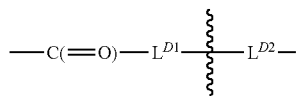

between $L^{D1}$ and $L^{D2}$ denotes direct or indirect attachment of $L^{D2}$ to $L^{D1}$;

each occurrence of

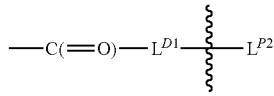

is independently a second linker not yet connected to the PBRM, in which $L^{P2}$ is a moiety containing a functional group that is capable of forming and not yet formed a covalent bond with a functional group of a PBRM, and the

in

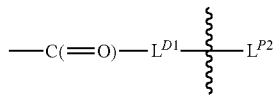

between $L^{D1}$ and $L^{P2}$ denotes direct or indirect attachment of $L^{P2}$ to $L^{D1}$, and each occurrence of the second linker is distinct from each occurrence of the first linker;

m is an integer from 1 to 2200,
$m_1$ is an integer from 1 to 660,
$m_2$ is an integer from 1 to 300,
$m_3$ is an integer from 1 to 110, and
the sum of m, $m_1$, $m_2$ and $m_3$ ranges from 15 to about 2200.

2. The scaffold of claim 1, wherein -A- is

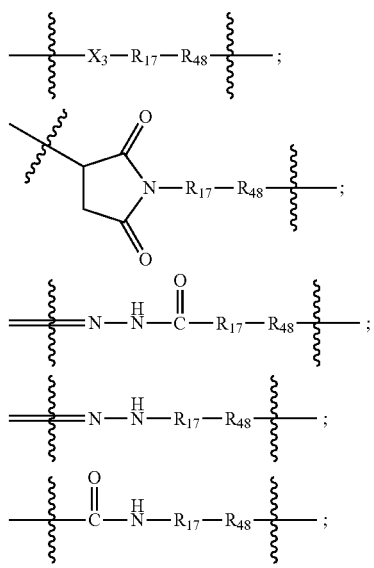

-continued

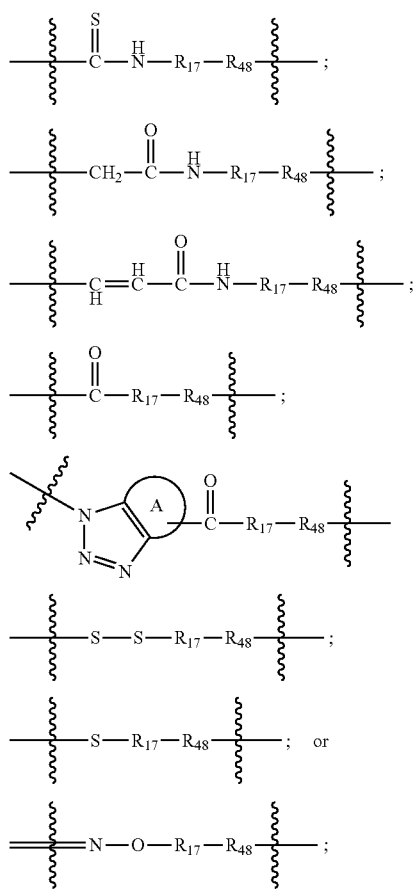

wherein
R₄₈ is proximal to D and is —C(O), NH or O;
X₃ is —O— or —NH;
R₁₇ is —C₁₋₁₀ alkylene-, —C₃₋₈ carbocyclo-, C₁₋₃₀ heteroalkylene, —O—(C₁₋₈alkyl)-, -arylene-, —C₁₋₁₀ alkylene-arylene-, -arylene-C₁₋₁₀ alkylene-, —C₁₋₁₀ alkylene-(C₃₋₈ carbocyclo)-, —(C₃₋₈ carbocyclo)-C₁₋₁₀ alkylene-, —C₃₋₈ heterocyclo-, —C₁₋₁₀ alkylene-(C₃₋₈ heterocyclo)-, —(C₃₋₈heterocyclo)-C₁₋₁₀ alkylene-, and —(CH₂CH₂O)ₕ—(CH₂)c, in which c is an integer from 0 to 3 and h is an integer from 1 to 12; and
ring A is cycloalkyl or heterocycloalkyl.

3. The scaffold of claim 2, wherein -A- is

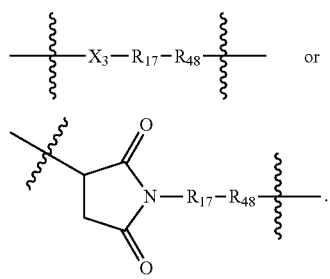

4. The scaffold of claim 1, wherein W is

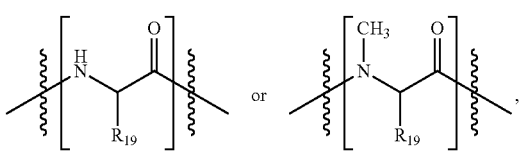

in which the carbonyl group is proximal to D and the amino group is proximal to the PHF; and R₁₉ is hydrogen, methyl, isopropyl, isobutyl, sec-butyl, benzyl, p-hydroxybenzyl, —CH₂OH, —CH(OH)CH₃, —CH₂CH₂SCH₃, —CH₂CONH₂, —CH₂COOH, —CH₂CH₂CONH₂, —CH₂CH₂COOH, —(CH₂)₃NHC(=NH)NH₂, —(CH₂)₃NH₂, —(CH₂)₃NHCOCH₃, —(CH₂)₃NHCHO, —(CH₂)₄NHC(=NH)NH₂, —(CH₂)₄NH₂, —(CH₂)₄NHCOCH₃, —(CH₂)₄NHCHO, —(CH₂)₃NHCONH₂, —(CH₂)₄NHCONH₂, —CH₂CH₂CH(OH)CH₂NH₂, 2-pyridylmethyl-, 3-pyridylmethyl-, 4-pyridylmethyl-, phenyl, cyclohexyl, or selected from

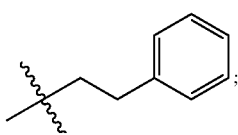

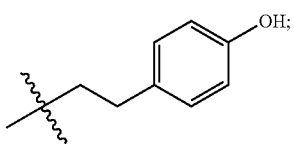

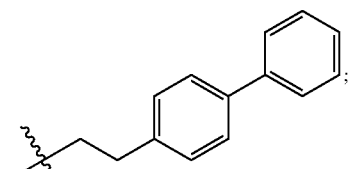

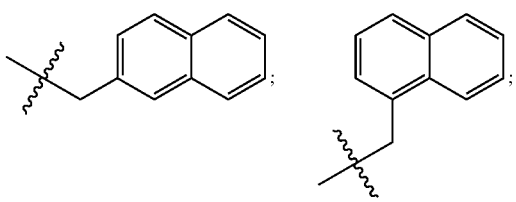

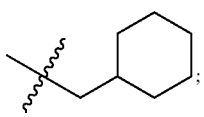

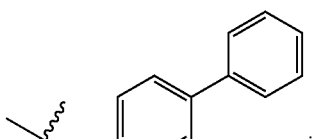

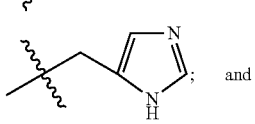 and

-continued

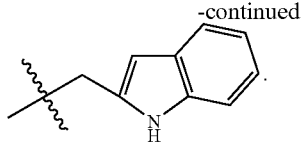

5. The scaffold of claim 4, wherein $R_{19}$ is isopropyl or —$(CH_2)_3NHCONH_2$.

6. The scaffold of claim 1, wherein Y is

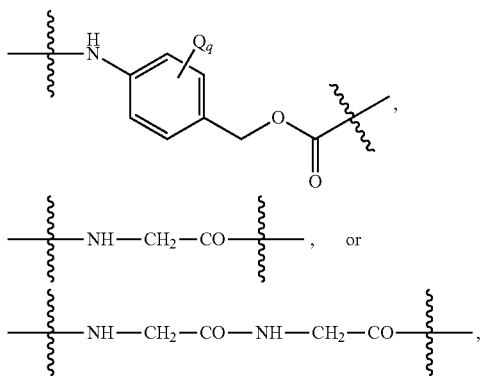

in which the carbonyl group is proximal to D; each Q independently is —$C_{1-8}$ alkyl, —O—($C_{1-8}$ alkyl), -halogen, -nitro or -cyano; and q is an integer from 0 to 4.

7. The scaffold of claim 6, wherein Y is

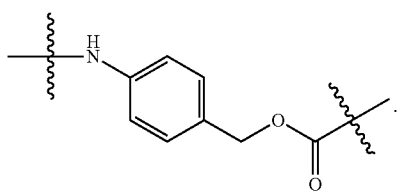 [SMILES: *Nc1ccc(COC(*)=O)cc1]

8. The scaffold of claim 1, wherein a is 0.

9. A polymeric scaffold of Formula (V1) or (V2):

wherein the POLYMER is a PHF scaffold having the structure

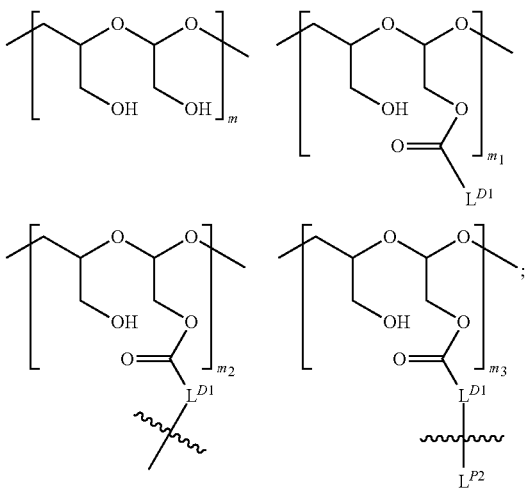

and the wavy line

between the POLYMER and amino acid denotes direct or indirect attachment;

$L^{D1}$ is a carbonyl-containing moiety;

(V1)

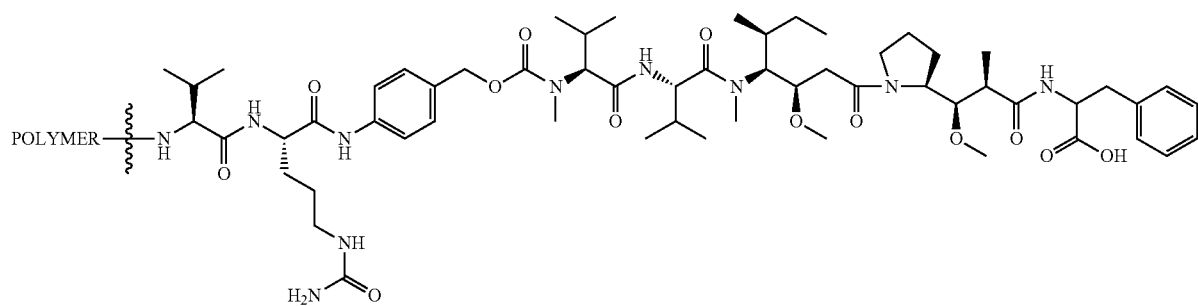

(V2)

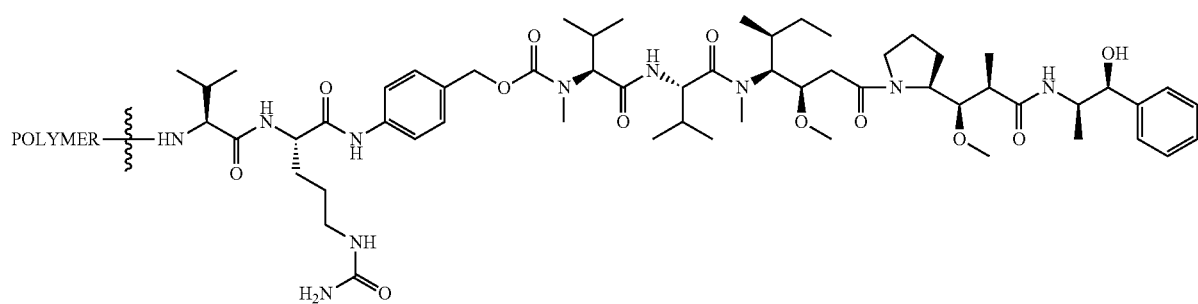

each occurrence of

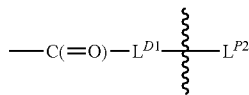

is independently a linker not yet connected to the PBRM, in which $L^{P2}$ is a moiety containing a functional group that is capable of forming and not yet formed a covalent bond with a functional group of a PBRM, and the

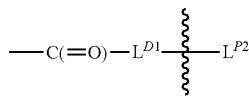

in

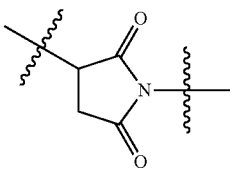 [SMILES: *C1CC(=O)N(*)C1=O]

between $L^{D1}$ and $L^{P2}$ denotes direct or indirect attachment of $L^{P2}$ to $L^{D1}$;

m is an integer from 1 to 2200,
$m_1$ is an integer from 1 to 660,
$m_2$ is an integer from 1 to 300,
$m_3$ is an integer from 1 to 110, and
the sum of m, $m_1$, $m_2$ and $m_3$ ranges from 15 to about 2200.

10. A polymeric scaffold of Formula (V3), (V4), (V5), or (V6):

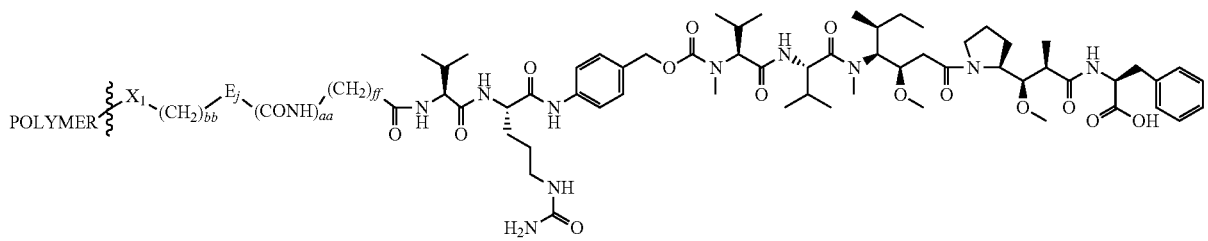

(V3)

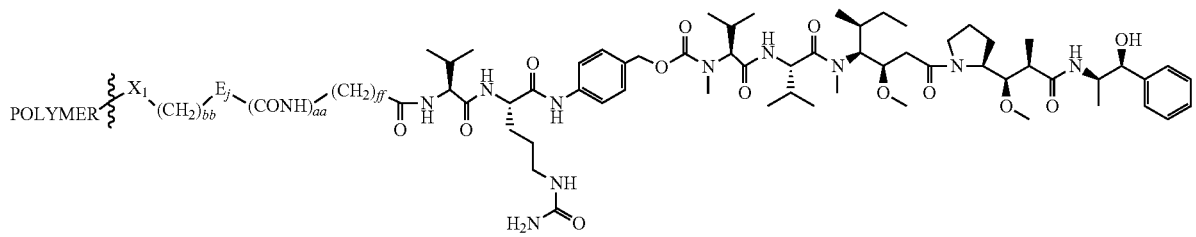

(V4)

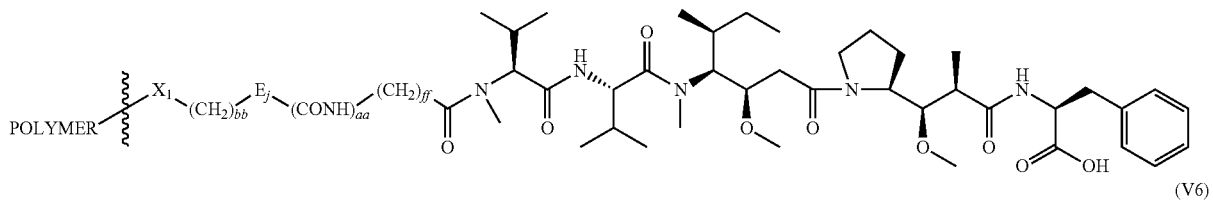

(V5)

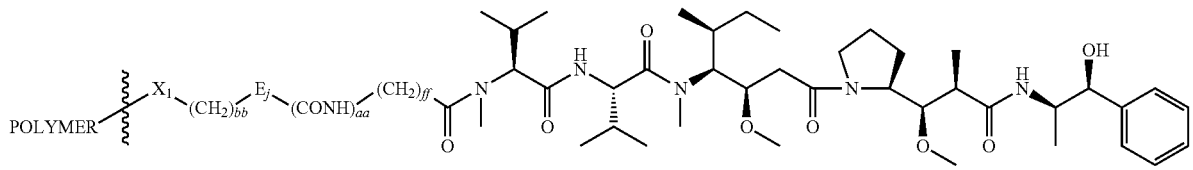

(V6)

wherein:
E is —$CH_2$— or —$OCH_2CH_2$—;
aa is an integer 0 or 1;
bb is an integer 0 or 2;
ff is an integer from 0 to 10;
j is an integer from 0 to 12; and
when E is —$CH_2$—, bb is 0 and j is an integer from 0 to 10; and when E is —$CH_2CH_2$—O—, bb is 2 and j is an integer from 1 to 12;
$X_1$ is NH, O or the POLYMER is a PHF scaffold having the structure wherein N— is distal to the POLYMER;

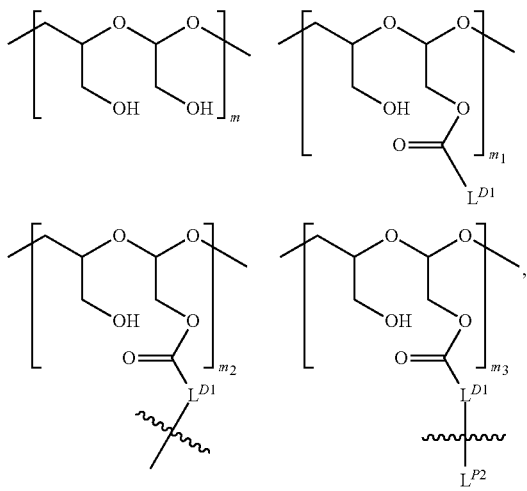

and
the wavy line

between the POLYMER and $X_1$ denotes direct or indirect attachment;

$L^{D1}$ is a carbonyl-containing moiety;

each occurrence of

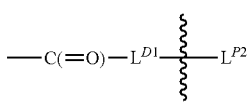

is independently a linker not yet connected to the PBRM, in which $L^{P2}$ is a moiety containing a functional group that is capable of forming and not yet formed a covalent bond with a functional group of a PBRM, and the

in

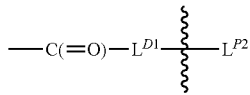

between $L^{D1}$ and $L^{P2}$ denotes direct or indirect attachment of $L^{P2}$ to $L^{D1}$;

m is an integer from 1 to 2200,
$m_1$ is an integer from 1 to 660,
$m_2$ is an integer from 1 to 300,
$m_3$ is an integer from 1 to 110, and
the sum of m, $m_1$, $m_2$ and $m_3$ ranges from 15 to about 2200.

11. The scaffold of claim 1, wherein the PHF has a molecular weight ranging from 20 kDa to 150 kDa when the PBRM to be conjugated with has a molecular weight of less than 80 kDa, $m_1$ is an integer from 1 to 330, $m_2$ is an integer from 3 to 150, $m_3$ is an integer from 1 to 55 and the sum of m, $m_1$, $m_2$ and $m_3$, ranging from about 150 to about 1100.

12. The scaffold of claim 11, wherein the PHF has a molecular weight ranging from 30 kDa to 100 kDa, $m_2$ is an integer from 3 to about 100, $m_3$ is an integer from 1 to 40, $m_1$ is an integer from 1 to 220 and the sum of m, $m_1$, $m_2$, and $m_3$ ranging from about 220 to about 740.

13. The scaffold of claim 1, wherein the PHF has a molecular weight ranging from 6 kDa to 20 kDa when the PBRM to be conjugated with has a molecular weight of greater than 40 kDa, $m_2$ is an integer from 2 to 20, $m_3$ is an integer from 1 to 9, $m_1$ is an integer from 1 to 75 and the sum of m, $m_1$, $m_2$, and $m_3$ ranging from about 45 to about 150.

14. The scaffold of claim 13, wherein the PHF has a molecular weight ranging from 8 kDa to 15 kDa, $m_2$ is an integer from 2 to 15, $m_3$ is an integer from 1 to 7, $m_1$ is an integer from 1 to 55 and the sum of m, $m_1$, $m_2$, and $m_3$ ranging from about 60 to about 110.

15. The scaffold of claim 1, wherein the functional group of $L^{P2}$ is selected from —$SR^P$, —S—LG, maleimido, and halo, in which LG is a leaving group and $R^P$ is H or a sulfur protecting group.

16. The scaffold of claim 1, wherein $L^{D1}$ comprises —X—$(CH_2)_v$—C(=O)— with X directly connected to the carbonyl group of

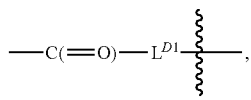

in which X is $CH_2$, O, or NH, and v is an integer from 1 to 6.

17. The scaffold of claim 1, wherein $L^{P2}$ contains a biodegradable bond.

18. The scaffold of claim 1, further comprising a PBRM connected to the polymeric carrier via $L^{P2}$.

19. The scaffold of claim 18, wherein ratio of D to PBRM is between 5:1 and 40:1.

* * * * *

UNITED STATES PATENT AND TRADEMARK OFFICE
CERTIFICATE OF CORRECTION

PATENT NO. : 10,226,535 B2
APPLICATION NO. : 14/651097
DATED : March 12, 2019
INVENTOR(S) : Aleksandr V. Yurkovetskiy et al.

Page 1 of 2

It is certified that error appears in the above-identified patent and that said Letters Patent is hereby corrected as shown below:

In the Claims

At Column 241, Line 40:
"$X_3$ is –O–or –NH;"
Should read:
-- $X_3$ is –O– or –NH; --

At Column 241, Line 47:
"heterocyclo)-, -($C_{3-8}$heterocyclo)-$C_{1-10}$ alkylene-,"
Should read:
-- heterocyclo)-, -($C_{3-8}$ heterocyclo)-$C_{1-10}$ alkylene-, --

At Column 242, Line 13:
"group is proximal to the PHF; and $R_{19}$is hydrogen, methyl"
Should read:
-- group is proximal to the PHF; and $R_{19}$ is hydrogen, methyl --

At Column 246, Line 6:
"the sum of m, $m_1$, $m_2$ and $m_3$ranges from 15 to about 2200."
Should read:
-- the sum of m, $m_1$, $m_2$ and $m_3$ ranges from 15 to about 2200. --

At Column 246, Line 66 through Column 247, Line 1:
"the POLYMER is a PHF scaffold having the structure
wherein N– is distal to the POLYMER;"
Should read:
-- wherein N– is distal to the POLYMER;
the POLYMER is a PHF scaffold having the structure --

Signed and Sealed this
Fourteenth Day of May, 2019

Andrei Iancu
*Director of the United States Patent and Trademark Office*

At Column 248, Line 39:
"of $L^{P2}$ is selected from –SR$^P$, –S–LG, maleimido, and"
Should read:
-- of $L^{P2}$ is selected from –SR$^P$, –S–S–LG, maleimido, and --